United States Patent
Mayer et al.

(10) Patent No.: US 6,908,884 B2
(45) Date of Patent: Jun. 21, 2005

(54) BENZAZOLONYLCARBONYLCYCLO-HEXENONES AND THEIR USE AS HERBICIDES

(75) Inventors: Guido Mayer, Neustadt (DE); Ulf Misslitz, Neustadt (DE); Ernst Baumann, Dudenhofen (DE); Wolfgang von Deyn, Neustadt (DE); Steffen Kudis, Mannheim (DE); Michael Hofmann, Ludwigshafen (DE); Thorsten Volk, Mannheim (DE); Matthias Witschel, Bad Dürkheim (DE); Cyrill Zagar, Ludwigshafen (DE); Andreas Landes, Römerberg (DE); Klaus Langemann, Schauenburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 109 days.

(21) Appl. No.: 10/433,013

(22) PCT Filed: Dec. 10, 2001

(86) PCT No.: PCT/EP01/14475

§ 371 (c)(1),
(2), (4) Date: May 29, 2003

(87) PCT Pub. No.: WO02/48121

PCT Pub. Date: Jun. 20, 2002

(65) Prior Publication Data

US 2004/0063584 A1 Apr. 1, 2004

(30) Foreign Application Priority Data

Dec. 11, 2000 (DE) .......................................... 100 61 551

(51) Int. Cl.$^7$ ..................... C07D 277/68; C07D 263/58; C07D 271/00; C07D 261/18; A01N 43/76
(52) U.S. Cl. ........................ 504/267; 504/271; 504/282; 548/131; 548/240; 514/314
(58) Field of Search .................................. 504/271, 282, 504/267; 548/240, 131; 514/314

(56) References Cited

U.S. PATENT DOCUMENTS

| 5,559,218 A | | 9/1996 | Kast et al. | |
|---|---|---|---|---|
| 5,744,425 A | | 4/1998 | Plath et al. | |
| 6,054,414 A | | 4/2000 | Otten et al. | |
| 6,153,759 A | * | 11/2000 | von Deyn et al. | 548/131 |
| 6,165,944 A | * | 12/2000 | von Deyn et al. | 504/271 |
| 6,262,074 B1 | * | 7/2001 | Otten et al. | 514/314 |
| 6,407,268 B1 | * | 6/2002 | Engel et al. | 549/511 |
| 6,500,750 B1 | * | 12/2002 | Shroff et al. | 438/622 |
| 6,506,708 B1 | * | 1/2003 | Neidlein et al. | 504/282 |
| 6,645,919 B1 | * | 11/2003 | Baumann et al. | 504/271 |
| 2004/0063584 A1 | * | 4/2004 | Mayer et al. | 504/267 |

FOREIGN PATENT DOCUMENTS

| CA | 2373137 | 11/2000 |
|---|---|---|
| EP | 283 261 | 9/1988 |
| EP | 1 120 413 | 8/2001 |

* cited by examiner

*Primary Examiner*—Sabiha Qazi
(74) *Attorney, Agent, or Firm*—Novak, Druce, DeLuca & Quigg

(57) ABSTRACT

Cyclohexenone derivatives of benzazolones of the formula I

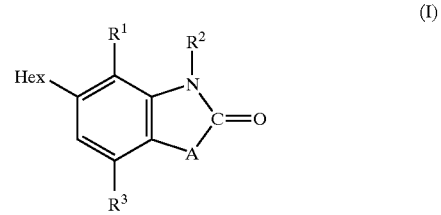

where the variables $R^1$, $R^2$, $R^3$, A and Hex are as defined in claim 1, and their salts, and their use for controlling harmful plants, are described.

13 Claims, No Drawings

BENZAZOLONYLCARBONYLCYCLO-HEXENONES AND THEIR USE AS HERBICIDES

The present invention relates to cycloyexenone derivatives of benzazolones (benzazolonylcarbonylcyclohexenones), to compositions comprising such compounds, and to the use of the cyclohexenone derivatives or of the compositions comprising them for controlling harmful plants. Moreover, the invention relates to benzazolonecarboxylic acids, which are important intermediates for preparing such cyclohexenone derivatives.

EP-A 283 261 discloses cyclohexane-1,3-diones in which the cyclohexenone ring in the 2-position is substituted by a heteroaromatic radical which is attached via a carbonyl group. Heteroaromatic radicals mentioned are sulfur-, nitrogen- and/or oxygen-containing 5-membered or 6-membered heterocycles.

WO 96/05182 discloses saccharin derivatives which have herbicidal action and are substituted on the benzene ring of the saccharin skeleton by a (2-cyclohexane-1,3-dione)carbonyl radical.

WO 97/09324 discloses cyclohexane-1,3-diones which have herbicidal action and, in the 2-position, a benzo-fused sulfur heterocycle, for example a thiochromane or a benzodihydrothiophene radical, which is attached via a carbonyl group.

WO 00/20408 describes inter alia herbicides based on cyclohexenone derivatives of the formula (a)

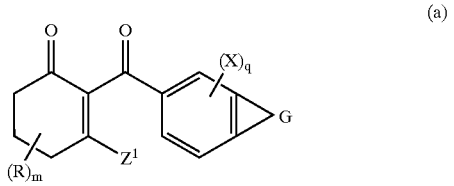

in which R is a methylene group, X is a hydrogen atom, a halogen atom or the like, G is a 3- to 5-membered chain which, together with the two carbons of the benzene ring to which G is attached, forms a 5- to 7-membered saturated or unsaturated fused ring, $Z^1$ is a halogen atom or the like, m is an integer from zero to four and q is either one or two.

PCT/EP 00/04042 discloses benzoheterocyclylcyclohexenones. Heterocyclic radicals mentioned are, inter alia, benzoxazolyl, benzimidazolyl, benzothiazolyl and benzotriazinyl. The compounds have herbicidal action.

However, the herbicidal properties of the compounds known from the publications mentioned and their compatibility with crop plants do not meet all of the criteria required from herbicides.

It is an object of the present invention to provide novel compounds having herbicidal action which preferably have greater activity than the herbicidal substances of the prior art and/or better selectivity for harmful plants.

We have found that this object is achieved by cyclohexenone derivatives of benzazolones of the formula I defined below.

Consequently, the present invention relates to cyclohexenone derivatives of benzo-fused, unsaturated 5-membered nitrogen heterocycles of the formula I

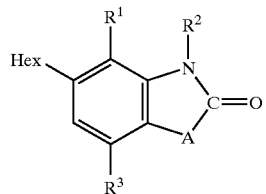

in which A, $R^1$, $R^2$, $R^3$ and Hex are as defined below:
A is O, S, SO, $SO_2$ or $NR^6$;
$R^1$ is halogen, $C_1$–$C_4$-alkyl, $C_1$–$C_4$-haloalkyl, $C_1$–$C_4$-hydroxyalkyl, $C_1$–$C_4$-alkoxy-$C_1$–$C_4$-alkyl, $C_1$–$C_4$-haloalkoxy-$C_1$–$C_4$-alkyl, $C_1$–$C_4$-haloalkylthio-$C_1$–$C_4$-alkyl, $C_1$–$C_4$-alkylthio-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, $C_1$–$C_4$-alkoxy, $C_1$–$C_4$-hydroxyalkoxy, $C_1$–$C_4$-haloalkoxy, $C_1$–$C_4$-alkoxy-$C_1$–$C_4$-alkoxy, $C_1$–$C_4$-haloalkoxy-$C_1$–$C_4$-alkoxy, $C_1$–$C_4$-alkylthio, $C_1$–$C_4$-haloalkylthio, $C_1$–$C_4$-alkylsulfonyl, $C_1$–$C_4$-haloalkylsulfonyl;
$R^2$ is hydrogen, hydroxyl, nitro, amino, $C_1$–$C_6$-alkylamino, di($C_1$–$C_6$-alkyl)amino, cyano, CHO, $C_1$–$C_6$-alkoxy, $C_1$–$C_6$-alkyl, $C_1$–$C_6$-hydroxyalkyl, $C_1$–$C_6$-haloalkyl, $C_1$–$C_6$-alkoxy-$C_1$–$C_6$-alkyl, $C_1$–$C_6$-haloalkoxy-$C_1$–$C_6$-alkyl, $C_2$–$C_6$-alkenyl, $C_2$–$C_6$-haloalkenyl, $C_1$–$C_6$-haloalkoxy-$C_2$–$C_6$-alkenyl, $C_1$–$C_6$-alkoxy-$C_2$–$C_6$-alkenyl, $C_2$–$C_6$-alkynyl, $C_2$–$C_6$-haloalkynyl, $C_1$–$C_6$-haloalkoxy-$C_2$–$C_6$-alkynyl, $C_1$–$C_6$-alkoxy-$C_2$–$C_6$-alkynyl, $C_1$–$C_6$-alkylsulfonyl, $C_1$–$C_6$-haloalkylsulfonyl, ($C_1$–$C_6$-alkyl)carbonyl, $C_1$–$C_6$-haloalkylcarbonyl, hydroxycarbonyl-$C_1$–$C_4$-alkyl, $C_1$–$C_6$-alkoxycarbonyl-$C_1$–$C_6$-alkyl, a radical of the formula $C(O)OR^4$, $CON(R^5)_2$ or $C(=NOR^{4a})R^{4b}$, aryl, aryl-$C_1$–$C_4$-alkyl, arylsulfonyl, arylcarbonyl, $C_3$–$C_6$-cycloalkyl, $C_3$–$C_6$-cycloalkenyl, 3-, 4-, 5-, 6- or 7-membered heterocyclyl, 3-, 4-, 5-, 6- or 7-membered heterocyclyl-$C_1$–$C_6$-alkyl, where each aryl, cycloalkyl, cycloalkenyl and each heterocyclyl radical may be unsubstituted or may carry one, two, three or four substituents, in each case selected from the group consisting of halogen, $C_1$–$C_4$-haloalkyl, $C_1$–$C_4$-alkoxy and $C_1$–$C_4$-haloalkoxy;
$R^3$ is hydrogen, $C_1$–$C_4$-alkyl, $C_1$–$C_4$-haloalkyl, $C_1$–$C_4$-alkoxy-$C_1$–$C_4$-alkyl, $C_1$–$C_4$-haloalkoxy-$C_1$–$C_4$-alkyl or halogen;
in which
$R^4$ is $C_1$–$C_6$-alkyl, $C_1$–$C_6$-haloalkyl, $C_1$–$C_6$-alkoxy-$C_1$–$C_6$-alkyl, $C_1$–$C_6$-haloalkoxy-$C_1$–$C_6$-alkyl, $C_2$–$C_6$-alkenyl, $C_2$–$C_6$-haloalkenyl, $C_1$–$C_6$-haloalkoxy-$C_2$–$C_6$-alkenyl, $C_1$–$C_6$-alkoxy-$C_2$–$C_6$-alkenyl, $C_2$–$C_6$-alkynyl, $C_2$–$C_6$-haloalkynyl, $C_1$–$C_6$-haloalkoxy-$C_2$–$C_6$-alkynyl, $C_1$–$C_6$-alkoxy-$C_2$–$C_6$-alkynyl;
$R^{4a}$, $R^{4b}$ independently of one another may have the meanings mentioned for $R^4$, and $R^{4b}$ may be hydrogen;
$R^5$ independently of one another are hydrogen, $C_1$–$C_6$-alkyl, $C_1$–$C_6$-haloalkyl, $C_1$–$C_6$-alkoxy-$C_1$–$C_6$-alkyl, ($C_1$–$C_6$-haloalkoxy)-$C_1$–$C_6$-alkyl, $C_2$–$C_6$-alkenyl, $C_2$–$C_6$-haloalkenyl, $C_1$–$C_6$-haloalkyl-$C_2$–$C_6$-alkenyl, $C_1$–$C_6$-haloalkoxy-$C_2$–$C_6$-alkenyl, $C_1$–$C_6$-alkoxy-$C_2$–$C_6$-alkenyl, $C_2$–$C_6$-alkynyl, $C_2$–$C_6$-haloalkynyl, $C_1$–$C_6$-haloalkyl-$C_2$–$C_6$-alkynyl, $C_1$–$C_6$-haloalkoxy-$C_2$–$C_6$-alkynyl, $C_1$–$C_6$-alkoxy-$C_2$–$C_6$-alkynyl, or together form a 3- to 7-membered heterocycle which may be partially or fully halogenated and/or may carry one, two or three substituents selected from the group consisting of $C_1$–$C_6$-alkyl, $C_1$–$C_6$-haloalkyl, $C_1$–$C_6$-alkoxy, $C_1$–$C_6$-haloalkoxy;

$R^6$ is hydrogen, $C_1$–$C_4$-alkyl, $C_1$–$C_4$-haloalkyl, $C_1$–$C_4$-haloalkoxy-$C_1$–$C_4$-alkyl, $C_1$–$C_4$-alkoxy-$C_1$–$C_4$-alkyl; and Hex is substituted (3-oxo-1-cyclohexen-2-yl)carbonyl of the formula IIa or substituted (1,3-dioxo-2-cyclohexyl) methylidene of the formula IIb

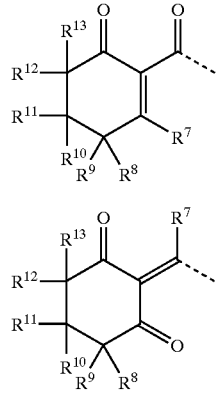

in which the variables $R^7$ to $R^{13}$ are as defined below:

$R^7$ is hydroxyl, mercapto, halogen, $OR^{14}$, $SR^{14}$, $SOR^{15}$, $SO_2R^{15}$, $OSO_2R^5$, $P(O)R^{16}R^{17}$, $OP(O)R^{16}R^{17}$, $P(S)R^{16}R^{17}$, $OP(S)R^{16}R^{17}$, $NR^{18}R^{19}$, $ONR^{18}R^{19}$ or N-bonded heterocyclyl which may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^8$, $R^{12}$ independently of one another are hydrogen, $C_1$–$C_4$-alkyl or $C_1$–$C_4$-alkoxycarbonyl;

$R^9$, $R^{11}$, $R^{13}$ independently of one another are hydrogen or $C_1$–$C_4$-alkyl;

$R^{10}$ is hydrogen, halogen, hydroxyl, $C_1$–$C_6$-alkyl, $C_1$–$C_6$-haloalkyl, di-($C_1$–$C_6$-alkoxy)-methyl, ($C_1$–$C_6$-alkoxy)-($C_1$–$C_6$-alkylthio)methyl, di-($C_1$–$C_6$-alkylthio)methyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkoxycarbonyl, $C_1$–$C_6$-halogenalkoxycarbonyl;

is 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the six lastmentioned radicals may be substituted by one to three $C_1$–$C_4$-alkyl radicals;

or $R^9$ and $R^{11}$ or $R^{11}$ and $R^{13}$ together form a π bond or a $C_1$–$C_5$-alkylene chain which may carry one, two or three radicals from the following group: halogen, cyano, $C_1$–$C_4$-alkyl, $C_1$–$C_4$-haloalkyl or $C_1$–$C_4$-alkoxycarbonyl;

or $R^9$ and $R^{13}$ together form a $C_1$–$C_4$-alkyl chain which may carry one, two or three radicals from the following group: halogen, cyano, $C_1$–$C_4$-alkyl, $C_1$–$C_4$-haloalkyl or $C_1$–$C_4$-alkoxycarbonyl;

or $R^{10}$ and $R^{11}$ together form a —O—$(CH_2)_p$—O—, —O—$(CH_2)_p$—S—, —S—$(CH_2)_p$—S—, —O—$(CH_2)_q$— or —S—$(CH_2)_q$— chain, in which p is 2, 3, 4 or 5 and q is 2, 3, 4, 5 or 6, which may be substituted by one, two or three radicals from the following group: halogen, cyano, $C_1$–$C_4$-alkyl, $C_1$–$C_4$-haloalkyl or $C_1$–$C_4$-alkoxycarbonyl;

or $R^{10}$ and $R^{11}$, together with the carbon to which they are attached, form a carbonyl group;

where $R^{14}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)amino-carbonyl, N-($C_1$–$C_6$-alkoxy)-N-($C_1$–$C_6$-alkyl)aminocarbonyl, N-($C_3$–$C_6$alkenyl)-N-($C_1$–$C_6$-alkoxy)aminocarbonyl, N-($C_3$–$C_6$-alkynyl)-N-($C_1$–$C_6$-alkoxy)aminocarbonyl, di($C_1$–$C_6$-alkyl)aminothiocarbonyl, $C_1$–$C_6$-alkoxyimino-$C_1$–$C_6$-alkyl, where the alkyl, cycloalkyl or alkoxy radicals mentioned may be partially or fully halogenated and/or may carry one, two or three of the following groups: cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, hydroxycarbonyl, $C_1$–$C_4$-alkylaminocarbonyl, di($C_1$–$C_4$-alkyl)-aminocarbonyl, aminocarbonyl, $C_1$–$C_4$-alkylcarbonyloxy or $C_3$–$C_6$-cycloalkyl;

is phenyl, phenyl-$C_1$–$C_6$-alkyl, phenylcarbonyl-$C_1$–$C_6$-alkyl, phenylcarbonyl, phenoxycarbonyl, phenyloxythiocarbonyl, phenylaminocarbonyl, N-($C_1$–$C_6$-alkyl)-N-phenylaminocarbonyl, phenyl-$C_2$–$C_6$-alkenylcarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl, heterocyclylaminocarbonyl, N-($C_1$–$C_6$-alkyl)-N-heterocyclylaminocarbonyl, or heterocyclyl-$C_1$–$C_6$-alkenylcarbonyl, where the phenyl and the heterocyclyl radical of the 18 lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{15}$ is $C_1$–$C_6$-alkyl, $C_3$–$C_6$-alkenyl, $C_3$–$C_6$-alkynyl or $C_3$–$C_6$-cycloalkyl, where the four radicals mentioned. may be partially or fully halogenated and/or may carry one, two or three of the following groups: cyano, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, $C_1$–$C_4$-alkoxycarbonyl or $C_1$–$C_4$-haloalkoxycarbonyl;

is phenyl, phenyl-$C_1$–$C_4$-alkyl, heterocyclyl or heterocyclyl-$C_1$–$C_4$-alkyl, where the phenyl and the heterocyclyl radical of the four lastmentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{16}$, $R^{17}$ independently of one another are hydrogen, hydroxyl, $C_1$–$C_6$-alkyl, $C_1$–$C_6$-alkoxy, $C_1$–$C_6$-alkylthio, phenyl, phenyl-$C_1$–$C_4$-alkyl or phenoxy, where the three lastmentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{18}$ is hydrogen, $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di($C_1$–$C_6$-alkyl)amino or $C_1$–$C_6$-alkylcarbonylamino, where the alkyl, cycloalkyl and alkoxy radicals mentioned may be partially or fully halogenated and/or may carry one, two or three of the following radicals: cyano, $C_1$–$C_4$-alkoxycarbonyl, $C_1$–$C_4$-alkylaminocarbonyl, di($C_1$–$C_4$-alkyl)-aminocarbonyl or $C_3$–$C_6$-cycloalkyl;

is phenyl, phenyl-$C_1$–$C_4$-alkyl, phenylcarbonyl, heterocyclyl, heterocyclyl-$C_1$–$C_4$-alkyl or heterocyclylcarbonyl, where the phenyl or heterocyclyl radical of the six lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{19}$ is hydrogen, $C_1$–$C_6$-alkyl, $C_3$–$C_6$-alkenyl or $C_3$–$C_6$-alkynyl;

and their agriculturally useful salts.

Furthermore we have found herbicidal compositions which comprise the cyclohexenone derivatives of the formula I and have very good herbicidal action. Moreover, we have found methods for controlling undesirable vegetation using the cyclohexenone derivatives of the formula I.

Depending on the substitution pattern, the compounds of the formula I may contain one or more chiral centers, in which case they are present as enantiomers or diasteromer mixtures. The invention provides both the pure enantiomers or diastereomers and their mixtures.

The compounds of the formula I may also be present in the form of their agriculturally useful salts, the type of salt generally being immaterial. In general, the salts of those cations and the acid addition salts of those acids are suitable whose cations and anions, respectively, do not negatively affect the herbicidal action of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)-eth-1-ylammonium, di(2-hydroxyeth-1-yl)ammonium, trimethylbenzylammonium, furthermore phosphonium ions, sulfonium ions, preferably tri($C_1$–$C_4$-alkyl)sulfonium, and sulfoxonium ions, preferably tri ($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, bicarbonate, carbonate, hexafluorosilicate, hexafluorophosphate, benzoate and the anions of $C_1$–$C_4$-alkanoic acids, preferably formate, acetate, propionate and butyrate.

For $R^7$=hydroxyl or mercapto {Y=O,S}, IIa also represents the tautomeric forms IIa', IIa" and IIa'".

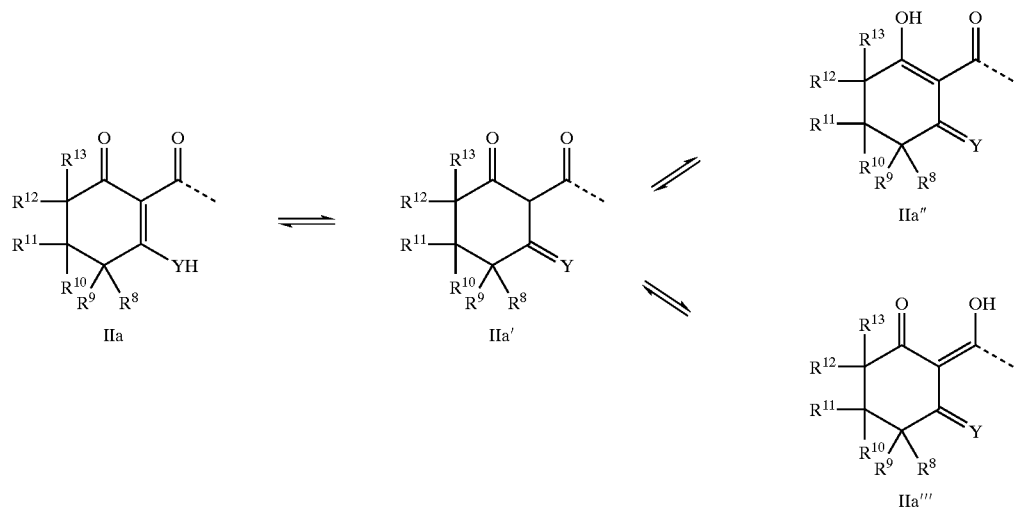

and IIb also represents the tautomeric forms IIb', IIb" and IIb'''.

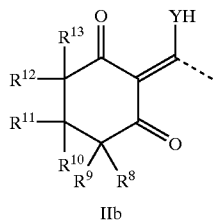

IIb

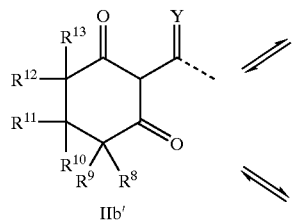

IIb'

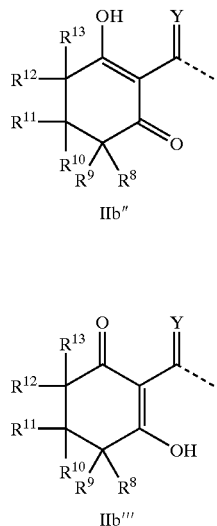

IIb"

IIb'''

The organic molecular moieties mentioned for the substituents $R^1$ to $R^{19}$ or as radicals on phenyl and heterocyclyl radicals are collective terms for individual enumerations of the particular group members. All hydrocarbon chains, i.e. all alkyl, haloalkyl, alkoxy, haloalkoxy, alkylthio, haloalkylthio, alkylsulfinyl, haloalkylsulfinyl, alkylsulfonyl, haloalkylsulfonyl, N-alkylamino, N,N-dialkylamino, N-haloalkylamino, N-alkoxyamino, N-alkoxy-N-alkylamino, N-alkylcarbonylamino, alkylcarbonyl, haloalkylcarbonyl, alkoxycarbonyl, haloalkoxycarbonyl, alkylthiocarbonyl, alkylcarbonyloxy, alkylaminocarbonyl, dialkylaminocarbonyl, dialkylaminothiocarbonyl, alkoxyalkyl, hydroxyalkoxyalkyl, alkoxyiminoalkyl, phenylalkylcarbonyl, heterocyclylalkylcarbonyl, phenylalkenylcarbonyl, heterocyclylalkenylcarbonyl, N-alkoxy-N-alkylaminocarbonyl, N-alkyl-N-phenylaminocarbonyl, N-alkyl-N-heterocyclylaminocarbonyl, phenylalkyl, heterocyclylalkyl, phenylcarbonylalkyl, heterocyclylcarbonylalkyl, alkoxyalkoxycarbonyl, alkenylcarbonyl, alkenyloxycarbonyl, alkenylaminocarbonyl, N-alkenyl-N-alkylaminocarbonyl, N-alkenyl-N-alkoxyaminocarbonyl, alkynylcarbonyl, alkynyloxycarbonyl, alkynylaminocarbonyl, N-alkynyl-N-alkylaminocarbonyl, N-alkynyl-N-alkoxyaminocarbonyl, alkenyl, alkynyl, haloalkenyl, haloalkynyl, alkenyloxy, alkynyloxy, alkanediyl, alkenediyl, alkadienediyl or alkynediyl moieties can be straight-chain or branched. Unless indicated otherwise, halogenated substituents preferably carry one to five identical or different halogen atoms. The expression halogen represents in each case fluorine, chlorine, bromine or iodine.

Examples of other meanings are:

$C_1$–$C_4$-alkyl: for example methyl, ethyl, propyl, 1-methylethyl, butyl, 1-methylpropyl, 2-methylpropyl or 1,1-dimethylethyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-alkyl, and the alkyl moieties of $C_1$–$C_6$-alkylamino, di($C_1$–$C_6$-alkyl)amino, N-($C_1$–$C_6$-alkoxy)-N-($C_1$–$C_6$-alkyl)-aminocarbonyl, N-($C_3$–$C_6$-alkenyl)-N-($C_1$–$C_6$-alkyl)aminocarbonyl, ($C_3$–$C_6$-alkynyl)-N-($C_1$–$C_6$-alkyl)aminocarbonyl, N-($C_1$–$C_6$-alkyl)-N-phenylaminocarbonyl, and also N-($C_1$–$C_6$-alkyl)-N-heterocyclylamino-carbonyl: $C_1$–$C_4$-alkyl as mentioned above, and also, for example, n-pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_6$-haloalkyl, and the haloalkyl moieties of N-$C_1$–$C_6$-haloalkylamino: $C_1$–$C_4$-haloalkyl, as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-alkoxy and the alkoxy moieties of hydroxy-$C_1$–$C_4$-alkoxy-$C_1$–$C_4$-alkyl, $C_1$–$C_4$-alkoxy-$C_1$–$C_4$-alkoxycarbonyl: for example methoxy, ethoxy, propoxy, 1-methylethoxy, butoxy, 1-methylpropoxy, 2-methylpropoxy or 1,1-dimethylethoxy;

$C_1$–$C_6$-alkoxy, and the alkoxy moieties of $C_1$–$C_6$-alkoxy-$C_3$–$C_6$-alkenyl, $C_1$–$C_6$-alkoxy-$C_3$–$C_6$-alkynyl, $C_1$–$C_6$-alkoxy-$C_2$–$C_6$-alkenyl, $C_1$–$C_6$-alkoxy-$C_2$–$C_6$-alkynyl, N-$C_1$–$C_6$-alkoxyamino, N-($C_1$–$C_6$-alkoxy)-N-($C_1$–$C_6$-alkyl)amino, $C_1$–$C_6$-alkoxyimino-$C_1$–$C_6$-alkyl, ($C_1$–$C_6$- alkoxy)($C_1$–$C_6$-alkylthio)methyl, N-($C_1$–$C_6$-alkoxy)-N-($C_1$–$C_6$-alkyl)aminocarbonyl, N-($C_3$–$C_6$-alkenyl)-N-($C_1$–$C_6$-alkoxy)aminocarbonyl and N-($C_3$–$C_6$-alkynyl)-N-($C_1$–$C_6$-alkoxy)aminocarbonyl: $C_1$–$C_4$-alkoxy as mentioned above, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_4$-haloalkoxy and the haloalkoxy moieties of $C_1$–$C_4$-haloalkoxy-$C_1$–$C_4$-alkyl, $C_1$–$C_4$-haloalkoxy-$C_1$–$C_4$-alkoxy, $C_1$–$C_4$-haloalkoxy-$C_1$–$C_6$-alkyl, $C_1$–$C_4$-haloalkoxy-$C_1$–$C_6$-alkoxy, $C_1$–$C_4$-haloalkoxy-$C_3$–$C_6$-alkenyl, $C_1$–$C_4$-haloalkoxy-$C_3$–$C_6$-alkynyl: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_6$-haloalkoxy: $C_1$–$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_4$-alkylthio ($C_1$–$C_4$-alkylsulfanyl: $C_1$–$C_4$-alkyl-S—) and the alkylthio moieties of $C_1$–$C_4$-alkylthio-$C_1$–$C_4$-alkyl: for example methylthio, ethylthio, propylthio, 1-methylethylthio, butylthio, 1-methylpropylthio, 2-methylpropylthio or 1,1-dimethylethylthio;

$C_1$–$C_6$-alkylthio, and the alkylthio moieties of di-($C_1$–$C_6$-alkylthio)methyl, $C_1$–$C_6$-alkylthiocarbonyl: $C_1$–$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_4$-haloalkylthio and the haloalkylthio moieties of $C_1$–$C_4$-haloalkylthio-$C_1$–$C_4$-alkyl: a $C_1$–$C_4$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio;

$C_1$–$C_6$-haloalkylthio: $C_1$–$C_4$-haloalkylthio as mentioned above, and also 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$–$C_4$-alkylsulfinyl ($C_1$–$C_4$-alkyl-S(=O)—): for example, methylsulfinyl, ethylsulfinyl, propylsulfinyl, 1-methylethylsulfinyl, butylsulfinyl, 1-methylpropylsulfinyl, 2-methylpropylsulfinyl or 1,1-dimethylethylsulfinyl;

$C_1$–$C_6$-alkylsulfinyl: $C_1$–$C_4$-alkylsulfinyl as mentioned above, and also pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl;

$C_1$–$C_4$-haloalkylsulfinyl: a $C_1$–$C_4$-alkylsulfinyl radical as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl or nonafluorobutylsulfinyl;

$C_1$–$C_6$-haloalkylsulfinyl: $C_1$–$C_4$-haloalkylsulfinyl as mentioned above, and also 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl;

$C_1$–$C_4$-alkylsulfonyl ($C_1$–$C_4$-alkyl-S(=O)$_2$—) and the alkylsulfonyl moieties of $C_1$–$C_4$-alkylsulfonyl-$C_1$–$C_4$-alkyl: for example methylsulfonyl, ethylsulfonyl, propylsulfonyl, 1-methylethylsulfonyl, butylsulfonyl, 1-methylpropylsulfonyl, 2-methylpropylsulfonyl or 1,1-dimethylethylsulfonyl;

$C_1$–$C_6$-alkylsulfonyl: $C_1$–$C_4$-alkylsulfonyl, as mentioned above, and also pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-$_1$-methylpropylsulfonyl or 1-ethyl-2-methylpropylsulfonyl;

$C_1$–$C_4$-haloalkylsulfonyl: a $C_1$–$C_4$-alkylsulfonyl radical as mentioned above which is partially or fully substituted by fluorine, chlorine, bromine and/or iodine, and also the haloalkylsulfonyl of $C_1$–$C_4$-haloalkylsulfonyl-$C_1$–$C_4$-alkyl: for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl or nonafluorobutylsulfonyl;

$C_1$–$C_6$-haloalkylsulfonyl and the haloalkylsulfonyl moieties of $C_1$–$C_6$-haloalkylsulfonyl-$C_1$–$C_6$-alkyl: $C_1$–$C_4$-haloalkylsulfonyl as mentioned above, and also 5-fluoropentylsulfonyl, 5-chloropentylsulfonyl, 5-bromopentylsulfonyl, 5-iodopentylsulfonyl, 6-fluorohexylsulfonyl, 6-chlorohexylsulfonyl, 6-bromohexylsulfonyl, 6-iodohexylsulfonyl or dodecafluorohexylsulfonyl;

$C_1$–$C_6$-alkylamino: methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

di($C_1$–$C_4$-alkyl)amino: for example N,N-dimethylamino, N,N-diethylamino, N,N-dipropylamino, N,N-di(1-methylethyl)-amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$–$C_6$-alkyl)amino: di($C_1$–$C_4$-alkyl)amino as mentioned above, and also N,N-dipentylamino, N,N-dihexylamino, N-methyl-N-pentylamino, N-ethyl-N-pentylamino, N-methyl-N-hexylamino or N-ethyl-N-hexylamino;

$C_1$–$C_4$-alkylcarbonyl: for example methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl;

$C_1$–$C_6$-alkylcarbonyl, and the alkylcarbonyl radicals of $C_1$–$C_6$-alkylcarbonylamino: $C_1$–$C_4$-alkylcarbonyl as mentioned above, and also, for example, pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_1$–$C_4$-haloalkylcarbonyl: a $C_1$–$C_4$-alkylcarbonyl radical as mentioned above which is partially or fully substituted by fluorine, chlorine, bromine and/or iodine, i.e. for example, chloroacetyl, dichloroacetyl, trichloroacetyl, fluoroacetyl, difluoroacetyl, trifluoroacetyl, chlorofluoroacetyl, dichlorofluoroacetyl, chlorodifluoroacetyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2- fluoroethylcarbonyl, 2,2,2-trichloroethylcarbonyl, pentafluoroethylcarbonyl, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, 2,2,3,3,3-pentafluoropropylcarbonyl, heptafluoropropylcarbonyl, 1-(fluoromethyl)-2-fluoroethylcarbonyl, 1-(chloromethyl)-2-chloroethylcarbonyl, 1-(bromomethyl)-2-bromoethylcarbonyl, 4-fluorobutylcarbonyl, 4-chlorobutylcarbonyl, 4-bromobutylcarbonyl or nonafluorobutylcarbonyl;

$C_1$–$C_6$-haloalkylcarbonyl: a $C_1$–$C_4$-haloalkylcarbonyl radical as mentioned above, and also 5-fluoropentylcarbonyl, 5-chloropentylcarbonyl, 5-bromopentylcarbonyl, perfluoropentylcarbonyl, 6-fluorohexylcarbonyl, 6-chlorohexylcarbonyl, 6-bromohexylcarbonyl or perfluorohexylcarbonyl;

$C_1$–$C_4$-alkoxycarbonyl: for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

$C_1$–$C_6$-alkoxycarbonyl and also the alkoxycarbonyl moieties of $C_1$–$C_6$-alkoxycarbonyl-$C_1$–$C_6$-alkyl: $C_1$–$C_4$-alkoxycarbonyl as mentioned above, and also, for example, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl;

$C_1$–$C_4$-haloalkoxycarbonyl: a $C_1$–$C_4$-alkoxycarbonyl radical as mentioned above which is partially or fully substituted by fluorine, chlorine, bromine and/or iodine, i.e., for example fluoromethoxycarbonyl, difluoromethoxycarbonyl, trifluoromethoxycarbonyl, chlorodifluoromethoxycarbonyl, bromodifluoromethoxycarbonyl, 2-fluoroethoxycarbonyl, 2-chloroethoxycarbonyl, 2-bromoethoxycarbonyl, 2-iodoethoxycarbonyl, 2,2-difluoroethoxycarbonyl, 2,2,2-trifluoroethoxycarbonyl, 2-chloro-2-fluoroethoxycarbonyl, 2-chloro-2,2-difluoroethoxycarbonyl, 2,2-dichloro-2-fluoroethoxycarbonyl, 2,2,2-trichloroethoxycarbonyl, pentafluoroethoxycarbonyl, 2-fluoropropoxycarbonyl, 3-fluoropropoxycarbonyl, 2-chloropropoxycarbonyl, 3-chloropropoxycarbonyl, 2-bromopropoxycarbonyl, 3-bromopropoxycarbonyl, 2,2-difluoropropoxycarbonyl, 2,3-difluoropropoxycarbonyl, 2,3-dichloropropoxycarbonyl, 3,3,3-trifluoropropoxycarbonyl, 3,3,3-trichloropropoxycarbonyl, 2,2,3,3,3-pentafluoropropoxycarbonyl, heptafluoropropoxycarbonyl, 1-(fluoromethyl)-2-fluoroethoxycarbonyl, 1-(chloromethyl)-2-chloroethoxycarbonyl, 1-(bromomethyl)-2-bromoethoxycarbonyl, 4-fluorobutoxycarbonyl, 4-chlorobutoxycarbonyl, 4-bromobutoxycarbonyl or 4-iodobutoxycarbonyl;

$C_1$–$C_6$-haloalkoxycarbonyl: a $C_1$–$C_4$-haloalkoxycarbonyl radical as mentioned above, and also 5-fluoropentoxycarbonyl, 5-chloropentoxycarbonyl, 5-bromopentoxycarbonyl, 6-fluorohexoxycarbonyl, 6-chlorohexoxycarbonyl or 6-bromohexoxycarbonyl;

($C_1$–$C_4$-alkyl)carbonyloxy: acetyloxy, ethylcarbonyloxy, propylcarbonyloxy, 1-methylethylcarbonyloxy, butylcarbonyloxy, 1-methylpropylcarbonyloxy, 2-methylpropylcarbonyloxy or 1,1-dimethylethylcarbonyloxy;

($C_1$–$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

($C_1$–$C_6$-alkylamino)carbonyl: ($C_1$–$C_4$-alkylamino)carbonyl as mentioned above, and also, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl;

di($C_1$–$C_4$-alkyl)aminocarbonyl: for example N,N-dimethylaminocarbonyl, N,N-diethylaminocarbonyl, N,N-di(1-methylethyl)aminocarbonyl, N,N-dipropylaminocarbonyl, N,N-dibutylaminocarbonyl, N,N-di(1-methylpropyl)-aminocarbonyl, N,N-di(2-methylpropyl)aminocarbonyl, N,N-di(1,1-dimethylethyl) aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)-aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)-aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

di($C_1$–$C_6$-alkyl)aminocarbonyl: di($C_1$–$C_4$-alkyl) aminocarbonyl as mentioned above, and also, for example, N-methyl-N-pentylaminocarbonyl, N-methyl-N-(1-methylbutyl)aminocarbonyl, N-methyl-N-(2-methylbutyl)aminocarbonyl, N-methyl-N-(3-methylbutyl)aminocarbonyl, N-methyl-N-(2,2-dimethylpropyl)aminocarbonyl, N-methyl-N-(1-ethylpropyl)-aminocarbonyl, N-methyl-N-hexylaminocarbonyl, N-methyl-N-(1,1-dimethylpropyl)aminocarbonyl, N-methyl-N-(1,2-dimethylpropyl)aminocarbonyl, N-methyl-N-(1-methylpentyl)aminocarbonyl, N-methyl-N-(2-methylpentyl)aminocarbonyl, N-methyl-N-(3-methylpentyl)aminocarbonyl, N-methyl-N-(4-methylpentyl)aminocarbonyl, N-methyl-N-(1,1-dimethylbutyl)aminocarbonyl, N-methyl-N-(1,2-dimethylbutyl)aminocarbonyl, N-methyl-N-(1,3-dimethylbutyl)aminocarbonyl, N-methyl-N-(2,2-dimethylbutyl)aminocarbonyl, N-methyl-N-(2,3-dimethylbutyl)aminocarbonyl, N-methyl-N-(3,3-dimethylbutyl)aminocarbonyl, N-methyl-N-(1-ethylbutyl)aminocarbonyl, N-methyl-N-(2-ethylbutyl)aminocarbonyl, N-methyl-N-(1,1,2-trimethylpropyl)aminocarbonyl, N-methyl-N-(1,2,2-trimethylpropyl)aminocarbonyl, N-methyl-N-(1-ethyl-1-methylpropyl)aminocarbonyl, N-methyl-N-(1-ethyl-2-methylpropyl)aminocarbonyl, N-ethyl-N-pentylaminocarbonyl, N-ethyl-N-(1-methylbutyl)aminocarbonyl, N-ethyl-N-(2-methylbutyl)aminocarbonyl, N-ethyl-N-(3-methylbutyl)aminocarbonyl, N-ethyl-N-(2,2-dimethylpropyl)aminocarbonyl, N-ethyl-N-(1-ethylpropyl)aminocarbonyl, N-ethyl-N-hexylaminocarbonyl, N-ethyl-N-(1,1-dimethylpropyl)aminocarbonyl, N-ethyl-N-(1,2-dimethylpropyl)aminocarbonyl, N-ethyl-N-(1-methylpentyl)aminocarbonyl, N-ethyl-N-(2-methylpentyl)aminocarbonyl, N-ethyl-N-(3-methylpentyl)aminocarbonyl, N-ethyl-N-(4-methylpentyl)aminocarbonyl, N-ethyl-N-(1,1-dimethylbutyl)aminocarbonyl, N-ethyl-N-(1,2-dimethylbutyl)aminocarbonyl, N-ethyl-N-(1,3-dimethylbutyl)aminocarbonyl, N-ethyl-N-(2,2-dimethylbutyl)aminocarbonyl, N-ethyl-N-(2,3-dimethylbutyl)aminocarbonyl, N-ethyl-N-(3,3-dimethylbutyl)aminocarbonyl, N-ethyl-N-(1-ethylbutyl)aminocarbonyl, N-ethyl-N-(2-ethylbutyl)aminocarbonyl, N-ethyl-N-(1,1,2-trimethylpropyl)aminocarbonyl, N-ethyl-N-(1,2,2-trimethylpropyl)aminocarbonyl, N-ethyl-N-(1-ethyl-1-methylpropyl)aminocarbonyl, N-ethyl-N-(1-ethyl-2-methylpropyl)aminocarbonyl, N-propyl-N-pentylaminocarbonyl, N-butyl-N-pentylaminocarbonyl, N,N-dipentylaminocarbonyl, N-propyl-N-hexylaminocarbonyl, N-butyl-N-hexylaminocarbonyl, N-pentyl-N-hexylaminocarbonyl or N,N-dihexylaminocarbonyl;

di($C_1$–$C_6$-alkyl)aminothiocarbonyl: for example N,N-dimethylaminothiocarbonyl, N,N-diethylaminothiocarbonyl, N,N-di(1-methylethyl)aminothiocarbonyl, N,N-dipropylaminothiocarbonyl, N,N-dibutylaminothiocarbonyl, N,N-di(1-methylpropyl)aminothiocarbonyl, N,N-di(2-methylpropyl)aminothiocarbonyl, N,N-di(1,1-dimethylethyl)aminothiocarbonyl, N-ethyl-N-methylaminothiocarbonyl, N-methyl-N-propylaminothiocarbonyl, N-methyl-N-(1-methylethyl)aminothiocarbonyl, N-butyl-N-methylaminothiocarbonyl, N-methyl-N-(1-methylpropyl)aminothiocarbonyl, N-methyl-N-(2-methylpropyl)aminothiocarbonyl, N-(1,1-dimethylethyl)-N-methylaminothiocarbonyl, N-ethyl-N-propylaminothiocarbonyl, N-ethyl-N-(1-methylethyl)aminothiocarbonyl, N-butyl-N-ethylaminothiocarbonyl, N-ethyl-N-(1-methylpropyl)aminothiocarbonyl, N-ethyl-N-(2-methylpropyl)aminothiocarbonyl, N-ethyl-N-(1,1-dimethylethyl)aminothiocarbonyl, N-(1-methylethyl)-N-propylaminothiocarbonyl, N-butyl-N-propylaminothiocarbonyl, N-(1-methylpropyl)-N-propylaminothiocarbonyl, N-(2-methylpropyl)-N-propylaminothiocarbonyl, N-(1,1-dimethylethyl)-N-propylaminothiocarbonyl, N-butyl-N-(1-methylethyl)aminothiocarbonyl, N-(1-methylethyl)-N-(1-methylpropyl)aminothiocarbonyl, N-(1-methylethyl)-N-(2-methylpropyl)aminothiocarbonyl, N-(1,1-dimethylethyl)-N-(1-methylethyl)aminothiocarbonyl, N-butyl-N-(1-methylpropyl)aminothiocarbonyl, N-butyl-N-(2-methylpropyl)aminothiocarbonyl, N-butyl-N-(1,1-dimethylethyl)aminothiocarbonyl, N-(1-methylpropyl)-N-(2-methylpropyl)aminothiocarbonyl, N-(1,1-dimethylethyl)-N-(1-methylpropyl)aminothiocarbonyl, N-(1,1-dimethylethyl)-N-(2-methylpropyl)aminothiocarbonyl, N-methyl-N-pentylaminothiocarbonyl, N-methyl-N-(1-methylbutyl)aminothiocarbonyl, N-methyl-N-(2-methylbutyl)aminothiocarbonyl, N-methyl-N-(3-methylbutyl)aminothiocarbonyl, N-methyl-N-(2,2-dimethylpropyl)aminothiocarbonyl, N-methyl-N-(1-ethylpropyl)aminothiocarbonyl, N-methyl-N-hexylaminothiocarbonyl, N-methyl-N-(1,1-dimethylpropyl)aminothiocarbonyl, N-methyl-N-(1,2-dimethylpropyl)aminothiocarbonyl, N-methyl-N-(1-methylpentyl)aminothiocarbonyl, N-methyl-N-(2-methylpentyl)aminothiocarbonyl, N-methyl-N-(3-methylpentyl)aminothiocarbonyl, N-methyl-N-(4-methylpentyl)aminothiocarbonyl, N-methyl-N-(1,1-dimethylbutyl)aminothiocarbonyl, N-methyl-N-(1,2-dimethylbutyl)aminothiocarbonyl, N-methyl-N-(1,3-dimethylbutyl)aminothiocarbonyl, N-methyl-N-(2,2-dimethylbutyl)aminothiocarbonyl, N-methyl-N-(2,3-dimethylbutyl)aminothiocarbonyl, N-methyl-N-(3,3-dimethylbutyl)aminothiocarbonyl, N-methyl-N-(1-ethylbutyl)aminothiocarbonyl, N-methyl-N-(2-ethylbutyl)aminothiocarbonyl, N-methyl-N-ethyl-N-(1,1,2-trimethylpropyl)aminothiocarbonyl, N-methyl-N-(1,2,2-trimethylpropyl)aminothiocarbonyl, N-methyl-N-(1-ethyl-1-methylpropyl)aminothiocarbonyl, N-methyl-N-(1-ethyl-2-methylpropyl)aminothiocarbonyl, N-ethyl-N-pentylaminothiocarbonyl, N-ethyl-N-(1-methylbutyl)aminothiocarbonyl, N-ethyl-N-(2-methylbutyl)aminothiocarbonyl, N-ethyl-N-(3-methylbutyl)aminothiocarbonyl, N-ethyl-N-(2,2-dimethylpropyl)aminothiocarbonyl, N-ethyl-N-(1-ethylpropyl)aminothiocarbonyl, N-ethyl-N-hexylaminothiocarbonyl, N-ethyl-N-(1,1-dimethylpropyl)aminothiocarbonyl, N-ethyl-N-(1,2-dimethylpropyl)aminothiocarbonyl, N-ethyl-N-(1-methylpentyl)aminothiocarbonyl, N-ethyl-N-(2-methylpentyl)aminothiocarbonyl, N-ethyl-N-(3-methylpentyl)aminothiocarbonyl, N-ethyl-N-(4-methylpentyl)aminothiocarbonyl, N-ethyl-N-(1,1-dimethylbutyl)aminothiocarbonyl, N-ethyl-N-(1,2-dimethylbutyl)aminothiocarbonyl, N-ethyl-N-(1,3-dimethylbutyl)aminothiocarbonyl, N-ethyl-N-(2,2-dimethylbutyl)aminothiocarbonyl, N-ethyl-N-(2-,3-dimethylbutyl)aminothiocarbonyl, N-ethyl-N-(3,3-dimethylbutyl)aminothiocarbonyl, N-ethyl-N-(1-ethylbutyl)aminothiocarbonyl, N-ethyl-N-(2-ethylbutyl)aminothiocarbonyl, N-ethyl-N-(1,1,2-trimethylpropyl)aminothiocarbonyl, N-ethyl-N-(1,2,2-trimethylpropyl)

aminothiocarbonyl, N-ethyl-N-(1-ethyl-1-methylpropyl) aminothiocarbonyl, N-ethyl-N-(1-ethyl-2-methylpropyl) aminothiocarbonyl, N-propyl-N-pentylaminothiocarbonyl, N-butyl-N-pentylaminothiocarbonyl, N,N-dipentylaminothiocarbonyl, N-propyl-N-hexylaminothiocarbonyl, N-butyl-N-hexylaminothiocarbonyl, N-pentyl-N-hexylaminothiocarbonyl or N,N-dihexylaminothiocarbonyl;

$C_1$–$C_6$-hydroxyalkyl: $C_1$–$C_6$-alkyl which is substituted by one to three OH groups, for example hydroxymethyl, 1-hydroxyethyl, 2-hydroxyethyl, 1,2-bishydroxyethyl, 1-hydroxypropyl, 2-hydroxypropyl, 3-hydroxypropyl, 4-hydroxybutyl, 2,2-dimethyl-3-hydroxypropyl;

phenyl-$C_1$–$C_6$-alkyl: $C_1$–$C_6$-alkyl which is substituted by a phenyl radical, for example benzyl, 1-phenylethyl and 2-phenylethyl, where the phenyl radical may, in the manner mentioned, be partially or fully halogenated or may carry one to three of the substituents mentioned above for phenyl; correspondingly, heterocyclyl-$C_1$–$C_6$-alkyl is a $C_1$–$C_6$-alkyl. which is substituted by a heterocyclyl radical;

$C_1$–$C_6$-alkoxy-$C_1$–$C_6$-alkyl: $C_1$–$C_6$-alkyl which is substituted by $C_1$–$C_6$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl or 4-(1,1-dimethylethoxy)butyl;

$C_1$–$C_6$-alkoxy-$C_1$–$C_6$-alkoxy, and the alkoxyalkoxy moieties of $C_1$–$C_6$-alkoxy-$C_1$–$C_6$-alkoxycarbonyl: $C_1$–$C_6$-alkoxy which is substituted by $C_1$–$C_6$-alkoxy as mentioned above, i.e, for example, methoxymethoxy, ethoxymethoxy, propoxymethoxy, (1-methylethoxy)methoxy, butoxymethoxy, (1-methylpropoxy)methoxy, (2-methylpropoxy)methoxy, (1,1-dimethylethoxy)methoxy, 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy)propoxy, 2-(1-methylethoxy)propoxy, 2-(butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(propoxy)propoxy, 3-(1-methylethoxy)propoxy, 3-(butoxy)propoxy, 3-(1-methylpropoxy)propoxy, 3-(2-methylpropoxy)propoxy, 3-(1,1-dimethylethoxy) propoxy, 2-(methoxy)butoxy, 2-(ethoxy)butoxy, 2-(propoxy)butoxy, 2-(1-methylethoxy)butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(propoxy)butoxy, 3-(1-methylethoxy)butoxy, 3-(butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(propoxy)butoxy, 4-(1-methylethoxy)butoxy, 4-(butoxy)butoxy, 4-(1-methylpropoxy)butoxy, 4-(2-methylpropoxy)butoxy or 4-(1,1-dimethylethoxy)butoxy;

$C_3$–$C_6$-alkenyl, and the alkenyl moieties of $C_3$–$C_6$-alkenylcarbonyl, $C_3$–$C_6$-alkenyloxy, $C_3$–$C_6$-alkenyloxycarbonyl, $C_3$–$C_6$-alkenylaminocarbonyl, N-($C_3$–$C_6$-alkenyl)-N-($C_1$–$C_6$-alkyl)aminocarbonyl, N-($C_3$–$C_6$-alkenyl)-N-($C_1$–$C_6$-alkoxy)aminocarbonyl: for example prop-2-en-1-yl, prop-1-en-3-yl, but-1-en-4-yl, 1-methylprop-2-en-1-yl, 2-methylprop-2-en-1-yl, 2-buten-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methyl-but-3-en-1-yl, 1,1-dimethylprop-2-en-1-yl, 1,2-dimethylprop-2-en-1-yl, 1-ethylprop-2-en-1-yl, hex-3-en-1-yl, hex-4-en-1-yl, hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl;

$C_2$–$C_6$-alkenyl, and the alkenyl moieties of $C_2$–$C_6$-alkenylcarbonyl, phenyl-$C_2$–$C_6$-alkenylcarbonyl and heterocyclyl-$C_2$–$C_6$-alkenylcarbonyl: $C_3$–$C_6$-alkenyl as mentioned above, and also ethenyl;

$C_3$–$C_6$-haloalkenyl: a $C_3$–$C_6$-alkenyl radical as mentioned above which is partially or fully substituted by fluorine, chlorine, bromine and/or iodine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

$C_3$–$C_6$-alkynyl, and the alkynyl moieties of $C_3$–$C_6$-alkynylcarbonyl, $C_3$–$C_6$-alkynyloxy, $C_3$–$C_6$-alkynyloxycarbonyl, $C_3$–$C_6$-alkynylaminocarbonyl, N-($C_3$–$C_6$-alkynyl)-N-($C_1$–$C_6$-alkyl)aminocarbonyl, N-($C_3$–$C_6$-alkynyl)-N-($C_1$–$C_6$-alkoxy)aminocarbonyl: for example propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_2$–$C_6$-alkynyl, and the alkynyl moieties of $C_2$–$C_6$-alkynylcarbonyl: $C_3$–$C_6$-alkynyl as mentioned above, and also ethynyl;

$C_3$–$C_6$-haloalkynyl: a $C_3$–$C_6$-alkynyl radical as mentioned above which is partially or fully substituted by fluorine, chlorine, bromine and/or iodine, i.e., for example, 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$–$C_6$-alkanediyl: methanediyl, ethane-1,1-diyl, ethane-1,2-diyl, propane-1,1-diyl, propane-1,2-diyl, propane-1,3-diyl, propane-2,2-diyl, butane-1,1-diyl, butane-1,2-diyl, butane-1,3-diyl, butane-1,4-diyl, 2-methylpropane-1,3-diyl, 2-methylpropane-1,2-diyl, 2-methylpropane-1,1-diyl, 1-methylpropane-1,2-diyl, 1-methylpropane-2,2-diyl, 1-methylpropane-1,1-diyl, pentane-1,1-diyl, pentane-1,2-diyl, pentane-1,3-diyl, pentane-1,5-diyl, pentane-2,3-diyl, pentane-2,2-diyl, 1-methylbutane-1,1-diyl, 1-methylbutane-1,2-diyl, 1-methylbutane-1,3-diyl, 1-methylbutane-1,4-diyl, 2-methylbutane-1,1-diyl, 2-methylbutane-.1,2-diyl, 2-methylbutane-1,3-diyl, 2-methylbutane-1,4-diyl, 2,2-dimethylpropane-1,1-diyl, 2,2-dimethylpropane-1,3-diyl, 1,1-dimethylpropane-1,3-diyl, 1,1-dimethylpropane-1,2-diyl, 2,3-dimethylpropane-1,3-diyl, 2,3-dimethylpropane-1,2-diyl, 1,3-dimethylpropane-1,3-diyl, hexane-1,1-diyl, hexane-1,2-diyl, hexane-1,3-diyl, hexane-1,4-diyl, hexane-1,5-diyl, hexane-1,6-diyl, hexane-2,5-diyl, 2-methylpentane-1,1-diyl, 1-methylpentane-1,2-diyl, 1-methylpentane-1,3-diyl, 1-methylpentane-1,4-diyl, 1-methylpentane-1,5-diyl, 2-methylpentane-1,1-diyl, 2-methylpentane-1,2-diyl, 2-methylpentane-1,3-diyl, 2-methylpentane-1,4-diyl, 2-methylpentane-1,5-diyl, 3-methylpentane-1,1-diyl, 3-methylpentane-1,2-diyl, 3-methylpentane-1,3-diyl, 3-methylpentane-1,4-diyl, 3-methylpentane-1,5-diyl, 1,1-dimethylbutane-1,2-diyl, 1,1-dimethylbutane-1,3-diyl, 1,1-dimethylbutane-1,4-diyl, 1,2-dimethylbutane-1,1-diyl, 1,2-dimethylbutane-1,2-diyl, 1,2-dimethylbutane-1,3-diyl, 1,2-dimethylbutane-1,4-diyl, 1,3-dimethylbutane-1,1-diyl, 1,3-dimethylbutane-1,2-diyl, 1,3-dimethylbutane-1,3-diyl, 1,3-dimethylbutane-1,4-diyl, 1-ethylbutane-1,1-diyl, 1-ethylbutane-1,2-diyl, 1-ethylbutane-1,3-diyl, 1-ethylbutane-1,4-diyl, 2-ethylbutane-1,1-diyl, 2-ethylbutane-1,2-diyl, 2-ethylbutane-1,3-diyl, 2-ethylbutane-1,4-diyl, 2-ethylbutane-2,3-diyl, 2,2-dimethylbutane-1,1-diyl, 2,2-dimethylbutane-1,3-diyl, 2,2-dimethylbutane-1,4-diyl, 1-isopropylpropane-1,1-diyl, 1-isopropylpropane-1,2-diyl, 1-isopropylpropane-1,3-diyl, 2-isopropylpropane-1,1-diyl, 2-isopropylpropane-1,2-diyl, 2-isopropylpropane-1,3-diyl, 1,2,3-trimethylpropane-1,1-diyl, 1,2,3-trimethylpropane-1,2-diyl or 1,2,3-trimethylpropane-1,3-diyl;

$C_2$–$C_6$-alkenediyl: ethene-1,1-diyl, ethene-1,2-diyl, 1-propene-1,1-diyl, 1-propene-1,2-diyl, 1-propene-1,3-diyl, 2-propene-1,1-diyl, 2-propene-1,2-diyl, 2-propene-1,3-diyl, 1-butene-1,1-diyl, 1-butene-1,2-diyl, 1-butene-1,3-diyl, 1-butene-1,4-diyl, 2-butene-1,1-diyl, 2-butene-1,2-diyl, 2-butene-1,3-diyl, 2-butene-1,4-diyl, 3-butene-1,1-diyl, 3-butene-1,2-diyl, 3-butene-1,3-diyl, 3-butene-1,4-diyl, 1-methyl-1-propene-1,2-diyl, 1-methyl-1-propene-1,3-diyl, 1-methyl-2-propene-1,1-diyl, 1-methyl-2-propene-1,2-diyl, 1-methyl-2-propene-1,3-diyl, 2-methyl-1,1-propene-1,1-diyl, 2-methyl-1-propene-1,3-diyl, 3-butene-1,1-diyl, 3-butene-1,2-diyl, 3-butene-1,3-diyl, 3-butene-1,1-diyl, 1-pentene-1,1-diyl, 1-pentene-1,2-diyl, 1-pentene-1,3-diyl, 1-pentene-1,4-diyl, 1-pentene-1,5-diyl, 1-hexene-1,1-diyl, 1-hexene-1,2-diyl, 1-hexene-1,3-diyl, 1-hexene-1,4-diyl, 1-hexene-1,5-diyl or 1-hexene-1,6-diyl;

$C_2$–$C_6$-alkadienediyl: 1,3-butadiene-1,1-diyl, 1,3-butadiene-1,2-diyl, 1,3-butadiene-1,3-diyl, 1,3-butadiene-1,4-diyl, 1,3-pentadiene-1,1-diyl, 1,3-pentadiene-1,2-diyl, 1,3-pentadiene-1,3-diyl, 1,3-pentadiene-1,4-diyl, 1,3-pentadiene-1,5-diyl, 2,4-pentadiene-1,1-diyl, 2,4-pentadiene-1,2-diyl, 2,4-pentadiene-1,3-diyl, 2,4-pentadiene-1,4-diyl, 2,4-pentadiene-1,5-diyl, 1-methyl-1,3-butadiene-1,4-diyl, 1,3-hexadiene-1,1-diyl, 1,3-hexadiene-1,2-diyl, 1,3-hexadiene-1,3-diyl, 1,3-hexadiene-1,4-diyl, 1,3-hexadiene-1,5-diyl, 1,3-hexadiene-1,6-diyl, 1-methyl-1,3-pentadiene-1,2-diyl, 1-methyl-1,3-pentadiene-1,3-diyl, 1-methyl-1,3-pentadiene-1,4-diyl or 1-methyl-1,3-pentadiene-1,5-diyl;

$C_2$–$C_6$-alkynediyl: ethyne-1,2-diyl, 1-propyne-1,3-diyl, 2-propyne-1,1-diyl, 2-propyne-1,3-diyl, 1-butyne-1,3-diyl, 1-butyne-1,4-diyl, 2-butyne-1,1-diyl, 2-butyne-1,4-diyl, 1-methyl-2-propyne-1,1-diyl, 1-methyl-2-propyne-1,3-diyl, 1-pentyne-1,3-diyl, 1-pentyne-1,4-diyl, 1-pentyne-1,5-diyl, 2-pentyne-1,1-diyl, 2-pentyne-1,4-diyl, 2-pentyne-1,5-diyl, 3-pentyne-1,1-diyl, 3-pentyne-1,2-diyl, 3-pentyne-1,5-diyl, 4-pentyne-1,1-diyl, 4-pentyne-1,2-diyl, 4-pentyne-1,3-diyl, 4-pentyne-1,5-diyl, 1-hexyne-1,3-diyl, 1-hexyne-1,4-diyl, 1-hexyne-1,5-diyl, 1-hexyne-1,6-diyl, 2-hexyne-1,1-diyl, 2-hexyne-1,4-diyl, 2-hexyne-1,5-diyl, 2-hexyne-1,6-diyl, 3-hexyne-1,1-diyl, 3-hexyne-1,2-diyl, 3-hexyne-1,5-diyl, 3-hexyne-1,6-diyl, 4-hexyne-1,1-diyl, 4-hexyne-1,2-diyl, 4-hexyne-1,3-diyl, 4-hexyne-1,6-diyl, 5-hexyne-1,1-diyl, 5-hexyne-1,2-diyl, 5-hexyne-1,3-diyl, 5-hexyne-1,4-diyl or 5-hexyne-1,6-diyl;

$C_3$–$C_6$-cycloalkyl, and the cycloalkyl moieties of $C_3$–$C_6$-cycloalkylamino and $C_3$–$C_6$-cycloalkylcarbonyl: for example cyclopropyl, cyclobutyl, cyclopentyl or cyclohexyl;

aryl is understood as meaning carbocyclic aromatic compounds such as phenyl or naphthyl;

a 3- to 7-membered heterocycle is understood as meaning a saturated, partially saturated or unsaturated 3-, 4-, 5-, 6- or 7-membered heterocyclic ring which contains one, two, three or four identical or different heteroatoms selected from the following group: oxygen, sulfur or nitrogen, i.e., for example, C-bonded 5-membered rings such as:

tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 2-furyl, 3-furyl, 2-thienyl, 3-thienyl, pyrrol-2-yl, pyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta^4$-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,3,2-dioxathiolan-4-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazol-2-yl, 1,2,3-triazol-4-yl, 1,2,4-triazol-3-yl, tetrazol-5-yl;

C-bonded 6-membered rings such as:
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydropyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, pyridin-2-yl, pyridin-3-yl, pyridin-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3- yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl, 3,4-dihydropyrimidin-6-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl or 1,2,4,5-tetrazin-3-yl;

N-bonded 5-membered rings such as:
tetrahydropyrrol-1-yl, 2,3-dihydro-1H-pyrrol-1-yl, 2,5-dihydro-1H-pyrrol-1-yl, pyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, pyrazol-1-yl, imidazol-1-yl, 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl, 1,2,3-triazol-1-yl, 1,2,4-triazol-1-yl, tetrazol-1-yl;

N-bonded 6-membered rings such as:
piperidin-1-yl, 1,2,3,4-tetrahydropyridin-1-yl, 1,2,5,6-tetrahydropyridin-1-yl, 1,4-dihydropyridin-1-yl, 1,2-dihydropyridin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl (morpholinyl), tetrahydro-1,2-oxazin-2-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

and also N-bonded cyclic imides such as:
phthalimide, tetrahydrophthalimide, succinimide, maleimide, glutarimide, 5-oxotriazolin-1-yl, 5-oxo-1,3,4-oxadiazolin-4-yl or 2,4-dioxo(1H,3H)pyrimidin-3-yl;

where, if appropriate, the sulfur of the heterocycles mentioned may be oxidized to S=O or S(=O)$_2$
and where a bicyclic ring system may be formed with a fused-on phenyl ring or with a $C_3$–$C_6$-carbocycle or with a further 5- to 6-membered heterocycle.

All phenyl rings or heterocyclyl radicals and all phenyl components in phenoxy, phenylalkyl, phenylcarbonylalkyl, phenylcarbonyl, phenylalkenylcarbonyl, phenoxycarbonyl, phenyloxythiocarbonyl, phenylaminocarbonyl and N-alkyl-N-phenylaminocarbonyl, phenylsulfonyl or phenoxysulfonyl or heterocyclyl components in heterocyclyloxy, heterocyclylalkyl, heterocyclylcarbonylalkyl, heterocyclylcarbonyl, heterocyclyloxythiocarbonyl, heterocyclylalkenylcarbonyl, heterocyclyloxycarbonyl, heterocyclylaminocarbonyl, N-alkyl-N-heterbcyclylaminocarbonyl, heterocyclylsulfonyl or heterocyclyloxysulfonyl are, unless stated otherwise, preferably unsubstituted, or they carry one, two or three halogen atoms and/or a nitro group, a cyano radical and/or one or two methyl, trifluoromethyl, methoxy or trifluoromethoxy substituents.

With respect to the use of the compounds of the formula I according to the invention as herbicides, the variables A, $R^1$ to $R^{19}$ preferably have the following meanings, in each case on their own or in combination:

A is O or $NR^6$, where $R^6$ is as defined above. $R^6$ is preferably not hydrogen. $R^6$ is in particular $C_1$–$C_4$-alkyl and very particularly preferably methyl. Another preferred class of the compounds I are those where A is S.

$R^1$ is halogen, $C_1$–$C_4$-alkyl, $C_1$–$C_4$-alkoxy, in particular methyl, methoxy or chlorine.

$R^2$ has the abovementioned meanings other than hydrogen, and is in particular $C_1$–$C_4$-alkyl, $C_1$–$C_4$-haloalkyl, hydroxyl, $C_1$–$C_4$-alkoxy, $C_1$–$C_4$-alkylsulfonyl, $C_1$–$C_4$-haloalkylsulfonyl, hydroxycarbonyl-$C_1$–$C_4$-alkyl, C(=N—O(—$C_1$–$C_4$-alkyl))-($C_1$–$C_4$-alkyl), $NH_2$, $C_1$–$C_4$-alkylamino, di($C_1$–$C_4$-alkyl)amino, phenyl, phenylcarbonyl or benzyl, where the phenyl rings of the three lastmentioned substituents may be substituted by one or two halogen atoms, methoxy groups or methyl groups, cyano, $C_1$–$C_4$-alkylcarbonyl, $C_1$–$C_4$-haloalkylcarbonyl, $C_1$–$C_4$-alkoxycarbonyl, $C_1$–$C_4$-alkoxycarbonyl-$C_1$–$C_4$-alkyl, $C_3$–$C_6$-alkenyl, $C_3$–$C_6$-alkynyl, 1,3-dioxolan-2-yl, 1,3-dithiolan-2-yl, 1,3-dioxan-2-yl, 1,3-dithian-2-yl, oxazolin-2-yl, oxazolidin-2-yl, 4,5-dihydroisoxazol-3-yl, 4,5-dihydroisoxazol-4-yl, isoxazol-3-yl, isoxazol-4-yl, methyl or ethyl substituted by one of the heterocycles mentioned above, such as in (1,3-dioxolan-2-yl)methyl, (1,3-dithiolan-2-yl)methyl, (1,3-dioxan-2-yl)methyl, (1,3-dithian-2-yl)methyl, (oxazolin-2-yl)methyl, (oxazolidin-2-yl)methyl, (4,5-dihydroisoxazol-3-yl) methyl, (4,5-dihydroisoxazol-4-yl)methyl, (isoxazol-3-yl)methyl, (isoxazol-4-yl)methyl, 2-(1,3-dioxolan-2-yl) ethyl, 2-(1,3-dithiolan-2-yl)ethyl, 2-(1,3-dioxan-2-yl) ethyl, 2-(1,3-dithian-2-yl)ethyl, 2-(oxazolin-2-yl)ethyl, 2-(oxazolidin-2-yl)ethyl, 2-(4,5-dihydroisoxazol-3-yl) ethyl, (4,5-dihydroisoxazol-4-yl)ethyl, 2-(isoxazol-3-yl) ethyl, 2-(isoxazol-4-yl)ethyl, where the abovementioned heterocycles may be mono-, di- or trisubstituted by $C_1$–$C_4$-alkyl, in particular methyl; and is especially $C_1$–$C_4$-alkyl, $C_3$–$C_6$-alkenyl, methoxymethyl, $CF_3$, $CHF_2$, CN, OH, $OCH_3$, $NH_2$, $NHCH_3$, $N(CH_3)_2$, $C_1$–$C_4$-alkoxy-carbonyl, acetyl, trifluoroacetyl, C(=$NOCH_3$) $CH_3$, $SO_2CH_3$, $SO_2CF_3$, $CH_2CO_2H$, $C_1$–$C_4$-alkoxycarbonyl-$C_1$–$C_4$-alkyl, cyclopropyl, cyclopentyl, cyclohexyl, 4,5-dihydroisoxazol-3-yl, 4,5-dihydroisoxazol-4-yl, isoxazol-3-yl, isoxazol-4-yl, where the abovementioned heterocycles may be monosubstituted by methyl, is phenyl, benzyl, benzoyl, 2-pyridyl.

$R^2$ is particularly preferably $C_1$–$C_6$-alkyl or $C_3$–$C_6$-alkenyl. Particular preference is also given to those compounds I in which $R^2$ is $C_3$–$C_6$-alkynyl, (1,3-dioxolan-2-yl)methyl, 2-(1,3-dioxolan-2-yl)ethyl or benzyl where the phenyl ring may be unsubstituted or carry 1 or 2 substituents, selected from the group consisting of halogen, methyl and methoxy.

$R^3$ is $C_1$–$C_4$-alkyl, halogen and in particular hydrogen.

In very particularly prefered compounds I, A is O or S, $R^1$ is methyl, $R^3$ is hydrogen and $R^3$ is a substituent different from hydrogen, in particular one of the substituents mentioned above as being preferred and specifically $C_1$–$C_6$-alkyl, $C_3$–$C_6$-alkynyl, $C_3$–$C_6$-alkenyl, (1,3-dioxolan-2-yl) methyl, 2-(1,3-dioxolan-2-yl)ethyl or benzyl where the phenyl ring may be unsubstituted or may carry 1 or 2 substituents selected from the group consisting of halogen, methyl and methoxy.

$R^7$, $R^8$, $R^9$, $R^{10}$, $R^{11}$, $R^{12}$ and $R^{13}$ preferably have the following meanings:

$R^7$ is hydroxyl, halogen, mercapto, $OR^{14}$, $SR^{14}$, $SO_2R^{15}$, $OSO_2R^{15}$, $NR^{18}R^{19}$, $ONR^{18}R^{19}$ or N-bonded heterocyclyl, such as pyrrolidinyl, piperidinyl, morpholinyl, pyrazolinyl or imidazolidinyl, which may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy or $C_1$–$C_4$-haloalkoxy; in particular hydroxyl, $OR^{14}$, $SR^{14}$, $N(OR^{18})$ $R^{19}$; particularly preferably hydroxyl, $C_1$–$C_4$-alkyloxy, $C_1$–$C_4$-alkylamino, di-$C_1$–$C_4$-alkylamino, N-$C_1$–$C_4$-alkoxy-$C_1$–$C_4$-alkylamino, $C_1$–$C_4$-alkylthio, phenylthio, O—$CH_2$-phenyl, phenylcarbonyloxy, 2-, 3- or 4-fluorophenylcarbonyloxy, $C_1$–$C_4$-sulfonyloxy, phenylsulfonyloxy and 2-, 3- or 4-methylphenylsulfonyloxy;

$R^8$, $R^{12}$ are hydrogen or $C_1$–$C_4$-alkyl, such as methyl, ethyl or propyl;

preferably hydrogen or methyl;

$R^9$, $R^{11}$, $R^{13}$ are hydrogen or $C_1$–$C_4$-alkyl, such as methyl, ethyl or propyl;

preferably hydrogen or methyl;

$R^{10}$ is hydrogen, hydroxyl, $C_1$–$C_6$-alkyl, di-$C_1$–$C_6$-alkoxy) methyl, ($C_1$–$C_6$-alkoxy)-($C_1$–$C_5$-alkylthio)methyl, di-($C_1$–$C_6$-alkylthio)methyl, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;

is 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the six lastmentioned radicals may be substituted by one, two or three $C_1$–$C_4$-alkyl radicals;

preferably hydrogen, hydroxyl or $C_1$–$C_4$-alkyl, such as methyl, ethyl or propyl;

or $R^9$ and $R^{11}$ or $R^{11}$ and $R^{13}$ together form a n bond or a $C_3$–$C_5$-alkyl chain which may carry one to three radicals from the following group: halogen, cyano, $C_1$–$C_4$-alkyl, $C_1$–$C_4$-haloalkyl or $C_1$–$C_4$-alkoxycarbonyl;

or $R^9$ and $R^{13}$ or $R^8$ and $R^{12}$ together form a $C_1$–$C_4$-alkyl chain which may carry one to three radicals from the following group: halogen, cyano, $C_1$–$C_4$-alkyl, $C_1$–$C_4$-haloalkyl or $C_1$–$C_4$-alkoxycarbonyl;

or $R^{10}$ and $R^{11}$ together form a —O—$(CH_2)_p$—O—, —O—$(CH_2)_p$—S— or —S—$(CH_2)_p$—S— chain which may be substituted by one to three radicals from the following group: halogen, cyano, $C_1$–$C_4$-alkyl, $C_1$–$C_4$-haloalkyl or $C_1$–$C_4$-alkoxycarbonyl;

or $R^{10}$ and $R^{11}$ together preferably form a —O—$(CH_2)_p$—O—, —O—$(CH_2)_p$—S— or —S—$(CH_2)_p$—S— chain which may be substituted by one to three radicals from the following group: $C_1$–$C_4$-haloalkyl or $C_1$–$C_4$-alkoxycarbonyl;

or $R^{10}$ and $R_{11}$ together with the carbons to which they are attached form a carbonyl group. The variable p is preferably 2 or 3 and the variable q is preferably 2, 3 or 4. Preferred meanings of $R^{14}$ to $R^{19}$ are:

$R^{14}$ is $C_1$–$C_6$-alkyl, $C_3$–$C_6$-alkenyl, $C_3$–$C_6$-haloalkenyl, $C_3$–$C_6$-alkynyl, $C_1$–$C_6$-alkylcarbonyl, $C_2$–$C_6$-alkenylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl) aminocarbonyl, N-($C_3$–$C_6$-alkenyl)-N-($C_1$–$C_6$-alkyl) aminocarbonyl, N-($C_3$–$C_6$-alkynyl)-N-($C_1$–$C_6$-alkyl) aminocarbonyl, N-($C_1$–$C_6$-alkoxy)-N-($C_1$–$C_6$-alkyl) aminocarbonyl, N-($C_3$–$C_6$-alkenyl)-N-($C_1$–$C_6$-alkoxy) aminocarbonyl, N-($C_3$–$C_6$-alkynyl)-N-($C_1$–$C_6$-alkoxy) aminocarbonyl, di-($C_1$–$C_6$-alkyl)aminothiocarbonyl, $C_1$–$C_6$-alkoxyimino-$C_1$–$C_6$-alkyl, where the alkyl, cycloalkyl or alkoxy radicals mentioned may be partially or fully halogenated and/or may carry one to three of the following groups: cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, hydroxycarbonyl, $C_1$–$C_4$-alkylaminocarbonyl, di-($C_1$–$C_4$-alkyl)aminocarbonyl, $C_1$–$C_4$-alkylcarbonyloxy or $C_3$–$C_6$-cycloalkyl;

is phenyl, phenyl-$C_1$–$C_6$-alkyl, phenylcarbonyl-$C_1$–$C_6$-alkyl, phenylcarbonyl, phenoxycarbonyl, phenoxythiocarbonyl, phenyl-$C_2$–$C_6$-alkenylcarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxy-carbonyl, heterocyclyloxythiocarbonyl or heterocyclyl-$C_1$–$C_6$-alkenylcarbonyl, where the phenyl or the heterocyclyl radical of the 14 lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

preferably $C_1$–$C_6$-alkyl, $C_3$–$C_6$-alkenyl, $C_3$–$C_6$-alkynyl, $C_1$–$C_6$-alkylcarbonyl, $C_1$–$C_6$-alkoxycarbonyl, $C_1$–$C_6$-alkylaminocarbonyl or N,N-di($C_1$–$C_6$-alkyl)aminocarbonyl, where the alkyl or alkoxy radicals mentioned may be partially or fully halogenated and/or may carry one to three of the following groups: cyano, $C_1$–$C_4$-alkoxy, $C_1$–$C_4$-alkylthio or $C_1$–$C_4$-alkoxycarbonyl;

phenyl, phenyl-$C_1$–$C_6$-alkyl, phenylcarbonyl-$C_1$–$C_6$-alkyl, phenylcarbonyl, phenoxycarbonyl, heterocyclyl, heterocyclyl-$C_1$–$C_6$-alkyl, heterocyclylcarbonyl-$C_1$–$C_6$-alkyl, heterocyclylcarbonyl or heterocyclyloxycarbonyl, where the phenyl or the heterocyclyl radical of the 10 lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{15}$ is $C_1$–$C_6$-alkyl, $C_3$–$C_6$-alkenyl or $C_3$–$C_6$-cycloalkyl, where the three radicals mentioned may be partially or fully halogenated and/or may carry one to three of the following groups: cyano, $C_1$–$C_4$-alkoxy, $C_1$–$C_4$-alkylthio, $C_1$–$C_4$-alkylcarbonyl or $C_1$–$C_4$-alkoxycarbonyl;

is phenyl, phenyl-$C_1$–$C_4$-alkyl, heterocyclyl or heterocyclyl-$C_1$–$C_4$-alkyl, where the phenyl or the heterocyclyl radical of the four lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{16}$, $R^{17}$ are hydroxyl, $C_1$–$C_6$-alkyl, $C_1$–$C_6$-alkoxy, phenyl, phenyl-$C_1$–$C_4$-alkyl or phenoxy, where the three lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{18}$ is $C_1$–$C_6$-alkyl, $C_3$–$C_6$-alkenyl, $C_3$–$C_6$-halogenalkenyl, $C_3$–$C_6$-cycloalkyl, $C_1$–$C_6$-alkoxy, $C_3$–$C_6$-alkenyloxy or di-($C_1$–$C_6$-alkyl)amino, where the alkyl, cycloalkyl or alkoxy radicals mentioned may be partially or fully halogenated and/or may carry one to three of the following radicals: cyano, $C_1$–$C_4$-alkoxycarbonyl, $C_1$–$C_4$-alkylaminocarbonyl, di-($C_1$–$C_4$-alkyl)aminocarbonyl or $C_3$–$C_6$-cycloalkyl;

is phenyl, phenyl-$C_1$–$C_4$-alkyl, phenylcarbonyl, heterocyclyl, heterocyclyl-$C_1$–$C_4$-alkyl or heterocyclylcarbonyl, where the phenyl or heterocyclyl radical of the six lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{19}$ is $C_1$–$C_6$-alkyl or $C_3$–$C_6$-alkenyl.

Preference is given to compounds of the formula I in which Hexk is a compound of the formula IIa or IIb".

Examples of preferred radicals Hex have the formulae IIa-1 to IIa-8.

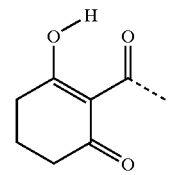

IIa-1

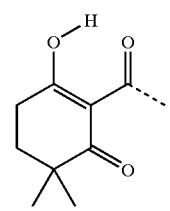

IIa-2

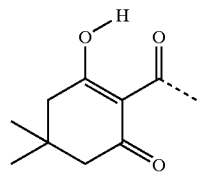

IIa-3

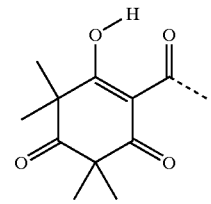

IIa-4

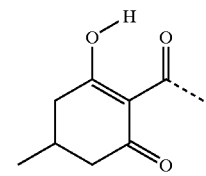

IIa-5

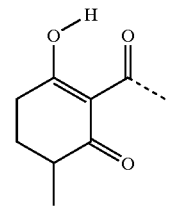

IIa-6

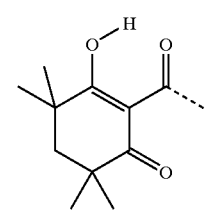

IIa-7

IIa-8

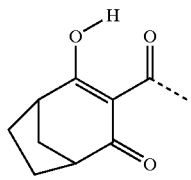

where the OH group in these radicals may also be replaced by one of the following groups: O—CH$_3$, N(CH$_3$)$_2$, N(OCH$_3$)CH$_3$, pyrrolidinyl, piperidinyl, morpholinyl, imidazolinyl, pyrazolinyl or S-phenyl. A particularly preferred group of the compounds I has a radical Hex of the formula IIa-4.

Examples of preferred compounds of the formula I are the benzazolonylcarbonylcyclohexenones I listed in Tables 1 to 25 below, where A, R$^1$, R$^2$ and R$^3$ in each case have the meanings given in one row of the table.

TABLE A

| No. | R$^1$ | R$^2$ | R$^3$ | A |
|---|---|---|---|---|
| 1 | CH$_3$ | H | H | O |
| 2 | CH$_3$ | CH$_3$ | H | O |
| 3 | CH$_3$ | C$_2$H$_5$ | H | O |
| 4 | CH$_3$ | n-C$_3$H$_7$ | H | O |
| 5 | CH$_3$ | i-C$_3$H$_7$ | H | O |
| 6 | CH$_3$ | n-C$_4$H$_9$ | H | O |
| 7 | CH$_3$ | i-C$_4$H$_9$ | H | O |
| 8 | CH$_3$ | s-C$_4$H$_9$ | H | O |
| 9 | CH$_3$ | t-C$_4$H$_9$ | H | O |
| 10 | CH$_3$ | CH$_2$OCH$_3$ | H | O |
| 11 | CH$_3$ | CF$_3$ | H | O |
| 12 | CH$_3$ | CF$_2$H | H | O |
| 13 | CH$_3$ | CN | H | O |
| 14 | CH$_3$ | OH | H | O |
| 15 | CH$_3$ | OCH$_3$ | H | O |
| 16 | CH$_3$ | NH$_2$ | H | O |
| 17 | CH$_3$ | NHCH$_3$ | H | O |
| 18 | CH$_3$ | N(CH$_3$)$_2$ | H | O |
| 19 | CH$_3$ | CO$_2$CH$_3$ | H | O |
| 20 | CH$_3$ | CO$_2$C$_2$H$_5$ | H | O |
| 21 | CH$_3$ | C(O)CH$_3$ | H | O |
| 22 | CH$_3$ | C(O)CF$_3$ | H | O |
| 23 | CH$_3$ | C(=NOCH$_3$)CH$_3$ | H | O |
| 24 | CH$_3$ | SO$_2$CH$_3$ | H | O |
| 25 | CH$_3$ | SO$_2$CF$_3$ | H | O |
| 26 | CH$_3$ | CH$_2$CO$_2$H | H | O |
| 27 | CH$_3$ | CH$_2$COOCH$_3$ | H | O |
| 28 | CH$_3$ | CH$_2$COOC$_2$H$_5$ | H | O |
| 29 | CH$_3$ | prop-1-en-3-yl | H | O |
| 30 | CH$_3$ | trans-but-2-en-1-yl | H | O |
| 31 | CH$_3$ | cis-but-2-en-1-yl | H | O |
| 32 | CH$_3$ | cis-3-methyl-but-2-en-1-yl | H | O |
| 33 | CH$_3$ | cyclopropyl | H | O |
| 34 | CH$_3$ | cyclopentyl | H | O |
| 35 | CH$_3$ | cyclohexyl | H | O |
| 36 | CH$_3$ | 4,5-dihydroisoxazol-3-yl | H | O |
| 37 | CH$_3$ | 4-methyl-4,5-dihydro-isoxazol-3-yl | H | O |
| 38 | CH$_3$ | isoxazol-3-yl | H | O |
| 39 | CH$_3$ | 4-methylisoxazol-3-yl | H | O |
| 40 | CH$_3$ | 4,5-dihydroisoxazol-4-yl | H | O |
| 41 | CH$_3$ | 3-methyl-4,5-dihydro-isoxazol-4-yl | H | O |
| 42 | CH$_3$ | isoxazol-4-yl | H | O |
| 43 | CH$_3$ | 3-methylisoxazol-4-yl | H | O |
| 44 | CH$_3$ | phenyl | H | O |
| 45 | CH$_3$ | benzyl | H | O |
| 46 | CH$_3$ | benzoyl | H | O |
| 47 | CH$_3$ | 2-pyridyl | H | O |

TABLE A-continued

| No. | R$^1$ | R$^2$ | R$^3$ | A |
|---|---|---|---|---|
| 48 | CH$_3$ | H | CH$_3$ | O |
| 49 | CH$_3$ | CH$_3$ | CH$_3$ | O |
| 50 | CH$_3$ | C$_2$H$_5$ | CH$_3$ | O |
| 51 | CH$_3$ | n-C$_3$H$_7$ | CH$_3$ | O |
| 52 | CH$_3$ | i-C$_3$H$_7$ | CH$_3$ | O |
| 53 | CH$_3$ | n-C$_4$H$_9$ | CH$_3$ | O |
| 54 | CH$_3$ | i-C$_4$H$_9$ | CH$_3$ | O |
| 55 | CH$_3$ | s-C$_4$H$_9$ | CH$_3$ | O |
| 56 | CH$_3$ | t-C$_4$H$_9$ | CH$_3$ | O |
| 57 | CH$_3$ | CH$_2$OCH$_3$ | CH$_3$ | O |
| 58 | CH$_3$ | CF$_3$ | CH$_3$ | O |
| 59 | CH$_3$ | CF$_2$H | CH$_3$ | O |
| 60 | CH$_3$ | CN | CH$_3$ | O |
| 61 | CH$_3$ | OH | CH$_3$ | O |
| 62 | CH$_3$ | OCH$_3$ | CH$_3$ | O |
| 63 | CH$_3$ | NH$_2$ | CH$_3$ | O |
| 64 | CH$_3$ | NHCH$_3$ | CH$_3$ | O |
| 65 | CH$_3$ | N(CH$_3$)$_2$ | CH$_3$ | O |
| 66 | CH$_3$ | CO$_2$CH$_3$ | CH$_3$ | O |
| 67 | CH$_3$ | CO$_2$C$_2$H$_5$ | CH$_3$ | O |
| 68 | CH$_3$ | C(O)CH$_3$ | CH$_3$ | O |
| 69 | CH$_3$ | C(O)CF$_3$ | CH$_3$ | O |
| 70 | CH$_3$ | C(=NOCH$_3$)CH$_3$ | CH$_3$ | O |
| 71 | CH$_3$ | SO$_2$CH$_3$ | CH$_3$ | O |
| 72 | CH$_3$ | SO$_2$CF$_3$ | CH$_3$ | O |
| 73 | CH$_3$ | CH$_2$CO$_2$H | CH$_3$ | O |
| 74 | CH$_3$ | CH$_2$COOCH$_3$ | CH$_3$ | O |
| 75 | CH$_3$ | CH$_2$COOC$_2$H$_5$ | CH$_3$ | O |
| 76 | CH$_3$ | prop-1-en-3-yl | CH$_3$ | O |
| 77 | CH$_3$ | trans-but-2-en-1-yl | CH$_3$ | O |
| 78 | CH$_3$ | cis-but-2-en-1-yl | CH$_3$ | O |
| 79 | CH$_3$ | cis-3-methyl-but-2-en-1-yl | CH$_3$ | O |
| 80 | CH$_3$ | cyclopropyl | CH$_3$ | O |
| 81 | CH$_3$ | cyclopentyl | CH$_3$ | O |
| 82 | CH$_3$ | cyclohexyl | CH$_3$ | O |
| 83 | CH$_3$ | 4,5-dihydroisoxazol-3-yl | CH$_3$ | O |
| 84 | CH$_3$ | 4-methyl-4,5-dihydro-isoxazol-3-yl | CH$_3$ | O |
| 85 | CH$_3$ | isoxazol-3-yl | CH$_3$ | O |
| 86 | CH$_3$ | 4-methylisoxazol-3-yl | CH$_3$ | O |
| 87 | CH$_3$ | 4,5-dihydroisoxazol-4-yl | CH$_3$ | O |
| 88 | CH$_3$ | 3-methyl-4,5-dihydro-isoxazol-4-yl | CH$_3$ | O |
| 89 | CH$_3$ | isoxazol-4-yl | CH$_3$ | O |
| 90 | CH$_3$ | 3-methylisoxazol-4-yl | CH$_3$ | O |
| 91 | CH$_3$ | phenyl | CH$_3$ | O |
| 92 | CH$_3$ | benzyl | CH$_3$ | O |
| 93 | CH$_3$ | benzoyl | CH$_3$ | O |
| 94 | CH$_3$ | 2-pyridyl | CH$_3$ | O |
| 95 | CH$_3$ | H | Cl | O |
| 96 | CH$_3$ | CH$_3$ | Cl | O |
| 97 | CH$_3$ | C$_2$H$_5$ | Cl | O |
| 98 | CH$_3$ | n-C$_3$H$_7$ | Cl | O |
| 99 | CH$_3$ | i-C$_3$H$_7$ | Cl | O |
| 100 | CH$_3$ | n-C$_4$H$_9$ | Cl | O |
| 101 | CH$_3$ | i-C$_4$H$_9$ | Cl | O |
| 102 | CH$_3$ | s-C$_4$H$_9$ | Cl | O |
| 103 | CH$_3$ | t-C$_4$H$_9$ | Cl | O |
| 104 | CH$_3$ | CH$_2$OCH$_3$ | Cl | O |
| 105 | CH$_3$ | CF$_3$ | Cl | O |
| 106 | CH$_3$ | CF$_2$H | Cl | O |
| 107 | CH$_3$ | CN | Cl | O |
| 108 | CH$_3$ | OH | Cl | O |
| 109 | CH$_3$ | OCH$_3$ | Cl | O |
| 110 | CH$_3$ | NH$_2$ | Cl | O |
| 111 | CH$_3$ | NHCH$_3$ | Cl | O |
| 112 | CH$_3$ | N(CH$_3$)$_2$ | Cl | O |
| 113 | CH$_3$ | CO$_2$CH$_3$ | Cl | O |
| 114 | CH$_3$ | CO$_2$C$_2$H$_5$ | Cl | O |
| 115 | CH$_3$ | C(O)CH$_3$ | Cl | O |
| 116 | CH$_3$ | C(O)CF$_3$ | Cl | O |
| 117 | CH$_3$ | C(=NOCH$_3$)CH$_3$ | Cl | O |
| 118 | CH$_3$ | SO$_2$CH$_3$ | Cl | O |
| 119 | CH$_3$ | SO$_2$CF$_3$ | Cl | O |

TABLE A-continued

| No. | R¹ | R² | R³ | A |
|---|---|---|---|---|
| 120 | $CH_3$ | $CH_2CO_2H$ | Cl | O |
| 121 | $CH_3$ | $CH_2COOCH_3$ | Cl | O |
| 122 | $CH_3$ | $CH_2COOC_2H_5$ | Cl | O |
| 123 | $CH_3$ | prop-1-en-3-yl | Cl | O |
| 124 | $CH_3$ | trans-but-2-en-1-yl | Cl | O |
| 125 | $CH_3$ | cis-but-2-en-1-yl | Cl | O |
| 126 | $CH_3$ | cis-3-methyl-but-2-en-1-yl | Cl | O |
| 127 | $CH_3$ | cyclopropyl | Cl | O |
| 128 | $CH_3$ | cyclopentyl | Cl | O |
| 129 | $CH_3$ | cyclohexyl | Cl | O |
| 130 | $CH_3$ | 4,5-dihydroisoxazol-3-yl | Cl | O |
| 131 | $CH_3$ | 4-methyl-4,5-dihydro-isoxazol-3-yl | Cl | O |
| 132 | $CH_3$ | isoxazol-3-yl | Cl | O |
| 133 | $CH_3$ | 4-methylisoxazol-3-yl | Cl | O |
| 134 | $CH_3$ | 4,5-dihydroisoxazol-4-yl | Cl | O |
| 135 | $CH_3$ | 3-methyl-4,5-dihydro-isoxazol-4-yl | Cl | O |
| 136 | $CH_3$ | isoxazol-4-yl | Cl | O |
| 137 | $CH_3$ | 3-methylisoxazol-4-yl | Cl | O |
| 138 | $CH_3$ | phenyl | Cl | O |
| 139 | $CH_3$ | benzyl | Cl | O |
| 140 | $CH_3$ | benzoyl | Cl | O |
| 141 | $CH_3$ | 2-pyridyl | Cl | O |
| 142 | Cl | H | H | O |
| 143 | Cl | $CH_3$ | H | O |
| 144 | Cl | $C_2H_5$ | H | O |
| 145 | Cl | $n\text{-}C_3H_7$ | H | O |
| 146 | Cl | $i\text{-}C_3H_7$ | H | O |
| 147 | Cl | $n\text{-}C_4H_9$ | H | O |
| 148 | Cl | $i\text{-}C_4H_9$ | H | O |
| 149 | Cl | $s\text{-}C_4H_9$ | H | O |
| 150 | Cl | $t\text{-}C_4H_9$ | H | O |
| 151 | Cl | $CH_2OCH_3$ | H | O |
| 152 | Cl | $CF_3$ | H | O |
| 153 | Cl | $CF_2H$ | H | O |
| 154 | Cl | CN | H | O |
| 155 | Cl | OH | H | O |
| 156 | Cl | $OCH_3$ | H | O |
| 157 | Cl | $NH_2$ | H | O |
| 158 | Cl | $NHCH_3$ | H | O |
| 159 | Cl | $N(CH_3)_2$ | H | O |
| 160 | Cl | $CO_2CH_3$ | H | O |
| 161 | Cl | $CO_2C_2H_5$ | H | O |
| 162 | Cl | $C(O)CH_3$ | H | O |
| 163 | Cl | $C(O)CF_3$ | H | O |
| 164 | Cl | $C(=NOCH_3)CH_3$ | H | O |
| 165 | Cl | $SO_2CH_3$ | H | O |
| 166 | Cl | $SO_2CF_3$ | H | O |
| 167 | Cl | $CH_2CO_2H$ | H | O |
| 168 | Cl | $CH_2COOCH_3$ | H | O |
| 169 | Cl | $CH_2COOC_2H_5$ | H | O |
| 170 | Cl | prop-1-en-3-yl | H | O |
| 171 | Cl | trans-but-2-en-1-yl | H | O |
| 172 | Cl | cis-but-2-en-1-yl | H | O |
| 173 | Cl | cis-3-methyl-but-2-en-1-yl | H | O |
| 174 | Cl | cyclopropyl | H | O |
| 175 | Cl | cyclopentyl | H | O |
| 176 | Cl | cyclohexyl | H | O |
| 177 | Cl | 4,5-dihydroisoxazol-3-yl | H | O |
| 178 | Cl | 4-methyl-4,5-dihydro-isoxazol-3-yl | H | O |
| 179 | Cl | isoxazol-3-yl | H | O |
| 180 | Cl | 4-methylisoxazol-3-yl | H | O |
| 181 | Cl | 4,5-dihydroisoxazol-4-yl | H | O |
| 182 | Cl | 3-methyl-4,5-dihydro-isoxazol-4-yl | H | O |
| 183 | Cl | isoxazol-4-yl | H | O |
| 184 | Cl | 3-methylisoxazol-4-yl | H | O |
| 185 | Cl | phenyl | H | O |
| 186 | Cl | benzyl | H | O |
| 187 | Cl | benzoyl | H | O |
| 188 | Cl | 2-pyridyl | H | O |
| 189 | Cl | H | $CH_3$ | O |
| 190 | Cl | $CH_3$ | $CH_3$ | O |
| 191 | Cl | $C_2H_5$ | $CH_3$ | O |
| 192 | Cl | $n\text{-}C_3H_7$ | $CH_3$ | O |
| 193 | Cl | $i\text{-}C_3H_7$ | $CH_3$ | O |
| 194 | Cl | $n\text{-}C_4H_9$ | $CH_3$ | O |
| 195 | Cl | $i\text{-}C_4H_9$ | $CH_3$ | O |
| 196 | Cl | $s\text{-}C_4H_9$ | $CH_3$ | O |
| 197 | Cl | $t\text{-}C_4H_9$ | $CH_3$ | O |
| 198 | Cl | $CH_2OCH_3$ | $CH_3$ | O |
| 199 | Cl | $CF_3$ | $CH_3$ | O |
| 200 | Cl | $CF_2H$ | $CH_3$ | O |
| 201 | Cl | CN | $CH_3$ | O |
| 202 | Cl | OH | $CH_3$ | O |
| 203 | Cl | $OCH_3$ | $CH_3$ | O |
| 204 | Cl | $NH_2$ | $CH_3$ | O |
| 205 | Cl | $NHCH_3$ | $CH_3$ | O |
| 206 | Cl | $N(CH_3)_2$ | $CH_3$ | O |
| 207 | Cl | $CO_2CH_3$ | $CH_3$ | O |
| 208 | Cl | $CO_2C_2H_5$ | $CH_3$ | O |
| 209 | Cl | $C(O)CH_3$ | $CH_3$ | O |
| 210 | Cl | $C(O)CF_3$ | $CH_3$ | O |
| 211 | Cl | $C(=NOCH_3)CH_3$ | $CH_3$ | O |
| 212 | Cl | $SO_2CH_3$ | $CH_3$ | O |
| 213 | Cl | $SO_2CF_3$ | $CH_3$ | O |
| 214 | Cl | $CH_2CO_2H$ | $CH_3$ | O |
| 215 | Cl | $CH_2COOCH_3$ | $CH_3$ | O |
| 216 | Cl | $CH_2COOC_2H_5$ | $CH_3$ | O |
| 217 | Cl | prop-1-en-3-yl | $CH_3$ | O |
| 218 | Cl | trans-but-2-en-1-yl | $CH_3$ | O |
| 219 | Cl | cis-but-2-en-1-yl | $CH_3$ | O |
| 220 | Cl | cis-3-methyl-but-2-en-1-yl | $CH_3$ | O |
| 221 | Cl | cyclopropyl | $CH_3$ | O |
| 222 | Cl | cyclopentyl | $CH_3$ | O |
| 223 | Cl | cyclohexyl | $CH_3$ | O |
| 224 | Cl | 4,5-dihydroisoxazol-3-yl | $CH_3$ | O |
| 225 | Cl | 4-methyl-4,5-dihydro-isoxazol-3-yl | $CH_3$ | O |
| 226 | Cl | isoxazol-3-yl | $CH_3$ | O |
| 227 | Cl | 4-methylisoxazol-3-yl | $CH_3$ | O |
| 228 | Cl | 4,5-dihydroisoxazol-4-yl | $CH_3$ | O |
| 229 | Cl | 3-methyl-4,5-dihydro-isoxazol-4-yl | $CH_3$ | O |
| 230 | Cl | isoxazol-4-yl | $CH_3$ | O |
| 231 | Cl | 3-methylisoxazol-4-yl | $CH_3$ | O |
| 232 | Cl | phenyl | $CH_3$ | O |
| 233 | Cl | benzyl | $CH_3$ | O |
| 234 | Cl | benzoyl | $CH_3$ | O |
| 235 | Cl | 2-pyridyl | $CH_3$ | O |
| 236 | Cl | H | Cl | O |
| 237 | Cl | $CH_3$ | Cl | O |
| 238 | Cl | $C_2H_5$ | Cl | O |
| 239 | Cl | $n\text{-}C_3H_7$ | Cl | O |
| 240 | Cl | $i\text{-}C_3H_7$ | Cl | O |
| 241 | Cl | $n\text{-}C_4H_9$ | Cl | O |
| 242 | Cl | $i\text{-}C_4H_9$ | Cl | O |
| 243 | Cl | $s\text{-}C_4H_9$ | Cl | O |
| 244 | Cl | $t\text{-}C_4H_9$ | Cl | O |
| 245 | Cl | $CH_2OCH_3$ | Cl | O |
| 246 | Cl | $CF_3$ | Cl | O |
| 247 | Cl | $CF_2H$ | Cl | O |
| 248 | Cl | CN | Cl | O |
| 249 | Cl | OH | Cl | O |
| 250 | Cl | $OCH_3$ | Cl | O |
| 251 | Cl | $NH_2$ | Cl | O |
| 252 | Cl | $NHCH_3$ | Cl | O |
| 253 | Cl | $N(CH_3)_2$ | Cl | O |
| 254 | Cl | $CO_2CH_3$ | Cl | O |
| 255 | Cl | $CO_2C_2H_5$ | Cl | O |
| 256 | Cl | $C(O)CH_3$ | Cl | O |
| 257 | Cl | $C(O)CF_3$ | Cl | O |
| 258 | Cl | $C(=NOCH_3)CH_3$ | Cl | O |

TABLE A-continued

| No. | R$^1$ | R$^2$ | R$^3$ | A |
|---|---|---|---|---|
| 259 | Cl | SO$_2$CH$_3$ | Cl | O |
| 260 | Cl | SO$_2$CF$_3$ | Cl | O |
| 261 | Cl | CH$_2$CO$_2$H | Cl | O |
| 262 | Cl | CH$_2$COOCH$_3$ | Cl | O |
| 263 | Cl | CH$_2$COOC$_2$H$_5$ | Cl | O |
| 264 | Cl | prop-1-en-3-yl | Cl | O |
| 265 | Cl | trans-but-2-en-1-yl | Cl | O |
| 266 | Cl | cis-but-2-en-1-yl | Cl | O |
| 267 | Cl | cis-3-methyl-but-2-en-1-yl | Cl | O |
| 268 | Cl | cyclopropyl | Cl | O |
| 269 | Cl | cyclopentyl | Cl | O |
| 270 | Cl | cyclohexyl | Cl | O |
| 271 | Cl | 4,5-dihydroisoxazol-3-yl | Cl | O |
| 272 | Cl | 4-methyl-4,5-dihydro-isoxazol-3-yl | Cl | O |
| 273 | Cl | isoxazol-3-yl | Cl | O |
| 274 | Cl | 4-methylisoxazol-3-yl | Cl | O |
| 275 | Cl | 4,5-dihydroisoxazol-4-yl | Cl | O |
| 276 | Cl | 3-methyl-4,5-dihydro-isoxazol-4-yl | Cl | O |
| 277 | Cl | isoxazol-4-yl | Cl | O |
| 278 | Cl | 3-methylisoxazol-4-yl | Cl | O |
| 279 | Cl | phenyl | Cl | O |
| 280 | Cl | benzyl | Cl | O |
| 281 | Cl | benzoyl | Cl | O |
| 282 | Cl | 2-pyridyl | Cl | O |
| 283 | OCH$_3$ | H | H | O |
| 284 | OCH$_3$ | CH$_3$ | H | O |
| 285 | OCH$_3$ | C$_2$H$_5$ | H | O |
| 286 | OCH$_3$ | n-C$_3$H$_7$ | H | O |
| 287 | OCH$_3$ | i-C$_3$H$_7$ | H | O |
| 288 | OCH$_3$ | n-C$_4$H$_9$ | H | O |
| 289 | OCH$_3$ | i-C$_4$H$_9$ | H | O |
| 290 | OCH$_3$ | s-C$_4$H$_9$ | H | O |
| 291 | OCH$_3$ | t-C$_4$H$_9$ | H | O |
| 292 | OCH$_3$ | CH$_2$OCH$_3$ | H | O |
| 293 | OCH$_3$ | CF$_3$ | H | O |
| 294 | OCH$_3$ | CF$_2$H | H | O |
| 295 | OCH$_3$ | CN | H | O |
| 296 | OCH$_3$ | OH | H | O |
| 297 | OCH$_3$ | OCH$_3$ | H | O |
| 298 | OCH$_3$ | NH$_2$ | H | O |
| 299 | OCH$_3$ | NHCH$_3$ | H | O |
| 300 | OCH$_3$ | N(CH$_3$)$_2$ | H | O |
| 301 | OCH$_3$ | CO$_2$CH$_3$ | H | O |
| 302 | OCH$_3$ | CO$_2$C$_2$H$_5$ | H | O |
| 303 | OCH$_3$ | C(O)CH$_3$ | H | O |
| 304 | OCH$_3$ | C(O)CF$_3$ | H | O |
| 305 | OCH$_3$ | C(=NOCH$_3$)CH$_3$ | H | O |
| 306 | OCH$_3$ | SO$_2$CH$_3$ | H | O |
| 307 | OCH$_3$ | SO$_2$CF$_3$ | H | O |
| 308 | OCH$_3$ | CH$_2$CO$_2$H | H | O |
| 309 | OCH$_3$ | CH$_2$COOCH$_3$ | H | O |
| 310 | OCH$_3$ | CH$_2$COOC$_2$H$_5$ | H | O |
| 311 | OCH$_3$ | prop-1-en-3-yl | H | O |
| 312 | OCH$_3$ | trans-but-2-en-1-yl | H | O |
| 313 | OCH$_3$ | cis-but-2-en-1-yl | H | O |
| 314 | OCH$_3$ | cis-3-methyl-but-2-en-1-yl | H | O |
| 315 | OCH$_3$ | cyclopropyl | H | O |
| 316 | OCH$_3$ | cyclopentyl | H | O |
| 317 | OCH$_3$ | cyclohexyl | H | O |
| 318 | OCH$_3$ | 4,5-dihydroisoxazol-3-yl | H | O |
| 319 | OCH$_3$ | 4-methyl-4,5-dihydro-isoxazol-3-yl | H | O |
| 320 | OCH$_3$ | isoxazol-3-yl | H | O |
| 321 | OCH$_3$ | 4-methylisoxazol-3-yl | H | O |
| 322 | OCH$_3$ | 4,5-dihydroisoxazol-4-yl | H | O |
| 323 | OCH$_3$ | 3-methyl-4,5-dihydro-isoxazol-4-yl | H | O |
| 324 | OCH$_3$ | isoxazol-4-yl | H | O |
| 325 | OCH$_3$ | 3-methylisoxazol-4-yl | H | O |
| 326 | OCH$_3$ | phenyl | H | O |
| 327 | OCH$_3$ | benzyl | H | O |
| 328 | OCH$_3$ | benzoyl | H | O |
| 329 | OCH$_3$ | 2-pyridyl | H | O |
| 330 | OCH$_3$ | H | CH$_3$ | O |
| 331 | OCH$_3$ | CH$_3$ | CH$_3$ | O |
| 332 | OCH$_3$ | C$_2$H$_5$ | CH$_3$ | O |
| 333 | OCH$_3$ | n-C$_3$H$_7$ | CH$_3$ | O |
| 334 | OCH$_3$ | i-C$_3$H$_7$ | CH$_3$ | O |
| 335 | OCH$_3$ | n-C$_4$H$_9$ | CH$_3$ | O |
| 336 | OCH$_3$ | i-C$_4$H$_9$ | CH$_3$ | O |
| 337 | OCH$_3$ | s-C$_4$H$_9$ | CH$_3$ | O |
| 338 | OCH$_3$ | t-C$_4$H$_9$ | CH$_3$ | O |
| 339 | OCH$_3$ | CH$_2$OCH$_3$ | CH$_3$ | O |
| 340 | OCH$_3$ | CF$_3$ | CH$_3$ | O |
| 341 | OCH$_3$ | CF$_2$H | CH$_3$ | O |
| 342 | OCH$_3$ | CN | CH$_3$ | O |
| 343 | OCH$_3$ | OH | CH$_3$ | O |
| 344 | OCH$_3$ | OCH$_3$ | CH$_3$ | O |
| 345 | OCH$_3$ | NH$_2$ | CH$_3$ | O |
| 346 | OCH$_3$ | NHCH$_3$ | CH$_3$ | O |
| 347 | OCH$_3$ | N(CH$_3$)$_2$ | CH$_3$ | O |
| 348 | OCH$_3$ | CO$_2$CH$_3$ | CH$_3$ | O |
| 349 | OCH$_3$ | CO$_2$C$_2$H$_5$ | CH$_3$ | O |
| 350 | OCH$_3$ | C(O)CH$_3$ | CH$_3$ | O |
| 351 | OCH$_3$ | C(O)CF$_3$ | CH$_3$ | O |
| 352 | OCH$_3$ | C(=NOCH$_3$)CH$_3$ | CH$_3$ | O |
| 353 | OCH$_3$ | SO$_2$CH$_3$ | CH$_3$ | O |
| 354 | OCH$_3$ | SO$_2$CF$_3$ | CH$_3$ | O |
| 355 | OCH$_3$ | CH$_2$CO$_2$H | CH$_3$ | O |
| 356 | OCH$_3$ | CH$_2$COOCH$_3$ | CH$_3$ | O |
| 357 | OCH$_3$ | CH$_2$COOC$_2$H$_5$ | CH$_3$ | O |
| 358 | OCH$_3$ | prop-1-en-3-yl | CH$_3$ | O |
| 359 | OCH$_3$ | trans-but-2-en-1-yl | CH$_3$ | O |
| 360 | OCH$_3$ | cis-but-2-en-1-yl | CH$_3$ | O |
| 361 | OCH$_3$ | cis-3-methyl-but-2-en-1-yl | CH$_3$ | O |
| 362 | OCH$_3$ | cyclopropyl | CH$_3$ | O |
| 363 | OCH$_3$ | cyclopentyl | CH$_3$ | O |
| 364 | OCH$_3$ | cyclohexyl | CH$_3$ | O |
| 365 | OCH$_3$ | 4,5-dihydroisoxazol-3-yl | CH$_3$ | O |
| 366 | OCH$_3$ | 4-methyl-4,5-dihydro-isoxazol-3-yl | CH$_3$ | O |
| 367 | OCH$_3$ | isoxazol-3-yl | CH$_3$ | O |
| 368 | OCH$_3$ | 4-methylisoxazol-3-yl | CH$_3$ | O |
| 369 | OCH$_3$ | 4,5-dihydroisoxazol-4-yl | CH$_3$ | O |
| 370 | OCH$_3$ | 3-methyl-4,5-dihydro-isoxazol-4-yl | CH$_3$ | O |
| 371 | OCH$_3$ | isoxazol-4-yl | CH$_3$ | O |
| 372 | OCH$_3$ | 3-methylisoxazol-4-yl | CH$_3$ | O |
| 373 | OCH$_3$ | phenyl | CH$_3$ | O |
| 374 | OCH$_3$ | benzyl | CH$_3$ | O |
| 375 | OCH$_3$ | benzoyl | CH$_3$ | O |
| 376 | OCH$_3$ | 2-pyridyl | CH$_3$ | O |
| 377 | OCH$_3$ | H | Cl | O |
| 378 | OCH$_3$ | CH$_3$ | Cl | O |
| 379 | OCH$_3$ | C$_2$H$_5$ | Cl | O |
| 380 | OCH$_3$ | n-C$_3$H$_7$ | Cl | O |
| 381 | OCH$_3$ | i-C$_3$H$_7$ | Cl | O |
| 382 | OCH$_3$ | n-C$_4$H$_9$ | Cl | O |
| 383 | OCH$_3$ | i-C$_4$H$_9$ | Cl | O |
| 384 | OCH$_3$ | s-C$_4$H$_9$ | Cl | O |
| 385 | OCH$_3$ | t-C$_4$H$_9$ | Cl | O |
| 386 | OCH$_3$ | CH$_2$OCH$_3$ | Cl | O |
| 387 | OCH$_3$ | CF$_3$ | Cl | O |
| 388 | OCH$_3$ | CF$_2$H | Cl | O |
| 389 | OCH$_3$ | CN | Cl | O |
| 390 | OCH$_3$ | OH | Cl | O |
| 391 | OCH$_3$ | OCH$_3$ | Cl | O |
| 392 | OCH$_3$ | NH$_2$ | Cl | O |
| 393 | OCH$_3$ | NHCH$_3$ | Cl | O |
| 394 | OCH$_3$ | N(CH$_3$)$_2$ | Cl | O |
| 395 | OCH$_3$ | CO$_2$CH$_3$ | Cl | O |
| 396 | OCH$_3$ | CO$_2$C$_2$H$_5$ | Cl | O |
| 397 | OCH$_3$ | C(O)CH$_3$ | Cl | O |

TABLE A-continued

| No. | R¹ | R² | R³ | A |
|---|---|---|---|---|
| 398 | OCH₃ | C(O)CF₃ | Cl | O |
| 399 | OCH₃ | C(=NOCH₃)CH₃ | Cl | O |
| 400 | OCH₃ | SO₂CH₃ | Cl | O |
| 401 | OCH₃ | SO₂CF₃ | Cl | O |
| 402 | OCH₃ | CH₂CO₂H | Cl | O |
| 403 | OCH₃ | CH₂COOCH₃ | Cl | O |
| 404 | OCH₃ | CH₂COOC₂H₅ | Cl | O |
| 405 | OCH₃ | prop-1-en-3-yl | Cl | O |
| 406 | OCH₃ | trans-but-2-en-1-yl | Cl | O |
| 407 | OCH₃ | cis-but-2-en-1-yl | Cl | O |
| 408 | OCH₃ | cis-3-methyl-but-2-en-1-yl | Cl | O |
| 409 | OCH₃ | cyclopropyl | Cl | O |
| 410 | OCH₃ | cyclopentyl | Cl | O |
| 411 | OCH₃ | cyclohexyl | Cl | O |
| 412 | OCH₃ | 4,5-dihydroisoxazol-3-yl | Cl | O |
| 413 | OCH₃ | 4-methyl-4,5-dihydro-isoxazol-3-yl | Cl | O |
| 414 | OCH₃ | isoxazol-3-yl | Cl | O |
| 415 | OCH₃ | 4-methylisoxazol-3-yl | Cl | O |
| 416 | OCH₃ | 4,5-dihydroisoxazol-4-yl | Cl | O |
| 417 | OCH₃ | 3-methyl-4,5-dihydro-isoxazol-4-yl | Cl | O |
| 418 | OCH₃ | isoxazol-4-yl | Cl | O |
| 419 | OCH₃ | 3-methylisoxazol-4-yl | Cl | O |
| 420 | OCH₃ | phenyl | Cl | O |
| 421 | OCH₃ | benzyl | Cl | O |
| 422 | OCH₃ | benzoyl | Cl | O |
| 423 | OCH₃ | 2-pyridyl | Cl | O |
| 424 | OCF₃ | H | H | O |
| 425 | OCF₃ | CH₃ | H | O |
| 426 | OCF₃ | C₂H₅ | H | O |
| 427 | OCF₃ | n-C₃H₇ | H | O |
| 428 | OCF₃ | i-C₃H₇ | H | O |
| 429 | OCF₃ | n-C₄H₉ | H | O |
| 430 | OCF₃ | i-C₄H₉ | H | O |
| 431 | OCF₃ | s-C₄H₉ | H | O |
| 432 | OCF₃ | t-C₄H₉ | H | O |
| 433 | OCF₃ | CH₂OCH₃ | H | O |
| 434 | OCF₃ | CF₃ | H | O |
| 435 | OCF₃ | CF₂H | H | O |
| 436 | OCF₃ | CN | H | O |
| 437 | OCF₃ | OH | H | O |
| 438 | OCF₃ | OCH₃ | H | O |
| 439 | OCF₃ | NH₂ | H | O |
| 440 | OCF₃ | NHCH₃ | H | O |
| 441 | OCF₃ | N(CH₃)₂ | H | O |
| 442 | OCF₃ | CO₂CH₃ | H | O |
| 443 | OCF₃ | CO₂C₂H₅ | H | O |
| 444 | OCF₃ | C(O)CH₃ | H | O |
| 445 | OCF₃ | C(O)CF₃ | H | O |
| 446 | OCF₃ | C(=NOCH₃)CH₃ | H | O |
| 447 | OCF₃ | SO₂CH₃ | H | O |
| 448 | OCF₃ | SO₂CF₃ | H | O |
| 449 | OCF₃ | CH₂CO₂H | H | O |
| 450 | OCF₃ | CH₂COOCH₃ | H | O |
| 451 | OCF₃ | CH₂COOC₂H₅ | H | O |
| 452 | OCF₃ | prop-1-en-3-yl | H | O |
| 453 | OCF₃ | trans-but-2-en-1-yl | H | O |
| 454 | OCF₃ | cis-but-2-en-1-yl | H | O |
| 455 | OCF₃ | cis-3-methyl-but-2-en-1-yl | H | O |
| 456 | OCF₃ | cyclopropyl | H | O |
| 457 | OCF₃ | cyclopentyl | H | O |
| 458 | OCF₃ | cyclohexyl | H | O |
| 459 | OCF₃ | 4,5-dihydroisoxazol-3-yl | H | O |
| 460 | OCF₃ | 4-methyl-4,5-dihydro-isoxazol-3-yl | H | O |
| 461 | OCF₃ | isoxazol-3-yl | H | O |
| 462 | OCF₃ | 4-methylisoxazol-3-yl | H | O |
| 463 | OCF₃ | 4,5-dihydroisoxazol-4-yl | H | O |
| 464 | OCF₃ | 3-methyl-4,5-dihydro-isoxazol-4-yl | H | O |
| 465 | OCF₃ | isoxazol-4-yl | H | O |
| 466 | OCF₃ | 3-methylisoxazol-4-yl | H | O |
| 467 | OCF₃ | phenyl | H | O |
| 468 | OCF₃ | benzyl | H | O |
| 469 | OCF₃ | benzoyl | H | O |
| 470 | OCF₃ | 2-pyridyl | H | O |
| 471 | OCF₃ | H | CH₃ | O |
| 472 | OCF₃ | CH₃ | CH₃ | O |
| 473 | OCF₃ | C₂H₅ | CH₃ | O |
| 474 | OCF₃ | n-C₃H₇ | CH₃ | O |
| 475 | OCF₃ | i-C₃H₇ | CH₃ | O |
| 476 | OCF₃ | n-C₄H₉ | CH₃ | O |
| 477 | OCF₃ | i-C₄H₉ | CH₃ | O |
| 478 | OCF₃ | s-C₄H₉ | CH₃ | O |
| 479 | OCF₃ | t-C₄H₉ | CH₃ | O |
| 480 | OCF₃ | CH₂OCH₃ | CH₃ | O |
| 481 | OCF₃ | CF₃ | CH₃ | O |
| 482 | OCF₃ | CF₂H | CH₃ | O |
| 483 | OCF₃ | CN | CH₃ | O |
| 484 | OCF₃ | OH | CH₃ | O |
| 485 | OCF₃ | OCH₃ | CH₃ | O |
| 486 | OCF₃ | NH₂ | CH₃ | O |
| 487 | OCF₃ | NHCH₃ | CH₃ | O |
| 488 | OCF₃ | N(CH₃)₂ | CH₃ | O |
| 489 | OCF₃ | CO₂CH₃ | CH₃ | O |
| 490 | OCF₃ | CO₂C₂H₅ | CH₃ | O |
| 491 | OCF₃ | C(O)CH₃ | CH₃ | O |
| 492 | OCF₃ | C(O)CF₃ | CH₃ | O |
| 493 | OCF₃ | C(=NOCH₃)CH₃ | CH₃ | O |
| 494 | OCF₃ | SO₂CH₃ | CH₃ | O |
| 495 | OCF₃ | SO₂CF₃ | CH₃ | O |
| 496 | OCF₃ | CH₂CO₂H | CH₃ | O |
| 497 | OCF₃ | CH₂COOCH₃ | CH₃ | O |
| 498 | OCF₃ | CH₂COOC₂H₅ | CH₃ | O |
| 499 | OCF₃ | prop-1-en-3-yl | CH₃ | O |
| 500 | OCF₃ | trans-but-2-en-1-yl | CH₃ | O |
| 501 | OCF₃ | cis-but-2-en-1-yl | CH₃ | O |
| 502 | OCF₃ | cis-3-methyl-but-2-en-1-yl | CH₃ | O |
| 503 | OCF₃ | cyclopropyl | CH₃ | O |
| 504 | OCF₃ | cyclopentyl | CH₃ | O |
| 505 | OCF₃ | cyclohexyl | CH₃ | O |
| 506 | OCF₃ | 4,5-dihydroisoxazol-3-yl | CH₃ | O |
| 507 | OCF₃ | 4-methyl-4,5-dihydro-isoxazol-3-yl | CH₃ | O |
| 508 | OCF₃ | isoxazol-3-yl | CH₃ | O |
| 509 | OCF₃ | 4-methylisoxazol-3-yl | CH₃ | O |
| 510 | OCF₃ | 4,5-dihydroisoxazol-4-yl | CH₃ | O |
| 511 | OCF₃ | 3-methyl-4,5-dihydro-isoxazol-4-yl | CH₃ | O |
| 512 | OCF₃ | isoxazol-4-yl | CH₃ | O |
| 513 | OCF₃ | 3-methylisoxazol-4-yl | CH₃ | O |
| 514 | OCF₃ | phenyl | CH₃ | O |
| 515 | OCF₃ | benzyl | CH₃ | O |
| 516 | OCF₃ | benzoyl | CH₃ | O |
| 517 | OCF₃ | 2-pyridyl | CH₃ | O |
| 518 | OCF₃ | H | Cl | O |
| 519 | OCF₃ | CH₃ | Cl | O |
| 520 | OCF₃ | C₂H₅ | Cl | O |
| 521 | OCF₃ | n-C₃H₇ | Cl | O |
| 522 | OCF₃ | i-C₃H₇ | Cl | O |
| 523 | OCF₃ | n-C₄H₉ | Cl | O |
| 524 | OCF₃ | i-C₄H₉ | Cl | O |
| 525 | OCF₃ | s-C₄H₉ | Cl | O |
| 526 | OCF₃ | t-C₄H₉ | Cl | O |
| 527 | OCF₃ | CH₂OCH₃ | Cl | O |
| 528 | OCF₃ | CF₃ | Cl | O |
| 529 | OCF₃ | CF₂H | Cl | O |
| 530 | OCF₃ | CN | Cl | O |
| 531 | OCF₃ | OH | Cl | O |
| 532 | OCF₃ | OCH₃ | Cl | O |
| 533 | OCF₃ | NH₂ | Cl | O |
| 534 | OCF₃ | NHCH₃ | Cl | O |
| 535 | OCF₃ | N(CH₃)₂ | Cl | O |
| 536 | OCF₃ | CO₂CH₃ | Cl | O |

TABLE A-continued

| No. | R¹ | R² | R³ | A |
|---|---|---|---|---|
| 537 | OCF$_3$ | CO$_2$C$_2$H$_5$ | Cl | O |
| 538 | OCF$_3$ | C(O)CH$_3$ | Cl | O |
| 539 | OCF$_3$ | C(O)CF$_3$ | Cl | O |
| 540 | OCF$_3$ | C(=NOCH$_3$)CH$_3$ | Cl | O |
| 541 | OCF$_3$ | SO$_2$CH$_3$ | Cl | O |
| 542 | OCF$_3$ | SO$_2$CF$_3$ | Cl | O |
| 543 | OCF$_3$ | CH$_2$CO$_2$H | Cl | O |
| 544 | OCF$_3$ | CH$_2$COOCH$_3$ | Cl | O |
| 545 | OCF$_3$ | CH$_2$COOC$_2$H$_5$ | Cl | O |
| 546 | OCF$_3$ | prop-1-en-3-yl | Cl | O |
| 547 | OCF$_3$ | trans-but-2-en-1-yl | Cl | O |
| 548 | OCF$_3$ | cis-but-2-en-1-yl | Cl | O |
| 549 | OCF$_3$ | cis-3-methyl-but-2-en-1-yl | Cl | O |
| 550 | OCF$_3$ | cyclopropyl | Cl | O |
| 551 | OCF$_3$ | cyclopentyl | Cl | O |
| 552 | OCF$_3$ | cyclohexyl | Cl | O |
| 553 | OCF$_3$ | 4,5-dihydroisoxazol-3-yl | Cl | O |
| 554 | OCF$_3$ | 4-methyl-4,5-dihydro-isoxazol-3-yl | Cl | O |
| 555 | OCF$_3$ | isoxazol-3-yl | Cl | O |
| 556 | OCF$_3$ | 4-methylisoxazol-3-yl | Cl | O |
| 557 | OCF$_3$ | 4,5-dihydroisoxazol-4-yl | Cl | O |
| 558 | OCF$_3$ | 3-methyl-4,5-dihydro-isoxazol-4-yl | Cl | O |
| 559 | OCF$_3$ | isoxazol-4-yl | Cl | O |
| 560 | OCF$_3$ | 3-methylisoxazol-4-yl | Cl | O |
| 561 | OCF$_3$ | phenyl | Cl | O |
| 562 | OCF$_3$ | benzyl | Cl | O |
| 563 | OCF$_3$ | benzoyl | Cl | O |
| 564 | OCF$_3$ | 2-pyridyl | Cl | O |
| 565 | SCH$_3$ | H | H | O |
| 566 | SCH$_3$ | CH$_3$ | H | O |
| 567 | SCH$_3$ | C$_2$H$_5$ | H | O |
| 568 | SCH$_3$ | n-C$_3$H$_7$ | H | O |
| 569 | SCH$_3$ | i-C$_3$H$_7$ | H | O |
| 570 | SCH$_3$ | n-C$_4$H$_9$ | H | O |
| 571 | SCH$_3$ | i-C$_4$H$_9$ | H | O |
| 572 | SCH$_3$ | s-C$_4$H$_9$ | H | O |
| 573 | SCH$_3$ | t-C$_4$H$_9$ | H | O |
| 574 | SCH$_3$ | CH$_2$OCH$_3$ | H | O |
| 575 | SCH$_3$ | CF$_3$ | H | O |
| 576 | SCH$_3$ | CF$_2$H | H | O |
| 577 | SCH$_3$ | CN | H | O |
| 578 | SCH$_3$ | OH | H | O |
| 579 | SCH$_3$ | OCH$_3$ | H | O |
| 580 | SCH$_3$ | NH$_2$ | H | O |
| 581 | SCH$_3$ | NHCH$_3$ | H | O |
| 582 | SCH$_3$ | N(CH$_3$)$_2$ | H | O |
| 583 | SCH$_3$ | CO$_2$CH$_3$ | H | O |
| 584 | SCH$_3$ | CO$_2$C$_2$H$_5$ | H | O |
| 585 | SCH$_3$ | C(O)CH$_3$ | H | O |
| 586 | SCH$_3$ | C(O)CF$_3$ | H | O |
| 587 | SCH$_3$ | C(=NOCH$_3$)CH$_3$ | H | O |
| 588 | SCH$_3$ | SO$_2$CH$_3$ | H | O |
| 589 | SCH$_3$ | SO$_2$CF$_3$ | H | O |
| 590 | SCH$_3$ | CH$_2$CO$_2$H | H | O |
| 591 | SCH$_3$ | CH$_2$COOCH$_3$ | H | O |
| 592 | SCH$_3$ | CH$_2$COOC$_2$H$_5$ | H | O |
| 593 | SCH$_3$ | prop-1-en-3-yl | H | O |
| 594 | SCH$_3$ | trans-but-2-en-1-yl | H | O |
| 595 | SCH$_3$ | cis-but-2-en-1-yl | H | O |
| 596 | SCH$_3$ | cis-3-methyl-but-2-en-1-yl | H | O |
| 597 | SCH$_3$ | cyclopropyl | H | O |
| 598 | SCH$_3$ | cyclopentyl | H | O |
| 599 | SCH$_3$ | cyclohexyl | H | O |
| 600 | SCH$_3$ | 4,5-dihydroisoxazol-3-yl | H | O |
| 601 | SCH$_3$ | 4-methyl-4,5-dihydro-isoxazol-3-yl | H | O |
| 602 | SCH$_3$ | isoxazol-3-yl | H | O |
| 603 | SCH$_3$ | 4-methylisoxazol-3-yl | H | O |
| 604 | SCH$_3$ | 4,5-dihydroisoxazol-4-yl | H | O |
| 605 | SCH$_3$ | 3-methyl-4,5-dihydro-isoxazol-4-yl | H | O |
| 606 | SCH$_3$ | isoxazol-4-yl | H | O |
| 607 | SCH$_3$ | 3-methylisoxazol-4-yl | H | O |
| 608 | SCH$_3$ | phenyl | H | O |
| 609 | SCH$_3$ | benzyl | H | O |
| 610 | SCH$_3$ | benzoyl | H | O |
| 611 | SCH$_3$ | 2-pyridyl | H | O |
| 612 | SCH$_3$ | H | CH$_3$ | O |
| 613 | SCH$_3$ | CH$_3$ | CH$_3$ | O |
| 614 | SCH$_3$ | C$_2$H$_5$ | CH$_3$ | O |
| 615 | SCH$_3$ | n-C$_3$H$_7$ | CH$_3$ | O |
| 616 | SCH$_3$ | i-C$_3$H$_7$ | CH$_3$ | O |
| 617 | SCH$_3$ | n-C$_4$H$_9$ | CH$_3$ | O |
| 618 | SCH$_3$ | i-C$_4$H$_9$ | CH$_3$ | O |
| 619 | SCH$_3$ | s-C$_4$H$_9$ | CH$_3$ | O |
| 620 | SCH$_3$ | t-C$_4$H$_9$ | CH$_3$ | O |
| 621 | SCH$_3$ | CH$_2$OCH$_3$ | CH$_3$ | O |
| 622 | SCH$_3$ | CF$_3$ | CH$_3$ | O |
| 623 | SCH$_3$ | CF$_2$H | CH$_3$ | O |
| 624 | SCH$_3$ | CN | CH$_3$ | O |
| 625 | SCH$_3$ | OH | CH$_3$ | O |
| 626 | SCH$_3$ | OCH$_3$ | CH$_3$ | O |
| 627 | SCH$_3$ | NH$_2$ | CH$_3$ | O |
| 628 | SCH$_3$ | NHCH$_3$ | CH$_3$ | O |
| 629 | SCH$_3$ | N(CH$_3$)$_2$ | CH$_3$ | O |
| 630 | SCH$_3$ | CO$_2$CH$_3$ | CH$_3$ | O |
| 631 | SCH$_3$ | CO$_2$C$_2$H$_5$ | CH$_3$ | O |
| 632 | SCH$_3$ | C(O)CH$_3$ | CH$_3$ | O |
| 633 | SCH$_3$ | C(O)CF$_3$ | CH$_3$ | O |
| 634 | SCH$_3$ | C(=NOCH$_3$)CH$_3$ | CH$_3$ | O |
| 635 | SCH$_3$ | SO$_2$CH$_3$ | CH$_3$ | O |
| 636 | SCH$_3$ | SO$_2$CF$_3$ | CH$_3$ | O |
| 637 | SCH$_3$ | CH$_2$CO$_2$H | CH$_3$ | O |
| 638 | SCH$_3$ | CH$_2$COOCH$_3$ | CH$_3$ | O |
| 639 | SCH$_3$ | CH$_2$COOC$_2$H$_5$ | CH$_3$ | O |
| 640 | SCH$_3$ | prop-1-en-3-yl | CH$_3$ | O |
| 641 | SCH$_3$ | trans-but-2-en-1-yl | CH$_3$ | O |
| 642 | SCH$_3$ | cis-but-2-en-1-yl | CH$_3$ | O |
| 643 | SCH$_3$ | cis-3-methyl-but-2-en-1-yl | CH$_3$ | O |
| 644 | SCH$_3$ | cyclopropyl | CH$_3$ | O |
| 645 | SCH$_3$ | cyclopentyl | CH$_3$ | O |
| 646 | SCH$_3$ | cyclohexyl | CH$_3$ | O |
| 647 | SCH$_3$ | 4,5-dihydroisoxazol-3-yl | CH$_3$ | O |
| 648 | SCH$_3$ | 4-methyl-4,5-dihydro-isoxazol-3-yl | CH$_3$ | O |
| 649 | SCH$_3$ | isoxazol-3-yl | CH$_3$ | O |
| 650 | SCH$_3$ | 4-methylisoxazol-3-yl | CH$_3$ | O |
| 651 | SCH$_3$ | 4,5-dihydroisoxazol-4-yl | CH$_3$ | O |
| 652 | SCH$_3$ | 3-methyl-4,5-dihydro-isoxazol-4-yl | CH$_3$ | O |
| 653 | SCH$_3$ | isoxazol-4-yl | CH$_3$ | O |
| 654 | SCH$_3$ | 3-methylisoxazol-4-yl | CH$_3$ | O |
| 655 | SCH$_3$ | phenyl | CH$_3$ | O |
| 656 | SCH$_3$ | benzyl | CH$_3$ | O |
| 657 | SCH$_3$ | benzoyl | CH$_3$ | O |
| 658 | SCH$_3$ | 2-pyridyl | CH$_3$ | O |
| 659 | SCH$_3$ | H | Cl | O |
| 660 | SCH$_3$ | CH$_3$ | Cl | O |
| 661 | SCH$_3$ | C$_2$H$_5$ | Cl | O |
| 662 | SCH$_3$ | n-C$_3$H$_7$ | Cl | O |
| 663 | SCH$_3$ | i-C$_3$H$_7$ | Cl | O |
| 664 | SCH$_3$ | n-C$_4$H$_9$ | Cl | O |
| 665 | SCH$_3$ | i-C$_4$H$_9$ | Cl | O |
| 666 | SCH$_3$ | s-C$_4$H$_9$ | Cl | O |
| 667 | SCH$_3$ | t-C$_4$H$_9$ | Cl | O |
| 668 | SCH$_3$ | CH$_2$OCH$_3$ | Cl | O |
| 669 | SCH$_3$ | CF$_3$ | Cl | O |
| 670 | SCH$_3$ | CF$_2$H | Cl | O |
| 671 | SCH$_3$ | CN | Cl | O |
| 672 | SCH$_3$ | OH | Cl | O |
| 673 | SCH$_3$ | OCH$_3$ | Cl | O |
| 674 | SCH$_3$ | NH$_2$ | Cl | O |
| 675 | SCH$_3$ | NHCH$_3$ | Cl | O |

TABLE A-continued

| No. | R¹ | R² | R³ | A |
|---|---|---|---|---|
| 676 | SCH₃ | N(CH₃)₂ | Cl | O |
| 677 | SCH₃ | CO₂CH₃ | Cl | O |
| 678 | SCH₃ | CO₂C₂H₅ | Cl | O |
| 679 | SCH₃ | C(O)CH₃ | Cl | O |
| 680 | SCH₃ | C(O)CF₃ | Cl | O |
| 681 | SCH₃ | C(=NOCH₃)CH₃ | Cl | O |
| 682 | SCH₃ | SO₂CH₃ | Cl | O |
| 683 | SCH₃ | SO₂CF₃ | Cl | O |
| 684 | SCH₃ | CH₂CO₂H | Cl | O |
| 685 | SCH₃ | CH₂COOCH₃ | Cl | O |
| 686 | SCH₃ | CH₂COOC₂H₅ | Cl | O |
| 687 | SCH₃ | prop-1-en-3-yl | Cl | O |
| 688 | SCH₃ | trans-but-2-en-1-yl | Cl | O |
| 689 | SCH₃ | cis-but-2-en-1-yl | Cl | O |
| 690 | SCH₃ | cis-3-methyl-but-2-en-1-yl | Cl | O |
| 691 | SCH₃ | cyclopropyl | Cl | O |
| 692 | SCH₃ | cyclopentyl | Cl | O |
| 693 | SCH₃ | cyclohexyl | Cl | O |
| 694 | SCH₃ | 4,5-dihydroisoxazol-3-yl | Cl | O |
| 695 | SCH₃ | 4-methyl-4,5-dihydro-isoxazol-3-yl | Cl | O |
| 696 | SCH₃ | isoxazol-3-yl | Cl | O |
| 697 | SCH₃ | 4-methylisoxazol-3-yl | Cl | O |
| 698 | SCH₃ | 4,5-dihydroisoxazol-4-yl | Cl | O |
| 699 | SCH₃ | 3-methyl-4,5-dihydro-isoxazol-4-yl | Cl | O |
| 700 | SCH₃ | isoxazol-4-yl | Cl | O |
| 701 | SCH₃ | 3-methylisoxazol-4-yl | Cl | O |
| 702 | SCH₃ | phenyl | Cl | O |
| 703 | SCH₃ | benzyl | Cl | O |
| 704 | SCH₃ | benzoyl | Cl | O |
| 705 | SCH₃ | 2-pyridyl | Cl | O |
| 706 | SO₂CH₃ | H | H | O |
| 707 | SO₂CH₃ | CH₃ | H | O |
| 708 | SO₂CH₃ | C₂H₅ | H | O |
| 709 | SO₂CH₃ | n-C₃H₇ | H | O |
| 710 | SO₂CH₃ | i-C₃H₇ | H | O |
| 711 | SO₂CH₃ | n-C₄H₉ | H | O |
| 712 | SO₂CH₃ | i-C₄H₉ | H | O |
| 713 | SO₂CH₃ | s-C₄H₉ | H | O |
| 714 | SO₂CH₃ | t-C₄H₉ | H | O |
| 715 | SO₂CH₃ | CH₂OCH₃ | H | O |
| 716 | SO₂CH₃ | CF₃ | H | O |
| 717 | SO₂CH₃ | CF₂H | H | O |
| 718 | SO₂CH₃ | CN | H | O |
| 719 | SO₂CH₃ | OH | H | O |
| 720 | SO₂CH₃ | OCH₃ | H | O |
| 721 | SO₂CH₃ | NH₂ | H | O |
| 722 | SO₂CH₃ | NHCH₃ | H | O |
| 723 | SO₂CH₃ | N(CH₃)₂ | H | O |
| 724 | SO₂CH₃ | CO₂CH₃ | H | O |
| 725 | SO₂CH₃ | CO₂C₂H₅ | H | O |
| 726 | SO₂CH₃ | C(O)CH₃ | H | O |
| 727 | SO₂CH₃ | C(O)CF₃ | H | O |
| 728 | SO₂CH₃ | C(=NOCH₃)CH₃ | H | O |
| 729 | SO₂CH₃ | SO₂CH₃ | H | O |
| 730 | SO₂CH₃ | SO₂CF₃ | H | O |
| 731 | SO₂CH₃ | CH₂CO₂H | H | O |
| 732 | SO₂CH₃ | CH₂COOCH₃ | H | O |
| 733 | SO₂CH₃ | CH₂COOC₂H₅ | H | O |
| 734 | SO₂CH₃ | prop-1-en-3-yl | H | O |
| 735 | SO₂CH₃ | trans-but-2-en-1-yl | H | O |
| 736 | SO₂CH₃ | cis-but-2-en-1-yl | H | O |
| 737 | SO₂CH₃ | cis-3-methyl-but-2-en-1-yl | H | O |
| 738 | SO₂CH₃ | cyclopropyl | H | O |
| 739 | SO₂CH₃ | cyclopentyl | H | O |
| 740 | SO₂CH₃ | cyclohexyl | H | O |
| 741 | SO₂CH₃ | 4,5-dihydroisoxazol-3-yl | H | O |
| 742 | SO₂CH₃ | 4-methyl-4,5-dihydro-isoxazol-3-yl | H | O |
| 743 | SO₂CH₃ | isoxazol-3-yl | H | O |
| 744 | SO₂CH₃ | 4-methylisoxazol-3-yl | H | O |
| 745 | SO₂CH₃ | 4,5-dihydroisoxazol-4-yl | H | O |
| 746 | SO₂CH₃ | 3-methyl-4,5-dihydro-isoxazol-4-yl | H | O |
| 747 | SO₂CH₃ | isoxazol-4-yl | H | O |
| 748 | SO₂CH₃ | 3-methylisoxazol-4-yl | H | O |
| 749 | SO₂CH₃ | phenyl | H | O |
| 750 | SO₂CH₃ | benzyl | H | O |
| 751 | SO₂CH₃ | benzoyl | H | O |
| 752 | SO₂CH₃ | 2-pyridyl | H | O |
| 753 | SO₂CH₃ | H | CH₃ | O |
| 754 | SO₂CH₃ | CH₃ | CH₃ | O |
| 755 | SO₂CH₃ | C₂H₅ | CH₃ | O |
| 756 | SO₂CH₃ | n-C₃H₇ | CH₃ | O |
| 757 | SO₂CH₃ | i-C₃H₇ | CH₃ | O |
| 758 | SO₂CH₃ | n-C₄H₉ | CH₃ | O |
| 759 | SO₂CH₃ | i-C₄H₉ | CH₃ | O |
| 760 | SO₂CH₃ | s-C₄H₉ | CH₃ | O |
| 761 | SO₂CH₃ | t-C₄H₉ | CH₃ | O |
| 762 | SO₂CH₃ | CH₂OCH₃ | CH₃ | O |
| 763 | SO₂CH₃ | CF₃ | CH₃ | O |
| 764 | SO₂CH₃ | CF₂H | CH₃ | O |
| 765 | SO₂CH₃ | CN | CH₃ | O |
| 766 | SO₂CH₃ | OH | CH₃ | O |
| 767 | SO₂CH₃ | OCH₃ | CH₃ | O |
| 768 | SO₂CH₃ | NH₂ | CH₃ | O |
| 769 | SO₂CH₃ | NHCH₃ | CH₃ | O |
| 770 | SO₂CH₃ | N(CH₃)₂ | CH₃ | O |
| 771 | SO₂CH₃ | CO₂CH₃ | CH₃ | O |
| 772 | SO₂CH₃ | CO₂C₂H₅ | CH₃ | O |
| 773 | SO₂CH₃ | C(O)CH₃ | CH₃ | O |
| 774 | SO₂CH₃ | C(O)CF₃ | CH₃ | O |
| 775 | SO₂CH₃ | C(=NOCH₃)CH₃ | CH₃ | O |
| 776 | SO₂CH₃ | SO₂CH₃ | CH₃ | O |
| 777 | SO₂CH₃ | SO₂CF₃ | CH₃ | O |
| 778 | SO₂CH₃ | CH₂CO₂H | CH₃ | O |
| 779 | SO₂CH₃ | CH₂COOCH₃ | CH₃ | O |
| 780 | SO₂CH₃ | CH₂COOC₂H₅ | CH₃ | O |
| 781 | SO₂CH₃ | prop-1-en-3-yl | CH₃ | O |
| 782 | SO₂CH₃ | trans-but-2-en-1-yl | CH₃ | O |
| 783 | SO₂CH₃ | cis-but-2-en-1-yl | CH₃ | O |
| 784 | SO₂CH₃ | cis-3-methyl-but-2-en-1-yl | CH₃ | O |
| 785 | SO₂CH₃ | cyclopropyl | CH₃ | O |
| 786 | SO₂CH₃ | cyclopentyl | CH₃ | O |
| 787 | SO₂CH₃ | cyclohexyl | CH₃ | O |
| 788 | SO₂CH₃ | 4,5-dihydroisoxazol-3-yl | CH₃ | O |
| 789 | SO₂CH₃ | 4-methyl-4,5-dihydro-isoxazol-3-yl | CH₃ | O |
| 790 | SO₂CH₃ | isoxazol-3-yl | CH₃ | O |
| 791 | SO₂CH₃ | 4-methylisoxazol-3-yl | CH₃ | O |
| 792 | SO₂CH₃ | 4,5-dihydroisoxazol-4-yl | CH₃ | O |
| 793 | SO₂CH₃ | 3-methyl-4,5-dihydro-isoxazol-4-yl | CH₃ | O |
| 794 | SO₂CH₃ | isoxazol-4-yl | CH₃ | O |
| 795 | SO₂CH₃ | 3-methylisoxazol-4-yl | CH₃ | O |
| 796 | SO₂CH₃ | phenyl | CH₃ | O |
| 797 | SO₂CH₃ | benzyl | CH₃ | O |
| 798 | SO₂CH₃ | benzoyl | CH₃ | O |
| 799 | SO₂CH₃ | 2-pyridyl | CH₃ | O |
| 800 | SO₂CH₃ | H | Cl | O |
| 801 | SO₂CH₃ | CH₃ | Cl | O |
| 802 | SO₂CH₃ | C₂H₅ | Cl | O |
| 803 | SO₂CH₃ | n-C₃H₇ | Cl | O |
| 804 | SO₂CH₃ | i-C₃H₇ | Cl | O |
| 805 | SO₂CH₃ | n-C₄H₉ | Cl | O |
| 806 | SO₂CH₃ | i-C₄H₉ | Cl | O |
| 807 | SO₂CH₃ | S-C₄H₉ | Cl | O |
| 808 | SO₂CH₃ | t-C₄H₉ | Cl | O |
| 809 | SO₂CH₃ | CH₂OCH₃ | Cl | O |
| 810 | SO₂CH₃ | CF₃ | Cl | O |
| 811 | SO₂CH₃ | CF₂H | Cl | O |
| 812 | SO₂CH₃ | CN | Cl | O |
| 813 | SO₂CH₃ | OH | Cl | O |
| 814 | SO₂CH₃ | OCH₃ | Cl | O |

TABLE A-continued

| No. | R¹ | R² | R³ | A |
|---|---|---|---|---|
| 815 | SO₂CH₃ | NH₂ | Cl | O |
| 816 | SO₂CH₃ | NHCH₃ | Cl | O |
| 817 | SO₂CH₃ | N(CH₃)₂ | Cl | O |
| 818 | SO₂CH₃ | CO₂CH₃ | Cl | O |
| 819 | SO₂CH₃ | CO₂C₂H₅ | Cl | O |
| 820 | SO₂CH₃ | C(O)CH₃ | Cl | O |
| 821 | SO₂CH₃ | C(O)CF₃ | Cl | O |
| 822 | SO₂CH₃ | C(=NOCH₃)CH₃ | Cl | O |
| 823 | SO₂CH₃ | SO₂CH₃ | Cl | O |
| 824 | SO₂CH₃ | SO₂CF₃ | Cl | O |
| 825 | SO₂CH₃ | CH₂CO₂H | Cl | O |
| 826 | SO₂CH₃ | CH₂COOCH₃ | Cl | O |
| 827 | SO₂CH₃ | CH₂COOC₂H₅ | Cl | O |
| 828 | SO₂CH₃ | prop-1-en-3-yl | Cl | O |
| 829 | SO₂CH₃ | trans-but-2-en-1-yl | Cl | O |
| 830 | SO₂CH₃ | cis-but-2-en-1-yl | Cl | O |
| 831 | SO₂CH₃ | cis-3-methyl-but-2-en-1-yl | Cl | O |
| 832 | SO₂CH₃ | cyclopropyl | Cl | O |
| 833 | SO₂CH₃ | cyclopentyl | Cl | O |
| 834 | SO₂CH₃ | cyclohexyl | Cl | O |
| 835 | SO₂CH₃ | 4,5-dihydroisoxazol-3-yl | Cl | O |
| 836 | SO₂CH₃ | 4-methyl-4,5-dihydro-isoxazol-3-yl | Cl | O |
| 837 | SO₂CH₃ | isoxazol-3-yl | Cl | O |
| 838 | SO₂CH₃ | 4-methylisoxazol-3-yl | Cl | O |
| 839 | SO₂CH₃ | 4,5-dihydroisoxazol-4-yl | Cl | O |
| 840 | SO₂CH₃ | 3-methyl-4,5-dihydro-isoxazol-4-yl | Cl | O |
| 841 | SO₂CH₃ | isoxazol-4-yl | Cl | O |
| 842 | SO₂CH₃ | 3-methylisoxazol-4-yl | Cl | O |
| 843 | SO₂CH₃ | phenyl | Cl | O |
| 844 | SO₂CH₃ | benzyl | Cl | O |
| 845 | SO₂CH₃ | benzoyl | Cl | O |
| 846 | SO₂CH₃ | 2-pyridyl | Cl | O |
| 847 | CF₃ | H | H | O |
| 848 | CF₃ | CH₃ | H | O |
| 849 | CF₃ | C₂H₅ | H | O |
| 850 | CF₃ | n-C₃H₇ | H | O |
| 851 | CF₃ | i-C₃H₇ | H | O |
| 852 | CF₃ | n-C₄H₉ | H | O |
| 853 | CF₃ | i-C₄H₉ | H | O |
| 854 | CF₃ | s-C₄H₉ | H | O |
| 855 | CF₃ | t-C₄H₉ | H | O |
| 856 | CF₃ | CH₂OCH₃ | H | O |
| 857 | CF₃ | CF₃ | H | O |
| 858 | CF₃ | CF₂H | H | O |
| 859 | CF₃ | CN | H | O |
| 860 | CF₃ | OH | H | O |
| 861 | CF₃ | OCH₃ | H | O |
| 862 | CF₃ | NH₂ | H | O |
| 863 | CF₃ | NHCH₃ | H | O |
| 864 | CF₃ | N(CH₃)₂ | H | O |
| 865 | CF₃ | CO₂CH₃ | H | O |
| 866 | CF₃ | CO₂C₂H₅ | H | O |
| 867 | CF₃ | C(O)CH₃ | H | O |
| 868 | CF₃ | C(O)CF₃ | H | O |
| 869 | CF₃ | C(=NOCH₃)CH₃ | H | O |
| 870 | CF₃ | SO₂CH₃ | H | O |
| 871 | CF₃ | SO₂CF₃ | H | O |
| 872 | CF₃ | CH₂CO₂H | H | O |
| 873 | CF₃ | CH₂COOCH₃ | H | O |
| 874 | CF₃ | CH₂COOC₂H₅ | H | O |
| 875 | CF₃ | prop-1-en-3-yl | H | O |
| 876 | CF₃ | trans-but-2-en-1-yl | H | O |
| 877 | CF₃ | cis-but-2-en-1-yl | H | O |
| 878 | CF₃ | cis-3-methyl-but-2-en-1-yl | H | O |
| 879 | CF₃ | cyclopropyl | H | O |
| 880 | CF₃ | cyclopentyl | H | O |
| 881 | CF₃ | cyclohexyl | H | O |
| 882 | CF₃ | 4,5-dihydroisoxazol-3-yl | H | O |
| 883 | CF₃ | 4-methyl-4,5-dihydro-isoxazol-3-yl | H | O |
| 884 | CF₃ | isoxazol-3-yl | H | O |
| 885 | CF₃ | 4-methylisoxazol-3-yl | H | O |
| 886 | CF₃ | 4,5-dihydroisoxazol-4-yl | H | O |
| 887 | CF₃ | 3-methyl-4,5-dihydro-isoxazol-4-yl | H | O |
| 888 | CF₃ | isoxazol-4-yl | H | O |
| 889 | CF₃ | 3-methylisoxazol-4-yl | H | O |
| 890 | CF₃ | phenyl | H | O |
| 891 | CF₃ | benzyl | H | O |
| 892 | CF₃ | benzoyl | H | O |
| 893 | CF₃ | 2-pyridyl | H | O |
| 894 | CF₃ | H | CH₃ | O |
| 895 | CF₃ | CH₃ | CH₃ | O |
| 896 | CF₃ | C₂H₅ | CH₃ | O |
| 897 | CF₃ | n-C₃H₇ | CH₃ | O |
| 898 | CF₃ | i-C₃H₇ | CH₃ | O |
| 899 | CF₃ | n-C₄H₉ | CH₃ | O |
| 900 | CF₃ | i-C₄H₉ | CH₃ | O |
| 901 | CF₃ | s-C₄H₉ | CH₃ | O |
| 902 | CF₃ | t-C₄H₉ | CH₃ | O |
| 903 | CF₃ | CH₂OCH₃ | CH₃ | O |
| 904 | CF₃ | CF₃ | CH₃ | O |
| 905 | CF₃ | CF₂H | CH₃ | O |
| 906 | CF₃ | CN | CH₃ | O |
| 907 | CF₃ | OH | CH₃ | O |
| 908 | CF₃ | OCH₃ | CH₃ | O |
| 909 | CF₃ | NH₂ | CH₃ | O |
| 910 | CF₃ | NHCH₃ | CH₃ | O |
| 911 | CF₃ | N(CH₃)₂ | CH₃ | O |
| 912 | CF₃ | CO₂CH₃ | CH₃ | O |
| 913 | CF₃ | CO₂C₂H₅ | CH₃ | O |
| 914 | CF₃ | C(O)CH₃ | CH₃ | O |
| 915 | CF₃ | C(O)CF₃ | CH₃ | O |
| 916 | CF₃ | C(=NOCH₃)CH₃ | CH₃ | O |
| 917 | CF₃ | SO₂CH₃ | CH₃ | O |
| 918 | CF₃ | SO₂CF₃ | CH₃ | O |
| 919 | CF₃ | CH₂CO₂H | CH₃ | O |
| 920 | CF₃ | CH₂COOCH₃ | CH₃ | O |
| 921 | CF₃ | CH₂COOC₂H₅ | CH₃ | O |
| 922 | CF₃ | prop-1-en-3-yl | CH₃ | O |
| 923 | CF₃ | trans-but-2-en-1-yl | CH₃ | O |
| 924 | CF₃ | cis-but-2-en-1-yl | CH₃ | O |
| 925 | CF₃ | cis-3-methyl-but-2-en-1-yl | CH₃ | O |
| 926 | CF₃ | cyclopropyl | CH₃ | O |
| 927 | CF₃ | cyclopentyl | CH₃ | O |
| 928 | CF₃ | cyclohexyl | CH₃ | O |
| 929 | CF₃ | 4,5-dihydroisoxazol-3-yl | CH₃ | O |
| 930 | CF₃ | 4-methyl-4,5-dihydroisoxazol-3-yl | CH₃ | O |
| 931 | CF₃ | isoxazol-3-yl | CH₃ | O |
| 932 | CF₃ | 4-methylisoxazol-3-yl | CH₃ | O |
| 933 | CF₃ | 4,5-dihydroisoxazol-4-yl | CH₃ | O |
| 934 | CF₃ | 3-methyl-4,5-dihydroisoxazol-4-yl | CH₃ | O |
| 935 | CF₃ | isoxazol-4-yl | CH₃ | O |
| 936 | CF₃ | 3-methylisoxazol-4-yl | CH₃ | O |
| 937 | CF₃ | phenyl | CH₃ | O |
| 938 | CF₃ | benzyl | CH₃ | O |
| 939 | CF₃ | benzoyl | CH₃ | O |
| 940 | CF₃ | 2-pyridyl | CH₃ | O |
| 941 | CF₃ | H | Cl | O |
| 942 | CF₃ | CH₃ | Cl | O |
| 943 | CF₃ | C₂H₅ | Cl | O |
| 944 | CF₃ | n-C₃H₇ | Cl | O |
| 945 | CF₃ | i-C₃H₇ | Cl | O |
| 946 | CF₃ | n-C₄H₉ | Cl | O |
| 947 | CF₃ | i-C₄H₉ | Cl | O |
| 948 | CF₃ | s-C₄H₉ | Cl | O |
| 949 | CF₃ | t-C₄H₉ | Cl | O |
| 950 | CF₃ | CH₂OCH₃ | Cl | O |
| 951 | CF₃ | CF₃ | Cl | O |
| 952 | CF₃ | CF₂H | Cl | O |
| 953 | CF₃ | CN | Cl | O |

TABLE A-continued

| No. | R¹ | R² | R³ | A |
|---|---|---|---|---|
| 954 | $CF_3$ | OH | Cl | O |
| 955 | $CF_3$ | $OCH_3$ | Cl | O |
| 956 | $CF_3$ | $NH_2$ | Cl | O |
| 957 | $CF_3$ | $NHCH_3$ | Cl | O |
| 958 | $CF_3$ | $N(CH_3)_2$ | Cl | O |
| 959 | $CF_3$ | $CO_2CH_3$ | Cl | O |
| 960 | $CF_3$ | $CO_2C_2H_5$ | Cl | O |
| 961 | $CF_3$ | $C(O)CH_3$ | Cl | O |
| 962 | $CF_3$ | $C(O)CF_3$ | Cl | O |
| 963 | $CF_3$ | $C(=NOCH_3)CH_3$ | Cl | O |
| 964 | $CF_3$ | $SO_2CH_3$ | Cl | O |
| 965 | $CF_3$ | $SO_2CF_3$ | Cl | O |
| 966 | $CF_3$ | $CH_2CO_2H$ | Cl | O |
| 967 | $CF_3$ | $CH_2COOCH_3$ | Cl | O |
| 968 | $CF_3$ | $CH_2COOC_2H_5$ | Cl | O |
| 969 | $CF_3$ | prop-1-en-3-yl | Cl | O |
| 970 | $CF_3$ | trans-but-2-en-1-yl | Cl | O |
| 971 | $CF_3$ | cis-but-2-en-1-yl | Cl | O |
| 972 | $CF_3$ | cis-3-methyl-but-2-en-1-yl | Cl | O |
| 973 | $CF_3$ | cyclopropyl | Cl | O |
| 974 | $CF_3$ | cyclopentyl | Cl | O |
| 975 | $CF_3$ | cyclohexyl | Cl | O |
| 976 | $CF_3$ | 4,5-dihydroisoxazol-3-yl | Cl | O |
| 977 | $CF_3$ | 4-methyl-4,5-dihydroisoxazol-3-yl | Cl | O |
| 978 | $CF_3$ | isoxazol-3-yl | Cl | O |
| 979 | $CF_3$ | 4-methylisoxazol-3-yl | Cl | O |
| 980 | $CF_3$ | 4,5-dihydroisoxazol-4-yl | Cl | O |
| 981 | $CF_3$ | 3-methyl-4,5-dihydroisoxazol-4-yl | Cl | O |
| 982 | $CF_3$ | isoxazol-4-yl | Cl | O |
| 983 | $CF_3$ | 3-methylisoxazol-4-yl | Cl | O |
| 984 | $CF_3$ | phenyl | Cl | O |
| 985 | $CF_3$ | benzyl | Cl | O |
| 986 | $CF_3$ | benzoyl | Cl | O |
| 987 | $CF_3$ | 2-pyridyl | Cl | O |
| 988 | $C_2H_5$ | H | H | O |
| 989 | $C_2H_5$ | $CH_3$ | H | O |
| 990 | $C_2H_5$ | $C_2H_5$ | H | O |
| 991 | $C_2H_5$ | $n-C_3H_7$ | H | O |
| 992 | $C_2H_5$ | $i-C_3H_7$ | H | O |
| 993 | $C_2H_5$ | $n-C_4H_9$ | H | O |
| 994 | $C_2H_5$ | $i-C_4H_9$ | H | O |
| 995 | $C_2H_5$ | $s-C_4H_9$ | H | O |
| 996 | $C_2H_5$ | $t-C_4H_9$ | H | O |
| 997 | $C_2H_5$ | $CH_2OCH_3$ | H | O |
| 998 | $C_2H_5$ | $CF_3$ | H | O |
| 999 | $C_2H_5$ | $CF_2H$ | H | O |
| 1000 | $C_2H_5$ | CN | H | O |
| 1001 | $C_2H_5$ | OH | H | O |
| 1002 | $C_2H_5$ | $OCH_3$ | H | O |
| 1003 | $C_2H_5$ | $NH_2$ | H | O |
| 1004 | $C_2H_5$ | $NHCH_3$ | H | O |
| 1005 | $C_2H_5$ | $N(CH_3)_2$ | H | O |
| 1006 | $C_2H_5$ | $CO_2CH_3$ | H | O |
| 1007 | $C_2H_5$ | $CO_2C_2H_5$ | H | O |
| 1008 | $C_2H_5$ | $C(O)CH_3$ | H | O |
| 1009 | $C_2H_5$ | $C(O)CF_3$ | H | O |
| 1010 | $C_2H_5$ | $C(=NOCH_3)CH_3$ | H | O |
| 1011 | $C_2H_5$ | $SO_2CH_3$ | H | O |
| 1012 | $C_2H_5$ | $SO_2CF_3$ | H | O |
| 1013 | $C_2H_5$ | $CH_2CO_2H$ | H | O |
| 1014 | $C_2H_5$ | $CH_2COOCH_3$ | H | O |
| 1015 | $C_2H_5$ | $CH_2COOC_2H_5$ | H | O |
| 1016 | $C_2H_5$ | prop-1-en-3-yl | H | O |
| 1017 | $C_2H_5$ | trans-but-2-en-1-yl | H | O |
| 1018 | $C_2H_5$ | cis-but-2-en-1-yl | H | O |
| 1019 | $C_2H_5$ | cis-3-methyl-but-2-en-1-yl | H | O |
| 1020 | $C_2H_5$ | cyclopropyl | H | O |
| 1021 | $C_2H_5$ | cyclopentyl | H | O |
| 1022 | $C_2H_5$ | cyclohexyl | H | O |
| 1023 | $C_2H_5$ | 4,5-dihydroisoxazol-3-yl | H | O |
| 1024 | $C_2H_5$ | 4-methyl-4,5-dihydroisoxazol-3-yl | H | O |
| 1025 | $C_2H_5$ | isoxazol-3-yl | H | O |
| 1026 | $C_2H_5$ | 4-methylisoxazol-3-yl | H | O |
| 1027 | $C_2H_5$ | 4,5-dihydroisoxazol-4-yl | H | O |
| 1028 | $C_2H_5$ | 3-methyl-4,5-dihydroisoxazol-4-yl | H | O |
| 1029 | $C_2H_5$ | isoxazol-4-yl | H | O |
| 1030 | $C_2H_5$ | 3-methylisoxazol-4-yl | H | O |
| 1031 | $C_2H_5$ | phenyl | H | O |
| 1032 | $C_2H_5$ | benzyl | H | O |
| 1033 | $C_2H_5$ | benzoyl | H | O |
| 1034 | $C_2H_5$ | 2-pyridyl | H | O |
| 1035 | $C_2H_5$ | H | $CH_3$ | O |
| 1036 | $C_2H_5$ | $CH_3$ | $CH_3$ | O |
| 1037 | $C_2H_5$ | $C_2H_5$ | $CH_3$ | O |
| 1038 | $C_2H_5$ | $n-C_3H_7$ | $CH_3$ | O |
| 1039 | $C_2H_5$ | $i-C_3H_7$ | $CH_3$ | O |
| 1040 | $C_2H_5$ | $n-C_4H_9$ | $CH_3$ | O |
| 1041 | $C_2H_5$ | $i-C_4H_9$ | $CH_3$ | O |
| 1042 | $C_2H_5$ | $s-C_4H_9$ | $CH_3$ | O |
| 1043 | $C_2H_5$ | $t-C_4H_9$ | $CH_3$ | O |
| 1044 | $C_2H_5$ | $CH_2OCH_3$ | $CH_3$ | O |
| 1045 | $C_2H_5$ | $CF_3$ | $CH_3$ | O |
| 1046 | $C_2H_5$ | $CF_2H$ | $CH_3$ | O |
| 1047 | $C_2H_5$ | CN | $CH_3$ | O |
| 1048 | $C_2H_5$ | OH | $CH_3$ | O |
| 1049 | $C_2H_5$ | $OCH_3$ | $CH_3$ | O |
| 1050 | $C_2H_5$ | $NH_2$ | $CH_3$ | O |
| 1051 | $C_2H_5$ | $NHCH_3$ | $CH_3$ | O |
| 1052 | $C_2H_5$ | $N(CH_3)_2$ | $CH_3$ | O |
| 1053 | $C_2H_5$ | $CO_2CH_3$ | $CH_3$ | O |
| 1054 | $C_2H_5$ | $CO_2C_2H_5$ | $CH_3$ | O |
| 1055 | $C_2H_5$ | $C(O)CH_3$ | $CH_3$ | O |
| 1056 | $C_2H_5$ | $C(O)CF_3$ | $CH_3$ | O |
| 1057 | $C_2H_5$ | $C(=NOCH_3)CH_3$ | $CH_3$ | O |
| 1058 | $C_2H_5$ | $SO_2CH_3$ | $CH_3$ | O |
| 1059 | $C_2H_5$ | $SO_2CF_3$ | $CH_3$ | O |
| 1060 | $C_2H_5$ | $CH_2CO_2H$ | $CH_3$ | O |
| 1061 | $C_2H_5$ | $CH_2COOCH_3$ | $CH_3$ | O |
| 1062 | $C_2H_5$ | $CH_2COOC_2H_5$ | $CH_3$ | O |
| 1063 | $C_2H_5$ | prop-1-en-3-yl | $CH_3$ | O |
| 1064 | $C_2H_5$ | trans-but-2-en-1-yl | $CH_3$ | O |
| 1065 | $C_2H_5$ | cis-but-2-en-1-yl | $CH_3$ | O |
| 1066 | $C_2H_5$ | cis-3-methyl-but-2-en-1-yl | $CH_3$ | O |
| 1067 | $C_2H_5$ | cyclopropyl | $CH_3$ | O |
| 1068 | $C_2H_5$ | cyclopentyl | $CH_3$ | O |
| 1069 | $C_2H_5$ | cyclohexyl | $CH_3$ | O |
| 1070 | $C_2H_5$ | 4,5-dihydroisoxazol-3-yl | $CH_3$ | O |
| 1071 | $C_2H_5$ | 4-methyl-4,5-dihydroisoxazol-3-yl | $CH_3$ | O |
| 1072 | $C_2H_5$ | isoxazol-3-yl | $CH_3$ | O |
| 1073 | $C_2H_5$ | 4-methylisoxazol-3-yl | $CH_3$ | O |
| 1074 | $C_2H_5$ | 4,5-dihydroisoxazol-4-yl | $CH_3$ | O |
| 1075 | $C_2H_5$ | 3-methyl-4,5-dihydroisoxazol-4-yl | $CH_3$ | O |
| 1076 | $C_2H_5$ | isoxazol-4-yl | $CH_3$ | O |
| 1077 | $C_2H_5$ | 3-methylisoxazol-4-yl | $CH_3$ | O |
| 1078 | $C_2H_5$ | phenyl | $CH_3$ | O |
| 1079 | $C_2H_5$ | benzyl | $CH_3$ | O |
| 1080 | $C_2H_5$ | benzoyl | $CH_3$ | O |
| 1081 | $C_2H_5$ | 2-pyridyl | $CH_3$ | O |
| 1082 | $C_2H_5$ | H | Cl | O |
| 1083 | $C_2H_5$ | $CH_3$ | Cl | O |
| 1084 | $C_2H_5$ | $C_2H_5$ | Cl | O |
| 1085 | $C_2H_5$ | $n-C_3H_7$ | Cl | O |
| 1086 | $C_2H_5$ | $i-C_3H_7$ | Cl | O |
| 1087 | $C_2H_5$ | $n-C_4H_9$ | Cl | O |
| 1088 | $C_2H_5$ | $i-C_4H_9$ | Cl | O |
| 1089 | $C_2H_5$ | $s-C_4H_9$ | Cl | O |
| 1090 | $C_2H_5$ | $t-C_4H_9$ | Cl | O |
| 1091 | $C_2H_5$ | $CH_2OCH_3$ | Cl | O |
| 1092 | $C_2H_5$ | $CF_3$ | Cl | O |

TABLE A-continued

| No. | R$^1$ | R$^2$ | R$^3$ | A |
|---|---|---|---|---|
| 1093 | C$_2$H$_5$ | CF$_2$H | Cl | O |
| 1094 | C$_2$H$_5$ | CN | Cl | O |
| 1095 | C$_2$H$_5$ | OH | Cl | O |
| 1096 | C$_2$H$_5$ | OCH$_3$ | Cl | O |
| 1097 | C$_2$H$_5$ | NH$_2$ | Cl | O |
| 1098 | C$_2$H$_5$ | NHCH$_3$ | Cl | O |
| 1099 | C$_2$H$_5$ | N(CH$_3$)$_2$ | Cl | O |
| 1100 | C$_2$H$_5$ | CO$_2$CH$_3$ | Cl | O |
| 1101 | C$_2$H$_5$ | CO$_2$C$_2$H$_5$ | Cl | O |
| 1102 | C$_2$H$_5$ | C(O)CH$_3$ | Cl | O |
| 1103 | C$_2$H$_5$ | C(O)CF$_3$ | Cl | O |
| 1104 | C$_2$H$_5$ | C(=NOCH$_3$)CH$_3$ | Cl | O |
| 1105 | C$_2$H$_5$ | SO$_2$CH$_3$ | Cl | O |
| 1106 | C$_2$H$_5$ | SO$_2$CF$_3$ | Cl | O |
| 1107 | C$_2$H$_5$ | CH$_2$CO$_2$H | Cl | O |
| 1108 | C$_2$H$_5$ | CH$_2$COOCH$_3$ | Cl | O |
| 1109 | C$_2$H$_5$ | CH$_2$COOC$_2$H$_5$ | Cl | O |
| 1110 | C$_2$H$_5$ | prop-1-en-3-yl | Cl | O |
| 1111 | C$_2$H$_5$ | trans-but-2-en-1-yl | Cl | O |
| 1112 | C$_2$H$_5$ | cis-but-2-en-1-yl | Cl | O |
| 1113 | C$_2$H$_5$ | cis-3-methyl-but-2-en-1-yl | Cl | O |
| 1114 | C$_2$H$_5$ | cyclopropyl | Cl | O |
| 1115 | C$_2$H$_5$ | cyclopentyl | Cl | O |
| 1116 | C$_2$H$_5$ | cyclohexyl | Cl | O |
| 1117 | C$_2$H$_5$ | 4,5-dihydroisoxazol-3-yl | Cl | O |
| 1118 | C$_2$H$_5$ | 4-methyl-4,5-dihydroisoxazol-3-yl | Cl | O |
| 1119 | C$_2$H$_5$ | isoxazol-3-yl | Cl | O |
| 1120 | C$_2$H$_5$ | 4-methylisoxazol-3-yl | Cl | O |
| 1121 | C$_2$H$_5$ | 4,5-dihydroisoxazol-4-yl | Cl | O |
| 1122 | C$_2$H$_5$ | 3-methyl-4,5-dihydroisoxazol-4-yl | Cl | O |
| 1123 | C$_2$H$_5$ | isoxazol-4-yl | Cl | O |
| 1124 | C$_2$H$_5$ | 3-methylisoxazol-4-yl | Cl | O |
| 1125 | C$_2$H$_5$ | phenyl | Cl | O |
| 1126 | C$_2$H$_5$ | benzyl | Cl | O |
| 1127 | C$_2$H$_5$ | benzoyl | Cl | O |
| 1128 | C$_2$H$_5$ | 2-pyridyl | Cl | O |
| 1129 | CH$_3$ | CH$_3$ | H | S |
| 1130 | CH$_3$ | H | H | S |
| 1131 | CH$_3$ | C$_2$H$_5$ | H | S |
| 1132 | CH$_3$ | n-C$_3$H$_7$ | H | S |
| 1133 | CH$_3$ | i-C$_3$H$_7$ | H | S |
| 1134 | CH$_3$ | n-C$_4$H$_9$ | H | S |
| 1135 | CH$_3$ | i-C$_4$H$_9$ | H | S |
| 1136 | CH$_3$ | s-C$_4$H$_9$ | H | S |
| 1137 | CH$_3$ | t-C$_4$H$_9$ | H | S |
| 1138 | CH$_3$ | CH$_2$OCH$_3$ | H | S |
| 1139 | CH$_3$ | CF$_3$ | H | S |
| 1140 | CH$_3$ | CF$_2$H | H | S |
| 1141 | CH$_3$ | CN | H | S |
| 1142 | CH$_3$ | OH | H | S |
| 1143 | CH$_3$ | OCH$_3$ | H | S |
| 1144 | CH$_3$ | NH$_2$ | H | S |
| 1145 | CH$_3$ | NHCH$_3$ | H | S |
| 1146 | CH$_3$ | N(CH$_3$)$_2$ | H | S |
| 1147 | CH$_3$ | CO$_2$CH$_3$ | H | S |
| 1148 | CH$_3$ | CO$_2$C$_2$H$_5$ | H | S |
| 1149 | CH$_3$ | C(O)CH$_3$ | H | S |
| 1150 | CH$_3$ | C(O)CF$_3$ | H | S |
| 1151 | CH$_3$ | C(=NOCH$_3$)CH$_3$ | H | S |
| 1152 | CH$_3$ | SO$_2$CH$_3$ | H | S |
| 1153 | CH$_3$ | SO$_2$CF$_3$ | H | S |
| 1154 | CH$_3$ | CH$_2$CO$_2$H | H | S |
| 1155 | CH$_3$ | CH$_2$COOCH$_3$ | H | S |
| 1156 | CH$_3$ | CH$_2$COOC$_2$H$_5$ | H | S |
| 1157 | CH$_3$ | prop-1-en-3-yl | H | S |
| 1158 | CH$_3$ | trans-but-2-en-1-yl | H | S |
| 1159 | CH$_3$ | cis-but-2-en-1-yl | H | S |
| 1160 | CH$_3$ | cis-3-methyl-but-2-en-1-yl | H | S |
| 1161 | CH$_3$ | cyclopropyl | H | S |
| 1162 | CH$_3$ | cyclopentyl | H | S |
| 1163 | CH$_3$ | cyclohexyl | H | S |
| 1164 | CH$_3$ | 4,5-dihydroisoxazol-3-yl | H | S |
| 1165 | CH$_3$ | 4-methyl-4,5-dihydro-isoxazol-3-yl | H | S |
| 1166 | CH$_3$ | isoxazol-3-yl | H | S |
| 1167 | CH$_3$ | 4-methylisoxazol-3-yl | H | S |
| 1168 | CH$_3$ | 4,5-dihydroisoxazol-4-yl | H | S |
| 1169 | CH$_3$ | 3-methyl-4,5-dihydro-isoxazol-4-yl | H | S |
| 1170 | CH$_3$ | isoxazol-4-yl | H | S |
| 1171 | CH$_3$ | 3-methylisoxazol-4-yl | H | S |
| 1172 | CH$_3$ | phenyl | H | S |
| 1173 | CH$_3$ | benzyl | H | S |
| 1174 | CH$_3$ | benzoyl | H | S |
| 1175 | CH$_3$ | 2-pyridyl | H | S |
| 1176 | CH$_3$ | H | CH$_3$ | S |
| 1177 | CH$_3$ | CH$_3$ | CH$_3$ | S |
| 1178 | CH$_3$ | C$_2$H$_5$ | CH$_3$ | S |
| 1179 | CH$_3$ | n-C$_3$H$_7$ | CH$_3$ | S |
| 1180 | CH$_3$ | i-C$_3$H$_7$ | CH$_3$ | S |
| 1181 | CH$_3$ | n-C$_4$H$_9$ | CH$_3$ | S |
| 1182 | CH$_3$ | i-C$_4$H$_9$ | CH$_3$ | S |
| 1183 | CH$_3$ | s-C$_4$H$_9$ | CH$_3$ | S |
| 1184 | CH$_3$ | t-C$_4$H$_9$ | CH$_3$ | S |
| 1185 | CH$_3$ | CH$_2$OCH$_3$ | CH$_3$ | S |
| 1186 | CH$_3$ | CF$_3$ | CH$_3$ | S |
| 1187 | CH$_3$ | CF$_2$H | CH$_3$ | S |
| 1188 | CH$_3$ | CN | CH$_3$ | S |
| 1189 | CH$_3$ | OH | CH$_3$ | S |
| 1190 | CH$_3$ | OCH$_3$ | CH$_3$ | S |
| 1191 | CH$_3$ | NH$_2$ | CH$_3$ | S |
| 1192 | CH$_3$ | NHCH$_3$ | CH$_3$ | S |
| 1193 | CH$_3$ | N(CH$_3$)$_2$ | CH$_3$ | S |
| 1194 | CH$_3$ | CO$_2$CH$_3$ | CH$_3$ | S |
| 1195 | CH$_3$ | CO$_2$C$_2$H$_5$ | CH$_3$ | S |
| 1196 | CH$_3$ | C(O)CH$_3$ | CH$_3$ | S |
| 1197 | CH$_3$ | C(O)CF$_3$ | CH$_3$ | S |
| 1198 | CH$_3$ | C(=NOCH$_3$)CH$_3$ | CH$_3$ | S |
| 1199 | CH$_3$ | SO$_2$CH$_3$ | CH$_3$ | S |
| 1200 | CH$_3$ | SO$_2$CF$_3$ | CH$_3$ | S |
| 1201 | CH$_3$ | CH$_2$CO$_2$H | CH$_3$ | S |
| 1202 | CH$_3$ | CH$_2$COOCH$_3$ | CH$_3$ | S |
| 1203 | CH$_3$ | CH$_2$COOC$_2$H$_5$ | CH$_3$ | S |
| 1204 | CH$_3$ | prop-1-en-3-yl | CH$_3$ | S |
| 1205 | CH$_3$ | trans-but-2-en-1-yl | CH$_3$ | S |
| 1206 | CH$_3$ | cis-but-2-en-1-yl | CH$_3$ | S |
| 1207 | CH$_3$ | cis-3-methyl-but-2-en-1-yl | CH$_3$ | S |
| 1208 | CH$_3$ | cyclopropyl | CH$_3$ | S |
| 1209 | CH$_3$ | cyclopentyl | CH$_3$ | S |
| 1210 | CH$_3$ | cyclohexyl | CH$_3$ | S |
| 1211 | CH$_3$ | 4,5-dihydroisoxazol-3-yl | CH$_3$ | S |
| 1212 | CH$_3$ | 4-methyl-4,5-dihydro-isoxazol-3-yl | CH$_3$ | S |
| 1213 | CH$_3$ | isoxazol-3-yl | CH$_3$ | S |
| 1214 | CH$_3$ | 4-methylisoxazol-3-yl | CH$_3$ | S |
| 1215 | CH$_3$ | 4,5-dihydroisoxazol-4-yl | CH$_3$ | S |
| 1216 | CH$_3$ | 3-methyl-4,5-dihydro-isoxazol-4-yl | CH$_3$ | S |
| 1217 | CH$_3$ | isoxazol-4-yl | CH$_3$ | S |
| 1218 | CH$_3$ | 3-methylisoxazol-4-yl | CH$_3$ | S |
| 1219 | CH$_3$ | phenyl | CH$_3$ | S |
| 1220 | CH$_3$ | benzyl | CH$_3$ | S |
| 1221 | CH$_3$ | benzoyl | CH$_3$ | S |
| 1222 | CH$_3$ | 2-pyridyl | CH$_3$ | S |
| 1223 | CH$_3$ | H | Cl | S |
| 1224 | CH$_3$ | CH$_3$ | Cl | S |
| 1225 | CH$_3$ | C$_2$H$_5$ | Cl | S |
| 1226 | CH$_3$ | n-C$_3$H$_7$ | Cl | S |
| 1227 | CH$_3$ | i-C$_3$H$_7$ | Cl | S |
| 1228 | CH$_3$ | n-C$_4$H$_9$ | Cl | S |
| 1229 | CH$_3$ | i-C$_4$H$_9$ | Cl | S |
| 1230 | CH$_3$ | s-C$_4$H$_9$ | Cl | S |
| 1231 | CH$_3$ | t-C$_4$H$_9$ | Cl | S |

TABLE A-continued

| No. | R¹ | R² | R³ | A |
|---|---|---|---|---|
| 1232 | $CH_3$ | $CH_2OCH_3$ | Cl | S |
| 1233 | $CH_3$ | $CF_3$ | Cl | S |
| 1234 | $CH_3$ | $CF_2H$ | Cl | S |
| 1235 | $CH_3$ | CN | Cl | S |
| 1236 | $CH_3$ | OH | Cl | S |
| 1237 | $CH_3$ | $OCH_3$ | Cl | S |
| 1238 | $CH_3$ | $NH_2$ | Cl | S |
| 1239 | $CH_3$ | $NHCH_3$ | Cl | S |
| 1240 | $CH_3$ | $N(CH_3)_2$ | Cl | S |
| 1241 | $CH_3$ | $CO_2CH_3$ | Cl | S |
| 1242 | $CH_3$ | $CO_2C_2H_5$ | Cl | S |
| 1243 | $CH_3$ | $C(O)CH_3$ | Cl | S |
| 1244 | $CH_3$ | $C(O)CF_3$ | Cl | S |
| 1245 | $CH_3$ | $C(=NOCH_3)CH_3$ | Cl | S |
| 1246 | $CH_3$ | $SO_2CH_3$ | Cl | S |
| 1247 | $CH_3$ | $SO_2CF_3$ | Cl | S |
| 1248 | $CH_3$ | $CH_2CO_2H$ | Cl | S |
| 1249 | $CH_3$ | $CH_2COOCH_3$ | Cl | S |
| 1250 | $CH_3$ | $CH_2COOC_2H_5$ | Cl | S |
| 1251 | $CH_3$ | prop-1-en-3-yl | Cl | S |
| 1252 | $CH_3$ | trans-but-2-en-1-yl | Cl | S |
| 1253 | $CH_3$ | cis-but-2-en-1-yl | Cl | S |
| 1254 | $CH_3$ | cis-3-methyl-but-2-en-1-yl | Cl | S |
| 1255 | $CH_3$ | cyclopropyl | Cl | S |
| 1256 | $CH_3$ | cyclopentyl | Cl | S |
| 1257 | $CH_3$ | cyclohexyl | Cl | S |
| 1258 | $CH_3$ | 4,5-dihydroisoxazol-3-yl | Cl | S |
| 1259 | $CH_3$ | 4-methyl-4,5-dihydro-isoxazol-3-yl | Cl | S |
| 1260 | $CH_3$ | isoxazol-3-yl | Cl | S |
| 1261 | $CH_3$ | 4-methylisoxazol-3-yl | Cl | S |
| 1262 | $CH_3$ | 4,5-dihydroisoxazol-4-yl | Cl | S |
| 1263 | $CH_3$ | 3-methyl-4,5-dihydro-isoxazol-4-yl | Cl | S |
| 1264 | $CH_3$ | isoxazol-4-yl | Cl | S |
| 1265 | $CH_3$ | 3-methylisoxazol-4-yl | Cl | S |
| 1266 | $CH_3$ | phenyl | Cl | S |
| 1267 | $CH_3$ | benzyl | Cl | S |
| 1268 | $CH_3$ | benzoyl | Cl | S |
| 1269 | $CH_3$ | 2-pyridyl | Cl | S |
| 1270 | Cl | H | H | S |
| 1271 | Cl | $CH_3$ | H | S |
| 1272 | Cl | $C_2H_5$ | H | S |
| 1273 | Cl | $n-C_3H_7$ | H | S |
| 1274 | Cl | $i-C_3H_7$ | H | S |
| 1275 | Cl | $n-C_4H_9$ | H | S |
| 1276 | Cl | $i-C_4H_9$ | H | S |
| 1277 | Cl | $s-C_4H_9$ | H | S |
| 1278 | Cl | $t-C_4H_9$ | H | S |
| 1279 | Cl | $CH_2OCH_3$ | H | S |
| 1280 | Cl | $CF_3$ | H | S |
| 1281 | Cl | $CF_2H$ | H | S |
| 1282 | Cl | CN | H | S |
| 1283 | Cl | OH | H | S |
| 1284 | Cl | $OCH_3$ | H | S |
| 1285 | Cl | $NH_2$ | H | S |
| 1286 | Cl | $NHCH_3$ | H | S |
| 1287 | Cl | $N(CH_3)_2$ | H | S |
| 1288 | Cl | $CO_2CH_3$ | H | S |
| 1289 | Cl | $CO_2C_2H_5$ | H | S |
| 1290 | Cl | $C(O)CH_3$ | H | S |
| 1291 | Cl | $C(O)CF_3$ | H | S |
| 1292 | Cl | $C(=NOCH_3)CH_3$ | H | S |
| 1293 | Cl | $SO_2CH_3$ | H | S |
| 1294 | Cl | $SO_2CF_3$ | H | S |
| 1295 | Cl | $CH_2CO_2H$ | H | S |
| 1296 | Cl | $CH_2COOCH_3$ | H | S |
| 1297 | Cl | $CH_2COOC_2H_5$ | H | S |
| 1298 | Cl | Prop-1-en-3-yl | H | S |
| 1299 | Cl | trans-but-2-en-1-yl | H | S |
| 1300 | Cl | cis-but-2-en-1-yl | H | S |
| 1301 | Cl | cis-3-methyl-but-2-en-1-yl | H | S |
| 1302 | Cl | cyclopropyl | H | S |
| 1303 | Cl | cyclopentyl | H | S |
| 1304 | Cl | cyclohexyl | H | S |
| 1305 | Cl | 4,5-dihydroisoxazol-3-yl | H | S |
| 1306 | Cl | 4-methyl-4,5-dihydro-isoxazol-3-yl | H | S |
| 1307 | Cl | isoxazol-3-yl | H | S |
| 1308 | Cl | 4-methylisoxazol-3-yl | H | S |
| 1309 | Cl | 4,5-dihydroisoxazol-4-yl | H | S |
| 1310 | Cl | 3-methyl-4,5-dihydro-isoxazol-4-yl | H | S |
| 1311 | Cl | isoxazol-4-yl | H | S |
| 1312 | Cl | 3-methylisoxazol-4-yl | H | S |
| 1313 | Cl | phenyl | H | S |
| 1314 | Cl | benzyl | H | S |
| 1315 | Cl | benzoyl | H | S |
| 1316 | Cl | 2-pyridyl | H | S |
| 1317 | Cl | H | $CH_3$ | S |
| 1318 | Cl | $CH_3$ | $CH_3$ | S |
| 1319 | Cl | $C_2H_5$ | $CH_3$ | S |
| 1320 | Cl | $n-C_3H_7$ | $CH_3$ | S |
| 1321 | Cl | $i-C_3H_7$ | $CH_3$ | S |
| 1322 | Cl | $n-C_4H_9$ | $CH_3$ | S |
| 1323 | Cl | $i-C_4H_9$ | $CH_3$ | S |
| 1324 | Cl | $s-C_4H_9$ | $CH_3$ | S |
| 1325 | Cl | $t-C_4H_9$ | $CH_3$ | S |
| 1326 | Cl | $CH_2OCH_3$ | $CH_3$ | S |
| 1327 | Cl | $CF_3$ | $CH_3$ | S |
| 1328 | Cl | $CF_2H$ | $CH_3$ | S |
| 1329 | Cl | CN | $CH_3$ | S |
| 1330 | Cl | OH | $CH_3$ | S |
| 1331 | Cl | $OCH_3$ | $CH_3$ | S |
| 1332 | Cl | $NH_2$ | $CH_3$ | S |
| 1333 | Cl | $NHCH_3$ | $CH_3$ | S |
| 1334 | Cl | $N(CH_3)_2$ | $CH_3$ | S |
| 1335 | Cl | $CO_2CH_3$ | $CH_3$ | S |
| 1336 | Cl | $CO_2C_2H_5$ | $CH_3$ | S |
| 1337 | Cl | $C(O)CH_3$ | $CH_3$ | S |
| 1338 | Cl | $C(O)CF_3$ | $CH_3$ | S |
| 1339 | Cl | $C(=NOCH_3)CH_3$ | $CH_3$ | S |
| 1340 | Cl | $SO_2CH_3$ | $CH_3$ | S |
| 1341 | Cl | $SO_2CF_3$ | $CH_3$ | S |
| 1342 | Cl | $CH_2CO_2H$ | $CH_3$ | S |
| 1343 | Cl | $CH_2COOCH_3$ | $CH_3$ | S |
| 1344 | Cl | $CH_2COOC_2H_5$ | $CH_3$ | S |
| 1345 | Cl | prop-1-en-3-yl | $CH_3$ | S |
| 1346 | Cl | trans-but-2-en-1-yl | $CH_3$ | S |
| 1347 | Cl | cis-but-2-en-1-yl | $CH_3$ | S |
| 1348 | Cl | cis-3-methyl-but-2-en-1-yl | $CH_3$ | S |
| 1349 | Cl | cyclopropyl | $CH_3$ | S |
| 1350 | Cl | cyclopentyl | $CH_3$ | S |
| 1351 | Cl | cyclohexyl | $CH_3$ | S |
| 1352 | Cl | 4,5-dihydroisoxazol-3-yl | $CH_3$ | S |
| 1353 | Cl | 4-methyl-4,5-dihydro-isoxazol-3-yl | $CH_3$ | S |
| 1354 | Cl | isoxazol-3-yl | $CH_3$ | S |
| 1355 | Cl | 4-methylisoxazol-3-yl | $CH_3$ | S |
| 1356 | Cl | 4,5-dihydroisoxazol-4-yl | $CH_3$ | S |
| 1357 | Cl | 3-methyl-4,5-dihydro-isoxazol-4-yl | $CH_3$ | S |
| 1358 | Cl | isoxazol-4-yl | $CH_3$ | S |
| 1359 | Cl | 3-methylisoxazol-4-yl | $CH_3$ | S |
| 1360 | Cl | phenyl | $CH_3$ | S |
| 1361 | Cl | benzyl | $CH_3$ | S |
| 1362 | Cl | benzoyl | $CH_3$ | S |
| 1363 | Cl | 2-pyridyl | $CH_3$ | S |
| 1364 | Cl | H | Cl | S |
| 1365 | Cl | $CH_3$ | Cl | S |
| 1366 | Cl | $C_2H_5$ | Cl | S |
| 1367 | Cl | $n-C_3H_7$ | Cl | S |
| 1368 | Cl | $i-C_3H_7$ | Cl | S |
| 1369 | Cl | $n-C_4H_9$ | Cl | S |
| 1370 | Cl | $i-C_4H_9$ | Cl | S |

TABLE A-continued

| No. | R¹ | R² | R³ | A |
|---|---|---|---|---|
| 1371 | Cl | s-C₄H₉ | Cl | S |
| 1372 | Cl | t-C₄H₉ | Cl | S |
| 1373 | Cl | CH₂OCH₃ | Cl | S |
| 1374 | Cl | CF₃ | Cl | S |
| 1375 | Cl | CF₂H | Cl | S |
| 1376 | Cl | CN | Cl | S |
| 1377 | Cl | OH | Cl | S |
| 1378 | Cl | OCH₃ | Cl | S |
| 1379 | Cl | NH₂ | Cl | S |
| 1380 | Cl | NHCH₃ | Cl | S |
| 1381 | Cl | N(CH₃)₂ | Cl | S |
| 1382 | Cl | CO₂CH₃ | Cl | S |
| 1383 | Cl | CO₂C₂H₅ | Cl | S |
| 1384 | Cl | C(O)CH₃ | Cl | S |
| 1385 | Cl | C(O)CF₃ | Cl | S |
| 1386 | Cl | C(=NOCH₃)CH₃ | Cl | S |
| 1387 | Cl | SO₂CH₃ | Cl | S |
| 1388 | Cl | SO₂CF₃ | Cl | S |
| 1389 | Cl | CH₂CO₂H | Cl | S |
| 1390 | Cl | CH₂COOCH₃ | Cl | S |
| 1391 | Cl | CH₂COOC₂H₅ | Cl | S |
| 1392 | Cl | prop-1-en-3-yl | Cl | S |
| 1393 | Cl | trans-but-2-en-1-yl | Cl | S |
| 1394 | Cl | cis-but-2-en-1-yl | Cl | S |
| 1395 | Cl | cis-3-methyl-but-2-en-1-yl | Cl | S |
| 1396 | Cl | cyclopropyl | Cl | S |
| 1397 | Cl | cyclopentyl | Cl | S |
| 1398 | Cl | cyclohexyl | Cl | S |
| 1399 | Cl | 4,5-dihydroisoxazol-3-yl | Cl | S |
| 1400 | Cl | 4-methyl-4,5-dihydro-isoxazol-3-yl | Cl | S |
| 1401 | Cl | isoxazol-3-yl | Cl | S |
| 1402 | Cl | 4-methylisoxazol-3-yl | Cl | S |
| 1403 | Cl | 4,5-dihydroisoxazol-4-yl | Cl | S |
| 1404 | Cl | 3-methyl-4,5-dihydro-isoxazol-4-yl | Cl | S |
| 1405 | Cl | isoxazol-4-yl | Cl | S |
| 1406 | Cl | 3-methylisoxazol-4-yl | Cl | S |
| 1407 | Cl | phenyl | Cl | S |
| 1408 | Cl | benzyl | Cl | S |
| 1409 | Cl | benzoyl | Cl | S |
| 1410 | Cl | 2-pyridyl | Cl | s |
| 1411 | OCH₃ | H | H | S |
| 1412 | OCH₃ | CH₃ | H | S |
| 1413 | OCH₃ | C₂H₅ | H | S |
| 1414 | OCH₃ | n-C₃H₇ | H | S |
| 1415 | OCH₃ | i-C₃H₇ | H | S |
| 1416 | OCH₃ | n-C₄H₉ | H | S |
| 1417 | OCH₃ | i-C₄H₉ | H | S |
| 1418 | OCH₃ | s-C₄H₉ | H | S |
| 1419 | OCH₃ | t-C₄H₉ | H | S |
| 1420 | OCH₃ | CH₂OCH₃ | H | S |
| 1421 | OCH₃ | CF₃ | H | S |
| 1422 | OCH₃ | CF₂H | H | S |
| 1423 | OCH₃ | CN | H | S |
| 1424 | OCH₃ | OH | H | S |
| 1425 | OCH₃ | OCH₃ | H | S |
| 1426 | OCH₃ | NH₂ | H | S |
| 1427 | OCH₃ | NHCH₃ | H | S |
| 1428 | OCH₃ | N(CH₃)₂ | H | S |
| 1429 | OCH₃ | CO₂CH₃ | H | S |
| 1430 | OCH₃ | CO₂C₂H₅ | H | S |
| 1431 | OCH₃ | C(O)CH₃ | H | S |
| 1432 | OCH₃ | C(O)CF₃ | H | S |
| 1433 | OCH₃ | C(=NOCH₃)CH₃ | H | S |
| 1434 | OCH₃ | SO₂CH₃ | H | S |
| 1435 | OCH₃ | SO₂CF₃ | H | S |
| 1436 | OCH₃ | CH₂CO₂H | H | S |
| 1437 | OCH₃ | CH₂COOCH₃ | H | S |
| 1438 | OCH₃ | CH₂COOC₂H₅ | H | S |
| 1439 | OCH₃ | prop-1-en-3-yl | H | S |
| 1440 | OCH₃ | trans-but-2-en-1-yl | H | S |
| 1441 | OCH₃ | cis-but-2-en-1-yl | H | S |
| 1442 | OCH₃ | cis-3-methyl-but-2-en-1-yl | H | S |
| 1443 | OCH₃ | cyclopropyl | H | S |
| 1444 | OCH₃ | cyclopentyl | H | S |
| 1445 | OCH₃ | cyclohexyl | H | S |
| 1446 | OCH₃ | 4,5-dihydroisoxazol-3-yl | H | S |
| 1447 | OCH₃ | 4-methyl-4,5-dihydro-isoxazol-3-yl | H | S |
| 1448 | OCH₃ | isoxazol-3-yl | H | S |
| 1449 | OCH₃ | 4-methylisoxazol-3-yl | H | S |
| 1450 | OCH₃ | 4,5-dihydroisoxazol-4-yl | H | S |
| 1451 | OCH₃ | 3-methyl-4,5-dihydro-isoxazol-4-yl | H | S |
| 1452 | OCH₃ | isoxazol-4-yl | H | S |
| 1453 | OCH₃ | 3-methylisoxazol-4-yl | H | S |
| 1454 | OCH₃ | phenyl | H | S |
| 1455 | OCH₃ | benzyl | H | S |
| 1456 | OCH₃ | benzoyl | H | S |
| 1457 | OCH₃ | 2-pyridyl | H | S |
| 1458 | OCH₃ | H | CH₃ | S |
| 1459 | OCH₃ | CH₃ | CH₃ | S |
| 1460 | OCH₃ | C₂H₅ | CH₃ | S |
| 1461 | OCH₃ | n-C₃H₇ | CH₃ | S |
| 1462 | OCH₃ | i-C₃H₇ | CH₃ | S |
| 1463 | OCH₃ | n-C₄H₉ | CH₃ | S |
| 1464 | OCH₃ | i-C₄H₉ | CH₃ | S |
| 1465 | OCH₃ | s-C₄H₉ | CH₃ | S |
| 1466 | OCH₃ | t-C₄H₉ | CH₃ | S |
| 1467 | OCH₃ | CH₂OCH₃ | CH₃ | S |
| 1468 | OCH₃ | CF₃ | CH₃ | S |
| 1469 | OCH₃ | CF₂H | CH₃ | S |
| 1470 | OCH₃ | CN | CH₃ | S |
| 1471 | OCH₃ | OH | CH₃ | S |
| 1472 | OCH₃ | OCH₃ | CH₃ | S |
| 1473 | OCH₃ | NH₂ | CH₃ | S |
| 1474 | OCH₃ | NHCH₃ | CH₃ | S |
| 1475 | OCH₃ | N(CH₃)₂ | CH₃ | S |
| 1476 | OCH₃ | CO₂CH₃ | CH₃ | S |
| 1477 | OCH₃ | CO₂C₂H₅ | CH₃ | S |
| 1478 | OCH₃ | C(O)CH₃ | CH₃ | S |
| 1479 | OCH₃ | C(O)CF₃ | CH₃ | S |
| 1480 | OCH₃ | C(=NOCH₃)CH₃ | CH₃ | S |
| 1481 | OCH₃ | SO₂CH₃ | CH₃ | S |
| 1482 | OCH₃ | SO₂CF₃ | CH₃ | S |
| 1483 | OCH₃ | CH₂CO₂H | CH₃ | S |
| 1484 | OCH₃ | CH₂COOCH₃ | CH₃ | S |
| 1485 | OCH₃ | CH₂COOC₂H₅ | CH₃ | S |
| 1486 | OCH₃ | prop-1-en-3-yl | CH₃ | S |
| 1487 | OCH₃ | trans-but-2-en-1-yl | CH₃ | S |
| 1488 | OCH₃ | cis-but-2-en-1-yl | CH₃ | S |
| 1489 | OCH₃ | cis-3-methyl-but-2-en-1-yl | CH₃ | S |
| 1490 | OCH₃ | cyclopropyl | CH₃ | S |
| 1491 | OCH₃ | cyclopentyl | CH₃ | S |
| 1492 | OCH₃ | cyclohexyl | CH₃ | S |
| 1493 | OCH₃ | 4,5-dihydroisoxazol-3-yl | CH₃ | S |
| 1494 | OCH₃ | 4-methyl-4,5-dihydro-isoxazol-3-yl | CH₃ | S |
| 1495 | OCH₃ | isoxazol-3-yl | CH₃ | S |
| 1496 | OCH₃ | 4-methylisoxazol-3-yl | CH₃ | S |
| 1497 | OCH₃ | 4,5-dihydroisoxazol-4-yl | CH₃ | S |
| 1498 | OCH₃ | 3-methyl-4,5-dihydro-isoxazol-4-yl | CH₃ | S |
| 1499 | OCH₃ | isoxazol-4-yl | CH₃ | S |
| 1500 | OCH₃ | 3-methylisoxazol-4-yl | CH₃ | S |
| 1501 | OCH₃ | phenyl | CH₃ | S |
| 1502 | OCH₃ | benzyl | CH₃ | S |
| 1503 | OCH₃ | benzoyl | CH₃ | S |
| 1504 | OCH₃ | 2-pyridyl | CH₃ | S |
| 1505 | OCH₃ | H | Cl | S |
| 1506 | OCH₃ | CH₃ | Cl | S |
| 1507 | OCH₃ | C₂H₅ | Cl | S |
| 1508 | OCH₃ | n-C₃H₇ | Cl | S |

TABLE A-continued

| No. | R¹ | R² | R³ | A |
|---|---|---|---|---|
| 1509 | OCH₃ | i-C₃H₇ | Cl | S |
| 1510 | OCH₃ | n-C₄H₉ | Cl | S |
| 1511 | OCH₃ | i-C₄H₉ | Cl | S |
| 1512 | OCH₃ | s-C₄H₉ | Cl | S |
| 1513 | OCH₃ | t-C₄H₉ | Cl | S |
| 1514 | OCH₃ | CH₂OCH₃ | Cl | S |
| 1515 | OCH₃ | CF₃ | Cl | S |
| 1516 | OCH₃ | CF₂H | Cl | S |
| 1517 | OCH₃ | CN | Cl | S |
| 1518 | OCH₃ | OH | Cl | S |
| 1519 | OCH₃ | OCH₃ | Cl | S |
| 1520 | OCH₃ | NH₂ | Cl | S |
| 1521 | OCH₃ | NHCH₃ | Cl | S |
| 1522 | OCH₃ | N(CH₃)₂ | Cl | S |
| 1523 | OCH₃ | CO₂CH₃ | Cl | S |
| 1524 | OCH₃ | CO₂C₂H₅ | Cl | S |
| 1525 | OCH₃ | C(O)CH₃ | Cl | S |
| 1526 | OCH₃ | C(O)CF₃ | Cl | S |
| 1527 | OCH₃ | C(=NOCH₃)CH₃ | Cl | S |
| 1528 | OCH₃ | SO₂CH₃ | Cl | S |
| 1529 | OCH₃ | SO₂CF₃ | Cl | S |
| 1530 | OCH₃ | CH₂CO₂H | Cl | S |
| 1531 | OCH₃ | CH₂COOCH₃ | Cl | S |
| 1532 | OCH₃ | CH₂COOC₂H₅ | Cl | S |
| 1533 | OCH₃ | prop-1-en-3-yl | Cl | S |
| 1534 | OCH₃ | trans-but-2-en-1-yl | Cl | S |
| 1535 | OCH₃ | cis-but-2-en-1-yl | Cl | S |
| 1536 | OCH₃ | cis-3-methyl-but-2-en-1-yl | Cl | S |
| 1537 | OCH₃ | cyclopropyl | Cl | S |
| 1538 | OCH₃ | cyclopentyl | Cl | S |
| 1539 | OCH₃ | cyclohexyl | Cl | S |
| 1540 | OCH₃ | 4,5-dihydroisoxazol-3-yl | Cl | S |
| 1541 | OCH₃ | 4-methyl-4,5-dihydro-isoxazol-3-yl | Cl | S |
| 1542 | OCH₃ | isoxazol-3-yl | Cl | S |
| 1543 | OCH₃ | 4-methylisoxazol-3-yl | Cl | S |
| 1544 | OCH₃ | 4,5-dihydroisoxazol-4-yl | Cl | S |
| 1545 | OCH₃ | 3-methyl-4,5-dihydro-isoxazol-4-yl | Cl | S |
| 1546 | OCH₃ | isoxazol-4-yl | Cl | S |
| 1547 | OCH₃ | 3-methylisoxazol-4-yl | Cl | S |
| 1548 | OCH₃ | phenyl | Cl | S |
| 1549 | OCH₃ | benzyl | Cl | S |
| 1550 | OCH₃ | benzoyl | Cl | S |
| 1551 | OCH₃ | 2-pyridyl | Cl | S |
| 1552 | OCF₃ | H | H | S |
| 1553 | OCF₃ | CH₃ | H | S |
| 1554 | OCF₃ | C₂H₅ | H | S |
| 1555 | OCF₃ | n-C₃H₇ | H | S |
| 1556 | OCF₃ | i-C₃H₇ | H | S |
| 1557 | OCF₃ | n-C₄H₉ | H | S |
| 1558 | OCF₃ | i-C₄H₉ | H | S |
| 1559 | OCF₃ | s-C₄H₉ | H | S |
| 1560 | OCF₃ | t-C₄H₉ | H | S |
| 1561 | OCF₃ | CH₂OCH₃ | H | S |
| 1562 | OCF₃ | CF₃ | H | S |
| 1563 | OCF₃ | CF₂H | H | S |
| 1564 | OCF₃ | CN | H | S |
| 1565 | OCF₃ | OH | H | S |
| 1566 | OCF₃ | OCH₃ | H | S |
| 1567 | OCF₃ | NH₂ | H | S |
| 1568 | OCF₃ | NHCH₃ | H | S |
| 1569 | OCF₃ | N(CH₃)₂ | H | S |
| 1570 | OCF₃ | CO₂CH₃ | H | S |
| 1571 | OCF₃ | CO₂C₂H₅ | H | S |
| 1572 | OCF₃ | C(O)CH₃ | H | S |
| 1573 | OCF₃ | C(O)CF₃ | H | S |
| 1574 | OCF₃ | C(=NOCH₃)CH₃ | H | S |
| 1575 | OCF₃ | SO₂CH₃ | H | S |
| 1576 | OCF₃ | SO₂CF₃ | H | S |
| 1577 | OCF₃ | CH₂CO₂H | H | S |
| 1578 | OCF₃ | CH₂COOCH₃ | H | S |
| 1579 | OCF₃ | CH₂COOC₂H₅ | H | S |
| 1580 | OCF₃ | prop-1-en-3-yl | H | S |
| 1581 | OCF₃ | trans-but-2-en-1-yl | H | S |
| 1582 | OCF₃ | cis-but-2-en-1-yl | H | S |
| 1583 | OCF₃ | cis-3-methyl-but-2-en-1-yl | H | S |
| 1584 | OCF₃ | cyclopropyl | H | S |
| 1585 | OCF₃ | cyclopentyl | H | S |
| 1586 | OCF₃ | cyclohexyl | H | S |
| 1587 | OCF₃ | 4,5-dihydroisoxazol-3-yl | H | S |
| 1588 | OCF₃ | 4-methyl-4,5-dihydro-isoxazol-3-yl | H | S |
| 1589 | OCF₃ | isoxazol-3-yl | H | S |
| 1590 | OCF₃ | 4-methylisoxazol-3-yl | H | S |
| 1591 | OCF₃ | 4,5-dihydroisoxazol-4-yl | H | S |
| 1592 | OCF₃ | 3-methyl-4,5-dihydro-isoxazol-4-yl | H | S |
| 1593 | OCF₃ | isoxazol-4-yl | H | S |
| 1594 | OCF₃ | 3-methylisoxazol-4-yl | H | S |
| 1595 | OCF₃ | phenyl | H | S |
| 1596 | OCF₃ | benzyl | H | S |
| 1597 | OCF₃ | benzoyl | H | S |
| 1598 | OCF₃ | 2-pyridyl | H | S |
| 1599 | OCF₃ | H | CH₃ | S |
| 1600 | OCF₃ | CH₃ | CH₃ | S |
| 1601 | OCF₃ | C₂H₅ | CH₃ | S |
| 1602 | OCF₃ | n-C₃H₇ | CH₃ | S |
| 1603 | OCF₃ | i-C₃H₇ | CH₃ | S |
| 1604 | OCF₃ | n-C₄H₉ | CH₃ | S |
| 1605 | OCF₃ | i-C₄H₉ | CH₃ | S |
| 1606 | OCF₃ | s-C₄H₉ | CH₃ | S |
| 1607 | OCF₃ | t-C₄H₉ | CH₃ | S |
| 1608 | OCF₃ | CH₂OCH₃ | CH₃ | S |
| 1609 | OCF₃ | CF₃ | CH₃ | S |
| 1610 | OCF₃ | CF₂H | CH₃ | S |
| 1611 | OCF₃ | CN | CH₃ | S |
| 1612 | OCF₃ | OH | CH₃ | S |
| 1613 | OCF₃ | OCH₃ | CH₃ | S |
| 1614 | OCF₃ | NH₂ | CH₃ | S |
| 1615 | OCF₃ | NHCH₃ | CH₃ | S |
| 1616 | OCF₃ | N(CH₃)₂ | CH₃ | S |
| 1617 | OCF₃ | CO₂CH₃ | CH₃ | S |
| 1618 | OCF₃ | CO₂C₂H₅ | CH₃ | S |
| 1619 | OCF₃ | C(O)CH₃ | CH₃ | S |
| 1620 | OCF₃ | C(O)CF₃ | CH₃ | S |
| 1621 | OCF₃ | C(=NOCH₃)CH₃ | CH₃ | S |
| 1622 | OCF₃ | SO₂CH₃ | CH₃ | S |
| 1623 | OCF₃ | SO₂CF₃ | CH₃ | S |
| 1624 | OCF₃ | CH₂CO₂H | CH₃ | S |
| 1625 | OCF₃ | CH₂COOCH₃ | CH₃ | S |
| 1626 | OCF₃ | CH₂COOC₂H₅ | CH₃ | S |
| 1627 | OCF₃ | prop-1-en-3-yl | CH₃ | S |
| 1628 | OCF₃ | trans-but-2-en-1-yl | CH₃ | S |
| 1629 | OCF₃ | cis-but-2-en-1-yl | CH₃ | S |
| 1630 | OCF₃ | cis-3-methyl-but-2-en-1-yl | CH₃ | S |
| 1631 | OCF₃ | cyclopropyl | CH₃ | S |
| 1632 | OCF₃ | cyclopentyl | CH₃ | S |
| 1633 | OCF₃ | cyclohexyl | CH₃ | S |
| 1634 | OCF₃ | 4,5-dihydroisoxazol-3-yl | CH₃ | S |
| 1635 | OCF₃ | 4-methyl-4,5-dihydro-isoxazol-3-yl | CH₃ | S |
| 1636 | OCF₃ | isoxazol-3-yl | CH₃ | S |
| 1637 | OCF₃ | 4-methylisoxazol-3-yl | CH₃ | S |
| 1638 | OCF₃ | 4,5-dihydroisoxazol-4-yl | CH₃ | S |
| 1639 | OCF₃ | 3-methyl-4,5-dihydro-isoxazol-4-yl | CH₃ | S |
| 1640 | OCF₃ | isoxazol-4-yl | CH₃ | S |
| 1641 | OCF₃ | 3-methylisoxazol-4-yl | CH₃ | S |
| 1642 | OCF₃ | phenyl | CH₃ | S |
| 1643 | OCF₃ | benzyl | CH₃ | S |
| 1644 | OCF₃ | benzoyl | CH₃ | S |
| 1645 | OCF₃ | 2-pyridyl | CH₃ | S |
| 1646 | OCF₃ | H | Cl | S |
| 1647 | OCF₃ | CH₃ | Cl | S |

TABLE A-continued

| No. | R¹ | R² | R³ | A |
|---|---|---|---|---|
| 1648 | OCF₃ | C₂H₅ | Cl | S |
| 1649 | OCF₃ | n-C₃H₇ | Cl | S |
| 1650 | OCF₃ | i-C₃H₇ | Cl | S |
| 1651 | OCF₃ | n-C₄H₉ | Cl | S |
| 1652 | OCF₃ | i-C₄H₉ | Cl | S |
| 1653 | OCF₃ | s-C₄H₉ | Cl | S |
| 1654 | OCF₃ | t-C₄H₉ | Cl | S |
| 1655 | OCF₃ | CH₂OCH₃ | Cl | S |
| 1656 | OCF₃ | CF₃ | Cl | S |
| 1657 | OCF₃ | CF₂H | Cl | S |
| 1658 | OCF₃ | CN | Cl | S |
| 1659 | OCF₃ | OH | Cl | S |
| 1660 | OCF₃ | OCH₃ | Cl | S |
| 1661 | OCF₃ | NH₂ | Cl | S |
| 1662 | OCF₃ | NHCH₃ | Cl | S |
| 1663 | OCF₃ | N(CH₃)₂ | Cl | S |
| 1664 | OCF₃ | CO₂CH₃ | Cl | S |
| 1665 | OCF₃ | CO₂C₂H₅ | Cl | S |
| 1666 | OCF₃ | C(O)CH₃ | Cl | S |
| 1667 | OCF₃ | C(O)CF₃ | Cl | S |
| 1668 | OCF₃ | C(=NOCH₃)CH₃ | Cl | S |
| 1669 | OCF₃ | SO₂CH₃ | Cl | S |
| 1670 | OCF₃ | SO₂CF₃ | Cl | S |
| 1671 | OCF₃ | CH₂CO₂H | Cl | S |
| 1672 | OCF₃ | CH₂COOCH₃ | Cl | S |
| 1673 | OCF₃ | CH₂COOC₂H₅ | Cl | S |
| 1674 | OCF₃ | prop-1-en-3-yl | Cl | S |
| 1675 | OCF₃ | trans-but-2-en-1-yl | Cl | S |
| 1676 | OCF₃ | cis-but-2-en-1-yl | Cl | S |
| 1677 | OCF₃ | cis-3-methyl-but-2-en-1-yl | Cl | S |
| 1678 | OCF₃ | cyclopropyl | Cl | S |
| 1679 | OCF₃ | cyclopentyl | Cl | S |
| 1680 | OCF₃ | cyclohexyl | Cl | S |
| 1681 | OCF₃ | 4,5-dihydroisoxazol-3-yl | Cl | S |
| 1682 | OCF₃ | 4-methyl-4,5-dihydro-isoxazol-3-yl | Cl | S |
| 1683 | OCF₃ | isoxazol-3-yl | Cl | S |
| 1684 | OCF₃ | 4-methylisoxazol-3-yl | Cl | S |
| 1685 | OCF₃ | 4,5-dihydroisoxazol-4-yl | Cl | S |
| 1686 | OCF₃ | 3-methyl-4,5-dihydro-isoxazol-4-yl | Cl | S |
| 1687 | OCF₃ | isoxazol-4-yl | Cl | S |
| 1688 | OCF₃ | 3-methylisoxazol-4-yl | Cl | S |
| 1689 | OCF₃ | phenyl | Cl | S |
| 1690 | OCF₃ | benzyl | Cl | S |
| 1691 | OCF₃ | benzoyl | Cl | S |
| 1692 | OCF₃ | 2-pyridyl | Cl | S |
| 1693 | SCH₃ | H | H | S |
| 1694 | SCH₃ | CH₃ | H | S |
| 1695 | SCH₃ | C₂H₅ | H | S |
| 1696 | SCH₃ | n-C₃H₇ | H | S |
| 1697 | SCH₃ | i-C₃H₇ | H | S |
| 1698 | SCH₃ | n-C₄H₉ | H | S |
| 1699 | SCH₃ | i-C₄H₉ | H | S |
| 1700 | SCH₃ | s-C₄H₉ | H | S |
| 1701 | SCH₃ | t-C₄H₉ | H | S |
| 1702 | SCH₃ | CH₂OCH₃ | H | S |
| 1703 | SCH₃ | CF₃ | H | S |
| 1704 | SCH₃ | CF₂H | H | S |
| 1705 | SCH₃ | CN | H | S |
| 1706 | SCH₃ | OH | H | S |
| 1707 | SCH₃ | OCH₃ | H | S |
| 1708 | SCH₃ | NH₂ | H | S |
| 1709 | SCH₃ | NHCH₃ | H | S |
| 1710 | SCH₃ | N(CH₃)₂ | H | S |
| 1711 | SCH₃ | CO₂CH₃ | H | S |
| 1712 | SCH₃ | CO₂C₂H₅ | H | S |
| 1713 | SCH₃ | C(O)CH₃ | H | S |
| 1714 | SCH₃ | C(O)CF₃ | H | S |
| 1715 | SCH₃ | C(=NOCH₃)CH₃ | H | S |
| 1716 | SCH₃ | SO₂CH₃ | H | S |
| 1717 | SCH₃ | SO₂CF₃ | H | S |
| 1718 | SCH₃ | CH₂CO₂H | H | S |
| 1719 | SCH₃ | CH₂COOCH₃ | H | S |
| 1720 | SCH₃ | CH₂COOC₂H₅ | H | S |
| 1721 | SCH₃ | prop-1-en-3-yl | H | S |
| 1722 | SCH₃ | trans-but-2-en-1-yl | H | S |
| 1723 | SCH₃ | cis-but-2-en-1-yl | H | S |
| 1724 | SCH₃ | cis-3-methyl-but-2-en-1-yl | H | S |
| 1725 | SCH₃ | cyclopropyl | H | S |
| 1726 | SCH₃ | cyclopentyl | H | S |
| 1727 | SCH₃ | cyclohexyl | H | S |
| 1728 | SCH₃ | 4,5-dihydroisoxazol-3-yl | H | S |
| 1729 | SCH₃ | 4-methyl-4,5-dihydro-isoxazol-3-yl | H | S |
| 1730 | SCH₃ | isoxazol-3-yl | H | S |
| 1731 | SCH₃ | 4-methylisoxazol-3-yl | H | S |
| 1732 | SCH₃ | 4,5-dihydroisoxazol-4-yl | H | S |
| 1733 | SCH₃ | 3-methyl-4,5-dihydro-isoxazol-4-yl | H | S |
| 1734 | SCH₃ | isoxazol-4-yl | H | S |
| 1735 | SCH₃ | 3-methylisoxazol-4-yl | H | S |
| 1736 | SCH₃ | phenyl | H | S |
| 1737 | SCH₃ | benzyl | H | S |
| 1738 | SCH₃ | benzoyl | H | S |
| 1739 | SCH₃ | 2-pyridyl | H | S |
| 1740 | SCH₃ | H | CH₃ | S |
| 1741 | SCH₃ | CH₃ | CH₃ | S |
| 1742 | SCH₃ | C₂H₅ | CH₃ | S |
| 1743 | SCH₃ | n-C₃H₇ | CH₃ | S |
| 1744 | SCH₃ | i-C₃H₇ | CH₃ | S |
| 1745 | SCH₃ | n-C₄H₉ | CH₃ | S |
| 1746 | SCH₃ | i-C₄H₉ | CH₃ | S |
| 1747 | SCH₃ | s-C₄H₉ | CH₃ | S |
| 1748 | SCH₃ | t-C₄H₉ | CH₃ | S |
| 1749 | SCH₃ | CH₂OCH₃ | CH₃ | S |
| 1750 | SCH₃ | CF₃ | CH₃ | S |
| 1751 | SCH₃ | CF₂H | CH₃ | S |
| 1752 | SCH₃ | CN | CH₃ | S |
| 1753 | SCH₃ | OH | CH₃ | S |
| 1754 | SCH₃ | OCH₃ | CH₃ | S |
| 1755 | SCH₃ | NH₂ | CH₃ | S |
| 1756 | SCH₃ | NHCH₃ | CH₃ | S |
| 1757 | SCH₃ | N(CH₃)₂ | CH₃ | S |
| 1758 | SCH₃ | CO₂CH₃ | CH₃ | S |
| 1759 | SCH₃ | CO₂C₂H₅ | CH₃ | S |
| 1760 | SCH₃ | C(O)CH₃ | CH₃ | S |
| 1761 | SCH₃ | C(O)CF₃ | CH₃ | S |
| 1762 | SCH₃ | C(=NOCH₃)CH₃ | CH₃ | S |
| 1763 | SCH₃ | SO₂CH₃ | CH₃ | S |
| 1764 | SCH₃ | SO₂CF₃ | CH₃ | S |
| 1765 | SCH₃ | CH₂CO₂H | CH₃ | S |
| 1766 | SCH₃ | CH₂COOCH₃ | CH₃ | S |
| 1767 | SCH₃ | CH₂COOC₂H₅ | CH₃ | S |
| 1768 | SCH₃ | prop-1-en-3-yl | CH₃ | S |
| 1769 | SCH₃ | trans-but-2-en-1-yl | CH₃ | S |
| 1770 | SCH₃ | cis-but-2-en-1-yl | CH₃ | S |
| 1771 | SCH₃ | cis-3-methyl-but-2-en-1-yl | CH₃ | S |
| 1772 | SCH₃ | cyclopropyl | CH₃ | S |
| 1773 | SCH₃ | cyclopentyl | CH₃ | S |
| 1774 | SCH₃ | cyclohexyl | CH₃ | S |
| 1775 | SCH₃ | 4,5-dihydroisoxazol-3-yl | CH₃ | S |
| 1776 | SCH₃ | 4-methyl-4,5-dihydro-isoxazol-3-yl | CH₃ | S |
| 1777 | SCH₃ | isoxazol-3-yl | CH₃ | S |
| 1778 | SCH₃ | 4-methylisoxazol-3-yl | CH₃ | S |
| 1779 | SCH₃ | 4,5-dihydroisoxazol-4-yl | CH₃ | S |
| 1780 | SCH₃ | 3-methyl-4,5-dihydro-isoxazol-4-yl | CH₃ | S |
| 1781 | SCH₃ | isoxazol-4-yl | CH₃ | S |
| 1782 | SCH₃ | 3-methylisoxazol-4-yl | CH₃ | S |
| 1783 | SCH₃ | phenyl | CH₃ | S |
| 1784 | SCH₃ | benzyl | CH₃ | S |
| 1785 | SCH₃ | benzoyl | CH₃ | S |
| 1786 | SCH₃ | 2-pyridyl | CH₃ | S |

TABLE A-continued

| No. | R¹ | R² | R³ | A |
|---|---|---|---|---|
| 1787 | SCH₃ | H | Cl | S |
| 1788 | SCH₃ | CH₃ | Cl | S |
| 1789 | SCH₃ | C₂H₅ | Cl | S |
| 1790 | SCH₃ | n-C₃H₇ | Cl | S |
| 1791 | SCH₃ | i-C₃H₇ | Cl | S |
| 1792 | SCH₃ | n-C₄H₉ | Cl | S |
| 1793 | SCH₃ | i-C₄H₉ | Cl | S |
| 1794 | SCH₃ | s-C₄H₉ | Cl | S |
| 1795 | SCH₃ | t-C₄H₉ | Cl | S |
| 1796 | SCH₃ | CH₂OCH₃ | Cl | S |
| 1797 | SCH₃ | CF₃ | Cl | S |
| 1798 | SCH₃ | CF₂H | Cl | S |
| 1799 | SCH₃ | CN | Cl | S |
| 1800 | SCH₃ | OH | Cl | S |
| 1801 | SCH₃ | OCH₃ | Cl | S |
| 1802 | SCH₃ | NH₂ | Cl | S |
| 1803 | SCH₃ | NHCH₃ | Cl | S |
| 1804 | SCH₃ | N(CH₃)₂ | Cl | S |
| 1805 | SCH₃ | CO₂CH₃ | Cl | S |
| 1806 | SCH₃ | CO₂C₂H₅ | Cl | S |
| 1807 | SCH₃ | C(O)CH₃ | Cl | S |
| 1808 | SCH₃ | C(O)CF₃ | Cl | S |
| 1809 | SCH₃ | C(=NOCH₃)CH₃ | Cl | S |
| 1810 | SCH₃ | SO₂CH₃ | Cl | S |
| 1811 | SCH₃ | SO₂CF₃ | Cl | S |
| 1812 | SCH₃ | CH₂CO₂H | Cl | S |
| 1813 | SCH₃ | CH₂COOCH₃ | Cl | S |
| 1814 | SCH₃ | CH₂COOC₂H₅ | Cl | S |
| 1815 | SCH₃ | prop-1-en-3-yl | Cl | S |
| 1816 | SCH₃ | trans-but-2-en-1-yl | Cl | S |
| 1817 | SCH₃ | cis-but-2-en-1-yl | Cl | S |
| 1818 | SCH₃ | cis-3-methyl-but-2-en-1-yl | Cl | S |
| 1819 | SCH₃ | cyclopropyl | Cl | S |
| 1820 | SCH₃ | cyclopentyl | Cl | S |
| 1821 | SCH₃ | cyclohexyl | Cl | S |
| 1822 | SCH₃ | 4,5-dihydroisoxazol-3-yl | Cl | S |
| 1823 | SCH₃ | 4-methyl-4,5-dihydro-isoxazol-3-yl | Cl | S |
| 1824 | SCH₃ | isoxazol-3-yl | Cl | S |
| 1825 | SCH₃ | 4-methylisoxazol-3-yl | Cl | S |
| 1826 | SCH₃ | 4,5-dihydroisoxazol-4-yl | Cl | S |
| 1827 | SCH₃ | 3-methyl-4,5-dihydro-isoxazol-4-yl | Cl | S |
| 1828 | SCH₃ | isoxazol-4-yl | Cl | S |
| 1829 | SCH₃ | 3-methylisoxazol-4-yl | Cl | S |
| 1830 | SCH₃ | phenyl | Cl | S |
| 1831 | SCH₃ | benzyl | Cl | S |
| 1832 | SCH₃ | benzoyl | Cl | S |
| 1833 | SCH₃ | 2-pyridyl | Cl | S |
| 1834 | SO₂CH₃ | H | H | S |
| 1835 | SO₂CH₃ | CH₃ | H | S |
| 1836 | SO₂CH₃ | C₂H₅ | H | S |
| 1837 | SO₂CH₃ | n-C₃H₇ | H | S |
| 1838 | SO₂CH₃ | i-C₃H₇ | H | S |
| 1839 | SO₂CH₃ | n-C₄H₉ | H | S |
| 1840 | SO₂CH₃ | i-C₄H₉ | H | S |
| 1841 | SO₂CH₃ | s-C₄H₉ | H | S |
| 1842 | SO₂CH₃ | t-C₄H₉ | H | S |
| 1843 | SO₂CH₃ | CH₂OCH₃ | H | S |
| 1844 | SO₂CH₃ | CF₃ | H | S |
| 1845 | SO₂CH₃ | CF₂H | H | S |
| 1846 | SO₂CH₃ | CN | H | S |
| 1847 | SO₂CH₃ | OH | H | S |
| 1848 | SO₂CH₃ | OCH₃ | H | S |
| 1849 | SO₂CH₃ | NH₂ | H | S |
| 1850 | SO₂CH₃ | NHCH₃ | H | S |
| 1851 | SO₂CH₃ | N(CH₃)₂ | H | S |
| 1852 | SO₂CH₃ | CO₂CH₃ | H | S |
| 1853 | SO₂CH₃ | CO₂C₂H₅ | H | S |
| 1854 | SO₂CH₃ | C(O)CH₃ | H | S |
| 1855 | SO₂CH₃ | C(O)CF₃ | H | S |
| 1856 | SO₂CH₃ | C(=NOCH₃)CH₃ | H | S |
| 1857 | SO₂CH₃ | SO₂CH₃ | H | S |
| 1858 | SO₂CH₃ | SO₂CF₃ | H | S |
| 1859 | SO₂CH₃ | CH₂CO₂H | H | S |
| 1860 | SO₂CH₃ | CH₂COOCH₃ | H | S |
| 1861 | SO₂CH₃ | CH₂COOC₂H₅ | H | S |
| 1862 | SO₂CH₃ | prop-1-en-3-yl | H | S |
| 1863 | SO₂CH₃ | trans-but-2-en-1-yl | H | S |
| 1864 | SO₂CH₃ | cis-but-2-en-1-yl | H | S |
| 1865 | SO₂CH₃ | cis-3-methyl-but-2-en-1-yl | H | S |
| 1866 | SO₂CH₃ | cyclopropyl | H | S |
| 1867 | SO₂CH₃ | cyclopentyl | H | S |
| 1868 | SO₂CH₃ | cyclohexyl | H | S |
| 1869 | SO₂CH₃ | 4,5-dihydroisoxazol-3-yl | H | S |
| 1870 | SO₂CH₃ | 4-methyl-4,5-dihydro-isoxazol-3-yl | H | S |
| 1871 | SO₂CH₃ | isoxazol-3-yl | H | S |
| 1872 | SO₂CH₃ | 4-methylisoxazol-3-yl | H | S |
| 1873 | SO₂CH₃ | 4,5-dihydroisoxazol-4-yl | H | S |
| 1874 | SO₂CH₃ | 3-methyl-4,5-dihydro-isoxazol-4-yl | H | S |
| 1875 | SO₂CH₃ | isoxazol-4-yl | H | S |
| 1876 | SO₂CH₃ | 3-methylisoxazol-4-yl | H | S |
| 1877 | SO₂CH₃ | phenyl | H | S |
| 1878 | SO₂CH₃ | benzyl | H | S |
| 1879 | SO₂CH₃ | benzoyl | H | S |
| 1880 | SO₂CH₃ | 2-pyridyl | H | S |
| 1881 | SO₂CH₃ | H | CH₃ | S |
| 1882 | SO₂CH₃ | CH₃ | CH₃ | S |
| 1883 | SO₂CH₃ | C₂H₅ | CH₃ | S |
| 1884 | SO₂CH₃ | n-C₃H₇ | CH₃ | S |
| 1885 | SO₂CH₃ | i-C₃H₇ | CH₃ | S |
| 1886 | SO₂CH₃ | n-C₄H₉ | CH₃ | S |
| 1887 | SO₂CH₃ | i-C₄H₉ | CH₃ | S |
| 1888 | SO₂CH₃ | s-C₄H₉ | CH₃ | S |
| 1889 | SO₂CH₃ | t-C₄H₉ | CH₃ | S |
| 1890 | SO₂CH₃ | CH₂OCH₃ | CH₃ | S |
| 1891 | SO₂CH₃ | CF₃ | CH₃ | S |
| 1892 | SO₂CH₃ | CF₂H | CH₃ | S |
| 1893 | SO₂CH₃ | CN | CH₃ | S |
| 1894 | SO₂CH₃ | OH | CH₃ | S |
| 1895 | SO₂CH₃ | OCH₃ | CH₃ | S |
| 1896 | SO₂CH₃ | NH₂ | CH₃ | S |
| 1897 | SO₂CH₃ | NHCH₃ | CH₃ | S |
| 1898 | SO₂CH₃ | N(CH₃)₂ | CH₃ | S |
| 1899 | SO₂CH₃ | CO₂CH₃ | CH₃ | S |
| 1900 | SO₂CH₃ | CO₂C₂H₅ | CH₃ | S |
| 1901 | SO₂CH₃ | C(O)CH₃ | CH₃ | S |
| 1902 | SO₂CH₃ | C(O)CF₃ | CH₃ | S |
| 1903 | SO₂CH₃ | C(=NOCH₃)CH₃ | CH₃ | S |
| 1904 | SO₂CH₃ | SO₂CH₃ | CH₃ | S |
| 1905 | SO₂CH₃ | SO₂CF₃ | CH₃ | S |
| 1906 | SO₂CH₃ | CH₂CO₂H | CH₃ | S |
| 1907 | SO₂CH₃ | CH₂COOCH₃ | CH₃ | S |
| 1908 | SO₂CH₃ | CH₂COOC₂H₅ | CH₃ | S |
| 1909 | SO₂CH₃ | prop-1-en-3-yl | CH₃ | S |
| 1910 | SO₂CH₃ | trans-but-2-en-1-yl | CH₃ | S |
| 1911 | SO₂CH₃ | cis-but-2-en-1-yl | CH₃ | S |
| 1912 | SO₂CH₃ | cis-3-methyl-but-2-en-1-yl | CH₃ | S |
| 1913 | SO₂CH₃ | cyclopropyl | CH₃ | S |
| 1914 | SO₂CH₃ | cyclopentyl | CH₃ | S |
| 1915 | SO₂CH₃ | cyclohexyl | CH₃ | S |
| 1916 | SO₂CH₃ | 4,5-dihydroisoxazol-3-yl | CH₃ | S |
| 1917 | SO₂CH₃ | 4-methyl-4,5-dihydro-isoxazol-3-yl | CH₃ | S |
| 1918 | SO₂CH₃ | isoxazol-3-yl | CH₃ | S |
| 1919 | SO₂CH₃ | 4-methylisoxazol-3-yl | CH₃ | S |
| 1920 | SO₂CH₃ | 4,5-dihydroisoxazol-4-yl | CH₃ | S |
| 1921 | SO₂CH₃ | 3-methyl-4,5-dihydro-isoxazol-4-yl | CH₃ | S |
| 1922 | SO₂CH₃ | isoxazol-4-yl | CH₃ | S |
| 1923 | SO₂CH₃ | 3-methylisoxazol-4-yl | CH₃ | S |
| 1924 | SO₂CH₃ | phenyl | CH₃ | S |
| 1925 | SO₂CH₃ | benzyl | CH₃ | S |

TABLE A-continued

| No. | R¹ | R² | R³ | A |
|---|---|---|---|---|
| 1926 | SO₂CH₃ | benzoyl | CH₃ | S |
| 1927 | SO₂CH₃ | 2-pyridyl | CH₃ | S |
| 1928 | SO₂CH₃ | H | Cl | S |
| 1929 | SO₂CH₃ | CH₃ | Cl | S |
| 1930 | SO₂CH₃ | C₂H₅ | Cl | S |
| 1931 | SO₂CH₃ | n-C₃H₇ | Cl | S |
| 1932 | SO₂CH₃ | i-C₃H₇ | Cl | S |
| 1933 | SO₂CH₃ | n-C₄H₉ | Cl | S |
| 1934 | SO₂CH₃ | i-C₄H₉ | Cl | S |
| 1935 | SO₂CH₃ | s-C₄H₉ | Cl | S |
| 1936 | SO₂CH₃ | t-C₄H₉ | Cl | S |
| 1937 | SO₂CH₃ | CH₂OCH₃ | Cl | S |
| 1938 | SO₂CH₃ | CF₃ | Cl | S |
| 1939 | SO₂CH₃ | CF₂H | Cl | S |
| 1940 | SO₂CH₃ | CN | Cl | S |
| 1941 | SO₂CH₃ | OH | Cl | S |
| 1942 | SO₂CH₃ | OCH₃ | Cl | S |
| 1943 | SO₂CH₃ | NH₂ | Cl | S |
| 1944 | SO₂CH₃ | NHCH₃ | Cl | S |
| 1945 | SO₂CH₃ | N(CH₃)₂ | Cl | S |
| 1946 | SO₂CH₃ | CO₂CH₃ | Cl | S |
| 1947 | SO₂CH₃ | CO₂C₂H₅ | Cl | S |
| 1948 | SO₂CH₃ | C(O)CH₃ | Cl | S |
| 1949 | SO₂CH₃ | C(O)CF₃ | Cl | S |
| 1950 | SO₂CH₃ | C(=NOCH₃)CH₃ | Cl | S |
| 1951 | SO₂CH₃ | SO₂CH₃ | Cl | S |
| 1952 | SO₂CH₃ | SO₂CF₃ | Cl | S |
| 1953 | SO₂CH₃ | CH₂CO₂H | Cl | S |
| 1954 | SO₂CH₃ | CH₂COOCH₃ | Cl | S |
| 1955 | SO₂CH₃ | CH₂COOC₂H₅ | Cl | S |
| 1956 | SO₂CH₃ | prop-1-en-3-yl | Cl | S |
| 1957 | SO₂CH₃ | trans-but-2-en-1-yl | Cl | S |
| 1958 | SO₂CH₃ | cis-but-2-en-1-yl | Cl | S |
| 1959 | SO₂CH₃ | cis-3-methyl-but-2-en-1-yl | Cl | S |
| 1960 | SO₂CH₃ | cyclopropyl | Cl | S |
| 1961 | SO₂CH₃ | cyclopentyl | Cl | S |
| 1962 | SO₂CH₃ | cyclohexyl | Cl | S |
| 1963 | SO₂CH₃ | 4,5-dihydroisoxazol-3-yl | Cl | S |
| 1964 | SO₂CH₃ | 4-methyl-4,5-dihydro-isoxazol-3-yl | Cl | S |
| 1965 | SO₂CH₃ | isoxazol-3-yl | Cl | S |
| 1966 | SO₂CH₃ | 4-methylisoxazol-3-yl | Cl | S |
| 1967 | SO₂CH₃ | 4,5-dihydroisoxazol-4-yl | Cl | S |
| 1968 | SO₂CH₃ | 3-methyl-4,5-dihydro-isoxazol-4-yl | Cl | S |
| 1969 | SO₂CH₃ | isoxazol-4-yl | Cl | S |
| 1970 | SO₂CH₃ | 3-methylisoxazol-4-yl | Cl | S |
| 1971 | SO₂CH₃ | phenyl | Cl | S |
| 1972 | SO₂CH₃ | benzyl | Cl | S |
| 1973 | SO₂CH₃ | benzoyl | Cl | S |
| 1974 | SO₂CH₃ | 2-pyridyl | Cl | S |
| 1975 | CF₃ | H | H | S |
| 1976 | CF₃ | CH₃ | H | S |
| 1977 | CF₃ | C₂H₅ | H | S |
| 1978 | CF₃ | n-C₃H₇ | H | S |
| 1979 | CF₃ | i-C₃H₇ | H | S |
| 1980 | CF₃ | n-C₄H₉ | H | S |
| 1981 | CF₃ | i-C₄H₉ | H | S |
| 1982 | CF₃ | s-C₄H₉ | H | S |
| 1983 | CF₃ | t-C₄H₉ | H | S |
| 1984 | CF₃ | CH₂OCH₃ | H | S |
| 1985 | CF₃ | CF₃ | H | S |
| 1986 | CF₃ | CF₂H | H | S |
| 1987 | CF₃ | CN | H | S |
| 1988 | CF₃ | OH | H | S |
| 1989 | CF₃ | OCH₃ | H | S |
| 1990 | CF₃ | NH₂ | H | S |
| 1991 | CF₃ | NHCH₃ | H | S |
| 1992 | CF₃ | N(CH₃)₂ | H | S |
| 1993 | CF₃ | CO₂CH₃ | H | S |
| 1994 | CF₃ | CO₂C₂H₅ | H | S |
| 1995 | CF₃ | C(O)CH₃ | H | S |
| 1996 | CF₃ | C(O)CF₃ | H | S |
| 1997 | CF₃ | C(=NOCH₃)CH₃ | H | S |
| 1998 | CF₃ | SO₂CH₃ | H | S |
| 1999 | CF₃ | SO₂CF₃ | H | S |
| 2000 | CF₃ | CH₂CO₂H | H | S |
| 2001 | CF₃ | CH₂COOCH₃ | H | S |
| 2002 | CF₃ | CH₂COOC₂H₅ | H | S |
| 2003 | CF₃ | prop-1-en-3-yl | H | S |
| 2004 | CF₃ | trans-but-2-en-1-yl | H | S |
| 2005 | CF₃ | cis-but-2-en-1-yl | H | S |
| 2006 | CF₃ | cis-3-methyl-but-2-en-1-yl | H | S |
| 2007 | CF₃ | cyclopropyl | H | S |
| 2008 | CF₃ | cyclopentyl | H | S |
| 2009 | CF₃ | cyclohexyl | H | S |
| 2010 | CF₃ | 4,5-dihydroisoxazol-3-yl | H | S |
| 2011 | CF₃ | 4-methyl-4,5-dihydro-isoxazol-3-yl | H | S |
| 2012 | CF₃ | isoxazol-3-yl | H | S |
| 2013 | CF₃ | 4-methylisoxazol-3-yl | H | S |
| 2014 | CF₃ | 4,5-dihydroisoxazol-4-yl | H | S |
| 2015 | CF₃ | 3-methyl-4,5-dihydro-isoxazol-4-yl | H |   |
| 2016 | CF₃ | isoxazol-4-yl | H | S |
| 2017 | CF₃ | 3-methylisoxazol-4-yl | H | S |
| 2018 | CF₃ | phenyl | H | S |
| 2019 | CF₃ | benzyl | H | S |
| 2020 | CF₃ | benzoyl | H | S |
| 2021 | CF₃ | 2-pyridyl | H | S |
| 2022 | CF₃ | H | CH₃ | S |
| 2023 | CF₃ | CH₃ | CH₃ | S |
| 2024 | CF₃ | C₂H₅ | CH₃ | S |
| 2025 | CF₃ | n-C₃H₇ | CH₃ | S |
| 2026 | CF₃ | i-C₃H₇ | CH₃ | S |
| 2027 | CF₃ | n-C₄H₉ | CH₃ | S |
| 2028 | CF₃ | i-C₄H₉ | CH₃ | S |
| 2029 | CF₃ | s-C₄H₉ | CH₃ | S |
| 2030 | CF₃ | t-C₄H₉ | CH₃ | S |
| 2031 | CF₃ | CH₂OCH₃ | CH₃ | S |
| 2032 | CF₃ | CF₃ | CH₃ | S |
| 2033 | CF₃ | CF₂H | CH₃ | S |
| 2034 | CF₃ | CN | CH₃ | S |
| 2035 | CF₃ | OH | CH₃ | S |
| 2036 | CF₃ | OCH₃ | CH₃ | S |
| 2037 | CF₃ | NH₂ | CH₃ | S |
| 2038 | CF₃ | NHCH₃ | CH₃ | S |
| 2039 | CF₃ | N(CH₃)₂ | CH₃ | S |
| 2040 | CF₃ | CO₂CH₃ | CH₃ | S |
| 2041 | CF₃ | CO₂C₂H₅ | CH₃ | S |
| 2042 | CF₃ | C(O)CH₃ | CH₃ | S |
| 2043 | CF₃ | C(O)CF₃ | CH₃ | S |
| 2044 | CF₃ | C(=NOCH₃)CH₃ | CH₃ | S |
| 2045 | CF₃ | SO₂CH₃ | CH₃ | S |
| 2046 | CF₃ | SO₂CF₃ | CH₃ | S |
| 2047 | CF₃ | CH₂CO₂H | CH₃ | S |
| 2048 | CF₃ | CH₂COOCH₃ | CH₃ | S |
| 2049 | CF₃ | CH₂COOC₂H₅ | CH₃ | S |
| 2050 | CF₃ | prop-1-en-3-yl | CH₃ | S |
| 2051 | CF₃ | trans-but-2-en-1-yl | CH₃ | S |
| 2052 | CF₃ | cis-but-2-en-1-yl | CH₃ | S |
| 2053 | CF₃ | cis-3-methyl-but-2-en-1-yl | CH₃ | S |
| 2054 | CF₃ | cyclopropyl | CH₃ | S |
| 2055 | CF₃ | cyclopentyl | CH₃ | S |
| 2056 | CF₃ | cyclohexyl | CH₃ | S |
| 2057 | CF₃ | 4,5-dihydroisoxazol-3-yl | CH₃ | S |
| 2058 | CF₃ | 4-methyl-4,5-dihydro-isoxazol-3-yl | CH₃ | S |
| 2059 | CF₃ | isoxazol-3-yl | CH₃ | S |
| 2060 | CF₃ | 4-methylisoxazol-3-yl | CH₃ | S |
| 2061 | CF₃ | 4,5-dihydroisoxazol-4-yl | CH₃ | S |
| 2062 | CF₃ | 3-methyl-4,5-dihydro-isoxazol-4-yl | CH₃ | S |
| 2063 | CF₃ | isoxazol-4-yl | CH₃ | S |
| 2064 | CF₃ | 3-methylisoxazol-4-yl | CH₃ | S |

TABLE A-continued

| No. | R¹ | R² | R³ | A |
|---|---|---|---|---|
| 2065 | CF₃ | phenyl | CH₃ | S |
| 2066 | CF₃ | benzyl | CH₃ | S |
| 2067 | CF₃ | benzoyl | CH₃ | S |
| 2068 | CF₃ | 2-pyridyl | CH₃ | S |
| 2069 | CF₃ | H | Cl | S |
| 2070 | CF₃ | CH₃ | Cl | S |
| 2071 | CF₃ | C₂H₅ | Cl | S |
| 2072 | CF₃ | n-C₃H₇ | Cl | S |
| 2073 | CF₃ | i-C₃H₇ | Cl | S |
| 2074 | CF₃ | n-C₄H₉ | Cl | S |
| 2075 | CF₃ | i-C₄H₉ | Cl | S |
| 2076 | CF₃ | s-C₄H₉ | Cl | S |
| 2077 | CF₃ | t-C₄H₉ | Cl | S |
| 2078 | CF₃ | CH₂OCH₃ | Cl | S |
| 2079 | CF₃ | CF₃ | Cl | S |
| 2080 | CF₃ | CF₂H | Cl | S |
| 2081 | CF₃ | CN | Cl | S |
| 2082 | CF₃ | OH | Cl | S |
| 2083 | CF₃ | OCH₃ | Cl | S |
| 2084 | CF₃ | NH₂ | Cl | S |
| 2085 | CF₃ | NHCH₃ | Cl | S |
| 2086 | CF₃ | N(CH₃)₂ | Cl | S |
| 2087 | CF₃ | CO₂CH₃ | Cl | S |
| 2088 | CF₃ | CO₂C₂H₅ | Cl | S |
| 2089 | CF₃ | C(O)CH₃ | Cl | S |
| 2090 | CF₃ | C(O)CF₃ | Cl | S |
| 2091 | CF₃ | C(=NOCH₃)CH₃ | Cl | S |
| 2092 | CF₃ | SO₂CH₃ | Cl | S |
| 2093 | CF₃ | SO₂CF₃ | Cl | S |
| 2094 | CF₃ | CH₂CO₂H | Cl | S |
| 2095 | CF₃ | CH₂COOCH₃ | Cl | S |
| 2096 | CF₃ | CH₂COOC₂H₅ | Cl | S |
| 2097 | CF₃ | prop-1-en-3-yl | Cl | S |
| 2098 | CF₃ | trans-but-2-en-1-yl | Cl | S |
| 2099 | CF₃ | cis-but-2-en-1-yl | Cl | S |
| 2100 | CF₃ | cis-3-methyl-but-2-en-1-yl | Cl | S |
| 2101 | CF₃ | cyclopropyl | Cl | S |
| 2102 | CF₃ | cyclopentyl | Cl | S |
| 2103 | CF₃ | cyclohexyl | Cl | S |
| 2104 | CF₃ | 4,5-dihydroisoxazol-3-yl | Cl | S |
| 2105 | CF₃ | 4-methyl-4,5-dihydro-isoxazol-3-yl | Cl | S |
| 2106 | CF₃ | isoxazol-3-yl | Cl | S |
| 2107 | CF₃ | 4-methylisoxazol-3-yl | Cl | S |
| 2108 | CF₃ | 4,5-dihydroisoxazol-4-yl | Cl | S |
| 2109 | CF₃ | 3-methyl-4,5-dihydro-isoxazol-4-yl | Cl | S |
| 2110 | CF₃ | isoxazol-4-yl | Cl | S |
| 2111 | CF₃ | 3-methylisoxazol-4-yl | Cl | S |
| 2112 | CF₃ | phenyl | Cl | S |
| 2113 | CF₃ | benzyl | Cl | S |
| 2114 | CF₃ | benzoyl | Cl | S |
| 2115 | CF₃ | 2-pyridyl | Cl | S |
| 2116 | C₂H₅ | H | H | S |
| 2117 | C₂H₅ | CH₃ | H | S |
| 2118 | C₂H₅ | C₂H₅ | H | S |
| 2119 | C₂H₅ | n-C₃H₇ | H | S |
| 2120 | C₂H₅ | i-C₃H₇ | H | S |
| 2121 | C₂H₅ | n-C₄H₉ | H | S |
| 2122 | C₂H₅ | i-C₄H₉ | H | S |
| 2123 | C₂H₅ | s-C₄H₉ | H | S |
| 2124 | C₂H₅ | t-C₄H₉ | H | S |
| 2125 | C₂H₅ | CH₂OCH₃ | H | S |
| 2126 | C₂H₅ | CF₃ | H | S |
| 2127 | C₂H₅ | CF₂H | H | S |
| 2128 | C₂H₅ | CN | H | S |
| 2129 | C₂H₅ | OH | H | S |
| 2130 | C₂H₅ | OCH₃ | H | S |
| 2131 | C₂H₅ | NH₂ | H | S |
| 2132 | C₂H₅ | NHCH₃ | H | S |
| 2133 | C₂H₅ | N(CH₃)₂ | H | S |
| 2134 | C₂H₅ | CO₂CH₃ | H | S |
| 2135 | C₂H₅ | CO₂C₂H₅ | H | S |
| 2136 | C₂H₅ | C(O)CH₃ | H | S |
| 2137 | C₂H₅ | C(O)CF₃ | H | S |
| 2138 | C₂H₅ | C(=NOCH₃)CH₃ | H | S |
| 2139 | C₂H₅ | SO₂CH₃ | H | S |
| 2140 | C₂H₅ | SO₂CF₃ | H | S |
| 2141 | C₂H₅ | CH₂CO₂H | H | S |
| 2142 | C₂H₅ | CH₂COOCH₃ | H | S |
| 2143 | C₂H₅ | CH₂COOC₂H₅ | H | S |
| 2144 | C₂H₅ | prop-1-en-3-yl | H | S |
| 2145 | C₂H₅ | trans-but-2-en-1-yl | H | S |
| 2146 | C₂H₅ | cis-but-2-en-1-yl | H | S |
| 2147 | C₂H₅ | cis-3-methyl-but-2-en-1-yl | H | S |
| 2148 | C₂H₅ | cyclopropyl | H | S |
| 2149 | C₂H₅ | cyclopentyl | H | S |
| 2150 | C₂H₅ | cyclohexyl | H | S |
| 2151 | C₂H₅ | 4,5-dihydroisoxazol-3-yl | H | S |
| 2152 | C₂H₅ | 4-methyl-4,5-dihydro-isoxazol-3-yl | H | S |
| 2153 | C₂H₅ | isoxazol-3-yl | H | S |
| 2154 | C₂H₅ | 4-methylisoxazol-3-yl | H | S |
| 2155 | C₂H₅ | 4,5-dihydroisoxazol-4-yl | H | S |
| 2156 | C₂H₅ | 3-methyl-4,5-dihydro-isoxazol-4-yl | H | S |
| 2157 | C₂H₅ | isoxazol-4-yl | H | S |
| 2158 | C₂H₅ | 3-methylisoxazol-4-yl | H | S |
| 2159 | C₂H₅ | phenyl | H | S |
| 2160 | C₂H₅ | benzyl | H | S |
| 2161 | C₂H₅ | benzoyl | H | S |
| 2162 | C₂H₅ | 2-pyridyl | H | S |
| 2163 | C₂H₅ | H | CH₃ | S |
| 2164 | C₂H₅ | CH₃ | CH₃ | S |
| 2165 | C₂H₅ | C₂H₅ | CH₃ | S |
| 2166 | C₂H₅ | n-C₃H₇ | CH₃ | S |
| 2167 | C₂H₅ | i-C₃H₇ | CH₃ | S |
| 2168 | C₂H₅ | n-C₄H₉ | CH₃ | S |
| 2169 | C₂H₅ | i-C₄H₉ | CH₃ | S |
| 2170 | C₂H₅ | s-C₄H₉ | CH₃ | S |
| 2171 | C₂H₅ | t-C₄H₉ | CH₃ | S |
| 2172 | C₂H₅ | CH₂OCH₃ | CH₃ | S |
| 2173 | C₂H₅ | CF₃ | CH₃ | S |
| 2174 | C₂H₅ | CF₂H | CH₃ | S |
| 2175 | C₂H₅ | CN | CH₃ | S |
| 2176 | C₂H₅ | OH | CH₃ | S |
| 2177 | C₂H₅ | OCH₃ | CH₃ | S |
| 2178 | C₂H₅ | NH₂ | CH₃ | S |
| 2179 | C₂H₅ | NHCH₃ | CH₃ | S |
| 2180 | C₂H₅ | N(CH₃)₂ | CH₃ | S |
| 2181 | C₂H₅ | CO₂CH₃ | CH₃ | S |
| 2182 | C₂H₅ | CO₂C₂H₅ | CH₃ | S |
| 2183 | C₂H₅ | C(O)CH₃ | CH₃ | S |
| 2184 | C₂H₅ | C(O)CF₃ | CH₃ | S |
| 2185 | C₂H₅ | C(=NOCH₃)CH₃ | CH₃ | S |
| 2186 | C₂H₅ | SO₂CH₃ | CH₃ | S |
| 2187 | C₂H₅ | SO₂CF₃ | CH₃ | S |
| 2188 | C₂H₅ | CH₂CO₂H | CH₃ | S |
| 2189 | C₂H₅ | CH₂COOCH₃ | CH₃ | S |
| 2190 | C₂H₅ | CH₂COOC₂H₅ | CH₃ | S |
| 2191 | C₂H₅ | prop-1-en-3-yl | CH₃ | S |
| 2192 | C₂H₅ | trans-but-2-en-1-yl | CH₃ | S |
| 2193 | C₂H₅ | cis-but-2-en-1-yl | CH₃ | S |
| 2194 | C₂H₅ | cis-3-methyl-but-2-en-1-yl | CH₃ | S |
| 2195 | C₂H₅ | cyclopropyl | CH₃ | S |
| 2196 | C₂H₅ | cyclopentyl | CH₃ | S |
| 2197 | C₂H₅ | cyclohexyl | CH₃ | S |
| 2198 | C₂H₅ | 4,5-dihydroisoxazol-3-yl | CH₃ | S |
| 2199 | C₂H₅ | 4-methyl-4,5-dihydro-isoxazol-3-yl | CH₃ | S |
| 2200 | C₂H₅ | isoxazol-3-yl | CH₃ | S |
| 2201 | C₂H₅ | 4-methylisoxazol-3-yl | CH₃ | S |
| 2202 | C₂H₅ | 4,5-dihydroisoxazol-4-yl | CH₃ | S |
| 2203 | C₂H₅ | 3-methyl-4,5-dihydro-isoxazol-4-yl | CH₃ | S |

TABLE A-continued

| No. | R¹ | R² | R³ | A |
|---|---|---|---|---|
| 2204 | $C_2H_5$ | isoxazol-4-yl | $CH_3$ | S |
| 2205 | $C_2H_5$ | 3-methylisoxazol-4-yl | $CH_3$ | S |
| 2206 | $C_2H_5$ | phenyl | $CH_3$ | S |
| 2207 | $C_2H_5$ | benzyl | $CH_3$ | S |
| 2208 | $C_2H_5$ | benzoyl | $CH_3$ | S |
| 2209 | $C_2H_5$ | 2-pyridyl | $CH_3$ | S |
| 2210 | $C_2H_5$ | H | Cl | S |
| 2211 | $C_2H_5$ | $CH_3$ | Cl | S |
| 2212 | $C_2H_5$ | $C_2H_5$ | Cl | S |
| 2213 | $C_2H_5$ | n-$C_3H_7$ | Cl | S |
| 2214 | $C_2H_5$ | i-$C_3H_7$ | Cl | S |
| 2215 | $C_2H_5$ | n-$C_4H_9$ | Cl | S |
| 2216 | $C_2H_5$ | i-$C_4H_9$ | Cl | S |
| 2217 | $C_2H_5$ | s-$C_4H_9$ | Cl | S |
| 2218 | $C_2H_5$ | t-$C_4H_9$ | Cl | S |
| 2219 | $C_2H_5$ | $CH_2OCH_3$ | Cl | S |
| 2220 | $C_2H_5$ | $CF_3$ | Cl | S |
| 2221 | $C_2H_5$ | $CF_2H$ | Cl | S |
| 2222 | $C_2H_5$ | CN | Cl | S |
| 2223 | $C_2H_5$ | OH | Cl | S |
| 2224 | $C_2H_5$ | $OCH_3$ | Cl | S |
| 2225 | $C_2H_5$ | $NH_2$ | Cl | S |
| 2226 | $C_2H_5$ | $NHCH_3$ | Cl | S |
| 2227 | $C_2H_5$ | $N(CH_3)_2$ | Cl | S |
| 2228 | $C_2H_5$ | $CO_2CH_3$ | Cl | S |
| 2229 | $C_2H_5$ | $CO_2C_2H_5$ | Cl | S |
| 2230 | $C_2H_5$ | $C(O)CH_3$ | Cl | S |
| 2231 | $C_2H_5$ | $C(O)CF_3$ | Cl | S |
| 2232 | $C_2H_5$ | $C(=NOCH_3)CH_3$ | Cl | S |
| 2233 | $C_2H_5$ | $SO_2CH_3$ | Cl | S |
| 2234 | $C_2H_5$ | $SO_2CF_3$ | Cl | S |
| 2235 | $C_2H_5$ | $CH_2CO_2H$ | Cl | S |
| 2236 | $C_2H_5$ | $CH_2COOCH_3$ | Cl | S |
| 2237 | $C_2H_5$ | $CH_2COOC_2H_5$ | Cl | S |
| 2238 | $C_2H_5$ | prop-1-en-3-yl | Cl | S |
| 2239 | $C_2H_5$ | trans-but-2-en-1-yl | Cl | S |
| 2240 | $C_2H_5$ | cis-but-2-en-1-yl | Cl | S |
| 2241 | $C_2H_5$ | cis-3-methyl-but-2-en-1-yl | Cl | S |
| 2242 | $C_2H_5$ | cyclopropyl | Cl | S |
| 2243 | $C_2H_5$ | cyclopentyl | Cl | S |
| 2244 | $C_2H_5$ | cyclohexyl | Cl | S |
| 2245 | $C_2H_5$ | 4,5-dihydroisoxazol-3-yl | Cl | S |
| 2246 | $C_2H_5$ | 4-methyl-4,5-dihydro-isoxazol-3-yl | Cl | S |
| 2247 | $C_2H_5$ | isoxazol-3-yl | Cl | S |
| 2248 | $C_2H_5$ | 4-methylisoxazol-3-yl | Cl | S |
| 2249 | $C_2H_5$ | 4,5-dihydroisoxazol-4-yl | Cl | S |
| 2250 | $C_2H_5$ | 3-methyl-4,5-dihydro-isoxazol-4-yl | Cl | S |
| 2251 | $C_2H_5$ | isoxazol-4-yl | Cl | S |
| 2252 | $C_2H_5$ | 3-methylisoxazol-4-yl | Cl | S |
| 2253 | $C_2H_5$ | phenyl | Cl | S |
| 2254 | $C_2H_5$ | benzyl | Cl | S |
| 2255 | $C_2H_5$ | benzoyl | Cl | S |
| 2256 | $C_2H_5$ | 2-pyridyl | Cl | S |
| 2257 | $CH_3$ | H | H | $NCH_3$ |
| 2258 | $CH_3$ | $CH_3$ | H | $NCH_3$ |
| 2259 | $CH_3$ | $C_2H_5$ | H | $NCH_3$ |
| 2260 | $CH_3$ | n-$C_3H_7$ | H | $NCH_3$ |
| 2261 | $CH_3$ | i-$C_3H_7$ | H | $NCH_3$ |
| 2262 | $CH_3$ | n-$C_4H_9$ | H | $NCH_3$ |
| 2263 | $CH_3$ | i-$C_4H_9$ | H | $NCH_3$ |
| 2264 | $CH_3$ | s-$C_4H_9$ | H | $NCH_3$ |
| 2265 | $CH_3$ | t-$C_4H_9$ | H | $NCH_3$ |
| 2266 | $CH_3$ | $CH_2OCH_3$ | H | $NCH_3$ |
| 2267 | $CH_3$ | $CF_3$ | H | $NCH_3$ |
| 2268 | $CH_3$ | $CF_2H$ | H | $NCH_3$ |
| 2269 | $CH_3$ | CN | H | $NCH_3$ |
| 2270 | $CH_3$ | OH | H | $NCH_3$ |
| 2271 | $CH_3$ | $OCH_3$ | H | $NCH_3$ |
| 2272 | $CH_3$ | $NH_2$ | H | $NCH_3$ |
| 2273 | $CH_3$ | $NHCH_3$ | H | $NCH_3$ |
| 2274 | $CH_3$ | $N(CH_3)_2$ | H | $NCH_3$ |
| 2275 | $CH_3$ | $CO_2CH_3$ | H | $NCH_3$ |
| 2276 | $CH_3$ | $CO_2C_2H_5$ | H | $NCH_3$ |
| 2277 | $CH_3$ | $C(O)CH_3$ | H | $NCH_3$ |
| 2278 | $CH_3$ | $C(O)CF_3$ | H | $NCH_3$ |
| 2279 | $CH_3$ | $C(=NOCH_3)CH_3$ | H | $NCH_3$ |
| 2280 | $CH_3$ | $SO_2CH_3$ | H | $NCH_3$ |
| 2281 | $CH_3$ | $SO_2CF_3$ | H | $NCH_3$ |
| 2282 | $CH_3$ | $CH_2CO_2H$ | H | $NCH_3$ |
| 2283 | $CH_3$ | $CH_2COOCH_3$ | H | $NCH_3$ |
| 2284 | $CH_3$ | $CH_2COOC_2H_5$ | H | $NCH_3$ |
| 2285 | $CH_3$ | prop-1-en-3-yl | H | $NCH_3$ |
| 2286 | $CH_3$ | trans-but-2-en-1-yl | H | $NCH_3$ |
| 2287 | $CH_3$ | cis-but-2-en-1-yl | H | $NCH_3$ |
| 2288 | $CH_3$ | cis-3-methyl-but-2-en-1-yl | H | $NCH_3$ |
| 2289 | $CH_3$ | cyclopropyl | H | $NCH_3$ |
| 2290 | $CH_3$ | cyclopentyl | H | $NCH_3$ |
| 2291 | $CH_3$ | cyclohexyl | H | $NCH_3$ |
| 2292 | $CH_3$ | 4,5-dihydroisoxazol-3-yl | H | $NCH_3$ |
| 2293 | $CH_3$ | 4-methyl-4,5-dihydro-isoxazol-3-yl | H | $NCH_3$ |
| 2294 | $CH_3$ | isoxazol-3-yl | H | $NCH_3$ |
| 2295 | $CH_3$ | 4-methylisoxazol-3-yl | H | $NCH_3$ |
| 2296 | $CH_3$ | 4,5-dihydroisoxazol-4-yl | H | $NCH_3$ |
| 2297 | $CH_3$ | 3-methyl-4,5-dihydro-isoxazol-4-yl | H | $NCH_3$ |
| 2298 | $CH_3$ | isoxazol-4-yl | H | $NCH_3$ |
| 2299 | $CH_3$ | 3-methylisoxazol-4-yl | H | $NCH_3$ |
| 2300 | $CH_3$ | phenyl | H | $NCH_3$ |
| 2301 | $CH_3$ | benzyl | H | $NCH_3$ |
| 2302 | $CH_3$ | benzoyl | H | $NCH_3$ |
| 2303 | $CH_3$ | 2-pyridyl | H | $NCH_3$ |
| 2304 | $CH_3$ | H | $CH_3$ | $NCH_3$ |
| 2305 | $CH_3$ | $CH_3$ | $CH_3$ | $NCH_3$ |
| 2306 | $CH_3$ | $C_2H_5$ | $CH_3$ | $NCH_3$ |
| 2307 | $CH_3$ | n-$C_3H_7$ | $CH_3$ | $NCH_3$ |
| 2308 | $CH_3$ | i-$C_3H_7$ | $CH_3$ | $NCH_3$ |
| 2309 | $CH_3$ | n-$C_4H_9$ | $CH_3$ | $NCH_3$ |
| 2310 | $CH_3$ | i-$C_4H_9$ | $CH_3$ | $NCH_3$ |
| 2311 | $CH_3$ | s-$C_4H_9$ | $CH_3$ | $NCH_3$ |
| 2312 | $CH_3$ | t-$C_4H_9$ | $CH_3$ | $NCH_3$ |
| 2313 | $CH_3$ | $CH_2OCH_3$ | $CH_3$ | $NCH_3$ |
| 2314 | $CH_3$ | $CF_3$ | $CH_3$ | $NCH_3$ |
| 2315 | $CH_3$ | $CF_2H$ | $CH_3$ | $NCH_3$ |
| 2316 | $CH_3$ | CN | $CH_3$ | $NCH_3$ |
| 2317 | $CH_3$ | OH | $CH_3$ | $NCH_3$ |
| 2318 | $CH_3$ | $OCH_3$ | $CH_3$ | $NCH_3$ |
| 2319 | $CH_3$ | $NH_2$ | $CH_3$ | $NCH_3$ |
| 2320 | $CH_3$ | $NHCH_3$ | $CH_3$ | $NCH_3$ |
| 2321 | $CH_3$ | $N(CH_3)_2$ | $CH_3$ | $NCH_3$ |
| 2322 | $CH_3$ | $CO_2CH_3$ | $CH_3$ | $NCH_3$ |
| 2323 | $CH_3$ | $CO_2C_2H_5$ | $CH_3$ | $NCH_3$ |
| 2324 | $CH_3$ | $C(O)CH_3$ | $CH_3$ | $NCH_3$ |
| 2325 | $CH_3$ | $C(O)CF_3$ | $CH_3$ | $NCH_3$ |
| 2326 | $CH_3$ | $C(=NOCH_3)CH_3$ | $CH_3$ | $NCH_3$ |
| 2327 | $CH_3$ | $SO_2CH_3$ | $CH_3$ | $NCH_3$ |
| 2328 | $CH_3$ | $SO_2CF_3$ | $CH_3$ | $NCH_3$ |
| 2329 | $CH_3$ | $CH_2CO_2H$ | $CH_3$ | $NCH_3$ |
| 2330 | $CH_3$ | $CH_2COOCH_3$ | $CH_3$ | $NCH_3$ |
| 2331 | $CH_3$ | $CH_2COOC_2H_5$ | $CH_3$ | $NCH_3$ |
| 2332 | $CH_3$ | prop-1-en-3-yl | $CH_3$ | $NCH_3$ |
| 2333 | $CH_3$ | trans-but-2-en-1-yl | $CH_3$ | $NCH_3$ |
| 2334 | $CH_3$ | cis-but-2-en-1-yl | $CH_3$ | $NCH_3$ |
| 2335 | $CH_3$ | cis-3-methyl-but-2-en-1-yl | $CH_3$ | $NCH_3$ |
| 2336 | $CH_3$ | cyclopropyl | $CH_3$ | $NCH_3$ |
| 2337 | $CH_3$ | cyclopentyl | $CH_3$ | $NCH_3$ |
| 2338 | $CH_3$ | cyclohexyl | $CH_3$ | $NCH_3$ |
| 2339 | $CH_3$ | 4,5-dihydroisoxazol-3-yl | $CH_3$ | $NCH_3$ |
| 2340 | $CH_3$ | 4-methyl-4,5-dihydro-isoxazol-3-yl | $CH_3$ | $NCH_3$ |
| 2341 | $CH_3$ | isoxazol-3-yl | $CH_3$ | $NCH_3$ |
| 2342 | $CH_3$ | 4-methylisoxazol-3-yl | $CH_3$ | $NCH_3$ |

TABLE A-continued

| No. | R¹ | R² | R³ | A |
|---|---|---|---|---|
| 2343 | $CH_3$ | 4,5-dihydroisoxazol-4-yl | $CH_3$ | $NCH_3$ |
| 2344 | $CH_3$ | 3-methyl-4,5-dihydro-isoxazol-4-yl | $CH_3$ | $NCH_3$ |
| 2345 | $CH_3$ | isoxazol-4-yl | $CH_3$ | $NCH_3$ |
| 2346 | $CH_3$ | 3-methylisoxazol-4-yl | $CH_3$ | $NCH_3$ |
| 2347 | $CH_3$ | phenyl | $CH_3$ | $NCH_3$ |
| 2348 | $CH_3$ | benzyl | $CH_3$ | $NCH_3$ |
| 2349 | $CH_3$ | benzoyl | $CH_3$ | $NCH_3$ |
| 2350 | $CH_3$ | 2-pyridyl | $CH_3$ | $NCH_3$ |
| 2351 | $CH_3$ | H | Cl | $NCH_3$ |
| 2352 | $CH_3$ | $CH_3$ | Cl | $NCH_3$ |
| 2353 | $CH_3$ | $C_2H_5$ | Cl | $NCH_3$ |
| 2354 | $CH_3$ | $n-C_3H_7$ | Cl | $NCH_3$ |
| 2355 | $CH_3$ | $i-C_3H_7$ | Cl | $NCH_3$ |
| 2356 | $CH_3$ | $n-C_4H_9$ | Cl | $NCH_3$ |
| 2357 | $CH_3$ | $i-C_4H_9$ | Cl | $NCH_3$ |
| 2358 | $CH_3$ | $s-C_4H_9$ | Cl | $NCH_3$ |
| 2359 | $CH_3$ | $t-C_4H_9$ | Cl | $NCH_3$ |
| 2360 | $CH_3$ | $CH_2OCH_3$ | Cl | $NCH_3$ |
| 2361 | $CH_3$ | $CF_3$ | Cl | $NCH_3$ |
| 2362 | $CH_3$ | $CF_2H$ | Cl | $NCH_3$ |
| 2363 | $CH_3$ | CN | Cl | $NCH_3$ |
| 2364 | $CH_3$ | OH | Cl | $NCH_3$ |
| 2365 | $CH_3$ | $OCH_3$ | Cl | $NCH_3$ |
| 2366 | $CH_3$ | $NH_2$ | Cl | $NCH_3$ |
| 2367 | $CH_3$ | $NHCH_3$ | Cl | $NCH_3$ |
| 2368 | $CH_3$ | $N(CH_3)_2$ | Cl | $NCH_3$ |
| 2369 | $CH_3$ | $CO_2CH_3$ | Cl | $NCH_3$ |
| 2370 | $CH_3$ | $CO_2C_2H_5$ | Cl | $NCH_3$ |
| 2371 | $CH_3$ | $C(O)CH_3$ | Cl | $NCH_3$ |
| 2372 | $CH_3$ | $C(O)CF_3$ | Cl | $NCH_3$ |
| 2373 | $CH_3$ | $C(=NOCH_3)CH_3$ | Cl | $NCH_3$ |
| 2374 | $CH_3$ | $SO_2CH_3$ | Cl | $NCH_3$ |
| 2375 | $CH_3$ | $SO_2CF_3$ | Cl | $NCH_3$ |
| 2376 | $CH_3$ | $CH_2CO_2H$ | Cl | $NCH_3$ |
| 2377 | $CH_3$ | $CH_2COOCH_3$ | Cl | $NCH_3$ |
| 2378 | $CH_3$ | $CH_2COOC_2H_5$ | Cl | $NCH_3$ |
| 2379 | $CH_3$ | prop-1-en-3-yl | Cl | $NCH_3$ |
| 2380 | $CH_3$ | trans-but-2-en-1-yl | Cl | $NCH_3$ |
| 2381 | $CH_3$ | cis-but-2-en-1-yl | Cl | $NCH_3$ |
| 2382 | $CH_3$ | cis-3-methyl-but-2-en-1-yl | Cl | $NCH_3$ |
| 2383 | $CH_3$ | cyclopropyl | Cl | $NCH_3$ |
| 2384 | $CH_3$ | cyclopentyl | Cl | $NCH_3$ |
| 2385 | $CH_3$ | cyclohexyl | Cl | $NCH_3$ |
| 2386 | $CH_3$ | 4,5-dihydroisoxazol-3-yl | Cl | $NCH_3$ |
| 2387 | $CH_3$ | 4-methyl-4,5-dihydro-isoxazol-3-yl | Cl | $NCH_3$ |
| 2388 | $CH_3$ | isoxazol-3-yl | Cl | $NCH_3$ |
| 2389 | $CH_3$ | 4-methylisoxazol-3-yl | Cl | $NCH_3$ |
| 2390 | $CH_3$ | 4,5-dihydroisoxazol-4-yl | Cl | $NCH_3$ |
| 2391 | $CH_3$ | 3-methyl-4,5-dihydro-isoxazol-4-yl | Cl | $NCH_3$ |
| 2392 | $CH_3$ | isoxazol-4-yl | Cl | $NCH_3$ |
| 2393 | $CH_3$ | 3-methylisoxazol-4-yl | Cl | $NCH_3$ |
| 2394 | $CH_3$ | phenyl | Cl | $NCH_3$ |
| 2395 | $CH_3$ | benzyl | Cl | $NCH_3$ |
| 2396 | $CH_3$ | benzoyl | Cl | $NCH_3$ |
| 2397 | $CH_3$ | 2-pyridyl | Cl | $NCH_3$ |
| 2398 | Cl | H | H | $NCH_3$ |
| 2399 | Cl | $CH_3$ | H | $NCH_3$ |
| 2400 | Cl | $C_2H_5$ | H | $NCH_3$ |
| 2401 | Cl | $n-C_3H_7$ | H | $NCH_3$ |
| 2402 | Cl | $i-C_3H_7$ | H | $NCH_3$ |
| 2403 | Cl | $n-C_4H_9$ | H | $NCH_3$ |
| 2404 | Cl | $i-C_4H_9$ | H | $NCH_3$ |
| 2405 | Cl | $s-C_4H_9$ | H | $NCH_3$ |
| 2406 | Cl | $t-C_4H_9$ | H | $NCH_3$ |
| 2407 | Cl | $CH_2OCH_3$ | H | $NCH_3$ |
| 2408 | Cl | $CF_3$ | H | $NCH_3$ |
| 2409 | Cl | $CF_2H$ | H | $NCH_3$ |
| 2410 | Cl | CN | H | $NCH_3$ |
| 2411 | Cl | OH | H | $NCH_3$ |
| 2412 | Cl | $OCH_3$ | H | $NCH_3$ |
| 2413 | Cl | $NH_2$ | H | $NCH_3$ |
| 2414 | Cl | $NHCH_3$ | H | $NCH_3$ |
| 2415 | Cl | $N(CH_3)_2$ | H | $NCH_3$ |
| 2416 | Cl | $CO_2CH_3$ | H | $NCH_3$ |
| 2417 | Cl | $CO_2C_2H_5$ | H | $NCH_3$ |
| 2418 | Cl | $C(O)CH_3$ | H | $NCH_3$ |
| 2419 | Cl | $C(O)CF_3$ | H | $NCH_3$ |
| 2420 | Cl | $C(=NOCH_3)CH_3$ | H | $NCH_3$ |
| 2421 | Cl | $SO_2CH_3$ | H | $NCH_3$ |
| 2422 | Cl | $SO_2CF_3$ | H | $NCH_3$ |
| 2423 | Cl | $CH_2CO_2H$ | H | $NCH_3$ |
| 2424 | Cl | $CH_2COOCH_3$ | H | $NCH_3$ |
| 2425 | Cl | $CH_2COOC_2H_5$ | H | $NCH_3$ |
| 2426 | Cl | prop-1-en-3-yl | H | $NCH_3$ |
| 2427 | Cl | trans-but-2-en-1-yl | H | $NCH_3$ |
| 2428 | Cl | cis-but-2-en-1-yl | H | $NCH_3$ |
| 2429 | Cl | cis-3-methyl-but-2-en-1-yl | H | $NCH_3$ |
| 2430 | Cl | cyclopropyl | H | $NCH_3$ |
| 2431 | Cl | cyclopentyl | H | $NCH_3$ |
| 2432 | Cl | cyclohexyl | H | $NCH_3$ |
| 2433 | Cl | 4,5-dihydroisoxazol-3-yl | H | $NCH_3$ |
| 2434 | Cl | 4-methyl-4,5-dihydro-isoxazol-3-yl | H | $NCH_3$ |
| 2435 | Cl | isoxazol-3-yl | H | $NCH_3$ |
| 2436 | Cl | 4-methylisoxazol-3-yl | H | $NCH_3$ |
| 2437 | Cl | 4,5-dihydroisoxazol-4-yl | H | $NCH_3$ |
| 2438 | Cl | 3-methyl-4,5-dihydro-isoxazol-4-yl | H | $NCH_3$ |
| 2439 | Cl | isoxazol-4-yl | H | $NCH_3$ |
| 2440 | Cl | 3-methylisoxazol-4-yl | H | $NCH_3$ |
| 2441 | Cl | phenyl | H | $NCH_3$ |
| 2442 | Cl | benzyl | H | $NCH_3$ |
| 2443 | Cl | benzoyl | H | $NCH_3$ |
| 2444 | Cl | 2-pyridyl | H | $NCH_3$ |
| 2445 | Cl | H | $CH_3$ | $NCH_3$ |
| 2446 | Cl | $CH_3$ | $CH_3$ | $NCH_3$ |
| 2447 | Cl | $C_2H_5$ | $CH_3$ | $NCH_3$ |
| 2448 | Cl | $n-C_3H_7$ | $CH_3$ | $NCH_3$ |
| 2449 | Cl | $i-C_3H_7$ | $CH_3$ | $NCH_3$ |
| 2450 | Cl | $n-C_4H_9$ | $CH_3$ | $NCH_3$ |
| 2451 | Cl | $i-C_4H_9$ | $CH_3$ | $NCH_3$ |
| 2452 | Cl | $s-C_4H_9$ | $CH_3$ | $NCH_3$ |
| 2453 | Cl | $t-C_4H_9$ | $CH_3$ | $NCH_3$ |
| 2454 | Cl | $CH_2OCH_3$ | $CH_3$ | $NCH_3$ |
| 2455 | Cl | $CF_3$ | $CH_3$ | $NCH_3$ |
| 2456 | Cl | $CF_2H$ | $CH_3$ | $NCH_3$ |
| 2457 | Cl | CN | $CH_3$ | $NCH_3$ |
| 2458 | Cl | OH | $CH_3$ | $NCH_3$ |
| 2459 | Cl | $OCH_3$ | $CH_3$ | $NCH_3$ |
| 2460 | Cl | $NH_2$ | $CH_3$ | $NCH_3$ |
| 2461 | Cl | $NHCH_3$ | $CH_3$ | $NCH_3$ |
| 2462 | Cl | $N(CH_3)_2$ | $CH_3$ | $NCH_3$ |
| 2463 | Cl | $CO_2CH_3$ | $CH_3$ | $NCH_3$ |
| 2464 | Cl | $CO_2C_2H_5$ | $CH_3$ | $NCH_3$ |
| 2465 | Cl | $C(O)CH_3$ | $CH_3$ | $NCH_3$ |
| 2466 | Cl | $C(O)CF_3$ | $CH_3$ | $NCH_3$ |
| 2467 | Cl | $C(=NOCH_3)CH_3$ | $CH_3$ | $NCH_3$ |
| 2468 | Cl | $SO_2CH_3$ | $CH_3$ | $NCH_3$ |
| 2469 | Cl | $SO_2CF_3$ | $CH_3$ | $NCH_3$ |
| 2470 | Cl | $CH_2CO_2H$ | $CH_3$ | $NCH_3$ |
| 2471 | Cl | $CH_2COOCH_3$ | $CH_3$ | $NCH_3$ |
| 2472 | Cl | $CH_2COOC_2H_5$ | $CH_3$ | $NCH_3$ |
| 2473 | Cl | prop-1-en-3-yl | $CH_3$ | $NCH_3$ |
| 2474 | Cl | trans-but-2-en-1-yl | $CH_3$ | $NCH_3$ |
| 2475 | Cl | cis-but-2-en-1-yl | $CH_3$ | $NCH_3$ |
| 2476 | Cl | cis-3-methyl-but-2-en-1-yl | $CH_3$ | $NCH_3$ |
| 2477 | Cl | cyclopropyl | $CH_3$ | $NCH_3$ |
| 2478 | Cl | cyclopentyl | $CH_3$ | $NCH_3$ |
| 2479 | Cl | cyclohexyl | $CH_3$ | $NCH_3$ |
| 2480 | Cl | 4,5-dihydroisoxazol-3-yl | $CH_3$ | $NCH_3$ |
| 2481 | Cl | 4-methyl-4,5-dihydro-isoxazol-3-yl | $CH_3$ | $NCH_3$ |

TABLE A-continued

| No. | R¹ | R² | R³ | A |
|---|---|---|---|---|
| 2482 | Cl | isoxazol-3-yl | $CH_3$ | $NCH_3$ |
| 2483 | Cl | 4-methylisoxazol-3-yl | $CH_3$ | $NCH_3$ |
| 2484 | Cl | 4,5-dihydroisoxazol-4-yl | $CH_3$ | $NCH_3$ |
| 2485 | Cl | 3-methyl-4,5-dihydroisoxazol-4-yl | $CH_3$ | $NCH_3$ |
| 2486 | Cl | isoxazol-4-yl | $CH_3$ | $NCH_3$ |
| 2487 | Cl | 3-methylisoxazol-4-yl | $CH_3$ | $NCH_3$ |
| 2488 | Cl | phenyl | $CH_3$ | $NCH_3$ |
| 2489 | Cl | benzyl | $CH_3$ | $NCH_3$ |
| 2490 | Cl | benzoyl | $CH_3$ | $NCH_3$ |
| 2491 | Cl | 2-pyridyl | $CH_3$ | $NCH_3$ |
| 2492 | Cl | H | Cl | $NCH_3$ |
| 2493 | Cl | $CH_3$ | Cl | $NCH_3$ |
| 2494 | Cl | $C_2H_5$ | Cl | $NCH_3$ |
| 2495 | Cl | $n-C_3H_7$ | Cl | $NCH_3$ |
| 2496 | Cl | $i-C_3H_7$ | Cl | $NCH_3$ |
| 2497 | Cl | $n-C_4H_9$ | Cl | $NCH_3$ |
| 2498 | Cl | $i-C_4H_9$ | Cl | $NCH_3$ |
| 2499 | Cl | $s-C_4H_9$ | Cl | $NCH_3$ |
| 2500 | Cl | $t-C_4H_9$ | Cl | $NCH_3$ |
| 2501 | Cl | $CH_2OCH_3$ | Cl | $NCH_3$ |
| 2502 | Cl | $CF_3$ | Cl | $NCH_3$ |
| 2503 | Cl | $CF_2H$ | Cl | $NCH_3$ |
| 2504 | Cl | CN | Cl | $NCH_3$ |
| 2505 | Cl | OH | Cl | $NCH_3$ |
| 2506 | Cl | $OCH_3$ | Cl | $NCH_3$ |
| 2507 | Cl | $NH_2$ | Cl | $NCH_3$ |
| 2508 | Cl | $NHCH_3$ | Cl | $NCH_3$ |
| 2509 | Cl | $N(CH_3)_2$ | Cl | $NCH_3$ |
| 2510 | Cl | $CO_2CH_3$ | Cl | $NCH_3$ |
| 2511 | Cl | $CO_2C_2H_5$ | Cl | $NCH_3$ |
| 2512 | Cl | $C(O)CH_3$ | Cl | $NCH_3$ |
| 2513 | Cl | $C(O)CF_3$ | Cl | $NCH_3$ |
| 2514 | Cl | $C(=NOCH_3)CH_3$ | Cl | $NCH_3$ |
| 2515 | Cl | $SO_2CH_3$ | Cl | $NCH_3$ |
| 2516 | Cl | $SO_2CF_3$ | Cl | $NCH_3$ |
| 2517 | Cl | $CH_2CO_2H$ | Cl | $NCH_3$ |
| 2518 | Cl | $CH_2COOCH_3$ | Cl | $NCH_3$ |
| 2519 | Cl | $CH_2COOC_2H_5$ | Cl | $NCH_3$ |
| 2520 | Cl | prop-1-en-3-yl | Cl | $NCH_3$ |
| 2521 | Cl | trans-but-2-en-1-yl | Cl | $NCH_3$ |
| 2522 | Cl | cis-but-2-en-1-yl | Cl | $NCH_3$ |
| 2523 | Cl | cis-3-methyl-but-2-en-1-yl | Cl | $NCH_3$ |
| 2524 | Cl | cyclopropyl | Cl | $NCH_3$ |
| 2525 | Cl | cyclopentyl | Cl | $NCH_3$ |
| 2526 | Cl | cyclohexyl | Cl | $NCH_3$ |
| 2527 | Cl | 4,5-dihydroisoxazol-3-yl | Cl | $NCH_3$ |
| 2528 | Cl | 4-methyl-4,5-dihydroisoxazol-3-yl | Cl | $NCH_3$ |
| 2529 | Cl | isoxazol-3-yl | Cl | $NCH_3$ |
| 2530 | Cl | 4-methylisoxazol-3-yl | Cl | $NCH_3$ |
| 2531 | Cl | 4,5-dihydroisoxazol-4-yl | Cl | $NCH_3$ |
| 2532 | Cl | 3-methyl-4,5-dihydroisoxazol-4-yl | Cl | $NCH_3$ |
| 2533 | Cl | isoxazol-4-yl | Cl | $NCH_3$ |
| 2534 | Cl | 3-methylisoxazol-4-yl | Cl | $NCH_3$ |
| 2535 | Cl | phenyl | Cl | $NCH_3$ |
| 2536 | Cl | benzyl | Cl | $NCH_3$ |
| 2537 | Cl | benzoyl | Cl | $NCH_3$ |
| 2538 | Cl | 2-pyridyl | Cl | $NCH_3$ |
| 2539 | $OCH_3$ | H | H | $NCH_3$ |
| 2540 | $OCH_3$ | $CH_3$ | H | $NCH_3$ |
| 2541 | $OCH_3$ | $C_2H_5$ | H | $NCH_3$ |
| 2542 | $OCH_3$ | $n-C_3H_7$ | H | $NCH_3$ |
| 2543 | $OCH_3$ | $i-C_3H_7$ | H | $NCH_3$ |
| 2544 | $OCH_3$ | $n-C_4H_9$ | H | $NCH_3$ |
| 2545 | $OCH_3$ | $i-C_4H_9$ | H | $NCH_3$ |
| 2546 | $OCH_3$ | $s-C_4H_9$ | H | $NCH_3$ |
| 2547 | $OCH_3$ | $t-C_4H_9$ | H | $NCH_3$ |
| 2548 | $OCH_3$ | $CH_2OCH_3$ | H | $NCH_3$ |
| 2549 | $OCH_3$ | $CF_3$ | H | $NCH_3$ |
| 2550 | $OCH_3$ | $CF_2H$ | H | $NCH_3$ |
| 2551 | $OCH_3$ | CN | H | $NCH_3$ |
| 2552 | $OCH_3$ | OH | H | $NCH_3$ |
| 2553 | $OCH_3$ | $OCH_3$ | H | $NCH_3$ |
| 2554 | $OCH_3$ | $NH_2$ | H | $NCH_3$ |
| 2555 | $OCH_3$ | $NHCH_3$ | H | $NCH_3$ |
| 2556 | $OCH_3$ | $N(CH_3)_2$ | H | $NCH_3$ |
| 2557 | $OCH_3$ | $CO_2CH_3$ | H | $NCH_3$ |
| 2558 | $OCH_3$ | $CO_2C_2H_5$ | H | $NCH_3$ |
| 2559 | $OCH_3$ | $C(O)CH_3$ | H | $NCH_3$ |
| 2560 | $OCH_3$ | $C(O)CF_3$ | H | $NCH_3$ |
| 2561 | $OCH_3$ | $C(=NOCH_3)CH_3$ | H | $NCH_3$ |
| 2562 | $OCH_3$ | $SO_2CH_3$ | H | $NCH_3$ |
| 2563 | $OCH_3$ | $SO_2CF_3$ | H | $NCH_3$ |
| 2564 | $OCH_3$ | $CH_2CO_2H$ | H | $NCH_3$ |
| 2565 | $OCH_3$ | $CH_2COOCH_3$ | H | $NCH_3$ |
| 2566 | $OCH_3$ | $CH_2COOC_2H_5$ | H | $NCH_3$ |
| 2567 | $OCH_3$ | prop-1-en-3-yl | H | $NCH_3$ |
| 2568 | $OCH_3$ | trans-but-2-en-1-yl | H | $NCH_3$ |
| 2569 | $OCH_3$ | cis-but-2-en-1-yl | H | $NCH_3$ |
| 2570 | $OCH_3$ | cis-3-methyl-but-2-en-1-yl | H | $NCH_3$ |
| 2571 | $OCH_3$ | cyclopropyl | H | $NCH_3$ |
| 2572 | $OCH_3$ | cyclopentyl | H | $NCH_3$ |
| 2573 | $OCH_3$ | cyclohexyl | H | $NCH_3$ |
| 2574 | $OCH_3$ | 4,5-dihydroisoxazol-3-yl | H | $NCH_3$ |
| 2575 | $OCH_3$ | 4-methyl-4,5-dihydroisoxazol-3-yl | H | $NCH_3$ |
| 2576 | $OCH_3$ | isoxazol-3-yl | H | $NCH_3$ |
| 2577 | $OCH_3$ | 4-methylisoxazol-3-yl | H | $NCH_3$ |
| 2578 | $OCH_3$ | 4,5-dihydroisoxazol-4-yl | H | $NCH_3$ |
| 2579 | $OCH_3$ | 3-methyl-4,5-dihydroisoxazol-4-yl | H | $NCH_3$ |
| 2580 | $OCH_3$ | isoxazol-4-yl | H | $NCH_3$ |
| 2581 | $OCH_3$ | 3-methylisoxazol-4-yl | H | $NCH_3$ |
| 2582 | $OCH_3$ | phenyl | H | $NCH_3$ |
| 2583 | $OCH_3$ | benzyl | H | $NCH_3$ |
| 2584 | $OCH_3$ | benzoyl | H | $NCH_3$ |
| 2585 | $OCH_3$ | 2-pyridyl | H | $NCH_3$ |
| 2586 | $OCH_3$ | H | $CH_3$ | $NCH_3$ |
| 2587 | $OCH_3$ | $CH_3$ | $CH_3$ | $NCH_3$ |
| 2588 | $OCH_3$ | $C_2H_5$ | $CH_3$ | $NCH_3$ |
| 2589 | $OCH_3$ | $n-C_3H_7$ | $CH_3$ | $NCH_3$ |
| 2590 | $OCH_3$ | $i-C_3H_7$ | $CH_3$ | $NCH_3$ |
| 2591 | $OCH_3$ | $n-C_4H_9$ | $CH_3$ | $NCH_3$ |
| 2592 | $OCH_3$ | $i-C_4H_9$ | $CH_3$ | $NCH_3$ |
| 2593 | $OCH_3$ | $s-C_4H_9$ | $CH_3$ | $NCH_3$ |
| 2594 | $OCH_3$ | $t-C_4H_9$ | $CH_3$ | $NCH_3$ |
| 2595 | $OCH_3$ | $CH_2OCH_3$ | $CH_3$ | $NCH_3$ |
| 2596 | $OCH_3$ | $CF_3$ | $CH_3$ | $NCH_3$ |
| 2597 | $OCH_3$ | $CF_2H$ | $CH_3$ | $NCH_3$ |
| 2598 | $OCH_3$ | CN | $CH_3$ | $NCH_3$ |
| 2599 | $OCH_3$ | OH | $CH_3$ | $NCH_3$ |
| 2600 | $OCH_3$ | $OCH_3$ | $CH_3$ | $NCH_3$ |
| 2601 | $OCH_3$ | $NH_2$ | $CH_3$ | $NCH_3$ |
| 2602 | $OCH_3$ | $NHCH_3$ | $CH_3$ | $NCH_3$ |
| 2603 | $OCH_3$ | $N(CH_3)_2$ | $CH_3$ | $NCH_3$ |
| 2604 | $OCH_3$ | $CO_2CH_3$ | $CH_3$ | $NCH_3$ |
| 2605 | $OCH_3$ | $CO_2C_2H_5$ | $CH_3$ | $NCH_3$ |
| 2606 | $OCH_3$ | $C(O)CH_3$ | $CH_3$ | $NCH_3$ |
| 2607 | $OCH_3$ | $C(O)CF_3$ | $CH_3$ | $NCH_3$ |
| 2608 | $OCH_3$ | $C(=NOCH_3)CH_3$ | $CH_3$ | $NCH_3$ |
| 2609 | $OCH_3$ | $SO_2CH_3$ | $CH_3$ | $NCH_3$ |
| 2610 | $OCH_3$ | $SO_2CF_3$ | $CH_3$ | $NCH_3$ |
| 2611 | $OCH_3$ | $CH_2CO_2H$ | $CH_3$ | $NCH_3$ |
| 2612 | $OCH_3$ | $CH_2COOCH_3$ | $CH_3$ | $NCH_3$ |
| 2613 | $OCH_3$ | $CH_2COOC_2H_5$ | $CH_3$ | $NCH_3$ |
| 2614 | $OCH_3$ | prop-1-en-3-yl | $CH_3$ | $NCH_3$ |
| 2615 | $OCH_3$ | trans-but-2-en-1-yl | $CH_3$ | $NCH_3$ |
| 2616 | $OCH_3$ | cis-but-2-en-1-yl | $CH_3$ | $NCH_3$ |
| 2617 | $OCH_3$ | cis-3-methyl-but-2-en-1-yl | $CH_3$ | $NCH_3$ |
| 2618 | $OCH_3$ | cyclopropyl | $CH_3$ | $NCH_3$ |
| 2619 | $OCH_3$ | cyclopentyl | $CH_3$ | $NCH_3$ |
| 2620 | $OCH_3$ | cyclohexyl | $CH_3$ | $NCH_3$ |
| 2621 | $OCH_3$ | 4,5-dihydroisoxazol-3-yl | $CH_3$ | $NCH_3$ |

TABLE A-continued

| No. | R¹ | R² | R³ | A |
|---|---|---|---|---|
| 2622 | OCH₃ | 4-methyl-4,5-dihydroisoxazol-3-yl | CH₃ | NCH₃ |
| 2623 | OCH₃ | isoxazol-3-yl | CH₃ | NCH₃ |
| 2624 | OCH₃ | 4-methylisoxazol-3-yl | CH₃ | NCH₃ |
| 2625 | OCH₃ | 4,5-dihydroisoxazol-4-yl | CH₃ | NCH₃ |
| 2626 | OCH₃ | 3-methyl-4,5-dihydroisoxazol-4-yl | CH₃ | NCH₃ |
| 2627 | OCH₃ | isoxazol-4-yl | CH₃ | NCH₃ |
| 2628 | OCH₃ | 3-methylisoxazol-4-yl | CH₃ | NCH₃ |
| 2629 | OCH₃ | phenyl | CH₃ | NCH₃ |
| 2630 | OCH₃ | benzyl | CH₃ | NCH₃ |
| 2631 | OCH₃ | benzoyl | CH₃ | NCH₃ |
| 2632 | OCH₃ | 2-pyridyl | CH₃ | NCH₃ |
| 2633 | OCH₃ | H | Cl | NCH₃ |
| 2634 | OCH₃ | CH₃ | Cl | NCH₃ |
| 2635 | OCH₃ | C₂H₅ | Cl | NCH₃ |
| 2636 | OCH₃ | n-C₃H₇ | Cl | NCH₃ |
| 2637 | OCH₃ | i-C₃H₇ | Cl | NCH₃ |
| 2638 | OCH₃ | n-C₄H₉ | Cl | NCH₃ |
| 2639 | OCH₃ | i-C₄H₉ | Cl | NCH₃ |
| 2640 | OCH₃ | s-C₄H₉ | Cl | NCH₃ |
| 2641 | OCH₃ | t-C₄H₉ | Cl | NCH₃ |
| 2642 | OCH₃ | CH₂OCH₃ | Cl | NCH₃ |
| 2643 | OCH₃ | CF₃ | Cl | NCH₃ |
| 2644 | OCH₃ | CF₂H | Cl | NCH₃ |
| 2645 | OCH₃ | CN | Cl | NCH₃ |
| 2646 | OCH₃ | OH | Cl | NCH₃ |
| 2647 | OCH₃ | OCH₃ | Cl | NCH₃ |
| 2648 | OCH₃ | NH₂ | Cl | NCH₃ |
| 2649 | OCH₃ | NHCH₃ | Cl | NCH₃ |
| 2650 | OCH₃ | N(CH₃)₂ | Cl | NCH₃ |
| 2651 | OCH₃ | CO₂CH₃ | Cl | NCH₃ |
| 2652 | OCH₃ | CO₂C₂H₅ | Cl | NCH₃ |
| 2653 | OCH₃ | C(O)CH₃ | Cl | NCH₃ |
| 2654 | OCH₃ | C(O)CF₃ | Cl | NCH₃ |
| 2655 | OCH₃ | C(=NOCH₃)CH₃ | Cl | NCH₃ |
| 2656 | OCH₃ | SO₂CH₃ | Cl | NCH₃ |
| 2657 | OCH₃ | SO₂CF₃ | Cl | NCH₃ |
| 2658 | OCH₃ | CH₂CO₂H | Cl | NCH₃ |
| 2659 | OCH₃ | CH₂COOCH₃ | Cl | NCH₃ |
| 2660 | OCH₃ | CH₂COOC₂H₅ | Cl | NCH₃ |
| 2661 | OCH₃ | prop-1-en-3-yl | Cl | NCH₃ |
| 2662 | OCH₃ | trans-but-2-en-1-yl | Cl | NCH₃ |
| 2663 | OCH₃ | cis-but-2-en-1-yl | Cl | NCH₃ |
| 2664 | OCH₃ | cis-3-methyl-but-2-en-1-yl | Cl | NCH₃ |
| 2665 | OCH₃ | cyclopropyl | Cl | NCH₃ |
| 2666 | OCH₃ | cyclopentyl | Cl | NCH₃ |
| 2667 | OCH₃ | cyclohexyl | Cl | NCH₃ |
| 2668 | OCH₃ | 4,5-dihydroisoxazol-3-yl | Cl | NCH₃ |
| 2669 | OCH₃ | 4-methyl-4,5-dihydroisoxazol-3-yl | Cl | NCH₃ |
| 2670 | OCH₃ | isoxazol-3-yl | Cl | NCH₃ |
| 2671 | OCH₃ | 4-methylisoxazol-3-yl | Cl | NCH₃ |
| 2672 | OCH₃ | 4,5-dihydroisoxazol-4-yl | Cl | NCH₃ |
| 2673 | OCH₃ | 3-methyl-4,5-dihydroisoxazol-4-yl | Cl | NCH₃ |
| 2674 | OCH₃ | isoxazol-4-yl | Cl | NCH₃ |
| 2675 | OCH₃ | 3-methylisoxazol-4-yl | Cl | NCH₃ |
| 2676 | OCH₃ | phenyl | Cl | NCH₃ |
| 2677 | OCH₃ | benzyl | Cl | NCH₃ |
| 2678 | OCH₃ | benzoyl | Cl | NCH₃ |
| 2679 | OCH₃ | 2-pyridyl | Cl | NCH₃ |
| 2680 | OCF₃ | H | H | NCH₃ |
| 2681 | OCF₃ | CH₃ | H | NCH₃ |
| 2682 | OCF₃ | C₂H₅ | H | NCH₃ |
| 2683 | OCF₃ | n-C₃H₇ | H | NCH₃ |
| 2684 | OCF₃ | i-C₃H₇ | H | NCH₃ |
| 2685 | OCF₃ | n-C₄H₉ | H | NCH₃ |
| 2686 | OCF₃ | i-C₄H₉ | H | NCH₃ |
| 2687 | OCF₃ | s-C₄H₉ | H | NCH₃ |
| 2688 | OCF₃ | t-C₄H₉ | H | NCH₃ |
| 2689 | OCF₃ | CH₂OCH₃ | H | NCH₃ |
| 2690 | OCF₃ | CF₃ | H | NCH₃ |
| 2691 | OCF₃ | CF₂H | H | NCH₃ |
| 2692 | OCF₃ | CN | H | NCH₃ |
| 2693 | OCF₃ | OH | H | NCH₃ |
| 2694 | OCF₃ | OCH₃ | H | NCH₃ |
| 2695 | OCF₃ | NH₂ | H | NCH₃ |
| 2696 | OCF₃ | NHCH₃ | H | NCH₃ |
| 2697 | OCF₃ | N(CH₃)₂ | H | NCH₃ |
| 2698 | OCF₃ | CO₂CH₃ | H | NCH₃ |
| 2699 | OCF₃ | CO₂C₂H₅ | H | NCH₃ |
| 2700 | OCF₃ | C(O)CH₃ | H | NCH₃ |
| 2701 | OCF₃ | C(O)CF₃ | H | NCH₃ |
| 2702 | OCF₃ | C(=NOCH₃)CH₃ | H | NCH₃ |
| 2703 | OCF₃ | SO₂CH₃ | H | NCH₃ |
| 2704 | OCF₃ | SO₂CF₃ | H | NCH₃ |
| 2705 | OCF₃ | CH₂CO₂H | H | NCH₃ |
| 2706 | OCF₃ | CH₂COOCH₃ | H | NCH₃ |
| 2707 | OCF₃ | CH₂COOC₂H₅ | H | NCH₃ |
| 2708 | OCF₃ | prop-1-en-3-yl | H | NCH₃ |
| 2709 | OCF₃ | trans-but-2-en-1-yl | H | NCH₃ |
| 2710 | OCF₃ | cis-but-2-en-1-yl | H | NCH₃ |
| 2711 | OCF₃ | cis-3-methyl-but-2-en-1-yl | H | NCH₃ |
| 2712 | OCF₃ | cyclopropyl | H | NCH₃ |
| 2713 | OCF₃ | cyclopentyl | H | NCH₃ |
| 2714 | OCF₃ | cyclohexyl | H | NCH₃ |
| 2715 | OCF₃ | 4,5-dihydroisoxazol-3-yl | H | NCH₃ |
| 2716 | OCF₃ | 4-methyl-4,5-dihydroisoxazol-3-yl | H | NCH₃ |
| 2717 | OCF₃ | isoxazol-3-yl | H | NCH₃ |
| 2718 | OCF₃ | 4-methylisoxazol-3-yl | H | NCH₃ |
| 2719 | OCF₃ | 4,5-dihydroisoxazol-4-yl | H | NCH₃ |
| 2720 | OCF₃ | 3-methyl-4,5-dihydroisoxazol-4-yl | H | NCH₃ |
| 2721 | OCF₃ | isoxazol-4-yl | H | NCH₃ |
| 2722 | OCF₃ | 3-methylisoxazol-4-yl | H | NCH₃ |
| 2723 | OCF₃ | phenyl | H | NCH₃ |
| 2724 | OCF₃ | benzyl | H | NCH₃ |
| 2725 | OCF₃ | benzoyl | H | NCH₃ |
| 2726 | OCF₃ | 2-pyridyl | H | NCH₃ |
| 2727 | OCF₃ | H | CH₃ | NCH₃ |
| 2728 | OCF₃ | CH₃ | CH₃ | NCH₃ |
| 2729 | OCF₃ | C₂H₅ | CH₃ | NCH₃ |
| 2730 | OCF₃ | n-C₃H₇ | CH₃ | NCH₃ |
| 2731 | OCF₃ | i-C₃H₇ | CH₃ | NCH₃ |
| 2732 | OCF₃ | n-C₄H₉ | CH₃ | NCH₃ |
| 2733 | OCF₃ | i-C₄H₉ | CH₃ | NCH₃ |
| 2734 | OCF₃ | s-C₄H₉ | CH₃ | NCH₃ |
| 2735 | OCF₃ | t-C₄H₉ | CH₃ | NCH₃ |
| 2736 | OCF₃ | CH₂OCH₃ | CH₃ | NCH₃ |
| 2737 | OCF₃ | CF₃ | CH₃ | NCH₃ |
| 2738 | OCF₃ | CF₂H | CH₃ | NCH₃ |
| 2739 | OCF₃ | CN | CH₃ | NCH₃ |
| 2740 | OCF₃ | OH | CH₃ | NCH₃ |
| 2741 | OCF₃ | OCH₃ | CH₃ | NCH₃ |
| 2742 | OCF₃ | NH₂ | CH₃ | NCH₃ |
| 2743 | OCF₃ | NHCH₃ | CH₃ | NCH₃ |
| 2744 | OCF₃ | N(CH₃)₂ | CH₃ | NCH₃ |
| 2745 | OCF₃ | CO₂CH₃ | CH₃ | NCH₃ |
| 2746 | OCF₃ | CO₂C₂H₅ | CH₃ | NCH₃ |
| 2747 | OCF₃ | C(O)CH₃ | CH₃ | NCH₃ |
| 2748 | OCF₃ | C(O)CF₃ | CH₃ | NCH₃ |
| 2749 | OCF₃ | C(=NOCH₃)CH₃ | CH₃ | NCH₃ |
| 2750 | OCF₃ | SO₂CH₃ | CH₃ | NCH₃ |
| 2751 | OCF₃ | SO₂CF₃ | CH₃ | NCH₃ |
| 2752 | OCF₃ | CH₂CO₂H | CH₃ | NCH₃ |
| 2753 | OCF₃ | CH₂COOCH₃ | CH₃ | NCH₃ |
| 2754 | OCF₃ | CH₂COOC₂H₅ | CH₃ | NCH₃ |
| 2755 | OCF₃ | prop-1-en-3-yl | CH₃ | NCH₃ |
| 2756 | OCF₃ | trans-but-2-en-1-yl | CH₃ | NCH₃ |
| 2757 | OCF₃ | cis-but-2-en-1-yl | CH₃ | NCH₃ |
| 2758 | OCF₃ | cis-3-methyl-but-2-en-1-yl | CH₃ | NCH₃ |
| 2759 | OCF₃ | cyclopropyl | CH₃ | NCH₃ |
| 2760 | OCF₃ | cyclopentyl | CH₃ | NCH₃ |
| 2761 | OCF₃ | cyclohexyl | CH₃ | NCH₃ |

TABLE A-continued

| No. | R¹ | R² | R³ | A |
|---|---|---|---|---|
| 2762 | OCF₃ | 4,5-dihydroisoxazol-3-yl | CH₃ | NCH₃ |
| 2763 | OCF₃ | 4-methyl-4,5-dihydroisoxazol-3-yl | CH₃ | NCH₃ |
| 2764 | OCF₃ | isoxazol-3-yl | CH₃ | NCH₃ |
| 2765 | OCF₃ | 4-methylisoxazol-3-yl | CH₃ | NCH₃ |
| 2766 | OCF₃ | 4,5-dihydroisoxazol-4-yl | CH₃ | NCH₃ |
| 2767 | OCF₃ | 3-methyl-4,5-dihydroisoxazol-4-yl | CH₃ | NCH₃ |
| 2768 | OCF₃ | isoxazol-4-yl | CH₃ | NCH₃ |
| 2769 | OCF₃ | 3-methylisoxazol-4-yl | CH₃ | NCH₃ |
| 2770 | OCF₃ | phenyl | CH₃ | NCH₃ |
| 2771 | OCF₃ | benzyl | CH₃ | NCH₃ |
| 2772 | OCF₃ | benzoyl | CH₃ | NCH₃ |
| 2773 | OCF₃ | 2-pyridyl | CH₃ | NCH₃ |
| 2774 | OCF₃ | H | Cl | NCH₃ |
| 2775 | OCF₃ | CH₃ | Cl | NCH₃ |
| 2776 | OCF₃ | C₂H₅ | Cl | NCH₃ |
| 2777 | OCF₃ | n-C₃H₇ | Cl | NCH₃ |
| 2778 | OCF₃ | i-C₃H₇ | Cl | NCH₃ |
| 2779 | OCF₃ | n-C₄H₉ | Cl | NCH₃ |
| 2780 | OCF₃ | i-C₄H₉ | Cl | NCH₃ |
| 2781 | OCF₃ | s-C₄H₉ | Cl | NCH₃ |
| 2782 | OCF₃ | t-C₄H₉ | Cl | NCH₃ |
| 2783 | OCF₃ | CH₂OCH₃ | Cl | NCH₃ |
| 2784 | OCF₃ | CF₃ | Cl | NCH₃ |
| 2785 | OCF₃ | CF₂H | Cl | NCH₃ |
| 2786 | OCF₃ | CN | Cl | NCH₃ |
| 2787 | OCF₃ | OH | Cl | NCH₃ |
| 2788 | OCF₃ | OCH₃ | Cl | NCH₃ |
| 2789 | OCF₃ | NH₂ | Cl | NCH₃ |
| 2790 | OCF₃ | NHCH₃ | Cl | NCH₃ |
| 2791 | OCF₃ | N(CH₃)₂ | Cl | NCH₃ |
| 2792 | OCF₃ | CO₂CH₃ | Cl | NCH₃ |
| 2793 | OCF₃ | CO₂C₂H₅ | Cl | NCH₃ |
| 2794 | OCF₃ | C(O)CH₃ | Cl | NCH₃ |
| 2795 | OCF₃ | C(O)CF₃ | Cl | NCH₃ |
| 2796 | OCF₃ | C(=NOCH₃)CH₃ | Cl | NCH₃ |
| 2797 | OCF₃ | SO₂CH₃ | Cl | NCH₃ |
| 2798 | OCF₃ | SO₂CF₃ | Cl | NCH₃ |
| 2799 | OCF₃ | CH₂CO₂H | Cl | NCH₃ |
| 2800 | OCF₃ | CH₂COOCH₃ | Cl | NCH₃ |
| 2801 | OCF₃ | CH₂COOC₂H₅ | Cl | NCH₃ |
| 2802 | OCF₃ | prop-1-en-3-yl | Cl | NCH₃ |
| 2803 | OCF₃ | trans-but-2-en-1-yl | Cl | NCH₃ |
| 2804 | OCF₃ | cis-but-2-en-1-yl | Cl | NCH₃ |
| 2805 | OCF₃ | cis-3-methyl-but-2-en-1-yl | Cl | NCH₃ |
| 2806 | OCF₃ | cyclopropyl | Cl | NCH₃ |
| 2807 | OCF₃ | cyclopentyl | Cl | NCH₃ |
| 2808 | OCF₃ | cyclohexyl | Cl | NCH₃ |
| 2809 | OCF₃ | 4,5-dihydroisoxazol-3-yl | Cl | NCH₃ |
| 2810 | OCF₃ | 4-methyl-4,5-dihydroisoxazol-3-yl | Cl | NCH₃ |
| 2811 | OCF₃ | isoxazol-3-yl | Cl | NCH₃ |
| 2812 | OCF₃ | 4-methylisoxazol-3-yl | Cl | NCH₃ |
| 2813 | OCF₃ | 4,5-dihydroisoxazol-4-yl | Cl | NCH₃ |
| 2814 | OCF₃ | 3-methyl-4,5-dihydroisoxazol-4-yl | Cl | NCH₃ |
| 2815 | OCF₃ | isoxazol-4-yl | Cl | NCH₃ |
| 2816 | OCF₃ | 3-methylisoxazol-4-yl | Cl | NCH₃ |
| 2817 | OCF₃ | phenyl | Cl | NCH₃ |
| 2818 | OCF₃ | benzyl | Cl | NCH₃ |
| 2819 | OCF₃ | benzoyl | Cl | NCH₃ |
| 2820 | OCF₃ | 2-pyridyl | Cl | NCH₃ |
| 2821 | SCH₃ | H | H | NCH₃ |
| 2822 | SCH₃ | CH₃ | H | NCH₃ |
| 2823 | SCH₃ | C₂H₅ | H | NCH₃ |
| 2824 | SCH₃ | n-C₃H₇ | H | NCH₃ |
| 2825 | SCH₃ | i-C₃H₇ | H | NCH₃ |
| 2826 | SCH₃ | n-C₄H₉ | H | NCH₃ |
| 2827 | SCH₃ | i-C₄H₉ | H | NCH₃ |
| 2828 | SCH₃ | s-C₄H₉ | H | NCH₃ |
| 2829 | SCH₃ | t-C₄H₉ | H | NCH₃ |
| 2830 | SCH₃ | CH₂OCH₃ | H | NCH₃ |
| 2831 | SCH₃ | CF₃ | H | NCH₃ |
| 2832 | SCH₃ | CF₂H | H | NCH₃ |
| 2833 | SCH₃ | CN | H | NCH₃ |
| 2834 | SCH₃ | OH | H | NCH₃ |
| 2835 | SCH₃ | OCH₃ | H | NCH₃ |
| 2836 | SCH₃ | NH₂ | H | NCH₃ |
| 2837 | SCH₃ | NHCH₃ | H | NCH₃ |
| 2838 | SCH₃ | N(CH₃)₂ | H | NCH₃ |
| 2839 | SCH₃ | CO₂CH₃ | H | NCH₃ |
| 2840 | SCH₃ | CO₂C₂H₅ | H | NCH₃ |
| 2841 | SCH₃ | C(O)CH₃ | H | NCH₃ |
| 2842 | SCH₃ | C(O)CF₃ | H | NCH₃ |
| 2843 | SCH₃ | C(=NOCH₃)CH₃ | H | NCH₃ |
| 2844 | SCH₃ | SO₂CH₃ | H | NCH₃ |
| 2845 | SCH₃ | SO₂CF₃ | H | NCH₃ |
| 2846 | SCH₃ | CH₂CO₂H | H | NCH₃ |
| 2847 | SCH₃ | CH₂COOCH₃ | H | NCH₃ |
| 2848 | SCH₃ | CH₂COOC₂H₅ | H | NCH₃ |
| 2849 | SCH₃ | prop-1-en-3-yl | H | NCH₃ |
| 2850 | SCH₃ | trans-but-2-en-1-yl | H | NCH₃ |
| 2851 | SCH₃ | cis-but-2-en-1-yl | H | NCH₃ |
| 2852 | SCH₃ | cis-3-methyl-but-2-en-1-yl | H | NCH₃ |
| 2853 | SCH₃ | cyclopropyl | H | NCH₃ |
| 2854 | SCH₃ | cyclopentyl | H | NCH₃ |
| 2855 | SCH₃ | cyclohexyl | H | NCH₃ |
| 2856 | SCH₃ | 4,5-dihydroisoxazol-3-yl | H | NCH₃ |
| 2857 | SCH₃ | 4-methyl-4,5-dihydroisoxazol-3-yl | H | NCH₃ |
| 2858 | SCH₃ | isoxazol-3-yl | H | NCH₃ |
| 2859 | SCH₃ | 4-methylisoxazol-3-yl | H | NCH₃ |
| 2860 | SCH₃ | 4,5-dihydroisoxazol-4-yl | H | NCH₃ |
| 2861 | SCH₃ | 3-methyl-4,5-dihydroisoxazol-4-yl | H | NCH₃ |
| 2862 | SCH₃ | isoxazol-4-yl | H | NCH₃ |
| 2863 | SCH₃ | 3-methylisoxazol-4-yl | H | NCH₃ |
| 2864 | SCH₃ | phenyl | H | NCH₃ |
| 2865 | SCH₃ | benzyl | H | NCH₃ |
| 2866 | SCH₃ | benzoyl | H | NCH₃ |
| 2867 | SCH₃ | 2-pyridyl | H | NCH₃ |
| 2868 | SCH₃ | H | CH₃ | NCH₃ |
| 2869 | SCH₃ | CH₃ | CH₃ | NCH₃ |
| 2870 | SCH₃ | C₂H₅ | CH₃ | NCH₃ |
| 2871 | SCH₃ | n-C₃H₇ | CH₃ | NCH₃ |
| 2872 | SCH₃ | i-C₃H₇ | CH₃ | NCH₃ |
| 2873 | SCH₃ | n-C₄H₉ | CH₃ | NCH₃ |
| 2874 | SCH₃ | i-C₄H₉ | CH₃ | NCH₃ |
| 2875 | SCH₃ | s-C₄H₉ | CH₃ | NCH₃ |
| 2876 | SCH₃ | t-C₄H₉ | CH₃ | NCH₃ |
| 2877 | SCH₃ | CH₂OCH₃ | CH₃ | NCH₃ |
| 2878 | SCH₃ | CF₃ | CH₃ | NCH₃ |
| 2879 | SCH₃ | CF₂H | CH₃ | NCH₃ |
| 2880 | SCH₃ | CN | CH₃ | NCH₃ |
| 2881 | SCH₃ | OH | CH₃ | NCH₃ |
| 2882 | SCH₃ | OCH₃ | CH₃ | NCH₃ |
| 2883 | SCH₃ | NH₂ | CH₃ | NCH₃ |
| 2884 | SCH₃ | NHCH₃ | CH₃ | NCH₃ |
| 2885 | SCH₃ | N(CH₃)₂ | CH₃ | NCH₃ |
| 2886 | SCH₃ | CO₂CH₃ | CH₃ | NCH₃ |
| 2887 | SCH₃ | CO₂C₂H₅ | CH₃ | NCH₃ |
| 2888 | SCH₃ | C(O)CH₃ | CH₃ | NCH₃ |
| 2889 | SCH₃ | C(O)CF₃ | CH₃ | NCH₃ |
| 2890 | SCH₃ | C(=NOCH₃)CH₃ | CH₃ | NCH₃ |
| 2891 | SCH₃ | SO₂CH₃ | CH₃ | NCH₃ |
| 2892 | SCH₃ | SO₂CF₃ | CH₃ | NCH₃ |
| 2893 | SCH₃ | CH₂CO₂H | CH₃ | NCH₃ |
| 2894 | SCH₃ | CH₂COOCH₃ | CH₃ | NCH₃ |
| 2895 | SCH₃ | CH₂COOC₂H₅ | CH₃ | NCH₃ |
| 2896 | SCH₃ | prop-1-en-3-yl | CH₃ | NCH₃ |
| 2897 | SCH₃ | trans-but-2-en-1-yl | CH₃ | NCH₃ |
| 2898 | SCH₃ | cis-but-2-en-1-yl | CH₃ | NCH₃ |
| 2899 | SCH₃ | cis-3-methyl-but-2-en-1-yl | CH₃ | NCH₃ |
| 2900 | SCH₃ | cyclopropyl | CH₃ | NCH₃ |

TABLE A-continued

| No. | R¹ | R² | R³ | A |
|---|---|---|---|---|
| 2901 | SCH₃ | cyclopentyl | CH₃ | NCH₃ |
| 2902 | SCH₃ | cyclohexyl | CH₃ | NCH₃ |
| 2903 | SCH₃ | 4,5-dihydroisoxazol-3-yl | CH₃ | NCH₃ |
| 2904 | SCH₃ | 4-methyl-4,5-dihydroisoxazol-3-yl | CH₃ | NCH₃ |
| 2905 | SCH₃ | isoxazol-3-yl | CH₃ | NCH₃ |
| 2906 | SCH₃ | 4-methylisoxazol-3-yl | CH₃ | NCH₃ |
| 2907 | SCH₃ | 4,5-dihydroisoxazol-4-yl | CH₃ | NCH₃ |
| 2908 | SCH₃ | 3-methyl-4,5-dihydroisoxazol-4-yl | CH₃ | NCH₃ |
| 2909 | SCH₃ | isoxazol-4-yl | CH₃ | NCH₃ |
| 2910 | SCH₃ | 3-methylisoxazol-4-yl | CH₃ | NCH₃ |
| 2911 | SCH₃ | phenyl | CH₃ | NCH₃ |
| 2912 | SCH₃ | benzyl | CH₃ | NCH₃ |
| 2913 | SCH₃ | benzoyl | CH₃ | NCH₃ |
| 2914 | SCH₃ | 2-pyridyl | CH₃ | NCH₃ |
| 2915 | SCH₃ | H | Cl | NCH₃ |
| 2916 | SCH₃ | CH₃ | Cl | NCH₃ |
| 2917 | SCH₃ | C₂H₅ | Cl | NCH₃ |
| 2918 | SCH₃ | n-C₃H₇ | Cl | NCH₃ |
| 2919 | SCH₃ | i-C₃H₇ | Cl | NCH₃ |
| 2920 | SCH₃ | n-C₄H₉ | Cl | NCH₃ |
| 2921 | SCH₃ | i-C₄H₉ | Cl | NCH₃ |
| 2922 | SCH₃ | s-C₄H₉ | Cl | NCH₃ |
| 2923 | SCH₃ | t-C₄H₉ | Cl | NCH₃ |
| 2924 | SCH₃ | CH₂OCH₃ | Cl | NCH₃ |
| 2925 | SCH₃ | CF₃ | Cl | NCH₃ |
| 2926 | SCH₃ | CF₂H | Cl | NCH₃ |
| 2927 | SCH₃ | CN | Cl | NCH₃ |
| 2928 | SCH₃ | OH | Cl | NCH₃ |
| 2929 | SCH₃ | OCH₃ | Cl | NCH₃ |
| 2930 | SCH₃ | NH₂ | Cl | NCH₃ |
| 2931 | SCH₃ | NHCH₃ | Cl | NCH₃ |
| 2932 | SCH₃ | N(CH₃)₂ | Cl | NCH₃ |
| 2933 | SCH₃ | CO₂CH₃ | Cl | NCH₃ |
| 2934 | SCH₃ | CO₂C₂H₅ | Cl | NCH₃ |
| 2935 | SCH₃ | C(O)CH₃ | Cl | NCH₃ |
| 2936 | SCH₃ | C(O)CF₃ | Cl | NCH₃ |
| 2937 | SCH₃ | C(=NOCH₃)CH₃ | Cl | NCH₃ |
| 2938 | SCH₃ | SO₂CH₃ | Cl | NCH₃ |
| 2939 | SCH₃ | SO₂CF₃ | Cl | NCH₃ |
| 2940 | SCH₃ | CH₂CO₂H | Cl | NCH₃ |
| 2941 | SCH₃ | CH₂COOCH₃ | Cl | NCH₃ |
| 2942 | SCH₃ | CH₂COOC₂H₅ | Cl | NCH₃ |
| 2943 | SCH₃ | prop-1-en-3-yl | Cl | NCH₃ |
| 2944 | SCH₃ | trans-but-2-en-1-yl | Cl | NCH₃ |
| 2945 | SCH₃ | cis-but-2-en-1-yl | Cl | NCH₃ |
| 2946 | SCH₃ | cis-3-methyl-but-2-en-1-yl | Cl | NCH₃ |
| 2947 | SCH₃ | cyclopropyl | Cl | NCH₃ |
| 2948 | SCH₃ | cyclopentyl | Cl | NCH₃ |
| 2949 | SCH₃ | cyclohexyl | Cl | NCH₃ |
| 2950 | SCH₃ | 4,5-dihydroisoxazol-3-yl | Cl | NCH₃ |
| 2951 | SCH₃ | 4-methyl-4,5-dihydroisoxazol-3-yl | Cl | NCH₃ |
| 2952 | SCH₃ | isoxazol-3-yl | Cl | NCH₃ |
| 2953 | SCH₃ | 4-methylisoxazol-3-yl | Cl | NCH₃ |
| 2954 | SCH₃ | 4,5-dihydroisoxazol-4-yl | Cl | NCH₃ |
| 2955 | SCH₃ | 3-methyl-4,5-dihydroisoxazol-4-yl | Cl | NCH₃ |
| 2956 | SCH₃ | isoxazol-4-yl | Cl | NCH₃ |
| 2957 | SCH₃ | 3-methylisoxazol-4-yl | Cl | NCH₃ |
| 2958 | SCH₃ | phenyl | Cl | NCH₃ |
| 2959 | SCH₃ | benzyl | Cl | NCH₃ |
| 2960 | SCH₃ | benzoyl | Cl | NCH₃ |
| 2961 | SCH₃ | 2-pyridyl | Cl | NCH₃ |
| 2962 | SO₂CH₃ | H | H | NCH₃ |
| 2963 | SO₂CH₃ | CH₃ | H | NCH₃ |
| 2964 | SO₂CH₃ | C₂H₅ | H | NCH₃ |
| 2965 | SO₂CH₃ | n-C₃H₇ | H | NCH₃ |
| 2966 | SO₂CH₃ | i-C₃H₇ | H | NCH₃ |
| 2967 | SO₂CH₃ | n-C₄H₉ | H | NCH₃ |
| 2968 | SO₂CH₃ | i-C₄H₉ | H | NCH₃ |
| 2969 | SO₂CH₃ | s-C₄H₉ | H | NCH₃ |
| 2970 | SO₂CH₃ | t-C₄H₉ | H | NCH₃ |
| 2971 | SO₂CH₃ | CH₂OCH₃ | H | NCH₃ |
| 2972 | SO₂CH₃ | CF₃ | H | NCH₃ |
| 2973 | SO₂CH₃ | CF₂H | H | NCH₃ |
| 2974 | SO₂CH₃ | CN | H | NCH₃ |
| 2975 | SO₂CH₃ | OH | H | NCH₃ |
| 2976 | SO₂CH₃ | OCH₃ | H | NCH₃ |
| 2977 | SO₂CH₃ | NH₂ | H | NCH₃ |
| 2978 | SO₂CH₃ | NHCH₃ | H | NCH₃ |
| 2979 | SO₂CH₃ | N(CH₃)₂ | H | NCH₃ |
| 2980 | SO₂CH₃ | CO₂CH₃ | H | NCH₃ |
| 2981 | SO₂CH₃ | CO₂C₂H₅ | H | NCH₃ |
| 2982 | SO₂CH₃ | C(O)CH₃ | H | NCH₃ |
| 2983 | SO₂CH₃ | C(O)CF₃ | H | NCH₃ |
| 2984 | SO₂CH₃ | C(=NOCH₃)CH₃ | H | NCH₃ |
| 2985 | SO₂CH₃ | SO₂CH₃ | H | NCH₃ |
| 2986 | SO₂CH₃ | SO₂CF₃ | H | NCH₃ |
| 2987 | SO₂CH₃ | CH₂CO₂H | H | NCH₃ |
| 2988 | SO₂CH₃ | CH₂COOCH₃ | H | NCH₃ |
| 2989 | SO₂CH₃ | CH₂COOC₂H₅ | H | NCH₃ |
| 2990 | SO₂CH₃ | prop-1-en-3-yl | H | NCH₃ |
| 2991 | SO₂CH₃ | trans-but-2-en-1-yl | H | NCH₃ |
| 2992 | SO₂CH₃ | cis-but-2-en-1-yl | H | NCH₃ |
| 2993 | SO₂CH₃ | cis-3-methyl-but-2-en-1-yl | H | NCH₃ |
| 2994 | SO₂CH₃ | cyclopropyl | H | NCH₃ |
| 2995 | SO₂CH₃ | cyclopentyl | H | NCH₃ |
| 2996 | SO₂CH₃ | cyclohexyl | H | NCH₃ |
| 2997 | SO₂CH₃ | 4,5-dihydroisoxazol-3-yl | H | NCH₃ |
| 2998 | SO₂CH₃ | 4-methyl-4,5-dihydroisoxazol-3-yl | H | NCH₃ |
| 2999 | SO₂CH₃ | isoxazol-3-yl | H | NCH₃ |
| 3000 | SO₂CH₃ | 4-methylisoxazol-3-yl | H | NCH₃ |
| 3001 | SO₂CH₃ | 4,5-dihydroisoxazol-4-yl | H | NCH₃ |
| 3002 | SO₂CH₃ | 3-methyl-4,5-dihydroisoxazol-4-yl | H | NCH₃ |
| 3003 | SO₂CH₃ | isoxazol-4-yl | H | NCH₃ |
| 3004 | SO₂CH₃ | 3-methylisoxazol-4-yl | H | NCH₃ |
| 3005 | SO₂CH₃ | phenyl | H | NCH₃ |
| 3006 | SO₂CH₃ | benzyl | H | NCH₃ |
| 3007 | SO₂CH₃ | benzoyl | H | NCH₃ |
| 3008 | SO₂CH₃ | 2-pyridyl | H | NCH₃ |
| 3009 | SO₂CH₃ | H | CH₃ | NCH₃ |
| 3010 | SO₂CH₃ | CH₃ | CH₃ | NCH₃ |
| 3011 | SO₂CH₃ | C₂H₅ | CH₃ | NCH₃ |
| 3012 | SO₂CH₃ | n-C₃H₇ | CH₃ | NCH₃ |
| 3013 | SO₂CH₃ | i-C₃H₇ | CH₃ | NCH₃ |
| 3014 | SO₂CH₃ | n-C₄H₉ | CH₃ | NCH₃ |
| 3015 | SO₂CH₃ | i-C₄H₉ | CH₃ | NCH₃ |
| 3016 | SO₂CH₃ | s-C₄H₉ | CH₃ | NCH₃ |
| 3017 | SO₂CH₃ | t-C₄H₉ | CH₃ | NCH₃ |
| 3018 | SO₂CH₃ | CH₂OCH₃ | CH₃ | NCH₃ |
| 3019 | SO₂CH₃ | CF₃ | CH₃ | NCH₃ |
| 3020 | SO₂CH₃ | CF₂H | CH₃ | NCH₃ |
| 3021 | SO₂CH₃ | CN | CH₃ | NCH₃ |
| 3022 | SO₂CH₃ | OH | CH₃ | NCH₃ |
| 3023 | SO₂CH₃ | OCH₃ | CH₃ | NCH₃ |
| 3024 | SO₂CH₃ | NH₂ | CH₃ | NCH₃ |
| 3025 | SO₂CH₃ | NHCH₃ | CH₃ | NCH₃ |
| 3026 | SO₂CH₃ | N(CH₃)₂ | CH₃ | NCH₃ |
| 3027 | SO₂CH₃ | CO₂CH₃ | CH₃ | NCH₃ |
| 3028 | SO₂CH₃ | CO₂C₂H₅ | CH₃ | NCH₃ |
| 3029 | SO₂CH₃ | C(O)CH₃ | CH₃ | NCH₃ |
| 3030 | SO₂CH₃ | C(O)CF₃ | CH₃ | NCH₃ |
| 3031 | SO₂CH₃ | C(=NOCH₃)CH₃ | CH₃ | NCH₃ |
| 3032 | SO₂CH₃ | SO₂CH₃ | CH₃ | NCH₃ |
| 3033 | SO₂CH₃ | SO₂CF₃ | CH₃ | NCH₃ |
| 3034 | SO₂CH₃ | CH₂CO₂H | CH₃ | NCH₃ |
| 3035 | SO₂CH₃ | CH₂COOCH₃ | CH₃ | NCH₃ |
| 3036 | SO₂CH₃ | CH₂COOC₂H₅ | CH₃ | NCH₃ |
| 3037 | SO₂CH₃ | prop-1-en-3-yl | CH₃ | NCH₃ |
| 3038 | SO₂CH₃ | trans-but-2-en-1-yl | CH₃ | NCH₃ |
| 3039 | SO₂CH₃ | cis-but-2-en-1-yl | CH₃ | NCH₃ |

TABLE A-continued

| No. | R¹ | R² | R³ | A |
|---|---|---|---|---|
| 3040 | SO₂CH₃ | cis-3-methyl-but-2-en-1-yl | CH₃ | NCH₃ |
| 3041 | SO₂CH₃ | cyclopropyl | CH₃ | NCH₃ |
| 3042 | SO₂CH₃ | cyclopentyl | CH₃ | NCH₃ |
| 3043 | SO₂CH₃ | cyclohexyl | CH₃ | NCH₃ |
| 3044 | SO₂CH₃ | 4,5-dihydroisoxazol-3-yl | CH₃ | NCH₃ |
| 3045 | SO₂CH₃ | 4-methyl-4,5-dihydroisoxazol-3-yl | CH₃ | NCH₃ |
| 3046 | SO₂CH₃ | isoxazol-3-yl | CH₃ | NCH₃ |
| 3047 | SO₂CH₃ | 4-methylisoxazol-3-yl | CH₃ | NCH₃ |
| 3048 | SO₂CH₃ | 4,5-dihydroisoxazol-4-yl | CH₃ | NCH₃ |
| 3049 | SO₂CH₃ | 3-methyl-4,5-dihydroisoxazol-4-yl | CH₃ | NCH₃ |
| 3050 | SO₂CH₃ | isoxazol-4-yl | CH₃ | NCH₃ |
| 3051 | SO₂CH₃ | 3-methylisoxazol-4-yl | CH₃ | NCH₃ |
| 3052 | SO₂CH₃ | phenyl | CH₃ | NCH₃ |
| 3053 | SO₂CH₃ | benzyl | CH₃ | NCH₃ |
| 3054 | SO₂CH₃ | benzoyl | CH₃ | NCH₃ |
| 3055 | SO₂CH₃ | 2-pyridyl | CH₃ | NCH₃ |
| 3056 | SO₂CH₃ | H | Cl | NCH₃ |
| 3057 | SO₂CH₃ | CH₃ | Cl | NCH₃ |
| 3058 | SO₂CH₃ | C₂H₅ | Cl | NCH₃ |
| 3059 | SO₂CH₃ | n-C₃H₇ | Cl | NCH₃ |
| 3060 | SO₂CH₃ | i-C₃H₇ | Cl | NCH₃ |
| 3061 | SO₂CH₃ | n-C₄H₉ | Cl | NCH₃ |
| 3062 | SO₂CH₃ | i-C₄H₉ | Cl | NCH₃ |
| 3063 | SO₂CH₃ | s-C₄H₉ | Cl | NCH₃ |
| 3064 | SO₂CH₃ | t-C₄H₉ | Cl | NCH₃ |
| 3065 | SO₂CH₃ | CH₂OCH₃ | Cl | NCH₃ |
| 3066 | SO₂CH₃ | CF₃ | Cl | NCH₃ |
| 3067 | SO₂CH₃ | CF₂H | Cl | NCH₃ |
| 3068 | SO₂CH₃ | CN | Cl | NCH₃ |
| 3069 | SO₂CH₃ | OH | Cl | NCH₃ |
| 3070 | SO₂CH₃ | OCH₃ | Cl | NCH₃ |
| 3071 | SO₂CH₃ | NH₂ | Cl | NCH₃ |
| 3072 | SO₂CH₃ | NHCH₃ | Cl | NCH₃ |
| 3073 | SO₂CH₃ | N(CH₃)₂ | Cl | NCH₃ |
| 3074 | SO₂CH₃ | CO₂CH₃ | Cl | NCH₃ |
| 3075 | SO₂CH₃ | CO₂C₂H₅ | Cl | NCH₃ |
| 3076 | SO₂CH₃ | C(O)CH₃ | Cl | NCH₃ |
| 3077 | SO₂CH₃ | C(O)CF₃ | Cl | NCH₃ |
| 3078 | SO₂CH₃ | C(=NOCH₃)CH₃ | Cl | NCH₃ |
| 3079 | SO₂CH₃ | SO₂CH₃ | Cl | NCH₃ |
| 3080 | SO₂CH₃ | SO₂CF₃ | Cl | NCH₃ |
| 3081 | SO₂CH₃ | CH₂CO₂H | Cl | NCH₃ |
| 3082 | SO₂CH₃ | CH₂COOCH₃ | Cl | NCH₃ |
| 3083 | SO₂CH₃ | CH₂COOC₂H₅ | Cl | NCH₃ |
| 3084 | SO₂CH₃ | prop-1-en-3-yl | Cl | NCH₃ |
| 3085 | SO₂CH₃ | trans-but-2-en-1-yl | Cl | NCH₃ |
| 3086 | SO₂CH₃ | cis-but-2-en-1-yl | Cl | NCH₃ |
| 3087 | SO₂CH₃ | cis-3-methyl-but-2-en-1-yl | Cl | NCH₃ |
| 3088 | SO₂CH₃ | cyclopropyl | Cl | NCH₃ |
| 3089 | SO₂CH₃ | cyclopentyl | Cl | NCH₃ |
| 3090 | SO₂CH₃ | cyclohexyl | Cl | NCH₃ |
| 3091 | SO₂CH₃ | 4,5-dihydroisoxazol-3-yl | Cl | NCH₃ |
| 3092 | SO₂CH₃ | 4-methyl-4,5-dihydroisoxazol-3-yl | Cl | NCH₃ |
| 3093 | SO₂CH₃ | isoxazol-3-yl | Cl | NCH₃ |
| 3094 | SO₂CH₃ | 4-methylisoxazol-3-yl | Cl | NCH₃ |
| 3095 | SO₂CH₃ | 4,5-dihydroisoxazol-4-yl | Cl | NCH₃ |
| 3096 | SO₂CH₃ | 3-methyl-4,5-dihydroisoxazol-4-yl | Cl | NCH₃ |
| 3097 | SO₂CH₃ | isoxazol-4-yl | Cl | NCH₃ |
| 3098 | SO₂CH₃ | 3-methylisoxazol-4-yl | Cl | NCH₃ |
| 3099 | SO₂CH₃ | phenyl | Cl | NCH₃ |
| 3100 | SO₂CH₃ | benzyl | Cl | NCH₃ |
| 3101 | SO₂CH₃ | benzoyl | Cl | NCH₃ |
| 3102 | SO₂CH₃ | 2-pyridyl | Cl | NCH₃ |
| 3103 | CF₃ | H | H | NCH₃ |
| 3104 | CF₃ | CH₃ | H | NCH₃ |
| 3105 | CF₃ | C₂H₅ | H | NCH₃ |
| 3106 | CF₃ | n-C₃H₇ | H | NCH₃ |
| 3107 | CF₃ | i-C₃H₇ | H | NCH₃ |
| 3108 | CF₃ | n-C₄H₉ | H | NCH₃ |
| 3109 | CF₃ | i-C₄H₉ | H | NCH₃ |
| 3110 | CF₃ | s-C₄H₉ | H | NCH₃ |
| 3111 | CF₃ | t-C₄H₉ | H | NCH₃ |
| 3112 | CF₃ | CH₂OCH₃ | H | NCH₃ |
| 3113 | CF₃ | CF₃ | H | NCH₃ |
| 3114 | CF₃ | CF₂H | H | NCH₃ |
| 3115 | CF₃ | CN | H | NCH₃ |
| 3116 | CF₃ | OH | H | NCH₃ |
| 3117 | CF₃ | OCH₃ | H | NCH₃ |
| 3118 | CF₃ | NH₂ | H | NCH₃ |
| 3119 | CF₃ | NHCH₃ | H | NCH₃ |
| 3120 | CF₃ | N(CH₃)₂ | H | NCH₃ |
| 3121 | CF₃ | CO₂CH₃ | H | NCH₃ |
| 3122 | CF₃ | CO₂C₂H₅ | H | NCH₃ |
| 3123 | CF₃ | C(O)CH₃ | H | NCH₃ |
| 3124 | CF₃ | C(O)CF₃ | H | NCH₃ |
| 3125 | CF₃ | C(=NOCH₃)CH₃ | H | NCH₃ |
| 3126 | CF₃ | SO₂CH₃ | H | NCH₃ |
| 3127 | CF₃ | SO₂CF₃ | H | NCH₃ |
| 3128 | CF₃ | CH₂CO₂H | H | NCH₃ |
| 3129 | CF₃ | CH₂COOCH₃ | H | NCH₃ |
| 3130 | CF₃ | CH₂COOC₂H₅ | H | NCH₃ |
| 3131 | CF₃ | prop-1-en-3-yl | H | NCH₃ |
| 3132 | CF₃ | trans-but-2-en-1-yl | H | NCH₃ |
| 3133 | CF₃ | cis-but-2-en-1-yl | H | NCH₃ |
| 3134 | CF₃ | cis-3-methyl-but-2-en-1-yl | H | NCH₃ |
| 3135 | CF₃ | cyclopropyl | H | NCH₃ |
| 3136 | CF₃ | cyclopentyl | H | NCH₃ |
| 3137 | CF₃ | cyclohexyl | H | NCH₃ |
| 3138 | CF₃ | 4,5-dihydroisoxazol-3-yl | H | NCH₃ |
| 3139 | CF₃ | 4-methyl-4,5-dihydroisoxazol-3-yl | H | NCH₃ |
| 3140 | CF₃ | isoxazol-3-yl | H | NCH₃ |
| 3141 | CF₃ | 4-methylisoxazol-3-yl | H | NCH₃ |
| 3142 | CF₃ | 4,5-dihydroisoxazol-4-yl | H | NCH₃ |
| 3143 | CF₃ | 3-methyl-4,5-dihydroisoxazol-4-yl | H | NCH₃ |
| 3144 | CF₃ | isoxazol-4-yl | H | NCH₃ |
| 3145 | CF₃ | 3-methylisoxazol-4-yl | H | NCH₃ |
| 3146 | CF₃ | phenyl | H | NCH₃ |
| 3147 | CF₃ | benzyl | H | NCH₃ |
| 3148 | CF₃ | benzoyl | H | NCH₃ |
| 3149 | CF₃ | 2-pyridyl | H | NCH₃ |
| 3150 | CF₃ | H | CH₃ | NCH₃ |
| 3151 | CF₃ | CH₃ | CH₃ | NCH₃ |
| 3152 | CF₃ | C₂H₅ | CH₃ | NCH₃ |
| 3153 | CF₃ | n-C₃H₇ | CH₃ | NCH₃ |
| 3154 | CF₃ | i-C₃H₇ | CH₃ | NCH₃ |
| 3155 | CF₃ | n-C₄H₉ | CH₃ | NCH₃ |
| 3156 | CF₃ | i-C₄H₉ | CH₃ | NCH₃ |
| 3157 | CF₃ | s-C₄H₉ | CH₃ | NCH₃ |
| 3158 | CF₃ | t-C₄H₉ | CH₃ | NCH₃ |
| 3159 | CF₃ | CH₂OCH₃ | CH₃ | NCH₃ |
| 3160 | CF₃ | CF₃ | CH₃ | NCH₃ |
| 3161 | CF₃ | CF₂H | CH₃ | NCH₃ |
| 3162 | CF₃ | CN | CH₃ | NCH₃ |
| 3163 | CF₃ | OH | CH₃ | NCH₃ |
| 3164 | CF₃ | OCH₃ | CH₃ | NCH₃ |
| 3165 | CF₃ | NH₂ | CH₃ | NCH₃ |
| 3166 | CF₃ | NHCH₃ | CH₃ | NCH₃ |
| 3167 | CF₃ | N(CH₃)₂ | CH₃ | NCH₃ |
| 3168 | CF₃ | CO₂CH₃ | CH₃ | NCH₃ |
| 3169 | CF₃ | CO₂C₂H₅ | CH₃ | NCH₃ |
| 3170 | CF₃ | C(O)CH₃ | CH₃ | NCH₃ |
| 3171 | CF₃ | C(O)CF₃ | CH₃ | NCH₃ |
| 3172 | CF₃ | C(=NOCH₃)CH₃ | CH₃ | NCH₃ |
| 3173 | CF₃ | SO₂CH₃ | CH₃ | NCH₃ |
| 3174 | CF₃ | SO₂CF₃ | CH₃ | NCH₃ |
| 3175 | CF₃ | CH₂CO₂H | CH₃ | NCH₃ |
| 3176 | CF₃ | CH₂COOCH₃ | CH₃ | NCH₃ |
| 3177 | CF₃ | CH₂COOC₂H₅ | CH₃ | NCH₃ |
| 3178 | CF₃ | prop-1-en-3-yl | CH₃ | NCH₃ |

TABLE A-continued

| No. | R¹ | R² | R³ | A |
|---|---|---|---|---|
| 3179 | $CF_3$ | trans-but-2-en-1-yl | $CH_3$ | $NCH_3$ |
| 3180 | $CF_3$ | cis-but-2-en-1-yl | $CH_3$ | $NCH_3$ |
| 3181 | $CF_3$ | cis-3-methyl-but-2-en-1-yl | $CH_3$ | $NCH_3$ |
| 3182 | $CF_3$ | cyclopropyl | $CH_3$ | $NCH_3$ |
| 3183 | $CF_3$ | cyclopentyl | $CH_3$ | $NCH_3$ |
| 3184 | $CF_3$ | cyclohexyl | $CH_3$ | $NCH_3$ |
| 3185 | $CF_3$ | 4,5-dihydroisoxazol-3-yl | $CH_3$ | $NCH_3$ |
| 3186 | $CF_3$ | 4-methyl-4,5-dihydroisoxazol-3-yl | $CH_3$ | $NCH_3$ |
| 3187 | $CF_3$ | isoxazol-3-yl | $CH_3$ | $NCH_3$ |
| 3188 | $CF_3$ | 4-methylisoxazol-3-yl | $CH_3$ | $NCH_3$ |
| 3189 | $CF_3$ | 4,5-dihydroisoxazol-4-yl | $CH_3$ | $NCH_3$ |
| 3190 | $CF_3$ | 3-methyl-4,5-dihydroisoxazol-4-yl | $CH_3$ | $NCH_3$ |
| 3191 | $CF_3$ | isoxazol-4-yl | $CH_3$ | $NCH_3$ |
| 3192 | $CF_3$ | 3-methylisoxazol-4-yl | $CH_3$ | $NCH_3$ |
| 3193 | $CF_3$ | phenyl | $CH_3$ | $NCH_3$ |
| 3194 | $CF_3$ | benzyl | $CH_3$ | $NCH_3$ |
| 3195 | $CF_3$ | benzoyl | $CH_3$ | $NCH_3$ |
| 3196 | $CF_3$ | 2-pyridyl | $CH_3$ | $NCH_3$ |
| 3197 | $CF_3$ | H | Cl | $NCH_3$ |
| 3198 | $CF_3$ | $CH_3$ | Cl | $NCH_3$ |
| 3199 | $CF_3$ | $C_2H_5$ | Cl | $NCH_3$ |
| 3200 | $CF_3$ | n-$C_3H_7$ | Cl | $NCH_3$ |
| 3201 | $CF_3$ | i-$C_3H_7$ | Cl | $NCH_3$ |
| 3202 | $CF_3$ | n-$C_4H_9$ | Cl | $NCH_3$ |
| 3203 | $CF_3$ | i-$C_4H_9$ | Cl | $NCH_3$ |
| 3204 | $CF_3$ | s-$C_4H_9$ | Cl | $NCH_3$ |
| 3205 | $CF_3$ | t-$C_4H_9$ | Cl | $NCH_3$ |
| 3206 | $CF_3$ | $CH_2OCH_3$ | Cl | $NCH_3$ |
| 3207 | $CF_3$ | $CF_3$ | Cl | $NCH_3$ |
| 3208 | $CF_3$ | $CF_2H$ | Cl | $NCH_3$ |
| 3209 | $CF_3$ | CN | Cl | $NCH_3$ |
| 3210 | $CF_3$ | OH | Cl | $NCH_3$ |
| 3211 | $CF_3$ | $OCH_3$ | Cl | $NCH_3$ |
| 3212 | $CF_3$ | $NH_2$ | Cl | $NCH_3$ |
| 3213 | $CF_3$ | $NHCH_3$ | Cl | $NCH_3$ |
| 3214 | $CF_3$ | $N(CH_3)_2$ | Cl | $NCH_3$ |
| 3215 | $CF_3$ | $CO_2CH_3$ | Cl | $NCH_3$ |
| 3216 | $CF_3$ | $CO_2C_2H_5$ | Cl | $NCH_3$ |
| 3217 | $CF_3$ | $C(O)CH_3$ | Cl | $NCH_3$ |
| 3218 | $CF_3$ | $C(O)CF_3$ | Cl | $NCH_3$ |
| 3219 | $CF_3$ | $C(=NOCH_3)CH_3$ | Cl | $NCH_3$ |
| 3220 | $CF_3$ | $SO_2CH_3$ | Cl | $NCH_3$ |
| 3221 | $CF_3$ | $SO_2CF_3$ | Cl | $NCH_3$ |
| 3222 | $CF_3$ | $CH_2CO_2H$ | Cl | $NCH_3$ |
| 3223 | $CF_3$ | $CH_2COOCH_3$ | Cl | $NCH_3$ |
| 3224 | $CF_3$ | $CH_2COOC_2H_5$ | Cl | $NCH_3$ |
| 3225 | $CF_3$ | prop-1-en-3-yl | Cl | $NCH_3$ |
| 3226 | $CF_3$ | trans-but-2-en-1-yl | Cl | $NCH_3$ |
| 3227 | $CF_3$ | cis-but-2-en-1-yl | Cl | $NCH_3$ |
| 3228 | $CF_3$ | cis-3-methyl-but-2-en-1-yl | Cl | $NCH_3$ |
| 3229 | $CF_3$ | cyclopropyl | Cl | $NCH_3$ |
| 3230 | $CF_3$ | cyclopentyl | Cl | $NCH_3$ |
| 3231 | $CF_3$ | cyclohexyl | Cl | $NCH_3$ |
| 3232 | $CF_3$ | 4,5-dihydroisoxazol-3-yl | Cl | $NCH_3$ |
| 3233 | $CF_3$ | 4-methyl-4,5-dihydroisoxazol-3-yl | Cl | $NCH_3$ |
| 3234 | $CF_3$ | isoxazol-3-yl | Cl | $NCH_3$ |
| 3235 | $CF_3$ | 4-methylisoxazol-3-yl | Cl | $NCH_3$ |
| 3236 | $CF_3$ | 4,5-dihydroisoxazol-4-yl | Cl | $NCH_3$ |
| 3237 | $CF_3$ | 3-methyl-4,5-dihydroisoxazol-4-yl | Cl | $NCH_3$ |
| 3238 | $CF_3$ | isoxazol-4-yl | Cl | $NCH_3$ |
| 3239 | $CF_3$ | 3-methylisoxazol-4-yl | Cl | $NCH_3$ |
| 3240 | $CF_3$ | phenyl | Cl | $NCH_3$ |
| 3241 | $CF_3$ | benzyl | Cl | $NCH_3$ |
| 3242 | $CF_3$ | benzoyl | Cl | $NCH_3$ |
| 3243 | $CF_3$ | 2-pyridyl | Cl | $NCH_3$ |
| 3244 | $C_2H_5$ | H | H | $NCH_3$ |
| 3245 | $C_2H_5$ | $CH_3$ | H | $NCH_3$ |
| 3246 | $C_2H_5$ | $C_2H_5$ | H | $NCH_3$ |
| 3247 | $C_2H_5$ | n-$C_3H_7$ | H | $NCH_3$ |
| 3248 | $C_2H_5$ | i-$C_3H_7$ | H | $NCH_3$ |
| 3249 | $C_2H_5$ | n-$C_4H_9$ | H | $NCH_3$ |
| 3250 | $C_2H_5$ | i-$C_4H_9$ | H | $NCH_3$ |
| 3251 | $C_2H_5$ | s-$C_4H_9$ | H | $NCH_3$ |
| 3252 | $C_2H_5$ | t-$C_4H_9$ | H | $NCH_3$ |
| 3253 | $C_2H_5$ | $CH_2OCH_3$ | H | $NCH_3$ |
| 3254 | $C_2H_5$ | $CF_3$ | H | $NCH_3$ |
| 3255 | $C_2H_5$ | $CF_2H$ | H | $NCH_3$ |
| 3256 | $C_2H_5$ | CN | H | $NCH_3$ |
| 3257 | $C_2H_5$ | OH | H | $NCH_3$ |
| 3258 | $C_2H_5$ | $OCH_3$ | H | $NCH_3$ |
| 3259 | $C_2H_5$ | $NH_2$ | H | $NCH_3$ |
| 3260 | $C_2H_5$ | $NHCH_3$ | H | $NCH_3$ |
| 3261 | $C_2H_5$ | $N(CH_3)_2$ | H | $NCH_3$ |
| 3262 | $C_2H_5$ | $CO_2CH_3$ | H | $NCH_3$ |
| 3263 | $C_2H_5$ | $CO_2C_2H_5$ | H | $NCH_3$ |
| 3264 | $C_2H_5$ | $C(O)CH_3$ | H | $NCH_3$ |
| 3265 | $C_2H_5$ | $C(O)CF_3$ | H | $NCH_3$ |
| 3266 | $C_2H_5$ | $C(=NOCH_3)CH_3$ | H | $NCH_3$ |
| 3267 | $C_2H_5$ | $SO_2CH_3$ | H | $NCH_3$ |
| 3268 | $C_2H_5$ | $SO_2CF_3$ | H | $NCH_3$ |
| 3269 | $C_2H_5$ | $CH_2CO_2H$ | H | $NCH_3$ |
| 3270 | $C_2H_5$ | $CH_2COOCH_3$ | H | $NCH_3$ |
| 3271 | $C_2H_5$ | $CH_2COOC_2H_5$ | H | $NCH_3$ |
| 3272 | $C_2H_5$ | prop-1-en-3-yl | H | $NCH_3$ |
| 3273 | $C_2H_5$ | trans-but-2-en-1-yl | H | $NCH_3$ |
| 3274 | $C_2H_5$ | cis-but-2-en-1-yl | H | $NCH_3$ |
| 3275 | $C_2H_5$ | cis-3-methyl-but-2-en-1-yl | H | $NCH_3$ |
| 3276 | $C_2H_5$ | cyclopropyl | H | $NCH_3$ |
| 3277 | $C_2H_5$ | cyclopentyl | H | $NCH_3$ |
| 3278 | $C_2H_5$ | cyclohexyl | H | $NCH_3$ |
| 3279 | $C_2H_5$ | 4,5-dihydroisoxazol-3-yl | H | $NCH_3$ |
| 3280 | $C_2H_5$ | 4-methyl-4,5-dihydroisoxazol-3-yl | H | $NCH_3$ |
| 3281 | $C_2H_5$ | isoxazol-3-yl | H | $NCH_3$ |
| 3282 | $C_2H_5$ | 4-methylisoxazol-3-yl | H | $NCH_3$ |
| 3283 | $C_2H_5$ | 4,5-dihydroisoxazol-4-yl | H | $NCH_3$ |
| 3284 | $C_2H_5$ | 3-methyl-4,5-dihydroisoxazol-4-yl | H | $NCH_3$ |
| 3285 | $C_2H_5$ | isoxazol-4-yl | H | $NCH_3$ |
| 3286 | $C_2H_5$ | 3-methylisoxazol-4-yl | H | $NCH_3$ |
| 3287 | $C_2H_5$ | phenyl | H | $NCH_3$ |
| 3288 | $C_2H_5$ | benzyl | H | $NCH_3$ |
| 3289 | $C_2H_5$ | benzoyl | H | $NCH_3$ |
| 3290 | $C_2H_5$ | 2-pyridyl | H | $NCH_3$ |
| 3291 | $C_2H_5$ | H | $CH_3$ | $NCH_3$ |
| 3292 | $C_2H_5$ | $CH_3$ | $CH_3$ | $NCH_3$ |
| 3293 | $C_2H_5$ | $C_2H_5$ | $CH_3$ | $NCH_3$ |
| 3294 | $C_2H_5$ | n-$C_3H_7$ | $CH_3$ | $NCH_3$ |
| 3295 | $C_2H_5$ | i-$C_3H_7$ | $CH_3$ | $NCH_3$ |
| 3296 | $C_2H_5$ | n-$C_4H_9$ | $CH_3$ | $NCH_3$ |
| 3297 | $C_2H_5$ | i-$C_4H_9$ | $CH_3$ | $NCH_3$ |
| 3298 | $C_2H_5$ | s-$C_4H_9$ | $CH_3$ | $NCH_3$ |
| 3299 | $C_2H_5$ | t-$C_4H_9$ | $CH_3$ | $NCH_3$ |
| 3300 | $C_2H_5$ | $CH_2OCH_3$ | $CH_3$ | $NCH_3$ |
| 3301 | $C_2H_5$ | $CF_3$ | $CH_3$ | $NCH_3$ |
| 3302 | $C_2H_5$ | $CF_2H$ | $CH_3$ | $NCH_3$ |
| 3303 | $C_2H_5$ | CN | $CH_3$ | $NCH_3$ |
| 3304 | $C_2H_5$ | OH | $CH_3$ | $NCH_3$ |
| 3305 | $C_2H_5$ | $OCH_3$ | $CH_3$ | $NCH_3$ |
| 3306 | $C_2H_5$ | $NH_2$ | $CH_3$ | $NCH_3$ |
| 3307 | $C_2H_5$ | $NHCH_3$ | $CH_3$ | $NCH_3$ |
| 3308 | $C_2H_5$ | $N(CH_3)_2$ | $CH_3$ | $NCH_3$ |
| 3309 | $C_2H_5$ | $CO_2CH_3$ | $CH_3$ | $NCH_3$ |
| 3310 | $C_2H_5$ | $CO_2C_2H_5$ | $CH_3$ | $NCH_3$ |
| 3311 | $C_2H_5$ | $C(O)CH_3$ | $CH_3$ | $NCH_3$ |
| 3312 | $C_2H_5$ | $C(O)CF_3$ | $CH_3$ | $NCH_3$ |
| 3313 | $C_2H_5$ | $C(=NOCH_3)CH_3$ | $CH_3$ | $NCH_3$ |
| 3314 | $C_2H_5$ | $SO_2CH_3$ | $CH_3$ | $NCH_3$ |
| 3315 | $C_2H_5$ | $SO_2CF_3$ | $CH_3$ | $NCH_3$ |
| 3316 | $C_2H_5$ | $CH_2CO_2H$ | $CH_3$ | $NCH_3$ |
| 3317 | $C_2H_5$ | $CH_2COOCH_3$ | $CH_3$ | $NCH_3$ |

TABLE A-continued

| No. | R$^1$ | R$^2$ | R$^3$ | A |
|---|---|---|---|---|
| 3318 | C$_2$H$_5$ | CH$_2$COOC$_2$H$_5$ | CH$_3$ | NCH$_3$ |
| 3319 | C$_2$H$_5$ | prop-1-en-3-yl | CH$_3$ | NCH$_3$ |
| 3320 | C$_2$H$_5$ | trans-but-2-en-1-yl | CH$_3$ | NCH$_3$ |
| 3321 | C$_2$H$_5$ | cis-but-2-en-1-yl | CH$_3$ | NCH$_3$ |
| 3322 | C$_2$H$_5$ | cis-3-methyl-but-2-en-1-yl | CH$_3$ | NCH$_3$ |
| 3323 | C$_2$H$_5$ | cyclopropyl | CH$_3$ | NCH$_3$ |
| 3324 | C$_2$H$_5$ | cyclopentyl | CH$_3$ | NCH$_3$ |
| 3325 | C$_2$H$_5$ | cyclohexyl | CH$_3$ | NCH$_3$ |
| 3326 | C$_2$H$_5$ | 4,5-dihydroisoxazol-3-yl | CH$_3$ | NCH$_3$ |
| 3327 | C$_2$H$_5$ | 4-methyl-4,5-dihydroisoxazol-3-yl | CH$_3$ | NCH$_3$ |
| 3328 | C$_2$H$_5$ | isoxazol-3-yl | CH$_3$ | NCH$_3$ |
| 3329 | C$_2$H$_5$ | 4-methylisoxazol-3-yl | CH$_3$ | NCH$_3$ |
| 3330 | C$_2$H$_5$ | 4,5-dihydroisoxazol-4-yl | CH$_3$ | NCH$_3$ |
| 3331 | C$_2$H$_5$ | 3-methyl-4,5-dihydroisoxazol-4-yl | CH$_3$ | NCH$_3$ |
| 3332 | C$_2$H$_5$ | isoxazol-4-yl | CH$_3$ | NCH$_3$ |
| 3333 | C$_2$H$_5$ | 3-methylisoxazol-4-yl | CH$_3$ | NCH$_3$ |
| 3334 | C$_2$H$_5$ | phenyl | CH$_3$ | NCH$_3$ |
| 3335 | C$_2$H$_5$ | benzyl | CH$_3$ | NCH$_3$ |
| 3336 | C$_2$H$_5$ | benzoyl | CH$_3$ | NCH$_3$ |
| 3337 | C$_2$H$_5$ | 2-pyridyl | CH$_3$ | NCH$_3$ |
| 3338 | C$_2$H$_5$ | H | Cl | NCH$_3$ |
| 3339 | C$_2$H$_5$ | CH$_3$ | Cl | NCH$_3$ |
| 3340 | C$_2$H$_5$ | C$_2$H$_5$ | Cl | NCH$_3$ |
| 3341 | C$_2$H$_5$ | n-C$_3$H$_7$ | Cl | NCH$_3$ |
| 3342 | C$_2$H$_5$ | i-C$_3$H$_7$ | Cl | NCH$_3$ |
| 3343 | C$_2$H$_5$ | n-C$_4$H$_9$ | Cl | NCH$_3$ |
| 3344 | C$_2$H$_5$ | i-C$_4$H$_9$ | Cl | NCH$_3$ |
| 3345 | C$_2$H$_5$ | s-C$_4$H$_9$ | Cl | NCH$_3$ |
| 3346 | C$_2$H$_5$ | t-C$_4$H$_9$ | Cl | NCH$_3$ |
| 3347 | C$_2$H$_5$ | CH$_2$OCH$_3$ | Cl | NCH$_3$ |
| 3348 | C$_2$H$_5$ | CF$_3$ | Cl | NCH$_3$ |
| 3349 | C$_2$H$_5$ | CF$_2$H | Cl | NCH$_3$ |
| 3350 | C$_2$H$_5$ | CN | Cl | NCH$_3$ |
| 3351 | C$_2$H$_5$ | OH | Cl | NCH$_3$ |
| 3352 | C$_2$H$_5$ | OCH$_3$ | Cl | NCH$_3$ |
| 3353 | C$_2$H$_5$ | NH$_2$ | Cl | NCH$_3$ |
| 3354 | C$_2$H$_5$ | NHCH$_3$ | Cl | NCH$_3$ |
| 3355 | C$_2$H$_5$ | N(CH$_3$)$_2$ | Cl | NCH$_3$ |
| 3356 | C$_2$H$_5$ | CO$_2$CH$_3$ | Cl | NCH$_3$ |
| 3357 | C$_2$H$_5$ | CO$_2$C$_2$H$_5$ | Cl | NCH$_3$ |
| 3358 | C$_2$H$_5$ | C(O)CH$_3$ | Cl | NCH$_3$ |
| 3359 | C$_2$H$_5$ | C(O)CF$_3$ | Cl | NCH$_3$ |
| 3360 | C$_2$H$_5$ | C(=NOCH$_3$)CH$_3$ | Cl | NCH$_3$ |
| 3361 | C$_2$H$_5$ | SO$_2$CH$_3$ | Cl | NCH$_3$ |
| 3362 | C$_2$H$_5$ | SO$_2$CF$_3$ | Cl | NCH$_3$ |
| 3363 | C$_2$H$_5$ | CH$_2$CO$_2$H | Cl | NCH$_3$ |
| 3364 | C$_2$H$_5$ | CH$_2$COOCH$_3$ | Cl | NCH$_3$ |
| 3365 | C$_2$H$_5$ | CH$_2$COOC$_2$H$_5$ | Cl | NCH$_3$ |
| 3366 | C$_2$H$_5$ | prop-1-en-3-yl | Cl | NCH$_3$ |
| 3367 | C$_2$H$_5$ | trans-but-2-en-1-yl | Cl | NCH$_3$ |
| 3368 | C$_2$H$_5$ | cis-but-2-en-1-yl | Cl | NCH$_3$ |
| 3369 | C$_2$H$_5$ | cis-3-methyl-but-2-en-1-yl | Cl | NCH$_3$ |
| 3370 | C$_2$H$_5$ | cyclopropyl | Cl | NCH$_3$ |
| 3371 | C$_2$H$_5$ | cyclopentyl | Cl | NCH$_3$ |
| 3372 | C$_2$H$_5$ | cyclohexyl | Cl | NCH$_3$ |
| 3373 | C$_2$H$_5$ | 4,5-dihydroisoxazol-3-yl | Cl | NCH$_3$ |
| 3374 | C$_2$H$_5$ | 4-methyl-4,5-dihydroisoxazol-3-yl | Cl | NCH$_3$ |
| 3375 | C$_2$H$_5$ | isoxazol-3-yl | Cl | NCH$_3$ |
| 3376 | C$_2$H$_5$ | 4-methylisoxazol-3-yl | Cl | NCH$_3$ |
| 3377 | C$_2$H$_5$ | 4,5-dihydroisoxazol-4-yl | Cl | NCH$_3$ |
| 3378 | C$_2$H$_5$ | 3-methyl-4,5-dihydroisoxazol-4-yl | Cl | NCH$_3$ |
| 3379 | C$_2$H$_5$ | isoxazol-4-yl | Cl | NCH$_3$ |
| 3380 | C$_2$H$_5$ | 3-methylisoxazol-4-yl | Cl | NCH$_3$ |
| 3381 | C$_2$H$_5$ | phenyl | Cl | NCH$_3$ |
| 3382 | C$_2$H$_5$ | benzyl | Cl | NCH$_3$ |
| 3383 | C$_2$H$_5$ | benzoyl | Cl | NCH$_3$ |
| 3384 | C$_2$H$_5$ | 2-pyridyl | Cl | NCH$_3$ |
| 3385 | CH$_3$ | n-pentyl | H | O |
| 3386 | CH$_3$ | CH$_2$—C≡C—CH$_2$—CH$_3$ | H | O |
| 3387 | CH$_3$ | CH$_2$—CH$_2$—CH=CH$_2$ | H | O |
| 3388 | CH$_3$ | CH$_2$—CH$_2$—CH$_2$—CH=CH$_2$ | H | O |
| 3389 | CH$_3$ | CH$_2$-[(3-OCH$_3$)C$_6$H$_4$] | H | O |
| 3390 | CH$_3$ | CH$_2$—C≡C—CH$_3$ | H | O |
| 3391 | CH$_3$ | CH$_2$—CH$_2$-(1,3-dioxolan-2-yl) | H | O |
| 3392 | CH$_3$ | CH$_2$-(1,3-dioxolan-2-yl) | H | O |
| 3393 | CH$_3$ | n-pentyl | CH$_3$ | O |
| 3394 | CH$_3$ | CH$_2$—C≡C—CH$_2$—CH$_3$ | CH$_3$ | O |
| 3395 | CH$_3$ | CH$_2$—CH$_2$—CH=CH$_2$ | CH$_3$ | O |
| 3396 | CH$_3$ | CH$_2$—CH$_2$—CH$_2$—CH=CH$_2$ | CH$_3$ | O |
| 3397 | CH$_3$ | CH$_2$-[(3-OCH$_3$)C$_6$H$_4$] | CH$_3$ | O |
| 3398 | CH$_3$ | CH$_2$—C≡C—CH$_3$ | CH$_3$ | O |
| 3399 | CH$_3$ | CH$_2$—CH$_2$-(1,3-dioxolan-2-yl) | CH$_3$ | O |
| 3400 | CH$_3$ | CH$_2$-(1,3-dioxolan-2-yl) | CH$_3$ | O |
| 3401 | CH$_3$ | n-pentyl | Cl | O |
| 3402 | CH$_3$ | CH$_2$—C≡C—CH$_2$—CH$_3$ | Cl | O |
| 3403 | CH$_3$ | CH$_2$—CH$_2$—CH=CH$_2$ | Cl | O |
| 3404 | CH$_3$ | CH$_2$—CH$_2$—CH$_2$—CH=CH$_2$ | Cl | O |
| 3405 | CH$_3$ | CH$_2$-[(3-OCH$_3$)C$_6$H$_4$] | Cl | O |
| 3406 | CH$_3$ | CH$_2$—C≡C—CH$_3$ | Cl | O |
| 3407 | CH$_3$ | CH$_2$—CH$_2$-(1,3-dioxolan-2-yl) | Cl | O |
| 3408 | CH$_3$ | CH$_2$-(1,3-dioxolan-2-yl) | Cl | O |
| 3409 | Cl | n-pentyl | H | O |
| 3410 | Cl | CH$_2$—C≡C—CH$_2$—CH$_3$ | H | O |
| 3411 | Cl | CH$_2$—CH$_2$—CH=CH$_2$ | H | O |
| 3412 | Cl | CH$_2$—CH$_2$—CH$_2$—CH=CH$_2$ | H | O |
| 3413 | Cl | CH$_2$-[(3-OCH$_3$)C$_6$H$_4$] | H | O |
| 3414 | Cl | CH$_2$—C≡C—CH$_3$ | H | O |
| 3415 | Cl | CH$_2$—CH$_2$-(1,3-dioxolan-2-yl) | H | O |
| 3416 | Cl | CH$_2$-(1,3-dioxolan-2-yl) | H | O |
| 3417 | Cl | n-pentyl | CH$_3$ | O |
| 3418 | Cl | CH$_2$—C≡C—CH$_2$—CH$_3$ | CH$_3$ | O |
| 3419 | Cl | CH$_2$—CH$_2$—CH=CH$_2$ | CH$_3$ | O |
| 3420 | Cl | CH$_2$—CH$_2$—CH$_2$—CH=CH$_2$ | CH$_3$ | O |
| 3421 | Cl | CH$_2$-[(3-OCH$_3$)C$_6$H$_4$] | CH$_3$ | O |
| 3422 | Cl | CH$_2$—C≡C—CH$_3$ | CH$_3$ | O |
| 3423 | Cl | CH$_2$—CH$_2$-(1,3-dioxolan-2-yl) | CH$_3$ | O |
| 3424 | Cl | CH$_2$-(1,3-dioxolan-2-yl) | CH$_3$ | O |
| 3425 | Cl | n-pentyl | Cl | O |
| 3426 | Cl | CH$_2$—C≡C—CH$_2$—CH$_3$ | Cl | O |
| 3427 | Cl | CH$_2$—CH$_2$—CH=CH$_2$ | Cl | O |
| 3428 | Cl | CH$_2$—CH$_2$—CH$_2$—CH=CH$_2$ | Cl | O |
| 3429 | Cl | CH$_2$-[(3-OCH$_3$)C$_6$H$_4$] | Cl | O |
| 3430 | Cl | CH$_2$—C≡C—CH$_3$ | Cl | O |
| 3431 | Cl | CH$_2$—CH$_2$-(1,3-dioxolan-2-yl) | Cl | O |
| 3432 | Cl | CH$_2$-(1,3-dioxolan-2-yl) | Cl | O |
| 3433 | OCH$_3$ | n-pentyl | H | O |
| 3434 | OCH$_3$ | CH$_2$—C≡C—CH$_2$—CH$_3$ | H | O |
| 3435 | OCH$_3$ | CH$_2$—CH$_2$—CH=CH$_2$ | H | O |
| 3436 | OCH$_3$ | CH$_2$—CH$_2$—CH$_2$—CH=CH$_2$ | H | O |
| 3437 | OCH$_3$ | CH$_2$-[(3-OCH$_3$)C$_6$H$_4$] | H | O |
| 3438 | OCH$_3$ | CH$_2$—C≡C—CH$_3$ | H | O |
| 3439 | OCH$_3$ | CH$_2$—CH$_2$-(1,3-dioxolan-2-yl) | H | O |
| 3440 | OCH$_3$ | CH$_2$-(1,3-dioxolan-2-yl) | H | O |
| 3441 | OCH$_3$ | n-pentyl | CH$_3$ | O |
| 3442 | OCH$_3$ | CH$_2$—C≡C—CH$_2$—CH$_3$ | CH$_3$ | O |
| 3443 | OCH$_3$ | CH$_2$—CH$_2$—CH=CH$_2$ | CH$_3$ | O |
| 3444 | OCH$_3$ | CH$_2$—CH$_2$—CH$_2$—CH=CH$_2$ | CH$_3$ | O |
| 3445 | OCH$_3$ | CH$_2$-[(3-OCH$_3$)C$_6$H$_4$] | CH$_3$ | O |
| 3446 | OCH$_3$ | CH$_2$—C≡C—CH$_3$ | CH$_3$ | O |

TABLE A-continued

| No. | R¹ | R² | R³ | A |
|---|---|---|---|---|
| 3447 | OCH₃ | CH₂—CH₂-(1,3-dioxolan-2-yl) | CH₃ | O |
| 3448 | OCH₃ | CH₂-(1,3-dioxolan-2-yl) | CH₃ | O |
| 3449 | OCH₃ | n-pentyl | Cl | O |
| 3450 | OCH₃ | CH₂—C≡C—CH₂—CH₃ | Cl | O |
| 3451 | OCH₃ | CH₂—CH₂—CH=CH₂ | Cl | O |
| 3452 | OCH₃ | CH₂—CH₂—CH₂—CH=CH₂ | Cl | O |
| 3453 | OCH₃ | CH₂-[(3-OCH₃)C₆H₄] | Cl | O |
| 3454 | OCH₃ | CH₂—C≡C—CH₃ | Cl | O |
| 3455 | OCH₃ | CH₂—CH₂-(1,3-dioxolan-2-yl) | Cl | O |
| 3456 | OCH₃ | CH₂-(1,3-dioxolan-2-yl) | Cl | O |
| 3457 | OCF₃ | n-pentyl | H | O |
| 3458 | OCF₃ | CH₂—C≡C—CH₂—CH₃ | H | O |
| 3459 | OCF₃ | CH₂—CH₂—CH=CH₂ | H | O |
| 3460 | OCF₃ | CH₂—CH₂—CH₂—CH=CH₂ | H | O |
| 3461 | OCF₃ | CH₂-[(3-OCH₃)C₆H₄] | H | O |
| 3462 | OCF₃ | CH₂—C≡C—CH₃ | H | O |
| 3463 | OCF₃ | CH₂—CH₂-(1,3-dioxolan-2-yl) | H | O |
| 3464 | OCF₃ | CH₂-(1,3-dioxolan-2-yl) | H | O |
| 3465 | OCF₃ | n-pentyl | CH₃ | O |
| 3466 | OCF₃ | CH₂—C≡C—CH₂—CH₃ | CH₃ | O |
| 3467 | OCF₃ | CH₂—CH₂—CH=CH₂ | CH₃ | O |
| 3468 | OCF₃ | CH₂—CH₂—CH₂—CH=CH₂ | CH₃ | O |
| 3469 | OCF₃ | CH₂-[(3-OCH₃)C₆H₄] | CH₃ | O |
| 3470 | OCF₃ | CH₂—C≡C—CH₃ | CH₃ | O |
| 3471 | OCF₃ | CH₂—CH₂-(1,3-dioxolan-2-yl) | CH₃ | O |
| 3472 | OCF₃ | CH₂-(1,3-dioxolan-2-yl) | CH₃ | O |
| 3473 | OCF₃ | n-pentyl | Cl | O |
| 3474 | OCF₃ | CH₂—C≡C—CH₂—CH₃ | Cl | O |
| 3475 | OCF₃ | CH₂—CH₂—CH=CH₂ | Cl | O |
| 3476 | OCF₃ | CH₂—CH₂—CH₂—CH=CH₂ | Cl | O |
| 3477 | OCF₃ | CH₂-[(3-OCH₃)C₆H₄] | Cl | O |
| 3478 | OCF₃ | CH₂—C≡C—CH₃ | Cl | O |
| 3479 | OCF₃ | CH₂—CH₂-(1,3-dioxolan-2-yl) | Cl | O |
| 3480 | OCF₃ | CH₂-(1,3-dioxolan-2-yl) | Cl | O |
| 3481 | SCH₃ | n-pentyl | H | O |
| 3482 | SCH₃ | CH₂—C≡C—CH₂—CH₃ | H | O |
| 3483 | SCH₃ | CH₂—CH₂—CH=CH₂ | H | O |
| 3484 | SCH₃ | CH₂—CH₂—CH₂—CH=CH₂ | H | O |
| 3485 | SCH₃ | CH₂-[(3-OCH₃)C₆H₄] | H | O |
| 3486 | SCH₃ | CH₂—C≡C—CH₃ | H | O |
| 3487 | SCH₃ | CH₂—CH₂-(1,3-dioxolan-2-yl) | H | O |
| 3488 | SCH₃ | CH₂-(1,3-dioxolan-2-yl) | H | O |
| 3489 | SCH₃ | n-pentyl | CH₃ | O |
| 3490 | SCH₃ | CH₂—C≡C—CH₂—CH₃ | CH₃ | O |
| 3491 | SCH₃ | CH₂—CH₂—CH=CH₂ | CH₃ | O |
| 3492 | SCH₃ | CH₂—CH₂—CH₂—CH=CH₂ | CH₃ | O |
| 3493 | SCH₃ | CH₂-[(3-OCH₃)C₆H₄] | CH₃ | O |
| 3494 | SCH₃ | CH₂—C≡C—CH₃ | CH₃ | O |
| 3495 | SCH₃ | CH₂—CH₂-(1,3-dioxolan-2-yl) | CH₃ | O |
| 3496 | SCH₃ | CH₂-(1,3-dioxolan-2-yl) | CH₃ | O |
| 3497 | SCH₃ | n-pentyl | Cl | O |
| 3498 | SCH₃ | CH₂—C≡C—CH₂—CH₃ | Cl | O |
| 3499 | SCH₃ | CH₂—CH₂—CH=CH₂ | Cl | O |
| 3500 | SCH₃ | CH₂—CH₂—CH₂—CH=CH₂ | Cl | O |
| 3501 | SCH₃ | CH₂-[(3-OCH₃)C₆H₄] | Cl | O |
| 3502 | SCH₃ | CH₂—C≡C—CH₃ | Cl | O |
| 3503 | SCH₃ | CH₂—CH₂-(1,3-dioxolan-2-yl) | Cl | O |
| 3504 | SCH₃ | CH₂-(1,3-dioxolan-2-yl) | Cl | O |
| 3505 | SO₂CH₃ | n-pentyl | H | O |
| 3506 | SO₂CH₃ | CH₂—C≡C—CH₂—CH₃ | H | O |
| 3507 | SO₂CH₃ | CH₂—CH₂—CH=CH₂ | H | O |
| 3508 | SO₂CH₃ | CH₂—CH₂—CH₂—CH=CH₂ | H | O |
| 3509 | SO₂CH₃ | CH₂-[(3-OCH₃)C₆H₄] | H | O |
| 3510 | SO₂CH₃ | CH₂—C≡C—CH₃ | H | O |
| 3511 | SO₂CH₃ | CH₂—CH₂-(1,3-dioxolan-2-yl) | H | O |
| 3512 | SO₂CH₃ | CH₂-(1,3-dioxolan-2-yl) | H | O |
| 3513 | SO₂CH₃ | n-pentyl | CH₃ | O |
| 3514 | SO₂CH₃ | CH₂—C≡C—CH₂—CH₃ | CH₃ | O |
| 3515 | SO₂CH₃ | CH₂—CH₂—CH=CH₂ | CH₃ | O |
| 3516 | SO₂CH₃ | CH₂—CH₂—CH₂—CH=CH₂ | CH₃ | O |
| 3517 | SO₂CH₃ | CH₂-[(3-OCH₃)C₆H₄] | CH₃ | O |
| 3518 | SO₂CH₃ | CH₂—C≡C—CH₃ | CH₃ | O |
| 3519 | SO₂CH₃ | CH₂—CH₂-(1,3-dioxolan-2-yl) | CH₃ | O |
| 3520 | SO₂CH₃ | CH₂-(1,3-dioxolan-2-yl) | CH₃ | O |
| 3521 | SO₂CH₃ | n-pentyl | Cl | O |
| 3522 | SO₂CH₃ | CH₂—C≡C—CH₂—CH₃ | Cl | O |
| 3523 | SO₂CH₃ | CH₂—CH₂—CH=CH₂ | Cl | O |
| 3524 | SO₂CH₃ | CH₂—CH₂—CH₂—CH=CH₂ | Cl | O |
| 3525 | SO₂CH₃ | CH₂-[(3-OCH₃)C₆H₄] | Cl | O |
| 3526 | SO₂CH₃ | CH₂—C≡C—CH₃ | Cl | O |
| 3527 | SO₂CH₃ | CH₂—CH₂-(1,3-dioxolan-2-yl) | Cl | O |
| 3528 | SO₂CH₃ | CH₂-(1,3-dioxolan-2-yl) | Cl | O |
| 3529 | CF₃ | n-pentyl | H | O |
| 3530 | CF₃ | CH₂—C≡C—CH₂—CH₃ | H | O |
| 3531 | CF₃ | CH₂—CH₂—CH=CH₂ | H | O |
| 3532 | CF₃ | CH₂—CH₂—CH₂—CH=CH₂ | H | O |
| 3533 | CF₃ | CH₂-[(3-OCH₃)C₆H₄] | H | O |
| 3534 | CF₃ | CH₂—C≡C—CH₃ | H | O |
| 3535 | CF₃ | CH₂—CH₂-(1,3-dioxolan-2-yl) | H | O |
| 3536 | CF₃ | CH₂-(1,3-dioxolan-2-yl) | H | O |
| 3537 | CF₃ | n-pentyl | CH₃ | O |
| 3538 | CF₃ | CH₂—C≡C—CH₂—CH₃ | CH₃ | O |
| 3539 | CF₃ | CH₂—CH₂—CH=CH₂ | CH₃ | O |
| 3540 | CF₃ | CH₂—CH₂—CH₂—CH=CH₂ | CH₃ | O |
| 3541 | CF₃ | CH₂-[(3-OCH₃)C₆H₄] | CH₃ | O |
| 3542 | CF₃ | CH₂—C≡C—CH₃ | CH₃ | O |
| 3543 | CF₃ | CH₂—CH₂-(1,3-dioxolan-2-yl) | CH₃ | O |
| 3544 | CF₃ | CH₂-(1,3-dioxolan-2-yl) | CH₃ | O |
| 3545 | CF₃ | n-pentyl | Cl | O |
| 3546 | CF₃ | CH₂—C≡C—CH₂—CH₃ | Cl | O |
| 3547 | CF₃ | CH₂—CH₂—CH=CH₂ | Cl | O |
| 3548 | CF₃ | CH₂—CH₂—CH₂—CH=CH₂ | Cl | O |
| 3549 | CF₃ | CH₂-[(3-OCH₃)C₆H₄] | Cl | O |
| 3550 | CF₃ | CH₂—C≡C—CH₃ | Cl | O |
| 3551 | CF₃ | CH₂—CH₂-(1,3-dioxolan-2-yl) | Cl | O |
| 3552 | CF₃ | CH₂-(1,3-dioxolan-2-yl) | Cl | O |
| 3553 | C₂H₅ | n-pentyl | H | O |
| 3554 | C₂H₅ | CH₂—C≡C—CH₂—CH₃ | H | O |
| 3555 | C₂H₅ | CH₂—CH₂—CH=CH₂ | H | O |
| 3556 | C₂H₅ | CH₂—CH₂—CH₂—CH=CH₂ | H | O |
| 3557 | C₂H₅ | CH₂-[(3-OCH₃)C₆H₄] | H | O |
| 3558 | C₂H₅ | CH₂—C≡C—CH₃ | H | O |
| 3559 | C₂H₅ | CH₂—CH₂-(1,3-dioxolan-2-yl) | H | O |
| 3560 | C₂H₅ | CH₂-(1,3-dioxolan-2-yl) | H | O |
| 3561 | C₂H₅ | n-pentyl | CH₃ | O |
| 3562 | C₂H₅ | CH₂—C≡C—CH₂—CH₃ | CH₃ | O |
| 3563 | C₂H₅ | CH₂—CH₂—CH=CH₂ | CH₃ | O |
| 3564 | C₂H₅ | CH₂—CH₂—CH₂—CH=CH₂ | CH₃ | O |
| 3565 | C₂H₅ | CH₂-[(3-OCH₃)C₆H₄] | CH₃ | O |
| 3566 | C₂H₅ | CH₂—C≡C—CH₃ | CH₃ | O |
| 3567 | C₂H₅ | CH₂—CH₂-(1,3-dioxolan-2-yl) | CH₃ | O |
| 3568 | C₂H₅ | CH₂-(1,3-dioxolan-2-yl) | CH₃ | O |

TABLE A-continued

| No. | R¹ | R² | R³ | A |
|---|---|---|---|---|
| 3569 | $C_2H_5$ | n-pentyl | Cl | O |
| 3570 | $C_2H_5$ | $CH_2-C\equiv C-CH_2-CH_3$ | Cl | O |
| 3571 | $C_2H_5$ | $CH_2-CH_2-CH=CH_2$ | Cl | O |
| 3572 | $C_2H_5$ | $CH_2-CH_2-CH_2-CH=CH_2$ | Cl | O |
| 3573 | $C_2H_5$ | $CH_2-[(3-OCH_3)C_6H_4]$ | Cl | O |
| 3574 | $C_2H_5$ | $CH_2-C\equiv C-CH_3$ | Cl | O |
| 3575 | $C_2H_5$ | $CH_2-CH_2$-(1,3-dioxolan-2-yl) | Cl | O |
| 3576 | $C_2H_5$ | $CH_2$-(1,3-dioxolan-2-yl) | Cl | O |
| 3577 | $CH_3$ | n-pentyl | H | S |
| 3578 | $CH_3$ | $CH_2-C\equiv C-CH_2-CH_3$ | H | S |
| 3579 | $CH_3$ | $CH_2-CH_2-CH=CH_2$ | H | S |
| 3580 | $CH_3$ | $CH_2-CH_2-CH_2-CH=CH_2$ | H | S |
| 3581 | $CH_3$ | $CH_2-[(3-OCH_3)C_6H_4]$ | H | S |
| 3582 | $CH_3$ | $CH_2-C\equiv C-CH_3$ | H | S |
| 3583 | $CH_3$ | $CH_2-CH_2$-(1,3-dioxolan-2-yl) | H | S |
| 3584 | $CH_3$ | $CH_2$-(1,3-dioxolan-2-yl) | H | S |
| 3585 | $CH_3$ | n-pentyl | $CH_3$ | S |
| 3586 | $CH_3$ | $CH_2-C\equiv C-CH_2-CH_3$ | $CH_3$ | S |
| 3587 | $CH_3$ | $CH_2-CH_2-CH=CH_2$ | $CH_3$ | S |
| 3588 | $CH_3$ | $CH_2-CH_2-CH_2-CH=CH_2$ | $CH_3$ | S |
| 3589 | $CH_3$ | $CH_2-[(3-OCH_3)C_6H_4]$ | $CH_3$ | S |
| 3590 | $CH_3$ | $CH_2-C\equiv C-CH_3$ | $CH_3$ | S |
| 3591 | $CH_3$ | $CH_2-CH_2$-(1,3-dioxolan-2-yl) | $CH_3$ | S |
| 3592 | $CH_3$ | $CH_2$-(1,3-dioxolan-2-yl) | $CH_3$ | S |
| 3593 | $CH_3$ | n-pentyl | Cl | S |
| 3594 | $CH_3$ | $CH_2-C\equiv C-CH_2-CH_3$ | Cl | S |
| 3595 | $CH_3$ | $CH_2-CH_2-CH=CH_2$ | Cl | S |
| 3596 | $CH_3$ | $CH_2-CH_2-CH_2-CH=CH_2$ | Cl | S |
| 3597 | $CH_3$ | $CH_2-[(3-OCH_3)C_6H_4]$ | Cl | S |
| 3598 | $CH_3$ | $CH_2-C\equiv C-CH_3$ | Cl | S |
| 3599 | $CH_3$ | $CH_2-CH_2$-(1,3-dioxolan-2-yl) | Cl | S |
| 3600 | $CH_3$ | $CH_2$-(1,3-dioxolan-2-yl) | Cl | S |
| 3601 | Cl | n-pentyl | H | S |
| 3602 | Cl | $CH_2-C\equiv C-CH_2-CH_3$ | H | S |
| 3603 | Cl | $CH_2-CH_2-CH=CH_2$ | H | S |
| 3604 | Cl | $CH_2-CH_2-CH_2-CH=CH_2$ | H | S |
| 3605 | Cl | $CH_2-[(3-OCH_3)C_6H_4]$ | H | S |
| 3606 | Cl | $CH_2-C\equiv C-CH_3$ | H | S |
| 3607 | Cl | $CH_2-CH_2$-(1,3-dioxolan-2-yl) | H | S |
| 3608 | Cl | $CH_2$-(1,3-dioxolan-2-yl) | H | S |
| 3609 | Cl | n-pentyl | $CH_3$ | S |
| 3610 | Cl | $CH_2-C\equiv C-CH_2-CH_3$ | $CH_3$ | S |
| 3611 | Cl | $CH_2-CH_2-CH=CH_2$ | $CH_3$ | S |
| 3612 | Cl | $CH_2-CH_2-CH_2-CH=CH_2$ | $CH_3$ | S |
| 3613 | Cl | $CH_2-[(3-OCH_3)C_6H_4]$ | $CH_3$ | S |
| 3614 | Cl | $CH_2-C\equiv C-CH_3$ | $CH_3$ | S |
| 3615 | Cl | $CH_2-CH_2$-(1,3-dioxolan-2-yl) | $CH_3$ | S |
| 3616 | Cl | $CH_2$-(1,3-dioxolan-2-yl) | $CH_3$ | S |
| 3617 | Cl | n-pentyl | Cl | S |
| 3618 | Cl | $CH_2-C\equiv C-CH_2-CH_3$ | Cl | S |
| 3619 | Cl | $CH_2-CH_2-CH=CH_2$ | Cl | S |
| 3620 | Cl | $CH_2-CH_2-CH_2-CH=CH_2$ | Cl | S |
| 3621 | Cl | $CH_2-[(3-OCH_3)C_6H_4]$ | Cl | S |
| 3622 | Cl | $CH_2-C\equiv C-CH_3$ | Cl | S |
| 3623 | Cl | $CH_2-CH_2$-(1,3-dioxolan-2-yl) | Cl | S |
| 3624 | Cl | $CH_2$-(1,3-dioxolan-2-yl) | Cl | S |
| 3625 | $OCH_3$ | n-pentyl | H | S |
| 3626 | $OCH_3$ | $CH_2-C\equiv C-CH_2-CH_3$ | H | S |
| 3627 | $OCH_3$ | $CH_2-CH_2-CH=CH_2$ | H | S |
| 3628 | $OCH_3$ | $CH_2-CH_2-CH_2-CH=CH_2$ | H | S |
| 3629 | $OCH_3$ | $CH_2-[(3-OCH_3)C_6H_4]$ | H | S |
| 3630 | $OCH_3$ | $CH_2-C\equiv C-CH_3$ | H | S |
| 3631 | $OCH_3$ | $CH_2-CH_2$-(1,3-dioxolan-2-yl) | H | S |
| 3632 | $OCH_3$ | $CH_2$-(1,3-dioxolan-2-yl) | H | S |
| 3633 | $OCH_3$ | n-pentyl | $CH_3$ | S |
| 3634 | $OCH_3$ | $CH_2-C\equiv C-CH_2-CH_3$ | $CH_3$ | S |
| 3635 | $OCH_3$ | $CH_2-CH_2-CH=CH_2$ | $CH_3$ | S |
| 3636 | $OCH_3$ | $CH_2-CH_2-CH_2-CH=CH_2$ | $CH_3$ | S |
| 3637 | $OCH_3$ | $CH_2-[(3-OCH_3)C_6H_4]$ | $CH_3$ | S |
| 3638 | $OCH_3$ | $CH_2-C\equiv C-CH_3$ | $CH_3$ | S |
| 3639 | $OCH_3$ | $CH_2-CH_2$-(1,3-dioxolan-2-yl) | $CH_3$ | S |
| 3640 | $OCH_3$ | $CH_2$-(1,3-dioxolan-2-yl) | $CH_3$ | S |
| 3641 | $OCH_3$ | n-pentyl | Cl | S |
| 3642 | $OCH_3$ | $CH_2-C\equiv C-CH_2-CH_3$ | Cl | S |
| 3643 | $OCH_3$ | $CH_2-CH_2-CH=CH_2$ | Cl | S |
| 3644 | $OCH_3$ | $CH_2-CH_2-CH_2-CH=CH_2$ | Cl | S |
| 3645 | $OCH_3$ | $CH_2-[(3-OCH_3)C_6H_4]$ | Cl | S |
| 3646 | $OCH_3$ | $CH_2-C\equiv C-CH_3$ | Cl | S |
| 3647 | $OCH_3$ | $CH_2-CH_2$-(1,3-dioxolan-2-yl) | Cl | S |
| 3648 | $OCH_3$ | $CH_2$-(1,3-dioxolan-2-yl) | Cl | S |
| 3649 | $OCF_3$ | n-pentyl | H | S |
| 3650 | $OCF_3$ | $CH_2-C\equiv C-CH_2-CH_3$ | H | S |
| 3651 | $OCF_3$ | $CH_2-CH_2-CH=CH_2$ | H | S |
| 3652 | $OCF_3$ | $CH_2-CH_2-CH_2-CH=CH_2$ | H | S |
| 3653 | $OCF_3$ | $CH_2-[(3-OCH_3)C_6H_4]$ | H | S |
| 3654 | $OCF_3$ | $CH_2-C\equiv C-CH_3$ | H | S |
| 3655 | $OCF_3$ | $CH_2-CH_2$-(1,3-dioxolan-2-yl) | H | S |
| 3656 | $OCF_3$ | $CH_2$-(1,3-dioxolan-2-yl) | H | S |
| 3657 | $OCF_3$ | n-pentyl | $CH_3$ | S |
| 3658 | $OCF_3$ | $CH_2-C\equiv C-CH_2-CH_3$ | $CH_3$ | S |
| 3659 | $OCF_3$ | $CH_2-CH_2-CH=CH_2$ | $CH_3$ | S |
| 3660 | $OCF_3$ | $CH_2-CH_2-CH_2-CH=CH_2$ | $CH_3$ | S |
| 3661 | $OCF_3$ | $CH_2-[(3-OCH_3)C_6H_4]$ | $CH_3$ | S |
| 3662 | $OCF_3$ | $CH_2-C\equiv C-CH_3$ | $CH_3$ | S |
| 3663 | $OCF_3$ | $CH_2-CH_2$-(1,3-dioxolan-2-yl) | $CH_3$ | S |
| 3664 | $OCF_3$ | $CH_2$-(1,3-dioxolan-2-yl) | $CH_3$ | S |
| 3665 | $OCF_3$ | n-pentyl | Cl | S |
| 3666 | $OCF_3$ | $CH_2-C\equiv C-CH_2-CH_3$ | Cl | S |
| 3667 | $OCF_3$ | $CH_2-CH_2-CH=CH_2$ | Cl | S |
| 3668 | $OCF_3$ | $CH_2-CH_2-CH_2-CH=CH_2$ | Cl | S |
| 3669 | $OCF_3$ | $CH_2-[(3-OCH_3)C_6H_4]$ | Cl | S |
| 3670 | $OCF_3$ | $CH_2-C\equiv C-CH_3$ | Cl | S |
| 3671 | $OCF_3$ | $CH_2-CH_2$-(1,3-dioxolan-2-yl) | Cl | S |
| 3672 | $OCF_3$ | $CH_2$-(1,3-dioxolan-2-yl) | Cl | S |
| 3673 | $SCH_3$ | n-pentyl | H | S |
| 3674 | $SCH_3$ | $CH_2-C\equiv C-CH_2-CH_3$ | H | S |
| 3675 | $SCH_3$ | $CH_2-CH_2-CH=CH_2$ | H | S |
| 3676 | $SCH_3$ | $CH_2-CH_2-CH_2-CH=CH_2$ | H | S |
| 3677 | $SCH_3$ | $CH_2-[(3-OCH_3)C_6H_4]$ | H | S |
| 3678 | $SCH_3$ | $CH_2-C\equiv C-CH_3$ | H | S |
| 3679 | $SCH_3$ | $CH_2-CH_2$-(1,3-dioxolan-2-yl) | H | S |
| 3680 | $SCH_3$ | $CH_2$-(1,3-dioxolan-2-yl) | H | S |
| 3681 | $SCH_3$ | n-pentyl | $CH_3$ | S |
| 3682 | $SCH_3$ | $CH_2-C\equiv C-CH_2-CH_3$ | $CH_3$ | S |
| 3683 | $SCH_3$ | $CH_2-CH_2-CH=CH_2$ | $CH_3$ | S |
| 3684 | $SCH_3$ | $CH_2-CH_2-CH_2-CH=CH_2$ | $CH_3$ | S |
| 3685 | $SCH_3$ | $CH_2-[(3-OCH_3)C_6H_4]$ | $CH_3$ | S |
| 3686 | $SCH_3$ | $CH_2-C\equiv C-CH_3$ | $CH_3$ | S |
| 3687 | $SCH_3$ | $CH_2-CH_2$-(1,3-dioxolan-2-yl) | $CH_3$ | S |
| 3688 | $SCH_3$ | $CH_2$-(1,3-dioxolan-2-yl) | $CH_3$ | S |
| 3689 | $SCH_3$ | n-pentyl | Cl | S |
| 3690 | $SCH_3$ | $CH_2-C\equiv C-CH_2-CH_3$ | Cl | S |
| 3691 | $SCH_3$ | $CH_2-CH_2-CH=CH_2$ | Cl | S |

TABLE A-continued

| No. | R¹ | R² | R³ | A |
|---|---|---|---|---|
| 3692 | SCH$_3$ | CH$_2$—CH$_2$—CH$_2$—CH=CH$_2$ | Cl | S |
| 3693 | SCH$_3$ | CH$_2$-[(3-OCH$_3$)C$_6$H$_4$] | Cl | S |
| 3694 | SCH$_3$ | CH$_2$—C≡C—CH$_3$ | Cl | S |
| 3695 | SCH$_3$ | CH$_2$—CH$_2$-(1,3-dioxolan-2-yl) | Cl | S |
| 3696 | SCH$_3$ | CH$_2$-(1,3-dioxolan-2-yl) | Cl | S |
| 3697 | SO$_2$CH$_3$ | n-pentyl | H | S |
| 3698 | SO$_2$CH$_3$ | CH$_2$—C≡C—CH$_2$—CH$_3$ | H | S |
| 3699 | SO$_2$CH$_3$ | CH$_2$—CH$_2$—CH=CH$_2$ | H | S |
| 3700 | SO$_2$CH$_3$ | CH$_2$—CH$_2$—CH$_2$—CH=CH$_2$ | H | S |
| 3701 | SO$_2$CH$_3$ | CH$_2$-[(3-OCH$_3$)C$_6$H$_4$] | H | S |
| 3702 | SO$_2$CH$_3$ | CH$_2$—C≡C—CH$_3$ | H | S |
| 3703 | SO$_2$CH$_3$ | CH$_2$—CH$_2$-(1,3-dioxolan-2-yl) | H | S |
| 3704 | SO$_2$CH$_3$ | CH$_2$-(1,3-dioxolan-2-yl) | H | S |
| 3705 | SO$_2$CH$_3$ | n-pentyl | CH$_3$ | S |
| 3706 | SO$_2$CH$_3$ | CH$_2$—C≡C—CH$_2$—CH$_3$ | CH$_3$ | S |
| 3707 | SO$_2$CH$_3$ | CH$_2$—CH$_2$—CH=CH$_2$ | CH$_3$ | S |
| 3708 | SO$_2$CH$_3$ | CH$_2$—CH$_2$—CH$_2$—CH=CH$_2$ | CH$_3$ | S |
| 3709 | SO$_2$CH$_3$ | CH$_2$-[(3-OCH$_3$)C$_6$H$_4$] | CH$_3$ | S |
| 3710 | SO$_2$CH$_3$ | CH$_2$—C≡C—CH$_3$ | CH$_3$ | S |
| 3711 | SO$_2$CH$_3$ | CH$_2$—CH$_2$-(1,3-dioxolan-2-yl) | CH$_3$ | S |
| 3712 | SO$_2$CH$_3$ | CH$_2$-(1,3-dioxolan-2-yl) | CH$_3$ | S |
| 3713 | SO$_2$CH$_3$ | n-pentyl | Cl | S |
| 3714 | SO$_2$CH$_3$ | CH$_2$—C≡C—CH$_2$—CH$_3$ | Cl | S |
| 3715 | SO$_2$CH$_3$ | CH$_2$—CH$_2$—CH=CH$_2$ | Cl | S |
| 3716 | SO$_2$CH$_3$ | CH$_2$—CH$_2$—CH$_2$—CH=CH$_2$ | Cl | S |
| 3717 | SO$_2$CH$_3$ | CH$_2$-[(3-OCH$_3$)C$_6$H$_4$] | Cl | S |
| 3718 | SO$_2$CH$_3$ | CH$_2$—C≡C—CH$_3$ | Cl | S |
| 3719 | SO$_2$CH$_3$ | CH$_2$—CH$_2$-(1,3-dioxolan-2-yl) | Cl | S |
| 3720 | SO$_2$CH$_3$ | CH$_2$-(1,3-dioxolan-2-yl) | Cl | S |
| 3721 | CF$_3$ | n-pentyl | H | S |
| 3722 | CF$_3$ | CH$_2$—C≡C—CH$_2$—CH$_3$ | H | S |
| 3723 | CF$_3$ | CH$_2$—CH$_2$—CH=CH$_2$ | H | S |
| 3724 | CF$_3$ | CH$_2$—CH$_2$—CH$_2$—CH=CH$_2$ | H | S |
| 3725 | CF$_3$ | CH$_2$-[(3-OCH$_3$)C$_6$H$_4$] | H | S |
| 3726 | CF$_3$ | CH$_2$—C≡C—CH$_3$ | H | S |
| 3727 | CF$_3$ | CH$_2$—CH$_2$-(1,3-dioxolan-2-yl) | H | S |
| 3728 | CF$_3$ | CH$_2$-(1,3-dioxolan-2-yl) | H | S |
| 3729 | CF$_3$ | n-pentyl | CH$_3$ | S |
| 3730 | CF$_3$ | CH$_2$—C≡C—CH$_2$—CH$_3$ | CH$_3$ | S |
| 3731 | CF$_3$ | CH$_2$—CH$_2$—CH=CH$_2$ | CH$_3$ | S |
| 3732 | CF$_3$ | CH$_2$—CH$_2$—CH$_2$—CH=CH$_2$ | CH$_3$ | S |
| 3733 | CF$_3$ | CH$_2$-[(3-OCH$_3$)C$_6$H$_4$] | CH$_3$ | S |
| 3734 | CF$_3$ | CH$_2$—C≡C—CH$_3$ | CH$_3$ | S |
| 3735 | CF$_3$ | CH$_2$—CH$_2$-(1,3-dioxolan-2-yl) | CH$_3$ | S |
| 3736 | CF$_3$ | CH$_2$-(1,3-dioxolan-2-yl) | CH$_3$ | S |
| 3737 | CF$_3$ | n-pentyl | Cl | S |
| 3738 | CF$_3$ | CH$_2$—C≡C—CH$_2$—CH$_3$ | Cl | S |
| 3739 | CF$_3$ | CH$_2$—CH$_2$—CH=CH$_2$ | Cl | S |
| 3740 | CF$_3$ | CH$_2$—CH$_2$—CH$_2$—CH=CH$_2$ | Cl | S |
| 3741 | CF$_3$ | CH$_2$-[(3-OCH$_3$)C$_6$H$_4$] | Cl | S |
| 3742 | CF$_3$ | CH$_2$—C≡C—CH$_3$ | Cl | S |
| 3743 | CF$_3$ | CH$_2$—CH$_2$-(1,3-dioxolan-2-yl) | Cl | S |
| 3744 | CF$_3$ | CH$_2$-(1,3-dioxolan-2-yl) | Cl | S |
| 3745 | C$_2$H$_5$ | n-pentyl | H | S |
| 3746 | C$_2$H$_5$ | CH$_2$—C≡C—CH$_2$—CH$_3$ | H | S |
| 3747 | C$_2$H$_5$ | CH$_2$—CH$_2$—CH=CH$_2$ | H | S |
| 3748 | C$_2$H$_5$ | CH$_2$—CH$_2$—CH$_2$—CH=CH$_2$ | H | S |
| 3749 | C$_2$H$_5$ | CH$_2$-[(3-OCH$_3$)C$_6$H$_4$] | H | S |
| 3750 | C$_2$H$_5$ | CH$_2$—C≡C—CH$_3$ | H | S |
| 3751 | C$_2$H$_5$ | CH$_2$—CH$_2$-(1,3-dioxolan-2-yl) | H | S |
| 3752 | C$_2$H$_5$ | CH$_2$-(1,3-dioxolan-2-yl) | H | S |
| 3753 | C$_2$H$_5$ | n-pentyl | CH$_3$ | S |
| 3754 | C$_2$H$_5$ | CH$_2$—C≡C—CH$_2$—CH$_3$ | CH$_3$ | S |
| 3755 | C$_2$H$_5$ | CH$_2$—CH$_2$—CH=CH$_2$ | CH$_3$ | S |
| 3756 | C$_2$H$_5$ | CH$_2$—CH$_2$—CH$_2$—CH=CH$_2$ | CH$_3$ | S |
| 3757 | C$_2$H$_5$ | CH$_2$-[(3-OCH$_3$)C$_6$H$_4$] | CH$_3$ | S |
| 3758 | C$_2$H$_5$ | CH$_2$—C≡C—CH$_3$ | CH$_3$ | S |
| 3759 | C$_2$H$_5$ | CH$_2$—CH$_2$-(1,3-dioxolan-2-yl) | CH$_3$ | S |
| 3760 | C$_2$H$_5$ | CH$_2$-(1,3-dioxolan-2-yl) | CH$_3$ | S |
| 3761 | C$_2$H$_5$ | n-pentyl | Cl | S |
| 3762 | C$_2$H$_5$ | CH$_2$—C≡C—CH$_2$—CH$_3$ | Cl | S |
| 3763 | C$_2$H$_5$ | CH$_2$—CH$_2$—CH=CH$_2$ | Cl | S |
| 3764 | C$_2$H$_5$ | CH$_2$—CH$_2$—CH$_2$—CH=CH$_2$ | Cl | S |
| 3765 | C$_2$H$_5$ | CH$_2$-[(3-OCH$_3$)C$_6$H$_4$] | Cl | S |
| 3766 | C$_2$H$_5$ | CH$_2$—C≡C—CH$_3$ | Cl | S |
| 3767 | C$_2$H$_5$ | CH$_2$—CH$_2$-(1,3-dioxolan-2-yl) | Cl | S |
| 3768 | C$_2$H$_5$ | CH$_2$-(1,3-dioxolan-2-yl) | Cl | S |
| 3769 | CH$_3$ | n-pentyl | H | NCH$_3$ |
| 3770 | CH$_3$ | CH$_2$—C≡C—CH$_2$—CH$_3$ | H | NCH$_3$ |
| 3771 | CH$_3$ | CH$_2$—CH$_2$—CH=CH$_2$ | H | NCH$_3$ |
| 3772 | CH$_3$ | CH$_2$—CH$_2$—CH$_2$—CH=CH$_2$ | H | NCH$_3$ |
| 3773 | CH$_3$ | CH$_2$-[(3-OCH$_3$)C$_6$H$_4$] | H | NCH$_3$ |
| 3774 | CH$_3$ | CH$_2$—C≡C—CH$_3$ | H | NCH$_3$ |
| 3775 | CH$_3$ | CH$_2$—CH$_2$-(1,3-dioxolan-2-yl) | H | NCH$_3$ |
| 3776 | CH$_3$ | CH$_2$-(1,3-dioxolan-2-yl) | H | NCH$_3$ |
| 3777 | CH$_3$ | n-pentyl | CH$_3$ | NCH$_3$ |
| 3778 | CH$_3$ | CH$_2$—C≡C—CH$_2$—CH$_3$ | CH$_3$ | NCH$_3$ |
| 3779 | CH$_3$ | CH$_2$—CH$_2$—CH=CH$_2$ | CH$_3$ | NCH$_3$ |
| 3780 | CH$_3$ | CH$_2$—CH$_2$—CH$_2$—CH=CH$_2$ | CH$_3$ | NCH$_3$ |
| 3781 | CH$_3$ | CH$_2$-[(3-OCH$_3$)C$_6$H$_4$] | CH$_3$ | NCH$_3$ |
| 3782 | CH$_3$ | CH$_2$—C≡C—CH$_3$ | CH$_3$ | NCH$_3$ |
| 3783 | CH$_3$ | CH$_2$—CH$_2$-(1,3-dioxolan-2-yl) | CH$_3$ | NCH$_3$ |
| 3784 | CH$_3$ | CH$_2$-(1,3-dioxolan-2-yl) | CH$_3$ | NCH$_3$ |
| 3785 | CH$_3$ | n-pentyl | Cl | NCH$_3$ |
| 3786 | CH$_3$ | CH$_2$—C≡C—CH$_2$—CH$_3$ | Cl | NCH$_3$ |
| 3787 | CH$_3$ | CH$_2$—CH$_2$—CH=CH$_2$ | Cl | NCH$_3$ |
| 3788 | CH$_3$ | CH$_2$—CH$_2$—CH$_2$—CH=CH$_2$ | Cl | NCH$_3$ |
| 3789 | CH$_3$ | CH$_2$-[(3-OCH$_3$)C$_6$H$_4$] | Cl | NCH$_3$ |
| 3790 | CH$_3$ | CH$_2$—C≡C—CH$_3$ | Cl | NCH$_3$ |
| 3791 | CH$_3$ | CH$_2$—CH$_2$-(1,3-dioxolan-2-yl) | Cl | NCH$_3$ |
| 3792 | CH$_3$ | CH$_2$-(1,3-dioxolan-2-yl) | Cl | NCH$_3$ |
| 3793 | Cl | n-pentyl | H | NCH$_3$ |
| 3794 | Cl | CH$_2$—C≡C—CH$_2$—CH$_3$ | H | NCH$_3$ |
| 3795 | Cl | CH$_2$—CH$_2$—CH=CH$_2$ | H | NCH$_3$ |
| 3796 | Cl | CH$_2$—CH$_2$—CH$_2$—CH=CH$_2$ | H | NCH$_3$ |
| 3797 | Cl | CH$_2$-[(3-OCH$_3$)C$_6$H$_4$] | H | NCH$_3$ |
| 3798 | Cl | CH$_2$—C≡C—CH$_3$ | H | NCH$_3$ |
| 3799 | Cl | CH$_2$—CH$_2$-(1,3-dioxolan-2-yl) | H | NCH$_3$ |
| 3800 | Cl | CH$_2$-(1,3-dioxolan-2-yl) | H | NCH$_3$ |
| 3801 | Cl | n-pentyl | CH$_3$ | NCH$_3$ |
| 3802 | Cl | CH$_2$—C≡C—CH$_2$—CH$_3$ | CH$_3$ | NCH$_3$ |
| 3803 | Cl | CH$_2$—CH$_2$—CH=CH$_2$ | CH$_3$ | NCH$_3$ |
| 3804 | Cl | CH$_2$—CH$_2$—CH$_2$—CH=CH$_2$ | CH$_3$ | NCH$_3$ |
| 3805 | Cl | CH$_2$-[(3-OCH$_3$)C$_6$H$_4$] | CH$_3$ | NCH$_3$ |
| 3806 | Cl | CH$_2$—C≡C—CH$_3$ | CH$_3$ | NCH$_3$ |
| 3807 | Cl | CH$_2$—CH$_2$-(1,3-dioxolan-2-yl) | CH$_3$ | NCH$_3$ |
| 3808 | Cl | CH$_2$-(1,3-dioxolan-2-yl) | CH$_3$ | NCH$_3$ |
| 3809 | Cl | n-pentyl | Cl | NCH$_3$ |
| 3810 | Cl | CH$_2$—C≡C—CH$_2$—CH$_3$ | Cl | NCH$_3$ |
| 3811 | Cl | CH$_2$—CH$_2$—CH=CH$_2$ | Cl | NCH$_3$ |
| 3812 | Cl | CH$_2$—CH$_2$—CH$_2$—CH=CH$_2$ | Cl | NCH$_3$ |
| 3813 | Cl | CH$_2$-[(3-OCH$_3$)C$_6$H$_4$] | Cl | NCH$_3$ |
| 3814 | Cl | CH$_2$—C≡C—CH$_3$ | Cl | NCH$_3$ |

TABLE A-continued

| No. | R¹ | R² | R³ | A |
|---|---|---|---|---|
| 3815 | Cl | CH$_2$—CH$_2$-(1,3-dioxolan-2-yl) | Cl | NCH$_3$ |
| 3816 | Cl | CH$_2$-(1,3-dioxolan-2-yl) | Cl | NCH$_3$ |
| 3817 | OCH$_3$ | n-pentyl | H | NCH$_3$ |
| 3818 | OCH$_3$ | CH$_2$—C≡C—CH$_2$—CH$_3$ | H | NCH$_3$ |
| 3819 | OCH$_3$ | CH$_2$—CH$_2$—CH=CH$_2$ | H | NCH$_3$ |
| 3820 | OCH$_3$ | CH$_2$—CH$_2$—CH$_2$—CH=CH$_2$ | H | NCH$_3$ |
| 3821 | OCH$_3$ | CH$_2$-[(3-OCH$_3$)C$_6$H$_4$] | H | NCH$_3$ |
| 3822 | OCH$_3$ | CH$_2$—C≡C—CH$_3$ | H | NCH$_3$ |
| 3823 | OCH$_3$ | CH$_2$—CH$_2$-(1,3-dioxolan-2-yl) | H | NCH$_3$ |
| 3824 | OCH$_3$ | CH$_2$-(1,3-dioxolan-2-yl) | H | NCH$_3$ |
| 3825 | OCH$_3$ | n-pentyl | CH$_3$ | NCH$_3$ |
| 3826 | OCH$_3$ | CH$_2$—C≡C—CH$_2$—CH$_3$ | CH$_3$ | NCH$_3$ |
| 3827 | OCH$_3$ | CH$_2$—CH$_2$—CH=CH$_2$ | CH$_3$ | NCH$_3$ |
| 3828 | OCH$_3$ | CH$_2$—CH$_2$—CH$_2$—CH=CH$_2$ | CH$_3$ | NCH$_3$ |
| 3829 | OCH$_3$ | CH$_2$-[(3-OCH$_3$)C$_6$H$_4$] | CH$_3$ | NCH$_3$ |
| 3830 | OCH$_3$ | CH$_2$—C≡C—CH$_3$ | CH$_3$ | NCH$_3$ |
| 3831 | OCH$_3$ | CH$_2$—CH$_2$-(1,3-dioxolan-2-yl) | CH$_3$ | NCH$_3$ |
| 3832 | OCH$_3$ | CH$_2$-(1,3-dioxolan-2-yl) | CH$_3$ | NCH$_3$ |
| 3833 | OCH$_3$ | n-pentyl | Cl | NCH$_3$ |
| 3834 | OCH$_3$ | CH$_2$—C≡C—CH$_2$—CH$_3$ | Cl | NCH$_3$ |
| 3835 | OCH$_3$ | CH$_2$—CH$_2$—CH=CH$_2$ | Cl | NCH$_3$ |
| 3836 | OCH$_3$ | CH$_2$—CH$_2$—CH$_2$—CH=CH$_2$ | Cl | NCH$_3$ |
| 3837 | OCH$_3$ | CH$_2$-[(3-OCH$_3$)C$_6$H$_4$] | Cl | NCH$_3$ |
| 3838 | OCH$_3$ | CH$_2$—C≡C—CH$_3$ | Cl | NCH$_3$ |
| 3839 | OCH$_3$ | CH$_2$—CH$_2$-(1,3-dioxolan-2-yl) | Cl | NCH$_3$ |
| 3840 | OCH$_3$ | CH$_2$-(1,3-dioxolan-2-yl) | Cl | NCH$_3$ |
| 3841 | OCF$_3$ | n-pentyl | H | NCH$_3$ |
| 3842 | OCF$_3$ | CH$_2$—C≡C—CH$_2$—CH$_3$ | H | NCH$_3$ |
| 3843 | OCF$_3$ | CH$_2$—CH$_2$—CH=CH$_2$ | H | NCH$_3$ |
| 3844 | OCF$_3$ | CH$_2$—CH$_2$—CH$_2$—CH=CH$_2$ | H | NCH$_3$ |
| 3845 | OCF$_3$ | CH$_2$-[(3-OCH$_3$)C$_6$H$_4$] | H | NCH$_3$ |
| 3846 | OCF$_3$ | CH$_2$—C≡C—CH$_3$ | H | NCH$_3$ |
| 3847 | OCF$_3$ | CH$_2$—CH$_2$-(1,3-dioxolan-2-yl) | H | NCH$_3$ |
| 3848 | OCF$_3$ | CH$_2$-(1,3-dioxolan-2-yl) | H | NCH$_3$ |
| 3849 | OCF$_3$ | n-pentyl | CH$_3$ | NCH$_3$ |
| 3850 | OCF$_3$ | CH$_2$—C≡C—CH$_2$—CH$_3$ | CH$_3$ | NCH$_3$ |
| 3851 | OCF$_3$ | CH$_2$—CH$_2$—CH=CH$_2$ | CH$_3$ | NCH$_3$ |
| 3852 | OCF$_3$ | CH$_2$—CH$_2$—CH$_2$—CH=CH$_2$ | CH$_3$ | NCH$_3$ |
| 3853 | OCF$_3$ | CH$_2$-[(3-OCH$_3$)C$_6$H$_4$] | CH$_3$ | NCH$_3$ |
| 3854 | OCF$_3$ | CH$_2$—C≡C—CH$_3$ | CH$_3$ | NCH$_3$ |
| 3855 | OCF$_3$ | CH$_2$—CH$_2$-(1,3-dioxolan-2-yl) | CH$_3$ | NCH$_3$ |
| 3856 | OCF$_3$ | CH$_2$-(1,3-dioxolan-2-yl) | CH$_3$ | NCH$_3$ |
| 3857 | OCF$_3$ | n-pentyl | Cl | NCH$_3$ |
| 3858 | OCF$_3$ | CH$_2$—C≡C—CH$_2$—CH$_3$ | Cl | NCH$_3$ |
| 3859 | OCF$_3$ | CH$_2$—CH$_2$—CH=CH$_2$ | Cl | NCH$_3$ |
| 3860 | OCF$_3$ | CH$_2$—CH$_2$—CH$_2$—CH=CH$_2$ | Cl | NCH$_3$ |
| 3861 | OCF$_3$ | CH$_2$-[(3-OCH$_3$)C$_6$H$_4$] | Cl | NCH$_3$ |
| 3862 | OCF$_3$ | CH$_2$—C≡C—CH$_3$ | Cl | NCH$_3$ |
| 3863 | OCF$_3$ | CH$_2$—CH$_2$-(1,3-dioxolan-2-yl) | Cl | NCH$_3$ |
| 3864 | OCF$_3$ | CH$_2$-(1,3-dioxolan-2-yl) | Cl | NCH$_3$ |
| 3865 | SCH$_3$ | n-pentyl | H | NCH$_3$ |
| 3866 | SCH$_3$ | CH$_2$—C≡C—CH$_2$—CH$_3$ | H | NCH$_3$ |
| 3867 | SCH$_3$ | CH$_2$—CH$_2$—CH=CH$_2$ | H | NCH$_3$ |
| 3868 | SCH$_3$ | CH$_2$—CH$_2$—CH$_2$—CH=CH$_2$ | H | NCH$_3$ |
| 3869 | SCH$_3$ | CH$_2$-[(3-OCH$_3$)C$_6$H$_4$] | H | NCH$_3$ |
| 3870 | SCH$_3$ | CH$_2$—C≡C—CH$_3$ | H | NCH$_3$ |
| 3871 | SCH$_3$ | CH$_2$—CH$_2$-(1,3-dioxolan-2-yl) | H | NCH$_3$ |
| 3872 | SCH$_3$ | CH$_2$-(1,3-dioxolan-2-yl) | H | NCH$_3$ |
| 3873 | SCH$_3$ | n-pentyl | CH$_3$ | NCH$_3$ |
| 3874 | SCH$_3$ | CH$_2$—C≡C—CH$_2$—CH$_3$ | CH$_3$ | NCH$_3$ |
| 3875 | SCH$_3$ | CH$_2$—CH$_2$—CH=CH$_2$ | CH$_3$ | NCH$_3$ |
| 3876 | SCH$_3$ | CH$_2$—CH$_2$—CH$_2$—CH=CH$_2$ | CH$_3$ | NCH$_3$ |
| 3877 | SCH$_3$ | CH$_2$-[(3-OCH$_3$)C$_6$H$_4$] | CH$_3$ | NCH$_3$ |
| 3878 | SCH$_3$ | CH$_2$—C≡C—CH$_3$ | CH$_3$ | NCH$_3$ |
| 3879 | SCH$_3$ | CH$_2$—CH$_2$-(1,3-dioxolan-2-yl) | CH$_3$ | NCH$_3$ |
| 3880 | SCH$_3$ | CH$_2$-(1,3-dioxolan-2-yl) | CH$_3$ | NCH$_3$ |
| 3881 | SCH$_3$ | n-pentyl | Cl | NCH$_3$ |
| 3882 | SCH$_3$ | CH$_2$—C≡C—CH$_2$—CH$_3$ | Cl | NCH$_3$ |
| 3883 | SCH$_3$ | CH$_2$—CH$_2$—CH=CH$_2$ | Cl | NCH$_3$ |
| 3884 | SCH$_3$ | CH$_2$—CH$_2$—CH$_2$—CH=CH$_2$ | Cl | NCH$_3$ |
| 3885 | SCH$_3$ | CH$_2$-[(3-OCH$_3$)C$_6$H$_4$] | Cl | NCH$_3$ |
| 3886 | SCH$_3$ | CH$_2$—C≡C—CH$_3$ | Cl | NCH$_3$ |
| 3887 | SCH$_3$ | CH$_2$—CH$_2$-(1,3-dioxolan-2-yl) | Cl | NCH$_3$ |
| 3888 | SCH$_3$ | CH$_2$-(1,3-dioxolan-2-yl) | Cl | NCH$_3$ |
| 3889 | SO$_2$CH$_3$ | n-pentyl | H | NCH$_3$ |
| 3890 | SO$_2$CH$_3$ | CH$_2$—C≡C—CH$_2$—CH$_3$ | H | NCH$_3$ |
| 3891 | SO$_2$CH$_3$ | CH$_2$—CH$_2$—CH=CH$_2$ | H | NCH$_3$ |
| 3892 | SO$_2$CH$_3$ | CH$_2$—CH$_2$—CH$_2$—CH=CH$_2$ | H | NCH$_3$ |
| 3893 | SO$_2$CH$_3$ | CH$_2$-[(3-OCH$_3$)C$_6$H$_4$] | H | NCH$_3$ |
| 3894 | SO$_2$CH$_3$ | CH$_2$—C≡C—CH$_3$ | H | NCH$_3$ |
| 3895 | SO$_2$CH$_3$ | CH$_2$—CH$_2$-(1,3-dioxolan-2-yl) | H | NCH$_3$ |
| 3896 | SO$_2$CH$_3$ | CH$_2$-(1,3-dioxolan-2-yl) | H | NCH$_3$ |
| 3897 | SO$_2$CH$_3$ | n-pentyl | CH$_3$ | NCH$_3$ |
| 3898 | SO$_2$CH$_3$ | CH$_2$—C≡C—CH$_2$—CH$_3$ | CH$_3$ | NCH$_3$ |
| 3899 | SO$_2$CH$_3$ | CH$_2$—CH$_2$—CH=CH$_2$ | CH$_3$ | NCH$_3$ |
| 3900 | SO$_2$CH$_3$ | CH$_2$—CH$_2$—CH$_2$—CH=CH$_2$ | CH$_3$ | NCH$_3$ |
| 3901 | SO$_2$CH$_3$ | CH$_2$-[(3-OCH$_3$)C$_6$H$_4$] | CH$_3$ | NCH$_3$ |
| 3902 | SO$_2$CH$_3$ | CH$_2$—C≡C—CH$_3$ | CH$_3$ | NCH$_3$ |
| 3903 | SO$_2$CH$_3$ | CH$_2$—CH$_2$-(1,3-dioxolan-2-yl) | CH$_3$ | NCH$_3$ |
| 3904 | SO$_2$CH$_3$ | CH$_2$-(1,3-dioxolan-2-yl) | CH$_3$ | NCH$_3$ |
| 3905 | SO$_2$CH$_3$ | n-pentyl | Cl | NCH$_3$ |
| 3906 | SO$_2$CH$_3$ | CH$_2$—C≡C—CH$_2$—CH$_3$ | Cl | NCH$_3$ |
| 3907 | SO$_2$CH$_3$ | CH$_2$—CH$_2$—CH=CH$_2$ | Cl | NCH$_3$ |
| 3908 | SO$_2$CH$_3$ | CH$_2$—CH$_2$—CH$_2$—CH=CH$_2$ | Cl | NCH$_3$ |
| 3909 | SO$_2$CH$_3$ | CH$_2$-[(3-OCH$_3$)C$_6$H$_4$] | Cl | NCH$_3$ |
| 3910 | SO$_2$CH$_3$ | CH$_2$—C≡C—CH$_3$ | Cl | NCH$_3$ |
| 3911 | SO$_2$CH$_3$ | CH$_2$—CH$_2$-(1,3-dioxolan-2-yl) | Cl | NCH$_3$ |
| 3912 | SO$_2$CH$_3$ | CH$_2$-(1,3-dioxolan-2-yl) | Cl | NCH$_3$ |
| 3913 | CF$_3$ | n-pentyl | H | NCH$_3$ |
| 3914 | CF$_3$ | CH$_2$—C≡C—CH$_2$—CH$_3$ | H | NCH$_3$ |
| 3915 | CF$_3$ | CH$_2$—CH$_2$—CH=CH$_2$ | H | NCH$_3$ |
| 3916 | CF$_3$ | CH$_2$—CH$_2$—CH$_2$—CH=CH$_2$ | H | NCH$_3$ |
| 3917 | CF$_3$ | CH$_2$-[(3-OCH$_3$)C$_6$H$_4$] | H | NCH$_3$ |
| 3918 | CF$_3$ | CH$_2$—C≡C—CH$_3$ | H | NCH$_3$ |
| 3919 | CF$_3$ | CH$_2$—CH$_2$-(1,3-dioxolan-2-yl) | H | NCH$_3$ |
| 3920 | CF$_3$ | CH$_2$-(1,3-dioxolan-2-yl) | H | NCH$_3$ |
| 3921 | CF$_3$ | n-pentyl | CH$_3$ | NCH$_3$ |
| 3922 | CF$_3$ | CH$_2$—C≡C—CH$_2$—CH$_3$ | CH$_3$ | NCH$_3$ |
| 3923 | CF$_3$ | CH$_2$—CH$_2$—CH=CH$_2$ | CH$_3$ | NCH$_3$ |
| 3924 | CF$_3$ | CH$_2$—CH$_2$—CH$_2$—CH=CH$_2$ | CH$_3$ | NCH$_3$ |
| 3925 | CF$_3$ | CH$_2$-[(3-OCH$_3$)C$_6$H$_4$] | CH$_3$ | NCH$_3$ |
| 3926 | CF$_3$ | CH$_2$—C≡C—CH$_3$ | CH$_3$ | NCH$_3$ |
| 3927 | CF$_3$ | CH$_2$—CH$_2$-(1,3-dioxolan-2-yl) | CH$_3$ | NCH$_3$ |
| 3928 | CF$_3$ | CH$_2$-(1,3-dioxolan-2-yl) | CH$_3$ | NCH$_3$ |
| 3929 | CF$_3$ | n-pentyl | Cl | NCH$_3$ |
| 3930 | CF$_3$ | CH$_2$—C≡C—CH$_2$—CH$_3$ | Cl | NCH$_3$ |
| 3931 | CF$_3$ | CH$_2$—CH$_2$—CH=CH$_2$ | Cl | NCH$_3$ |
| 3932 | CF$_3$ | CH$_2$—CH$_2$—CH$_2$—CH=CH$_2$ | Cl | NCH$_3$ |
| 3933 | CF$_3$ | CH$_2$-[(3-OCH$_3$)C$_6$H$_4$] | Cl | NCH$_3$ |
| 3934 | CF$_3$ | CH$_2$—C≡C—CH$_3$ | Cl | NCH$_3$ |
| 3935 | CF$_3$ | CH$_2$—CH$_2$-(1,3-dioxolan-2-yl) | Cl | NCH$_3$ |
| 3936 | CF$_3$ | CH$_2$-(1,3-dioxolan-2-yl) | Cl | NCH$_3$ |

TABLE A-continued

| No. | R¹ | R² | R³ | A |
|---|---|---|---|---|
| 3937 | $C_2H_5$ | n-pentyl | H | $NCH_3$ |
| 3938 | $C_2H_5$ | $CH_2-C\equiv C-CH_2-CH_3$ | H | $NCH_3$ |
| 3939 | $C_2H_5$ | $CH_2-CH_2-CH=CH_2$ | H | $NCH_3$ |
| 3940 | $C_2H_5$ | $CH_2-CH_2-CH_2-CH=CH_2$ | H | $NCH_3$ |
| 3941 | $C_2H_5$ | $CH_2-[(3-OCH_3)C_6H_4]$ | H | $NCH_3$ |
| 3942 | $C_2H_5$ | $CH_2-C\equiv C-CH_3$ | H | $NCH_3$ |
| 3943 | $C_2H_5$ | $CH_2-CH_2$-(1,3-dioxolan-2-yl) | H | $NCH_3$ |
| 3944 | $C_2H_5$ | $CH_2$-(1,3-dioxolan-2-yl) | H | $NCH_3$ |
| 3945 | $C_2H_5$ | n-pentyl | $CH_3$ | $NCH_3$ |
| 3946 | $C_2H_5$ | $CH_2-C\equiv C-CH_2-CH_3$ | $CH_3$ | $NCH_3$ |
| 3947 | $C_2H_5$ | $CH_2-CH_2-CH=CH_2$ | $CH_3$ | $NCH_3$ |
| 3948 | $C_2H_5$ | $CH_2-CH_2-CH_2-CH=CH_2$ | $CH_3$ | $NCH_3$ |
| 3949 | $C_2H_5$ | $CH_2-[(3-OCH_3)C_6H_4]$ | $CH_3$ | $NCH_3$ |
| 3950 | $C_2H_5$ | $CH_2-C\equiv C-CH_3$ | $CH_3$ | $NCH_3$ |
| 3951 | $C_2H_5$ | $CH_2-CH_2$-(1,3-dioxolan-2-yl) | $CH_3$ | $NCH_3$ |
| 3952 | $C_2H_5$ | $CH_2$-(1,3-dioxolan-2-yl) | $CH_3$ | $NCH_3$ |
| 3953 | $C_2H_5$ | n-pentyl | Cl | $NCH_3$ |
| 3954 | $C_2H_5$ | $CH_2-C\equiv C-CH_2-CH_3$ | Cl | $NCH_3$ |
| 3955 | $C_2H_5$ | $CH_2-CH_2-CH=CH_2$ | Cl | $NCH_3$ |
| 3956 | $C_2H_5$ | $CH_2-CH_2-CH_2-CH=CH_2$ | Cl | $NCH_3$ |
| 3957 | $C_2H_5$ | $CH_2-[(3-OCH_3)C_6H_4]$ | Cl | $NCH_3$ |
| 3958 | $C_2H_5$ | $CH_2-C\equiv C-CH_3$ | Cl | $NCH_3$ |
| 3959 | $C_2H_5$ | $CH_2-CH_2$-(1,3-dioxolan-2-yl) | Cl | $NCH_3$ |
| 3960 | $C_2H_5$ | $CH_2$-(1,3-dioxolan-2-yl) | Cl | $NCH_3$ |

Examples of particularly preferred benzothiazol-5-ylcarbonyl derivatives of cyclohexenones according to the invention are the compounds listed in Tables 1 to 28.

TABLE 1

Compounds I-1a.1 to I-1a.3960

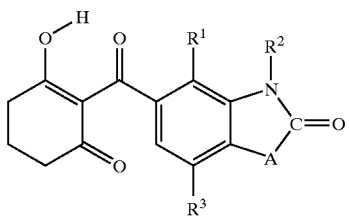

I-1a

Compounds of the formula I-1a in which the substituents A, $R^1$, $R^2$ and $R^3$ for each individual compound correspond in each case to one row of Table A.

TABLE 2

Compounds I-1b.1 to I-1b.3960

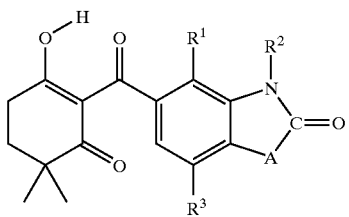

I-1b

Compounds of the formula I-1b in which the substituents A, $R^1$, $R^2$ and $R^3$ for each individual compound correspond in each case to one row of Table A.

TABLE 3

Compounds I-1c.1 to I-1c.3960

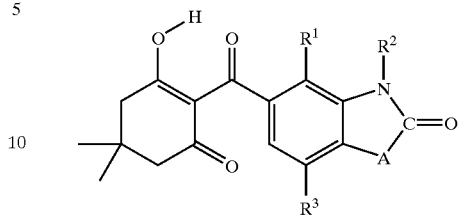

I-1c

Compounds of the formula I-1c in which the substituents A, $R^1$, $R^2$ and $R^3$ for each individual compound correspond in each case to one row of Table A.

TABLE 4

Compounds I-1d.1 to I-1d.3960

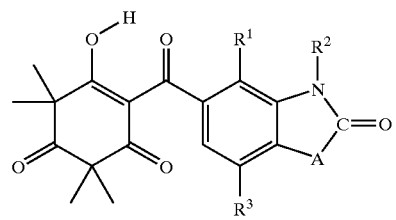

I-1d

Compounds of the formula I-1d in which the substituents A, $R^1$, $R^2$ and $R^3$ for each individual compound correspond in each case to one row of Table A.

TABLE 5

Compounds I-1e.1 to I-1e.3960

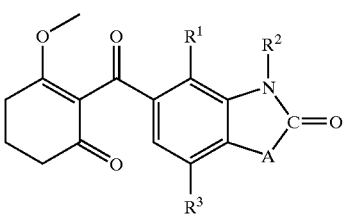

I-1e

Compounds of the formula I-1e in which the substituents A, $R^1$, $R^2$ and $R^3$ for each individual compound correspond in each case to one row of Table A.

TABLE 6

Compounds I-1f.1 to I-1f.3960

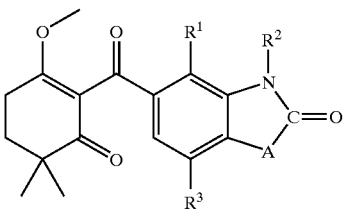

I-1f

Compounds of the formula I-1f in which the substituents A, $R^1$, $R^2$ and $R^3$ for each individual compound correspond in each case to one row of Table A.

TABLE 7

Compounds I-1g.1 to I-1g.3960

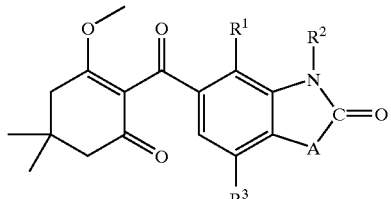
I-1g

Compounds of the formula I-1g in which the substituents A, R¹, R² and R³ for each individual compound correspond in each case to one row of Table A.

TABLE 8

Compounds I-1h.1 to I-1h.3960

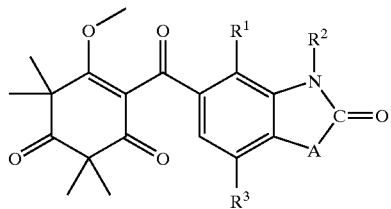
I-1h

Compounds of the formula I-1h in which the substituents A, R¹, R² and R³ for each individual compound correspond in each case to one row of Table A.

TABLE 9

Compounds I-1i.1 to I-1i.3960

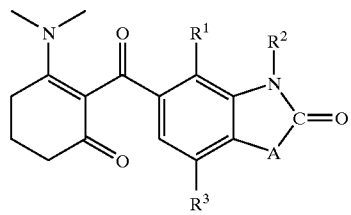
I-1i

Compounds of the formula I-1i in which the substituents A, R¹, R² and R³ for each individual compound correspond in each case to one row of Table A.

TABLE 10

Compounds I-1k.1 to I-1k.3960

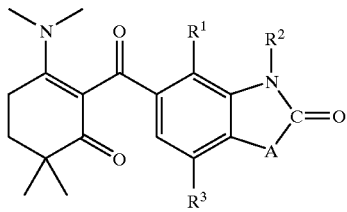
I-1k

Compounds of the formula I-1k in which the substituents A, R¹, R² and R³ for each individual compound correspond in each case to one row of Table A.

TABLE 11

Compounds I-1l.1 to I-1l.3960

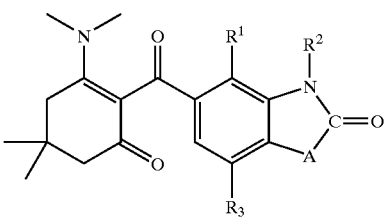
I-1l

Compounds of the formula I-1l in which the substituents A, R¹, R² and R³ for each individual compound correspond in each case to one row of Table A.

TABLE 12

Compounds I-1m.1 to I-1m.3960

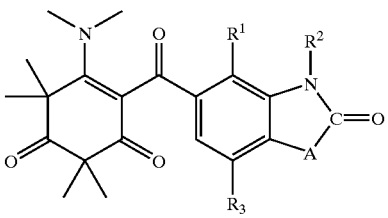
I-1m

Compounds of the formula I-1m in which the substituents A, R¹, R² and R³ for each individual compound correspond in each case to one row of Table A.

TABLE 13

Compounds I-1n.1 to I-1n.3960

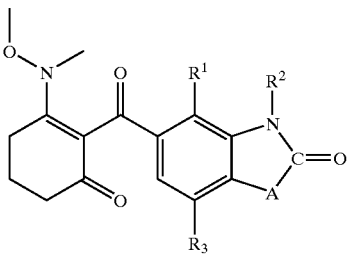
I-1n

Compounds of the formula I-1n in which the substituents A, R¹, R² and R³ for each individual compound correspond in each case to one row of Table A.

TABLE 14

Compounds I-1o.1 to I-1o.3960

I-1o

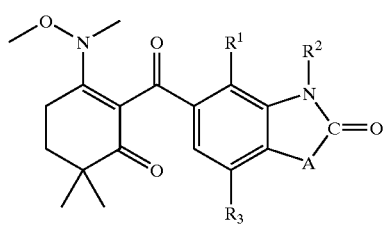

Compounds of the formula I-1o in which the substituents A, R¹, R² and R³ for each individual compound correspond in each case to one row of Table A.

TABLE 15

Compounds I-1p.1 to I-1p.3960

I-1p

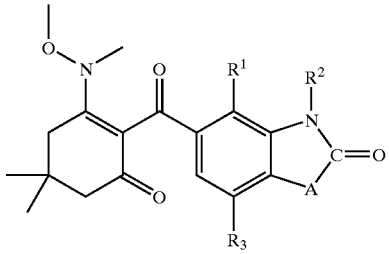

Compounds of the formula I-1p in which the substituents A, R¹, R² and R³ for each individual compound correspond in each case to one row of Table A.

TABLE 16

Compounds I-1q.1 to I-1q.3960

I-1q

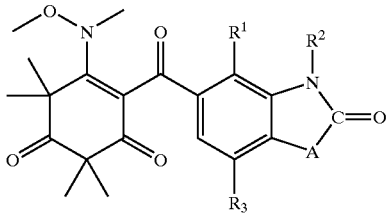

Compounds of the formula I-1q in which the substituents A, R¹, R² and R³ for each individual compound correspond in each case to one row of Table A.

TABLE 17

Compounds I-1r.1 to I-1r.3960

I-1r

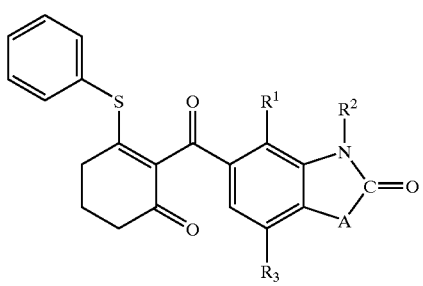

Compounds of the formula I-1r in which the substituents A, R¹, R² and R³ for each individual compound correspond in each case to one row of Table A.

TABLE 18

Compounds I-1s.1 to I-1s.3960

I-1s

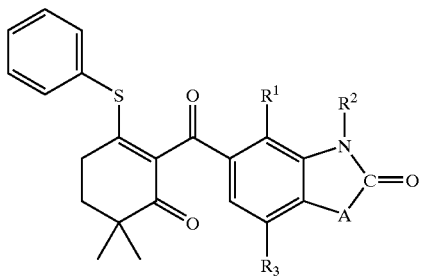

Compounds of the formula I-1s in which the substituents A, R¹, R² and R³ for each individual compound correspond in each case to one row of Table A.

TABLE 19

Compounds I-1t.1 to I-1t.3960

I-1t

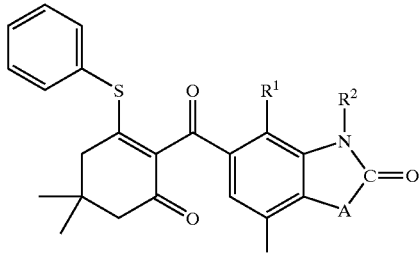

Compounds of the formula I-1t in which the substituents A, R¹, R² and R³ for each individual compound correspond in each case to one row of Table A.

TABLE 20

Compounds I-1u.1 to I-1u.3960

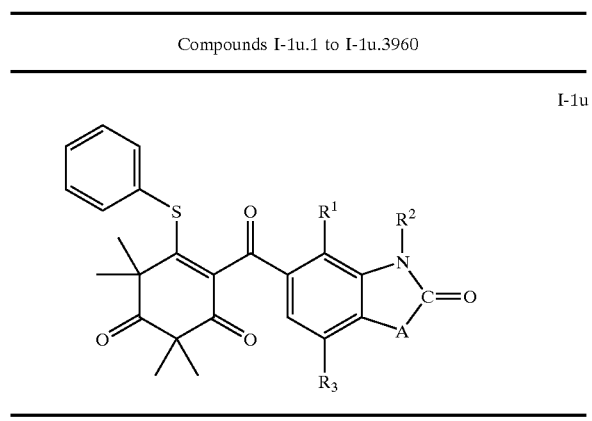

I-1u

Compounds of the formula I-1u in which the substituents A, R¹, R² and R³ for each individual compound correspond in each case to one row of Table A.

TABLE 21

Compounds I-1v.1 to I-1v.3960

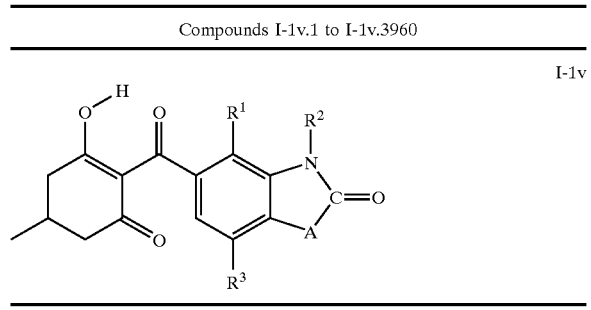

I-1v

Compounds of the formula I-1v in which the substituents A, R¹, R² and R³ for each individual compound correspond in each case to one row of Table A.

TABLE 22

Compounds I-1w.1 to I-1w.3960

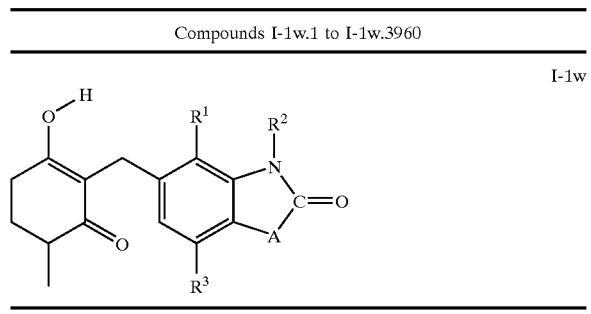

I-1w

Compounds of the formula I-1w in which the substituents A, R¹, R² and R³ for each individual compound correspond in each case to one row of Table A.

TABLE 23

Compounds I-1x.1 to I-1x.3960

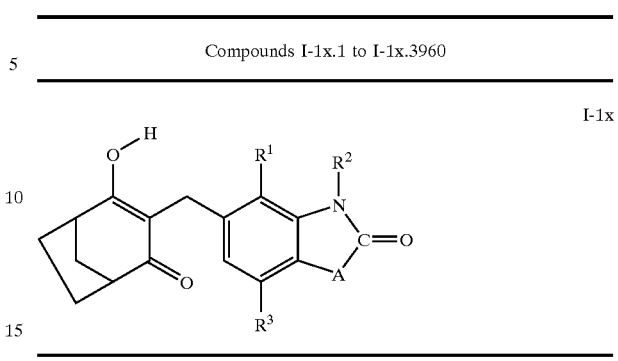

I-1x

Compounds of the formula I-1x in which the substituents A, R¹, R² and R³ for each individual compound correspond in each case to one row of Table A.

TABLE 24

Compounds I-1y.1 to I-1y.3960

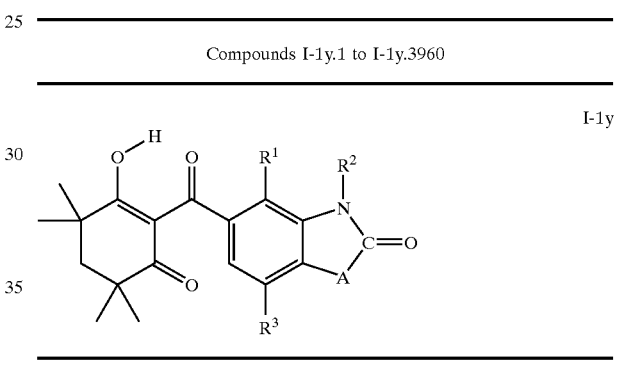

I-1y

Compounds of the formula I-1y in which the substituents A, R¹, R² and R³ for each individual compound correspond in each case to one row of Table A.

TABLE 25

Compounds I-1z.1 to I-1z.3960

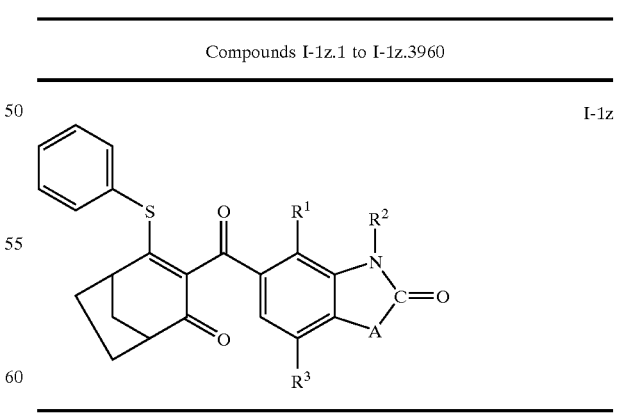

I-1z

Compounds of the formula I-1z in which the substituents A, R¹, R² and R³ for each individual compound correspond in each case to one row of Table A.

TABLE 26

Compounds I-1za.1 to I-1za.3960

I-1za

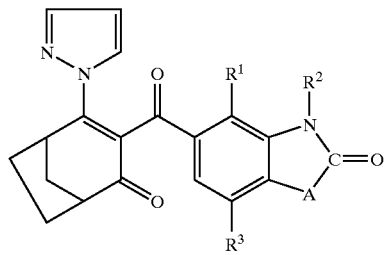

Compounds of the formula I-1za in which the substituents A, $R^1$, $R^2$ and $R^3$ for each individual compound correspond in each case to one row of Table A.

TABLE 27

Compounds I-1zb.1 to I-1zb.3960

I-1zb

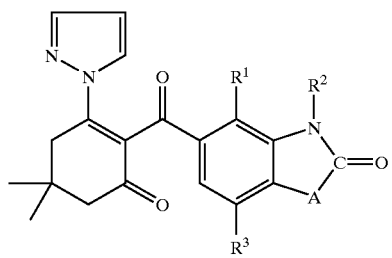

Compounds of the formula I-1zb in which the substituents A, $R^1$, $R^2$ and $R^3$ for each individual compound correspond in each case to one row of Table A.

TABLE 28

Compounds I-1zc.1 to I-1zc.3960

I-1zc

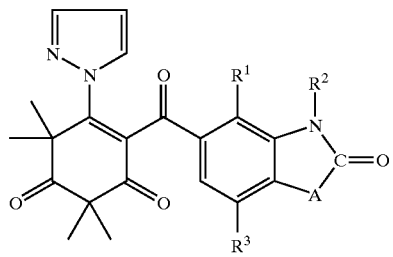

Compounds of the formula I-1zc in which the substituents A, $R^1$, $R^2$ and $R^3$ for each individual compound correspond in each case to one row of Table A.

The compound of the formula I where $R^7$ is hydroxyl is prepared by reacting an activated carboxylic acid IVb or a carboxylic acid IVa, which is preferably activated in situ, with a cyclohexane-1,3-dione of the formula III to give the acylation product, followed by rearrangement.

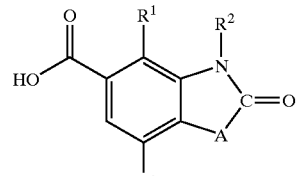

IVa

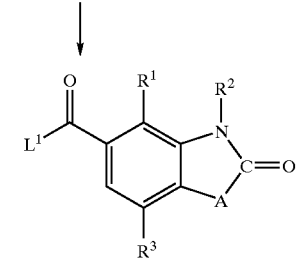

III          IVb

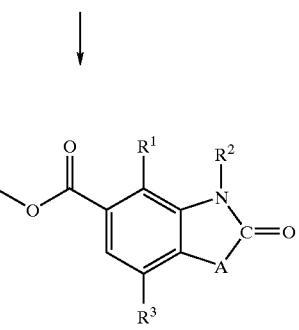

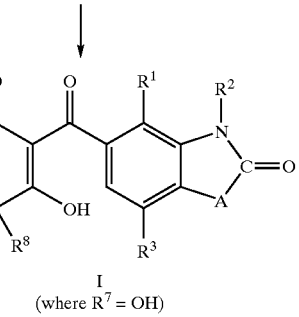

I
(where $R^7$ = OH)

$L^1$ is a nucleophilically replaceable leaving group, such as halogen, for example bromine or chlorine, hetaryl, for example imidazolyl or pyridyl, carboxylate, for example acetate or trifluoroacetate, etc.

The activated carboxylic acid Ivb can be employed directly, such as in the case of the benzoyl halides, or be generated in situ, for example using carbodiimides, such as ethyl-(3'-dimethylaminopropyl)carbodiimide, dicyclohexylcarbodiimide, triphenylphosphine/ azodicarboxylic ester, 2-pyridine disulfide/ triphenylphosphine, carbonyldiimidazole, etc.

If appropriate, it may be advantageous to carry out the acylation reaction in the presence of a base. Here, the reactants and the auxiliary base are advantageously employed in equimolar amounts. In some cases, it may be advantageous to employ a slight excess of the auxiliary base, for example from 1.2 to 1.5 molar equivalents, based on IVa or IVb.

Suitable auxiliary bases are tertiary alkylamines, pyridine or alkali metal carbonates. Suitable solvents are, for example, chlorinated hydrocarbons, such as methylene chloride or 1,2-dichloroethane, aromatic hydrocarbons, such as toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

If the activated carboxylic acid component used is a halide, it may be advantageous to cool the reaction mixture to 0–10° C. when adding this reactant. The mixture is subsequently stirred at 20–100° C., preferably at 25–50° C., until the reaction has gone to completion. Work-up is carried out in a customary manner, for example by pouring the reaction mixture into water and extracting the product of value. Solvents which are suitable for this purpose are, in particular, methylene chloride, diethyl ether and ethyl acetate. After the organic phase has been dried and the solvent has been removed, the crude ester can be employed for the rearrangement without further purification.

The rearrangement of the esters to give the compounds of the formula I is advantageously carried out at 20–100° C. in a solvent and in the presence of a base and, if appropriate, using a cyano compound as catalyst.

Suitable solvents are, for example, acetonitrile, methylene chloride, 1,2-dichloroethane, dioxane, ethyl acetate, toluene or mixtures of these. Preferred solvents are acetonitrile and dioxane.

Suitable bases are tertiary amines, such as triethylamine, aromatic amines, such as pyridine, or alkali metal carbonates, such as sodium carbonate or potassium carbonate, which are preferably employed in an equimolar amount or an up to 4-fold excess, based on the ester. Preference is given to using triethylamine or alkali metal carbonate, preferably in twice the equimolar amount, based on the ester.

Suitable cyano compounds are inorganic cyanides, such as sodium cyanide or potassium cyanide, and organic cyano compounds, such as acetonecyanohydrin or trimethylsilyl cyanide. They are employed in an amount of 1–50 mol percent, based on the ester. Preference is given to using acetonecyanohydrin or trimethylsilyl cyanide, for example in an amount of 5–15, preferably about 10, mol percent, based on the ester.

Work-up can be carried out in a manner known per se. The reaction mixture is, for example, acidified with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the precipitate that is formed is filtered off with suction and/or extracted with methylene chloride or ethyl acetate, dried and concentrated.

B. Preparation of Compounds of the Formula I where $R^7$=Halogen is Carried out by Reacting Cyclohexenone Derivatives of the Formula I (where $R^7$=Hydroxyl) with Halogenating Agents:

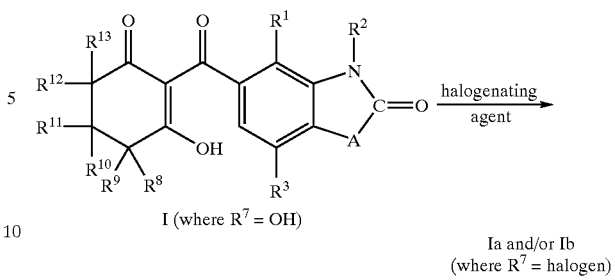

Here and below, "compound Ia" is a compound of the formula I where Hex is a radical of the formula IIa and, correspondingly, compound Ib is a compound of the formula I where Hex is a radical IIb.

Suitable halogenating agents are, for example, phosgene, diphosgene, triphosgene, thionyl chloride, oxalyl chloride, phosphorus oxychloride, phosphorus pentachloride, mesyl chloride, chloromethylene-N,N-dimethylammonium chloride, oxalyl bromide, phosphorus oxybromide, etc.

C. Preparation of Compounds of the Formula I where $R^7$=$OR^{14}$, $OSO_2R^{15}$, $OPOR^{16}R^{17}$ or $OPSR^{16}R^{17}$ by Reacting Cyclohexenone Derivatives of the Formula I (where $R^7$=hydroxyl) with Alkylating, Sulfonylating or Phosphonylating Agents Vα, Vβ, Vγ and Vδ, Respectively.

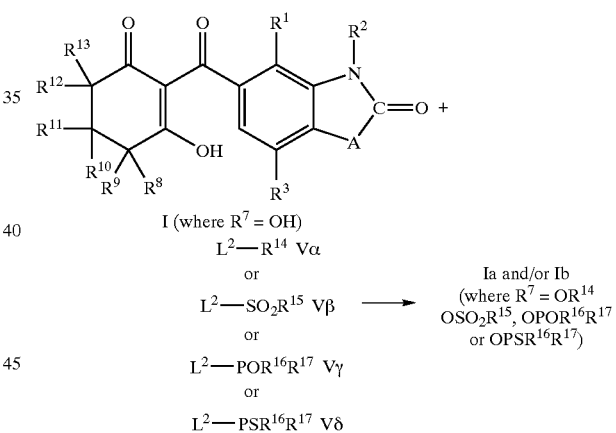

$L^2$ is a nucleophilically replaceable leaving group, such as halogen, for example chlorine or bromine, hetaryl, for example imidazolyl, carboxylate, for example acetate, or sulfonate, for example mesylate or triflate, etc.

Compounds of the formula Vα, Vβ, Vγ or Vδ can be employed directly, such as in the case of the carbonyl halides, or be generated in situ, for example activated carboxylic acids (using carboxylic acid and dicyclohexylcarbodiimide, etc.).

D. Compounds of the Formula I where $R^7$=$OR^{14}$, $SR^{14}$, $POR^{16}R^{17}$, $NR^{18}R^{19}$, $ONR^{18}R^{19}$ or N-Bonded Heterocyclyl are Prepared by Reacting Compounds of the Formula I where $R^7$=Halogen, $OSO_2R^{15}$ with Compounds of the Formula VIα, VIβ, VIγ, VIδ, VIε or VIη, if Appropriate in the Presence of a Base or with Prior Formation of Salt.

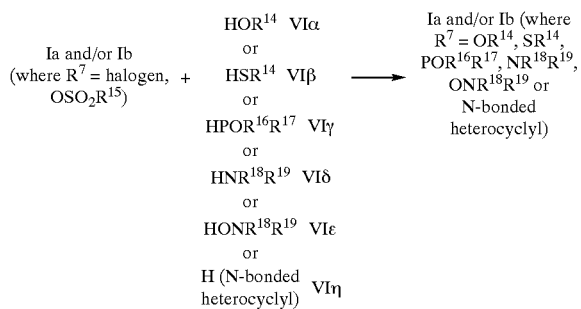

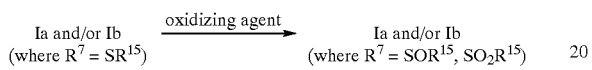

E. Compounds of the Formula I where $R^7=SOR^{15}$, $SO_2R^{15}$ are Prepared, for Example, by Reacting Compounds of the Formula I where $R^7=SR^{15}$ with an Oxidizing Agent.

Ia and/or Ib (where $R^7 = SR^{15}$) →[oxidizing agent] Ia and/or Ib (where $R^7 = SOR^{15}$, $SO_2R^{15}$)

Suitable oxidizing agents are, for example, m-chloroperbenzoic acid, peroxyacetic acid, trifluoroperoxyacetic acid, hydrogen peroxide, if appropriate in the presence of a catalyst, such as tungstate.

For the reactions mentioned under points B to E, the following conditions apply:

The starting materials are generally employed in equimolar amounts. However, it may also be advantageous to employ an excess of one or the other component.

If appropriate, it may be advantageous to carry out the reactions in the presence of a base. Reactants and base are advantageously employed in equimolar amounts.

With respect to the processes C and D, it may, in certain cases, be advantageous to employ an excess of base, for example 1.5 to 3 molar equivalents, in each case based on the starting material.

Suitable bases are tertiary alkylamines, such as triethylamine, aromatic amines, such as pyridine, alkali metal carbonates, for example sodium carbonate or potassium carbonate, alkali metal bicarbonates, such as sodium bicarbonate and potassium bicarbonate, alkali metal alkoxides, such as sodium methoxide, sodium ethoxide, potassium tert-butoxide, or alkali metal hydrides, for example sodium hydride. Preference is given to using triethylamine or pyridine.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

In general, the reaction temperature is in the range from 0° C. to the boiling point of the reaction mixture.

Work-up can be carried out in a manner known per se to give the product.

Depending on the reaction conditions, in the processes B to D the compounds Ia, Ib, or mixtures of these can be formed. The latter can be separated by classic separation methods, for example crystallization, chromatography, etc.

The cyclohexanediones of the formula III used as starting materials are known or can be prepared by processes known per se (e.g. EP-A 71 707, EP-A 142 741, EP-A 243 313, U.S. Pat. No. 4,249,937, WO 92/13821).

The alkylating agents Vα, sulfonylating agents Vβ, phosphonylating agents Vγ and Vδ, and the compounds VIα, VIβ, VIγ, VIδ and VIε are likewise known, or they can be prepared by known processes.

The carboxylic acids of the formula IVa and their activated derivatives IVb are novel and also form part of the subject-matter of the present invention.

Scheme 1 shows a general route to compounds of the formula IVa in which A is oxygen or $NR^6$.

Scheme 1:

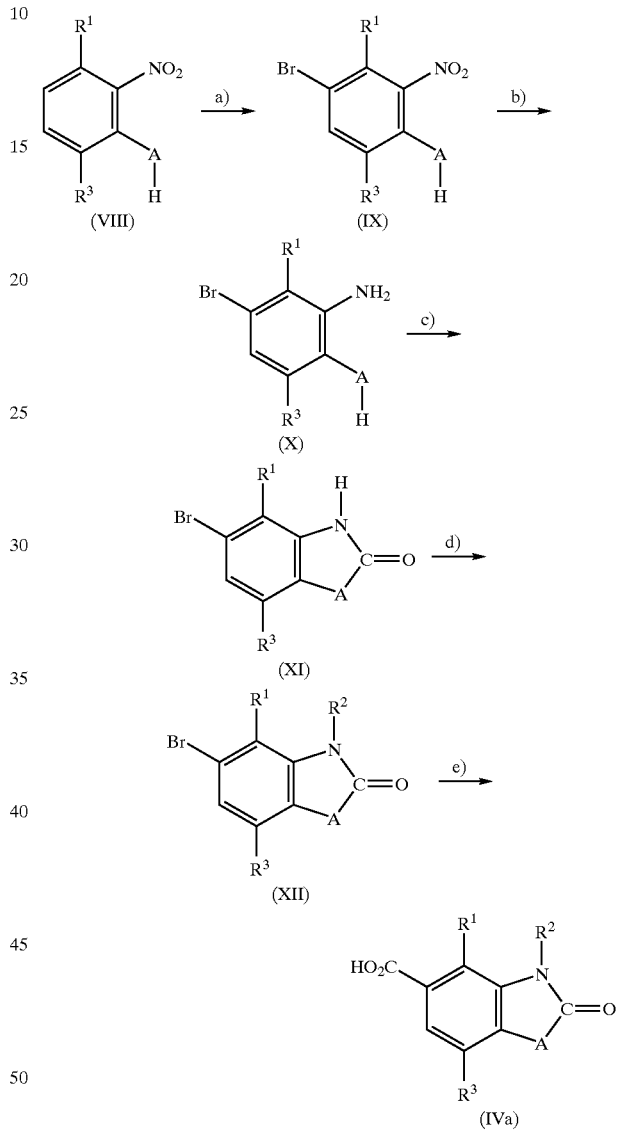

According to scheme 1, benzazolonecarboxylic acids of the formula IVa (A=O or $NR^6$) can be prepared from 2-nitroanilines or 2-nitrophenols of the formula VIII, which are substituted in position 3. In step a), the nitro compounds VIII are initially brominated in the position meta to the nitro group. Brominating agents which are customary for this purpose are bromine, N-bromosuccinimide, N-bromohydantoin or pyridinium perbromide which, if appropriate, are employed together with a Lewis acid such as $FeBr_3$. The bromination is usually carried out in an inert solvent. Suitable solvents are aliphatic or cycloaliphatic hydrocarbons, for example n-hexane or cyclohexane, halogenated hydrocarbons, for example dichloromethane, trichloromethane, carbon tetrachloride, trichloroethane, trichloroethylene, heteroaromatic compounds, such as pyridine, or anhydrous inorganic or organic acids, such as acetic acid. Customary reaction temperatures are in the range from −15° C. to 150° C., preferably in the range from −15° C. to 100° C. Methods for brominating nitro compounds are known, for example from Organikum, 16th ed., 1986, p. 315.

Subsequently, in step b), the nitro group of the compound IX is reduced to the amino group. Suitable reducing agents are, for example, hydrazines, metal hydrides, such as aluminum hydride, and complex hydrides derived therefrom, such as lithium aluminum hydride, diisobutyl aluminum hydride, or boranes, and also nascent hydrogen, for example iron, zinc or tin the presence of acids, such as hydrochloric acid or carboxylic acids, such as acetic acid. A further suitable reducing agent is hydrogen in the presence of catalytic amounts of transition metals such as nickel, palladium, platinum, ruthenium or rhodium. The transition metals can be used as such or in supported form, for example on activated carbon, in the form of activated metals, for example, Raney nickel, or in the form of soluble complex compounds. The reaction is preferably carried out in a solvent. Suitable solvents for the reduction are, depending on the solubility of the substrate to be hydrogenated and the chosen reducing agent, for example $C_1$–$C_4$-alcohols, such as methanol, ethanol, n-propanol, isopropanol or n-butanol, halogenated $C_1$–$C_6$-hydrocarbons, such as dichloromethane, trichloromethane, trichloroethane, trichloroethylene, aromatic hydrocarbons, such as benzene, toluene, xylenes, chlorobenzene, aqueous solutions of inorganic acids, such as aqueous hydrochloric acid, or organic acids, and mixtures thereof with water. The reduction is usually carried out at temperatures in the range from −15° C. to +100° C., preferably in the range from 0° C. to 40° C. The reduction with hydrogen is usually carried out at a hydrogen pressure in the range from 1 to 50 bar. Catalytic hydrogenations with hydrogen are preferably carried out in the range from 1 to 10 bar. For the catalytic hydrogenation of aromatic nitro groups, see, for example, Rylander in "Catalytic Hydrogenation over Platinum Metals", Academic Press, New York, 1967, 168–202; Furst et al., Chem. Rev. 65 (1965), 52; Tepko et al., J. Org. Chem. 45 (1980), 4992.

The 3-bromoaniline X is then, in step c), condensed to the heterocycle by reacting the compound X with a carbonic acid equivalent, such as methyl chloroformate, phosgene or its synthesis equivalents, such as diphosgene or triphosgene, under conditions which are customary for phosgenation. In general, the cyclization is carried out under neutral to acidic reaction conditions at temperatures in the range from 0° C. to 150° C. and preferably in the range from 20° C. to 120° C. The phosgenation is usually carried out in a solvent. Suitable solvents are, in particular, aliphatic or cycloaliphatic hydrocarbons, such as n-hexane or cyclohexane, halogenated hydrocarbons, such as dichloromethane, chloroform, trichloroethane, trichloroethylene, aromatic hydrocarbons, such as benzene, aliphatic ethers, such as diethyl ether, methyl tert-butyl ether, or cyclic ethers, such as tetrahydrofuran or dioxane. Phosgenation methods are known, see, for example, Justus Liebigs Ann. Chem., (2), 1978 193–213; J. Med. Chem., 30 (N 7) (1987), 1166–1176, J. Heterocycl. Chem. 28 (8) (1991), 1937–1939; J. Nat. Prod. 58 (3) (1995), 456–458.

In step d), the substituent $R^2$ is introduced, for example, by reacting the 5-bromobenzazol-2-one XI obtained in step c) with $R^2$-L or its precursor, L being a nucleophilically displaceable leaving group. Suitable leaving groups are, for example, halogen, such as chlorine, bromine or iodine, carboxylate, such as acetate or trifluoroacetate, or sulfonates, such as tosylate, mesylate or triflate. The reaction is preferably carried out in the presence of an auxiliary base, for example alkali metal carbonates or alkaline earth metal carbonates, such as sodium carbonate, potassium carbonate, magnesium carbonate or calcium carbonate, alkali metal hydrides or alkaline earth metal hydrides, for example sodium hydride, tertiary alkylamines, for example triethylamine, aromatic amines, for example pyridine, DMPU. The reaction is generally carried out at temperatures in the range from −15° C. to 150° C. and preferably at from 0° C. to 100° C. The reaction is usually carried out in a solvent. Suitable solvents are, for example, the abovementioned inert hydrocarbons, the abovementioned halogenated hydrocarbons, aromatic hydrocarbons, such as benzene, toluene, xylene or chlorobenzene, the abovementioned acyclic or cyclic ethers, furthermore polar aprotic solvents, such as dimethylformamide, acetonitrile or dimethyl sulfoxide. Methods for introducing a substituent at a heterocylic amide nitrogen atom are known, see also Eur. J. Med. Chem. 30 (9) (1995), 715–719; Tetrahedron 54 (9) (1998), 1763–1772.

Successive reaction of XII with magnesium or alkylmagnesium halides to the corresponding Grignard reagent and subsequent reaction of the Grignard reagent with carbon dioxide gives the carboxylic acid IVa (step e)). Customary reaction temperatures are in the range from −15° C. to 150° C., preferably in the range from −15° C. to 100° C. Suitable solvents are anhydrous solvents, in particular the abovementioned inert cyclic or acyclic hydrocarbons, the abovementioned aromatic hydrocarbons or the abovementioned acyclic or cyclic ethers. The benzazolone-5-carboxylic acid IVa is obtained by introducing dry carbon dioxide into the resulting solution of the Grignard reagent corresponding to XII and subsequent aqueous work-up. The carbon dioxide pressure is usually from 1 to 6 bar.

Alternatively, XII can be converted into carboxylic acid IVa by halogen-metal exchange using an alkali metal alkyl, for example a lithium alkyl, such as methyllithium, n-butyllithium or tert-butyllithium, and subsequent reaction of the lithiated product with $CO_2$. Customary reaction temperatures are in the range from −100° C. to 0° C., preferably in the range from −78° C. to −50° C. Suitable solvents are anhydrous solvents, in particular the abovementioned inert hydrocarbons, the abovementioned aromatic hydrocarbons or the abovementioned acyclic or cyclic ethers. Introduction of dry carbon dioxide into the solution of the lithiated product of XII gives the benzazolonecarboxylic acid IVa. The carbon dioxide pressure is usually from 1 to 6 bar.

Reaction step e) in scheme 1 can also be realized by reacting XII with carbon monoxide, a base and water, under elevated pressure in the presence of a palladium, nickel, cobalt or rhodium catalyst.

The catalysts nickel, cobalt, rhodium and in particular palladium can be present in metallic form or in the form of customary salts, such as in the form of halogen compounds, for example palladium(II) chloride, rhodium(III) chloride hydrate, acetates, for example palladium(II) acetate, cyanides, etc., in the known valence states. Metal complexes with tertiary phosphines, metal alkyl carbonyls, metal carbonyls, for example $CO_2(CO)_8$, $Ni(CO)_4$, metal carbonyl complexes with tertiary phosphines, for example $(PPh_3)_2Ni(CO)_2$, or transition metal salts complexed with tertiary phosphines can also be employed. The lastmentioned embodiment is preferred, in particular when the catalyst used is palladium. Here, the type of phosphine ligands is of minor importance. Suitable ligands are, for example, those of the formula:

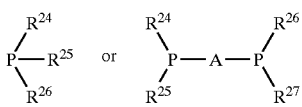

where the radicals $R^{24}$ to $R^{26}$ are low-molecular-weight alkyl, for example $C_1$–$C_6$-alkyl, aryl, $C_1$–$C_4$-alkylaryl, for example benzyl, phenethyl, or aryloxy. Aryl is, for example naphthyl, anthryl and preferably unsubstituted or substituted phenyl, where, with respect to the substituents, attention has to be paid only to their inertness to the carboxylation reaction, otherwise they can be varied widely and include all inert organocarbon radicals, such as $C_1$–$C_6$-alkyl radicals, for example methyl, carboxyl radicals, such as COOH, COOM (M is, for example, an alkali metal, alkaline earth metal or ammonium salt), or organocarbon radicals attached via oxygen, such as $C_1$–$C_6$-alkoxy radicals. A is a divalent organic radical, for example $C_1$–$C_4$-alkylene, 1,2-cycloalkylene, α,α'-ferrocenediyl, α,α-biphenyl or similar bifunctional groups.

The phosphine complexes can be prepared in a manner known per se, for example as described in the documents mentioned at the outset. For example, customary commercially available metal salts such as palladium(II) chloride or palladium(II) acetate are used as starting materials and the phosphine, for example $P(C_6H_5)_3$, $P(n-C_4H_9)_3$, $PCH_3(C_6H_5)_2$, 1,2-bis(diphenylphosphino)ethane, is added.

The amount of phosphine, based on the transition metal, is usually from 0 to 20, in particular from 0.1 to 10, molar equivalents, particularly preferably from 1 to 5 molar equivalents.

The amount of transition metal is not critical. Of course, for reasons of cost, preference is given to using a relatively small amount, for example from 0.1 to 10 mol %, in particular from 1 to 5 mol %, based on the starting material IVa.

For preparing the benzazolonecarboxylic acid IVa, the reaction is carried out with carbon monoxide and at least equimolar amounts of water, based on the bromide obtained in step d). The reaction component water can simultaneously also serve as solvent, i.e. the maximum amount is not critical.

However, depending on the nature of the starting materials and the catalysts used, it may also be advantageous for the solvent used to be, instead of the reaction component, another inert solvent or the base which is used for the carboxylation.

Suitable inert solvents for carboxylation reactions are customary solvents such as hydrocarbons, for example toluene, xylene, hexane, pentane, cyclohexane, ethers, for example methyl tert-butyl ether, tetrahydrofuran, dioxane, dimethoxyethane, substituted amides, such as dimethylformamide, persubstituted ureas, such as tetra-$C_1$–$C_4$-alkylureas, or nitrites, such as benzonitrile or acetonitrile.

In a preferred embodiment of the process, one of the reaction components, in particular the base, is used in an excess, so that no additional solvent is necessary.

Bases which are suitable for the process are all inert bases which are able to bind hydrogen iodide or hydrogen bromide liberated during the reaction. Examples which may be mentioned here are tertiary amines, such as tert-alkylamines, trialkylamines, such as triethylamine, cyclic amines, such as N-methylpiperidine or N,N'-dimethylpiperazine, pyridine, alkali metal carbonates or bicarbonates, or tetraalkyl-substituted urea derivatives, such as tetra-$C_1$–$C_4$-alkylurea, for example tetramethylurea.

The amount of base is not critical: customarily from 1 to 10, in particular from 1 to 5, mol are used. When the base is simultaneously used as solvent, the amount is generally such that the reaction components are dissolved, unnecessarily high excesses being avoided for reasons of practicability in order to save costs, to be able to employ small reaction vessels and to ensure that the reaction components have maximum contact.

During the reaction, the carbon monoxide pressure is adjusted such that an excess of CO, based on the bromide, is always present. At room temperature, the carbon monoxide pressure is preferably from 1 to 250 bar, in particular from 5 to 150 bar, of CO.

The carbonylation is generally carried out continuously or batchwise at from 20 to 250° C., in particular from 30 to 150° C. In the case of batchwise operation, carbon monoxide is advantageously continuously injected onto the reaction mixture to maintain a constant pressure.

It is, of course, also possible to carry out reaction step e) first and then reaction step d).

The 2-nitroanilines or 2-nitrophenols of the formula VIII, which are substituted in the 3-position, used as starting materials for the synthesis of the benzazolonecarboxylic acids IVa are known and can be prepared by processes known per se. Alternatively, the compounds IX in which A is oxygen can be prepared in the manner shown below in scheme 7.

A further general route to the benzazolonecarboxylic acids of the formula IVa is shown in scheme 2.

Scheme 2:

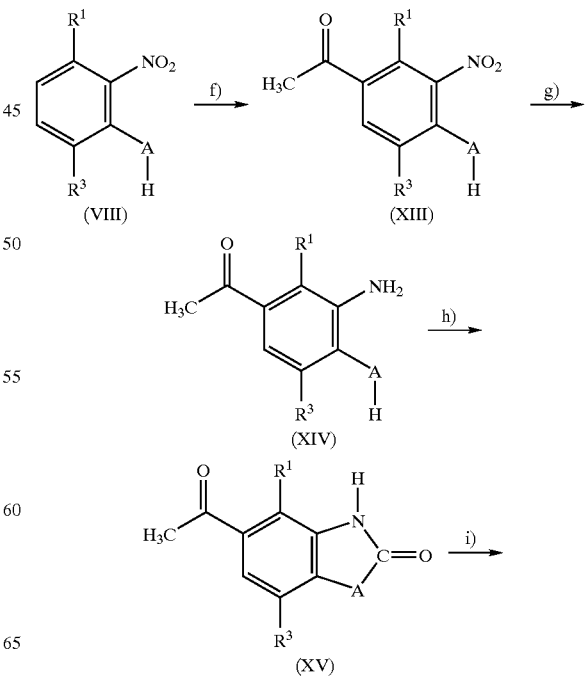

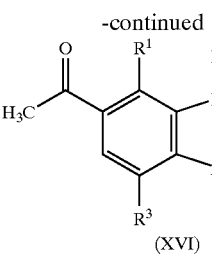

(XVI)

Starting with the 2-nitroanilines or 2-nitrophenols of the formula VIII, which are substituted in the 3-position, the substituted acetophenone XIII can be prepared by Friedel-Crafts acylation in step f). The acetyl group can be introduced in a known manner by reacting the compound VIII with acetic acid or activated acetic acid, such as acetic anhydride or acetyl chloride, in the presence of a Lewis acid such as aluminum trichloride, boron trichloride or trifluoroacetic acid, under anhydrous conditions. Usually, more than 1 mol of Lewis acid is required per mole of ketone formed, since the ketone formed binds the Lewis acid as a complex. After the reaction has ended, this complex is cleaved hydrolytically. Friedel-Crafts acylations are usually carried out in a solvent. Suitable solvents are the abovementioned cyclic and acyclic hydrocarbons, the abovementioned halogenated hydrocarbons, aromatic hydrocarbons, such as nitrobenzene, or the abovementioned ethers. The reaction temperatures are generally in the range from 0° C. to 150° C. and preferably in the range from 20° C. to 120° C. Methods for introducing acyl groups are known, see, for example, Organikum, 16th ed. 1986, p. 325.

In step g), the substituted acetophenone XIII is then reduced to the amino compound XIV. The reduction is carried out in the manner described in step b) in scheme 1. In step h), the aniline derivative XIV is then phosgenated in the manner described in step c) in scheme 1. The substituent $R^2$ can be introduced similarly to step d) in scheme 1 (step i) in scheme 2).

The compound XVI obtained in step i) in scheme 2 is converted into the benzazolonecarboxylic acid IVa with the aid of the haloform reaction. To this end, a halogenating agent, such as hypohalite, for example hypochlorite, or chlorine in alkaline solution is allowed to act on the compound XVI. Initially, a trihalomethylcarbonyl derivative is formed, which, under the alkaline reaction conditions, is cleaved hydrolytically with formation of the desired benzazolonecarboxylic acid IVa. Suitable bases are, in particular, alkali metal hydroxides, such as sodium hydroxide or potassium hydroxide. The reaction is usually carried out in solution. Suitable solvents are in particular water, mixtures of water and organic solvents, such as $C_1$–$C_4$-alcohols, for example methanol, ethanol, propanol, butanol, or the abovementioned ethers. Customary reaction temperatures are in the range from 0° C. to 150° C., preferably in the range from 20° C. to 120° C. For the haloform reaction, see, for example, Organikum, 16th ed. 1986, p. 375.

If A in formula IVa is sulfur, the benzazolonecarboxylic acids of the general formula IVa can also be prepared in the manner shown in scheme 3.

Scheme 3:

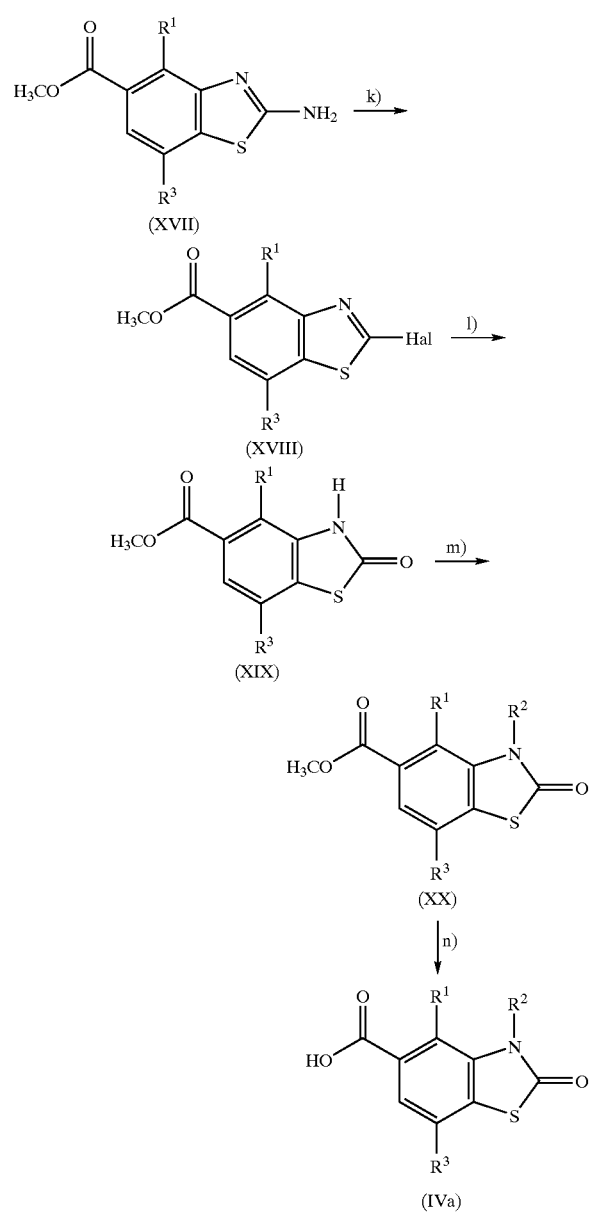

Hal = halogen, in particular Cl

According to scheme 3, the benzazolonecarboxylic acids of the formula IVa where A=sulfur can be prepared from the aminobenzothiazoles XVII. The 2-aminobenzothiazole XVII is converted into the 2-halobenzothiazole compound XVIII in a manner known per se under Sandmeyer conditions (step k)). In this manner, further functionalities can be introduced in the 2-position of the benzothiazole ring.

To this end, the 2-aminobenzothiazole XVII is initially reacted with inorganic or organic nitrite, such as sodium nitrite in the presence of acid, such as hydrochloric acid, or with tert-butyl nitrite. The resulting diazonium salt is then reacted with an inorganic halide, such as sodium chloride, with addition of copper or a Cu(I) halide, such as Cu(I) chloride. The reaction is generally carried out at temperatures in the range from 0° C. to 150° C. and preferably in the range from 20° C. to 100° C. Suitable solvents are in particular water or mixtures of water with organic solvents, such as the abovementioned alcohols or ethers. For preparing aromatic halides, in particular chlorides, according to Sandmeyer, see also Organikum, 16th ed. 1986, p. 545.

In step 1), the 2-halobenzothiazole compound XVIII can then be hydrolyzed under acidic or alkaline conditions to give the benzothiazolone. To this end, the compound XVIII is treated with a base, such as alkali metal hydroxide or alkaline earth metal hydroxide, for example sodium hydroxide, potassium hydroxide or magnesium hydroxide, or alkali metal alkoxide, such as sodium ethoxide or potassium methoxide, or with an acid, such as hydrochloric acid. The hydrolysis is usually carried out in a solvent. Suitable solvents are, depending on the base used, polar aprotic solvents, such as dimethylformamide, dimethyl sulfoxide, N-methylpyrrolidone or acetonitrile, ethers, such as tetrahydrofuran or dioxane, water and mixtures of water with the abovementioned alcohols, ethers or polar aprotic solvents. The hydrolysis is generally carried out at from 0° C. to 150° C. and preferably at from 20° C. to 120° C. For the hydrolysis of haloheteroaromatic compounds to keto compounds see also J. Med. Chem. 20 (No. 6) (1977), 791–796.

In step m), the substituent $R^2$ is introduced into the compound XIX as described in step d) in scheme 1. For the hydrolysis in step n), for example, the benzazolone methyl ester XX obtained in step m) is reacted with alkali metal hydroxide, for example lithium hydroxide, sodium hydroxide or potassium hydroxide, with alkaline earth metal hydroxide, such as magnesium hydroxide, or with alkali metal iodides, such as sodium iodide, in a suitable solvent, preferably in the absence of oxygen. Usual reaction temperatures are in the range from 0° C. to 200° C. and in particular in the range from 20° C. to 180° C. Suitable solvents are the abovementioned aliphatic or cycloaliphatic hydrocarbons, the halogenated hydrocarbons, the aromatic hydrocarbons, the abovementioned ethers and alcohols, aqueous monophasic systems, and also pyridine. For hydrolysis, see, for example, Organikum, 16th ed. 1986, p. 415, McMurry, Org. React. 24 (1976), 187; Taschner et al., Rocz. Chem. 30 (1956), 323; Houben-Weyl: "Methoden der organischen Chemie" [Methods of Organic Chemistry], volume E 8 b 1994; p. 1010 f.; J.Chem. Soc. Perkin Trans. 1, No. 12 (1976), 1291–1296; in particular A. R. Katritzky et al., J. Heterocycl. Chem., 30 (1) (1993) 135–139. The synthesis of the starting material XVII is described in PCT/EP 00/04042 and PCT/EP 00/04040.

A further route to the compounds of the formula IVa is shown in scheme 4.

Scheme 4:

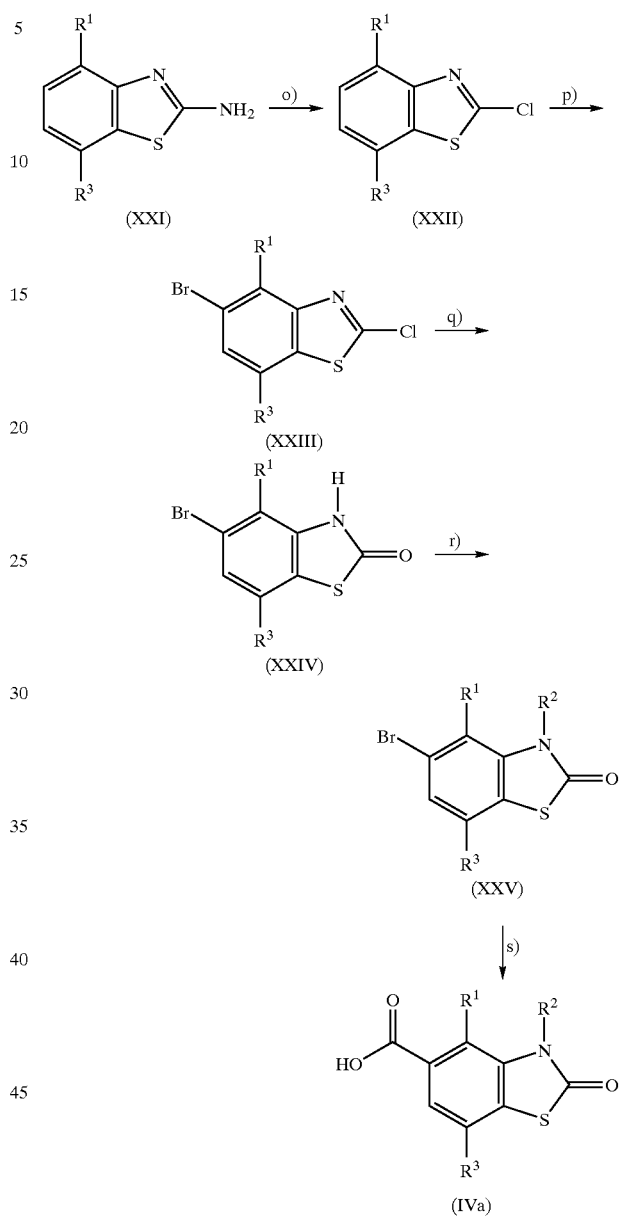

In step o), the 2-chlorobenzothiazole compounds XXII can be prepared in a Sandmeyer reaction from the 2-aminobenzothiazoles of the formula XXI, which are known per se. The reaction conditions required correspond to those for step k) in scheme 3. The 2-chlorobenzothiazole XXII can be brominated in a manner similar to that of step a) in scheme 1, the bromine substituent being introduced selectively in the position ortho to $R^1$ (step p)). The compound XXIII is then, under the conditions given for step 1) in scheme 3, subjected to basic hydrolysis (step q)). In step r), the substituent $R^2$ can be introduced into XXIV under the conditions described for step d) in scheme 1. The carboxyl group is introduced (step s)) according to the reaction conditions described in step e) in scheme 1.

A variant for preparing the benzothiazolonecarboxylic acid IVa (A=S) is shown in scheme 5.

Scheme 5:

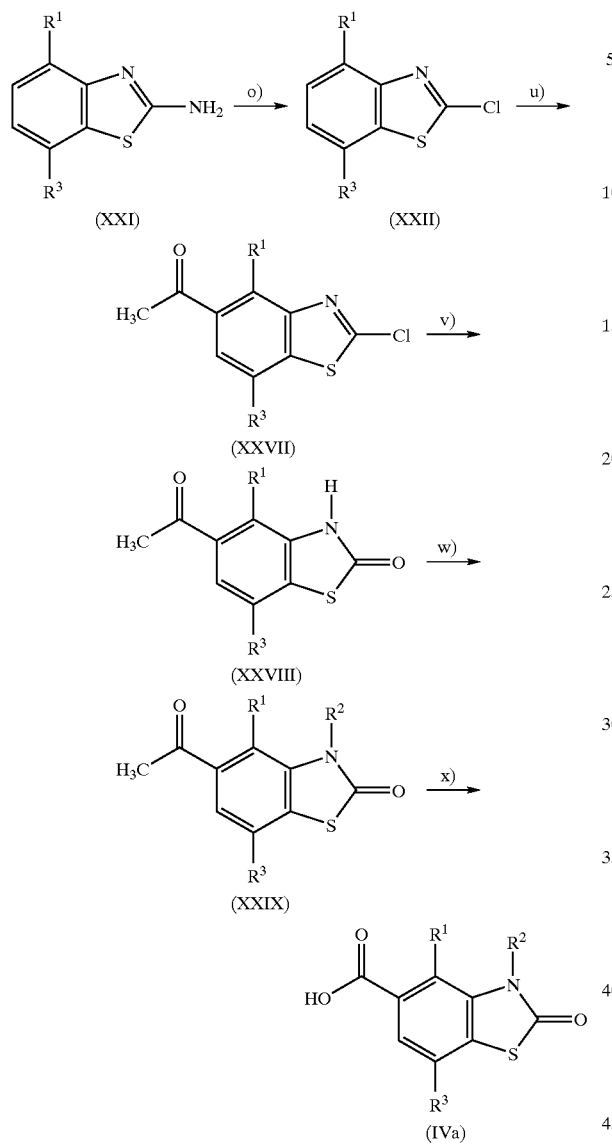

Scheme 6:

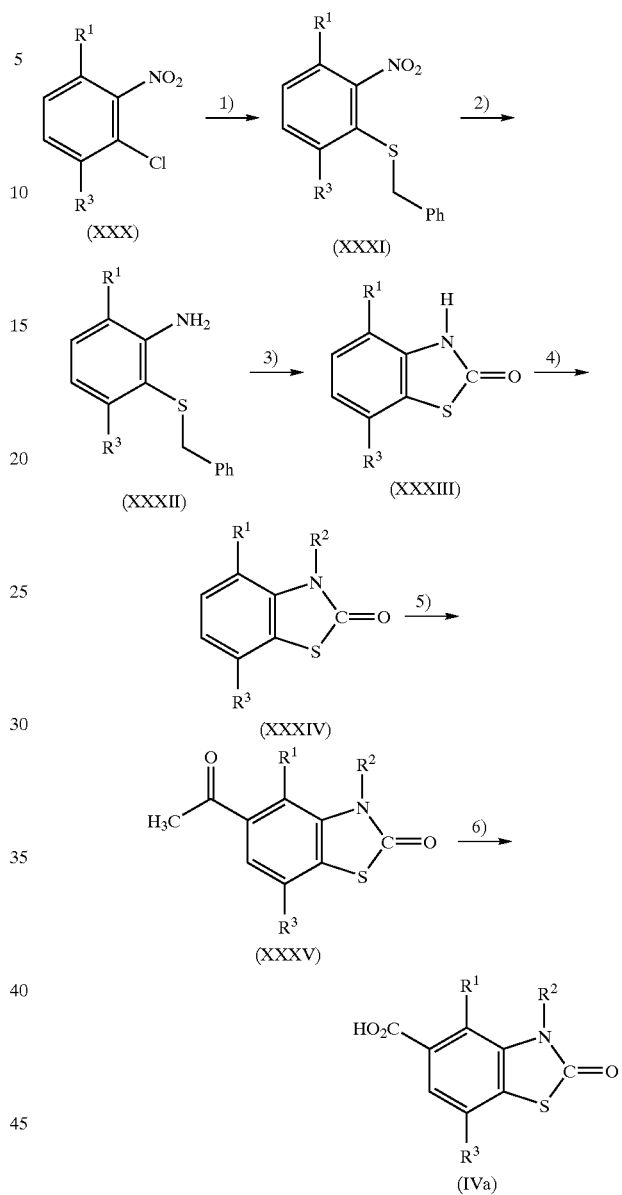

Again, the initial starting materials are substituted 2-aminobenzothiazoles XXI which are converted in the manner described above into the 2-chlorobenzothiazoles XXII (step o), see scheme 3). In step u), the 2-chlorobenzothiazoles XXII are then subjected to a Friedel-Crafts acylation under the conditions given in step f) in scheme 2, giving the compound XXVII. XXVII is hydrolyzed in a manner similar to that described for reaction step q) in scheme 4. In step w), the substituent $R^2$ is introduced into XXVIII in a manner known per se, for example as described in step d) in scheme 1. The substituted acetophenone XXIX is then, in the concluding haloform reaction in step x), under the conditions given in step j) in scheme 2, converted into the desired benzazolonecarboxylic acid IVa, with loss of a carbon.

A further route to benzazolonecarboxylic acids of the formula IVa (A=sulfur) is shown in scheme 6.

The o-chloronitrobenzenes of the formula XXX, which are known per se, are initially converted with alkali metal salts of benzyl ercaptan into the corresponding thioethers XXXI (step 1)). The substitution is usually carried out in one of the abovementioned aliphatic or cycloaliphatic hydrocarbons, halogenated hydrocarbons, aromatic hydrocarbons, ethers, in dimethylformamide, NMP, sulfolane or dimethyl sulfoxide. Customary reaction temperatures are in the range from 0° C. to 250° C. and preferably in the range from 50° C. to 175° C. Methods for nucleophilic substitution are known, see also A. Bagno et al., J. Chem. Soc. Perkin Trans. II, 1991 (5), 651–655; J. R. Beck et al., J. Org. Chem. 43 (10), (1978), 2048–2052.

In step 2), the compound XXXI is then reduced to amino compound XXXII. The required reaction conditions correspond to those for step b) in scheme 1. The amino compound XXXII is then cyclized under the reaction conditions described in step c) in scheme 1 using carbonic acid equivalents, to give the benzothiazolone XXXIII (step 3)).

The substituent R² is subsequently introduced under the reaction conditions described in step d) in scheme 1 (step 4)). The acetyl group is introduced in the position ortho to substituent R¹ by Friedel-Crafts acylation of the compound XXXIV (step 5)). The required reaction conditions correspond to those of step f) in scheme 2. The desired benzazolonecarboxylic acid IVa can be obtained from compound XXXV by haloform reaction (step 6)). The required reaction conditions correspond to those in step j) in scheme 2.

In a similar manner as in scheme 1, compounds of the formula IVa where A=sulfur can be obtained in a variant of this process starting with o-chloronitrobenzenes XXX by initially brominating the thioether XXXI obtained in step 1). The required reaction conditions correspond to those of step a) in scheme 1. The subsequent reduction of the nitro group to the amino group is carried out under the conditions mentioned in step b) in scheme 1. Condensation with carbonic acid equivalents gives the benzothiazolones. The required reaction conditions correspond to those of step c) in scheme 1. The substituent R² is introduced in the customary manner, analogously to step d) in scheme 1. The carboxyl group is introduced by the procedure described in step e) in scheme 1.

A further route to benzazolonecarboxylic acids where A=oxygen is shown in scheme 7.

Scheme 7:

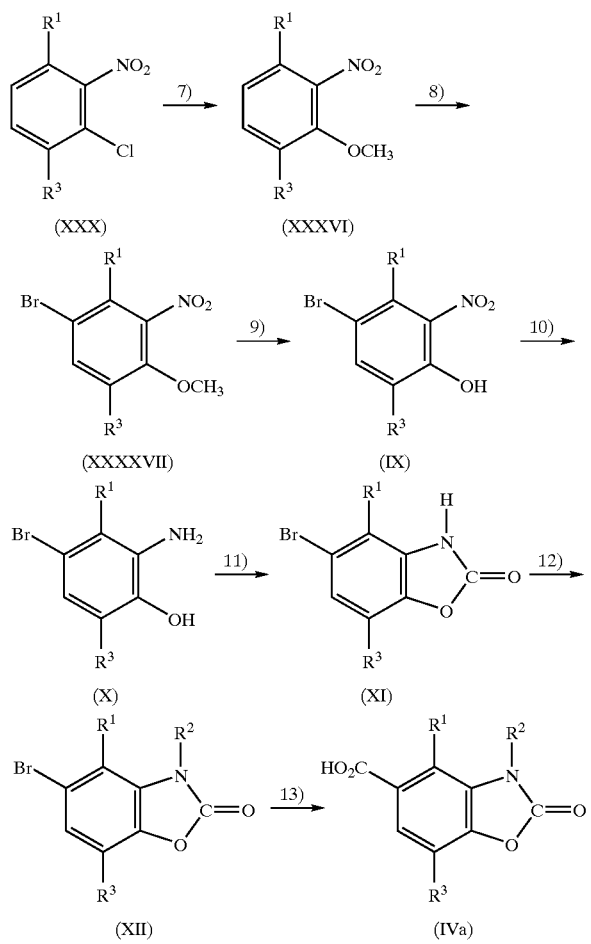

According to scheme 7, for example, o-chloronitrobenzenes of the formula XXX can be converted with alkali metal salts of alkoxides into the corresponding o-nitroethers XXXVI (step 7)). This nucleophilic substitution on the aromatic ring is generally carried out with exclusion of water, usually in a solvent. Suitable solvents are, in particular, the abovementioned aliphatic or cycloaliphatic hydrocarbons, halogenated hydrocarbons, aromatic hydrocarbons, ethers, DMF, NMP, sulfolane or dimethyl sulfoxide. The required reaction temperatures are generally in the range from 0° C. to 250° C. and preferably from 50° C. to 175° C. Methods for preparing aromatic ethers from o-nitrochloro compounds are known, see also A. Bagno et al., J.Chem. Soc. Perkin Trans. II, 1991 (5), 651–655; J. R. Beck et al., J. Org. Chem. 43 (10) (1978), 2048–2052.

The resulting o-nitroanisole XXXVI is brominated under the reaction conditions given in step a) in scheme 1, the bromine atom being introduced selectively in position para to the methoxy group (step 8)).

In step 9), the hydroxyl group is then exposed by ether cleavage under acidic reaction conditions in the presence of a Lewis acid, such as aluminum trichloride, aluminum tribromide or hydrohalic acids, such as hydriodic acid or hydrobromic acid, giving 4-bromo-2-nitrophenols of the formula IX. The ether cleavage is usually carried out in a solvent. Suitable solvents are the abovementioned acyclic and cyclic hydrocarbons, halogenated hydrocarbons, aromatic hydrocarbons or acids, such as acetic acid. The ether cleavage is generally carried out at temperatures in the range from −15° C. to 150° C., preferably in the range from 0° C. to 100° C. For the cleavage of phenol ethers, see also Organikum, 16th ed. 1986, p. 192.

The further reaction steps 10) to 13) in scheme 7 correspond to reaction steps b) to e) in scheme 1.

The examples below serve to illustrate the invention.

EXAMPLE 1

Preparation of 3,4-dimethyl-5-(1',3'-cyclohexanedion-2'-yl)carbonylbenzothiazol-2-one (Compound I-1a.1129)

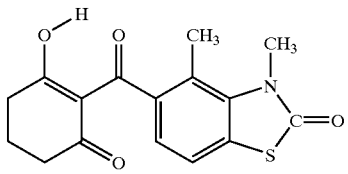

1.1 Methyl 2-chloro-4-methylbenzothiazole-5-carboxylate

A solution of 5 g (22.5 mmol) of methyl 2-amino-4-methyl-benzothiazole-5-carboxylate in 2 l of acetonitrile was admixed with 10 ml of water, 4.5 g (44.8 mmol) of copper(I) chloride, 6.6 g of sodium chloride (110 mmol) and 2 ml of 15-crown-5. A solution of 3 g (29 mmol) of tert-butyl nitrite was then added dropwise with stirring, the solution was heated at reflux for 15 h, the resulting precipitate was filtered off and the solution was concentrated under reduced pressure. The residue was then extracted three times with in each case 500 ml of ethyl acetate. To this end, the solvent was heated to boiling point and the solution was filtered whilst hot. The extracts were concentrated under reduced pressure. The residue was purified by trituration with n-hexane/diethyl ether. This gave 4.2 g (17.4 mmol, 77% yield) of methyl 2-chloro-4-methylbenzothiazole-5-carboxylate of m.p. 112° C.

¹H-NMR (CDCl₃): δ (ppm)=2.98 (s, 3H), 3.94 (s, 3H), 7.64 (d, 1H), 7.95 (d, 1H).

1.2 Methyl 4-methylbenzothiazol-2-one-5-carboxylate

A solution of 22.5 g (93 mmol) of methyl 2-chloro-4-methyl-benzothiazole-5-carboxylate in 360 ml of N-methylpyrrolidone was admixed with 13.6 g (186 mmol) of potassium methoxide and heated at 100° C. for 5 hours. After cooling, the resulting precipitate was filtered off with suction and the filtrate was admixed with water. The pH of the reaction solution was then adjusted to pH 1, the aqueous solution was extracted three times with ethyl acetate and the combined organic phases were washed and dried. The solvent was removed under reduced pressure and the residue was purified by trituration with methylene chloride/n-hexane. This gave, in a yield of 55%, 11.38 g (51 mmol) of methyl 4-methylbenzothiazol-2-one-5-carboxylate of m.p. 262° C.–266° C.

$^1$H-NMR (CDCl$_3$): δ (ppm)=2.64 (s, 3H), 3.91 (s, 3H), 7.28 (d, 1H), 7.74 (d, 1H), 9.94 (br s, 1H, NH).

1.3 Methyl 3,4-dimethylbenzothiazol-2-one-5-carboxylate

A solution of 11.38 g (51 mmol) of methyl 4-methylbenzo-thiazol-2-one-5-carboxylate in 400 ml of acetone was admixed with 14.18 g of potassium carbonate. 5.1 ml (54 mmol) of dimethyl sulfate were then added dropwise with stirring, and the mixture was stirred at 23° C. for 78 hours. The precipitated solid was filtered off and the solvent was removed under reduced pressure. Recrystallization from ether gave, in a yield of 84%, 10.15 g (43 mmol) of methyl 3,4-dimethylbenzothiazol-2-one-5-carboxylate of m.p. 97° C.–100° C.

$^1$H-NMR (CDCl$_3$): δ (ppm)=2.78 (s, 3H), 3.77 (s, 3H), 3.92 (s, 3H), 7.28 (d, 1H), 7.36 (d, 1H).

1.4 Methyl 3,4-dimethylbenzothiazol-2-one-5-carboxylic acid

A solution of 10.15 g (43 mmol) of methyl 3,4-dimethylbenzo-thiazol-2-one-5-carboxylate in 100 ml of tetrahydrofuran and 100 ml of water was admixed with 2.06 g (86 mmol) of lithium hydroxide. The solution was then heated at reflux for 2 hours. After cooling, the tetrahydrofuran was removed under reduced pressure, the remaining aqueous solution was acidified and the precipitated solid was filtered off with suction and dried. More product was obtained by extracting the mother liquor with ethyl acetate. This gave a total of 8 g (36 mmol, 83% yield) of 3,4-dimethylbenzothiazol-2-one-5-carboxylic acid of m.p. 235° C.–239° C.

$^1$H-NMR (DMSO-D$_6$): δ (ppm)=2.77 (s, 3H), 3.66 (s, 3H), 7.42 (d, 1H), 7.56 (d, 1H).

1.5 Cyclohexenon-3-yl 3,4-dimethylbenzothiazol-2-one-5-carboxylate 1.1 g (5 mmol) of 3,4-dimethylbenzothiazol-2-one-5-carboxylic acid, 0.58 g of 1,3-cyclohexanedione and 1.25 g of ethyl(3'-dimethylaminopropyl)carbodiimide were dissolved in 40 ml of acetonitrile, and the solution was stirred at 50° C. for 4 hours. After the reaction had ended, the precipitate was filtered off and the solution was concentrated. The residue was taken up in water and extracted with methylene chloride. The organic phase was washed and dried and the solvent was then removed. Chromatography of the residue on silica gel (mobile phase: cyclohexane/ethyl acetate, gradient from 100:0 to 50:50) gave 0.77 g (2.4 mmol, 48% yield) of cyclohexenone-3-yl 3,4-dimethylbenzothiazol-2-one-5-carboxylate of m.p. 144° C.–146° C.

$^1$H-NMR (CDCl$_3$): δ (ppm)=1.18 (s, 6H), 2.37 (s, 2H), 2.57 (s, 2H), 2.86 (s, 3H), 3.81 (s, 3H), 6.05 (s, 1H), 7.37 (d,1H), 7.68 (d, 1H).

1.6 3,4-Dimethyl-5-(1',3'-cyclohexanedion-2'-yl)carbonyl-benzothiazol-2-one

With stirring, 0.97 g of potassium carbonate and a drop of trimethylsilyl cyanide were added to a solution of 0.43 g (1.4 mmol) of cyclohexenon-3-yl 3,4-dimethyl-benzothiazol-2-one-5-carboxylate in 40 ml of acetonitrile. The reaction mixture was heated at 45° C. for 16 hours, the precipitated solid was filtered off, the solvent was removed under reduced pressure and the residue was then taken up in water. The aqueous phase was adjusted to pH 7 and extracted with methylene chloride. The solvent was removed, giving 0.09 g (0.3 mmol, 20% yield) of 3,4-dimethyl-5-(1',3'-cyclohexanedion-2'-yl)carbonylbenzo-thiazol-2-one as an oil.

$^1$H-NMR: δ (ppm)=7.31 (d), 6.86 (d), 3.80 (s), 2.83 (m), 2.60 (s), 2.47 (m), 2.10 (m).

EXAMPLE 2

Preparation of 3,4-dimethyl-5-(5',5'-dimethyl-1',3'-cyclohexanedion-2'-yl)-carbonylbenzothiazol-2-one (Compound I-1c.1129)

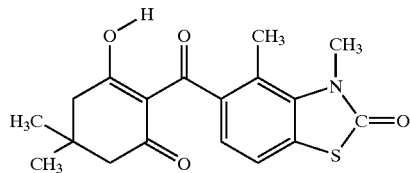

2.1 5',5'-Dimethylcyclohexenone-3'-yl 3,4-dimethylbenzothiazol-2-one-5-carboxylate The reaction was carried out similarly to the procedure described in Example 1.5 using, instead of 0.58 g of 1,3-cyclohexanedione, 0.72 g of 5,5-dimethyl-1,3-cyclohexanedione.

0.66 g (1.9 mmol, 39% yield) of 5,5-dimethylcyclohexenon-3-yl 3,4-dimethylbenzothiazol-2-one-5-carboxylate of m.p. 123°-126° C. was isolated.

$^1$H-NMR (CDCl$_3$): δ (ppm)=1.18 (s, 6H), 2.37 (s, 2H), 2.57 (s, 2H), 2.86 (s, 3H), 3.81 (s, 3H), 6.05 (s, 1H), 7.37 (d,1H), 7.68 (d, 1H).

2.2 3,4-Dimethyl-5-(5',5'-dimethyl-1',3'-cyclohexanedion-2'-yl)-carbonylbenzothiazol-2-one The reaction was carried out similarly to the procedure described in Example 1.6 using, instead of 0.43 g (1.4 mmol) of cyclohexenon-3-yl 3,4-dimethylbenzothiazol-2-one-5-carboxylate, 0.63 g (1.8 mmol) of 5,5-dimethylcyclohexenon-3-yl 3,4-dimethylbenzothiazol-2-one-5-carboxylate and using 1.24 g of potassium carbonate instead of 0.97 g of potassium carbonate.

0.35 g (1 mmol, 56% yield) of the title compound of m.p. 173° C.–176° C. was isolated.

$^1$H-NMR (CDCl$_3$): δ (ppm)=1.14 (s, 6H), 2.32 (s, 2H), 2.56 (s, 3H), 2.68 (s, 2H), 3.79 (s, 3H), 6.82 (d, 1H), 7.27 (d, 1H), 17.60 (s, 1H).

EXAMPLE 3

Preparation of 3,4-dimethyl-5-(4',4',6',6'-tetramethyl-1',3',5'-cyclohexane-trion-2'-yl)-carbonylbenzothiazol-2-one (Compound I-1d.1129)

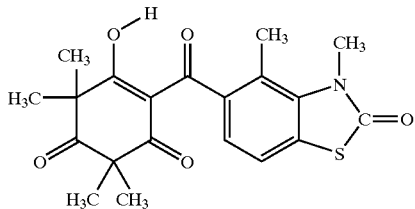

3.1 4',4',6',6'-Tetramethylcyclohexene-1',5'-dion-3'-yl 3,4-dimethylbenzothiazol-2-one-5-carboxylate The reaction was carried out similarly to the procedure described in Example 1.5 using, instead of 0.58 g of 1,3-cyclohexanedione, 0.94 g of 4,4,6,6-tetramethyl-1,3,5-cyclohexanetrione.

0.96 g (2.5 mmol, 50% yield) of 4,4,6,6-tetramethylcyclohexene-1,5-dion-3-yl 3,4-dimethylbenzothiazol-2-one-5-carboxylate of m.p. 145° C.–147° C. was isolated.

$^1$H-NMR (CDCl$_3$): δ (ppm)=1.40 (s, 6H), 1.48 (s, 6H), 2.86 (s, 3H), 3.82 (s, 3H), 6.28 (s, 1H), 7.39 (d, 1H), 7.72 (d, 1H).

3.2 3,4-Dimethyl-5-(4',4',6',6'-tetramethyl-1',3',5'-cyclohexanetrion-2'-yl)-carbonylbenzothiazol-2-one The reaction was carried out similarly to the procedure described in Example 1.6 using, instead of 0.43 g (1.4 mmol) of cyclohexenon-3-yl 3,4-dimethylbenzothiazol-2-one-5-carboxylate, 0.78 g (2 mmol) of 4,4,6,6-tetramethylcyclohexene-1,5-dion-3-yl 3,4-dimethylbenzothiazol-2-one-5-carboxylate and 1.24 g of potassium carbonate instead of 0.97 g of potassium carbonate.

This gave 0.17 g (0.4 mmol, 22% yield) of the title compound of m.p. 203° C. to 204° C.

$^1$H-NMR: δ (ppm)=7.28 (d), 6.84 (d), 3.80 (s), 2.62 (s), 1.56 (s), 1.36 (s).

In a similar manner, the compounds I of Examples 4 to 40 were prepared by reacting the respective carboxylic acid IV in a similar manner with the respective cyclohexane-1,3-dione, where in the preparation of the compounds I of Examples 20, 21 and 28 the triketone that was originally obtained was derivatized by reacting successively with oxazolyl chloride and then with pyrazole.

| Ex. | Structure/compound number | m.p. or $^1$H-NMR |
|---|---|---|
| 1 | I-1a.1129 | δ (ppm) = 7.31 (d), 6.86 (d), 3.80 (s), 2.83 (m), 2.60 (s), 2.47 (m), 2.10 (m). |
| 2 | I-1c.1129 | m.p. 173° C.–176° C. |
| 3 | I-1d.1129 | δ (ppm) = 7.28 (d), 6.84 (d), 3.80 (s), 2.62 (s), 1.56 (s), 1.36 (s) |
| 4 | I-1x.1129 | m.p. 101° C.–110° C. |

-continued
| Ex. | Structure/compound number | m.p. or ¹H-NMR |
|---|---|---|
| 5 | 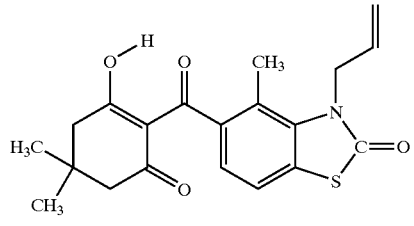 I-1c.1157 | m.p. 143° C.–150° C. |
| 6 | 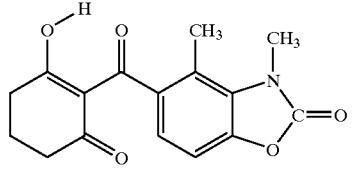 I-1a.2 | m.p. 207° C.–209° C. |
| 7 | 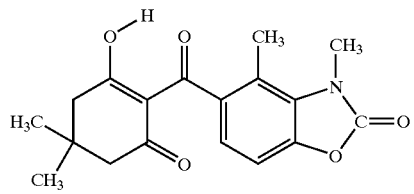 I-1c.2 | m.p. 139° C.–143° C. |
| 8 | 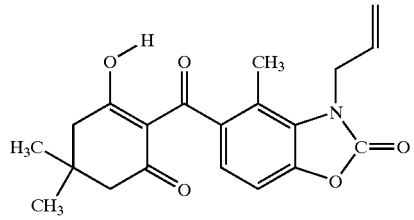 I-1c.29 | δ (ppm) = 7.12 (d), 6.82 (d), 6.00 (m), 5.30 8d), 5.17 (d), 4.63 (m), 2.68 (s), 2.33 8s), 2.29 (s), 1.12 (s) |
| 9 | 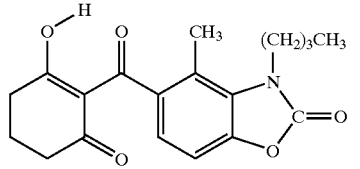 I-1a.6 | m.p. 128° –130° C. |
| 10 | 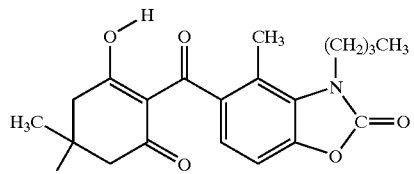 I-1c.6 | m.p. 115° C.–116° C. |

-continued

| Ex. | Structure/compound number | m.p. or $^1$H-NMR |
|---|---|---|
| 11 | I-1a.29 | δ (ppm) = 2.05 (m, 2H), 2.35 (s, 3H), 2.75 (m, 2H), 4.65 (d, 2H), 5.20 (m, 2H), 5.95 (m, 1H), 6.85 (d, 1H), 7.05 (d, 1H), 17.5 (s, 1H) |
| 12 | I-1a.3 | m.p. 150° C.–153° C. |
| 13 | I-1c.3 | δ (ppm) = 1.13 (s, 6H), 1.35 (t, 3H), 2.40 (s, 3H), 2.50 (s, 4H), 4.05 (m, 2H), 6.80 (m, 2H), 7.05 (d, 2H), 17 (s, 1H) |
| 14 | I-1x.1134 | δ (ppm) = 0.95 (t, 3H), 1.40 (m, 2H), 1.65–2.30 (m, 8H), 2.45 (s, 3H), 2.90 (M, 1H), 3.15 (m, 1H), 4.15 (m, 2H), 6.85 (d, 1H), 7.25 (d, 1H), 17.8 (s, 1H) |
| 15 | I-1d.1134 | δ (ppm) = 0.95 (t, 3H), 1.25–1.60 (m, 16H), 1.75 (m, 2H), 2.50 (s, 3H), 4.20 (m, 2H), 6.80 (d, 1H), 7.30 (d, 1H), 17.8 (s, 1H) |
| 16 | I-1c.1131 | δ (ppm) = 1.15 (s, 6H), 1.35 (t, 3H), 2.35 (s, 2H), 2.50 (s, 3H), 2.70 (s, 2H), 4.30 (m, 2H), 6.85 (d, 1H), 7.30 (d, 1H), 17.8 (s, 1H) |

-continued
| Ex. | Structure/compound number | m.p. or $^1$H-NMR |
|---|---|---|
| 17 | 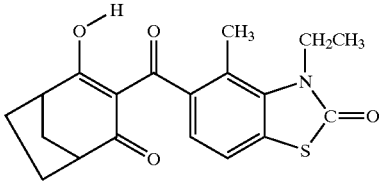<br>I-1x.1131 | m.p. 155° C.–157° C. |
| 18 | 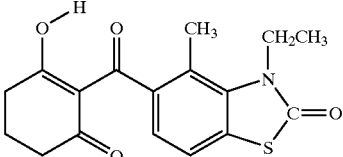<br>I-1a.1131 | m.p. 198° C.–200° C. |
| 19 | 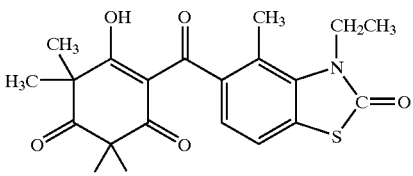<br>I-1d.1131 | m.p. 122° C.–123° C. |
| 20 | 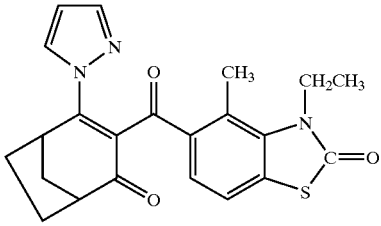<br>I-1za.1131 | δ (ppm) = 1.35 (t, 3H), 1.85–2.45 (m, 6H), 3.15 (m, 1H), 3.70 (m, 1H), 4.30 (m, 2H), 6.35 (s, 1H), 7.15 (m, 2H), 7.60 (s, 1H), 7.85 (s, 1H) |
| 21 | 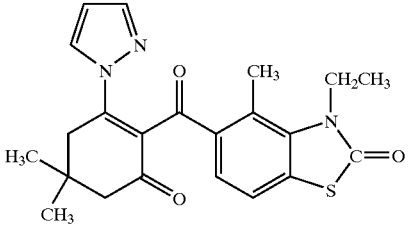<br>I-1zb.1131 | m.p. 150° C.–151° C. |
| 22 | 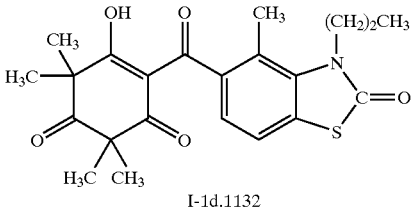<br>I-1d.1132 | δ (ppm) = 1.00 (t, 3H), 1.35 (s, 6H), 1.55 (s, 6H), 1.75 (m, 2H), 2.50 (s, 3H), 4.15 (m, 2H), 6.85 (d, 1H), 7.25 (d, 1H), 18.0 (s, 1H) |

-continued

| Ex. | Structure/compound number | m.p. or ¹H-NMR |
|---|---|---|
| 23 | I-1x.1173 | m.p. 160° C.–162° C. |
| 24 | I-1d.1173 | m.p. 158° C.–162° C. |
| 25 | I-1c.1132 | m.p. 129° C.–135° C. |
| 26 | I-1d.3582 | m.p. 135° C.–144° C. |
| 27 | I-1x.3583 | δ (ppm) = 1.75 (m, 2H), 1.95–2.30 (m, 2H), 2.45 (s, 3H), 2.90 (m, 1H), 3.15 (m, 1H), 3.80–4.00 (m, 4H), 4.35 (m, 2H), 5.00 (m, 1H), 6.85 (d, 1H), 7.30 (d, 1H), 17.6 (s, 1H) |
| 28 | I-1zc.1131 | δ (ppm) = 1.35 (t, 3H), 1.50 (s, 6H), 1.60 (s, 6H), 2.65 (s, 3H), 4.25 (m, 2H), 6.30 (s, 1H), 7.20 (d, 1H), 7.30 (d, 1H), 7.50–7.60 (m, 2H) |

| Ex. | Structure/compound number | m.p. or $^1$H-NMR |
|---|---|---|
| 29 | 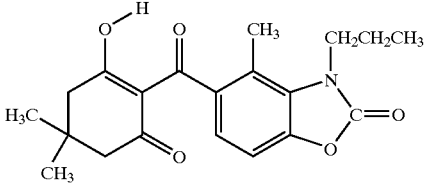 I-1c.4 | m.p. 189° C.–193° C. |
| 30 | 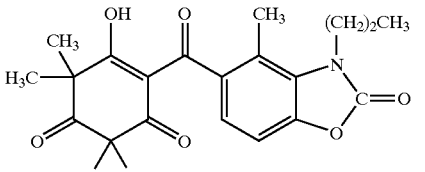 I-1d.4 | δ (ppm) = 1.00 (t, 3H), 1.35 (s, 6H), 1.55 (s, 6H), 1.80 (m, 2H), 2.45 (s, 3H), 3.95 (m, 2H), 6.80 (d, 1H), 7.10 (d, 1H), 17.8 (s, 1H) |
| 31 | 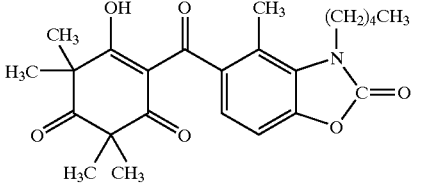 I-1d.3385 | δ (ppm) = 0.90 (t, 3H), 1.25–1.60 (m, 16H), 1.75 (m, 2H), 2.50 (s, 3H), 4.00 (m, 2H), 5.30, (s, 2H), 6.85 (d, 1H), 7.10 (d, 1H), 17.6 (s, 1H) |
| 32 | 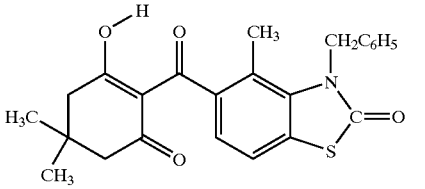 I-1c.1173 | m.p. 161° C.–166° C. |
| 33 | 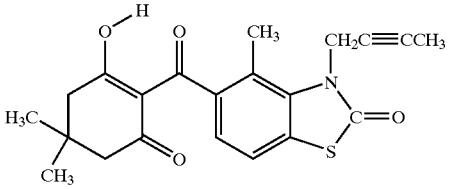 I-1c.3582 | m.p. 147° C.–149° C. |
| 34 | 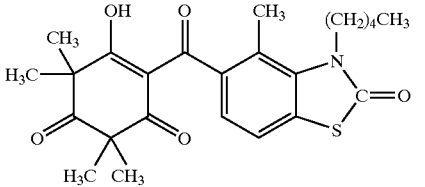 I-1d.3577 | δ (ppm) = 0.90 (t, 3H), 1.25–1.80 (m, 18H), 2.50 (s, 3H), 4.20 (m, 2H), 6.85 (d, 1H), 7.30 (d, 1H), 18.0 (s, 1H) |

-continued

| Ex. | Structure/compound number | m.p. or ¹H-NMR |
|---|---|---|
| 35 | I-1x.3577 | δ (ppm) = 0.90 (t, 3H), 1.35–2.25 (m, 12H), 2.90 (m, 1H), 3.15 (m, 1H), 4.15 (m, 2H), 6.85 (d, 1H), 7.30 (d, 1H), 18.0 (s, 1H) |
| 36 | I-1c.3577 | δ (ppm) = 0.90 (t, 3H), 1.15 (s, 6H), 1.50–1.80 (m, 6H), 2.30, (s, 2H), 2.40 (s, 3H), 2.70 (s, 2H), 4.00 (m, 2H), 6.80 (d, 1H), 7.10 (d, 1H), 17.8 (s, 1H) |
| 37 | I-1x.3580 | δ (ppm) = 1.65–2.10 (m, 10H), 2.90 (m, 1H), 3.20 (m, 1H), 4.20 (m, 1H), 5.05 (m, 2H), 5.80 (m, 2H), 6.85 (d, 1H), 7.30 (d, 1H), 17.8 (s, 1H) |
| 38 | I-1d.3581 | δ (ppm) = 1.25 (s, 6H), 1.50 (s, 6H), 2.30 (s, 3H), 3.75 (s, 3H), 5.45 (s, 2H), 6.60 (s, 1H), 6.65 (d, 1H), 6.75 (d, 1H), 6.85 (d, 1H), 7.25 (d, 1H), 7.35 (d, 1H), 17.8 (s, 1H) |
| 39 | I-1d.3579 | δ (ppm) = 1.30–1.65 (m, 12H), 2.45 (m, 2H), 2.50 (s, 3H), 4.25 (m, 2H), 5.05–5.15 (m, 2H), 5.85 (m, 1H), 6.85 (d, 1H), 7.30 (d, 1H), 17.8 (s, 1H) |
| 40 | I-1x.3579 | m.p. 129° C.–132° C. |

The compounds I and their agriculturally useful salts are suitable, both as isomer mixtures and in the form of the pure isomers, for use as herbicides. The herbicidal compositions comprising compounds I effect very good control of vegetation on non-crop areas, especially at high application rates. In crops such as wheat, rice, maize, soybeans and cotton, they act against broad-leaved weeds and grass weeds without causing any significant damage to the crop plants. This effect is observed in particular at low application rates.

Depending on the application method in question, the compounds I or the herbicidal compositions comprising them can additionally be employed in a further number of crop plants for eliminating undesirable plants. Suitable crops are, for example, the following:
*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum (N.rustica), Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera* and *Zea mays.*

In addition, the compounds I can also be used in crops which tolerate the action of herbicides due to breeding, including genetic engineering methods.

The compounds I, or the compositions comprising them, can be applied, for example, in the form of directly sprayable aqueous solutions, powders, suspensions, including highly-concentrated aqueous, oily or other suspensions or dispersions, emulsions, oil dispersions, pastes, dusts, mat rials for broadcasting or granules, by means of spraying, atomizing, dusting, broadcasting, pouring or seed dressing or mixing with the seed. The use forms depend on the intended purposes; in each case, they should ensure the finest possible distribution of the active compounds according to the invention. The herbicidal compositions comprise a herbicidally effective amount of at least one compound of the formula I or an agriculturally useful salt of I and auxiliaries which are customarily used for formulating crop protection agents.

Suitable inert additives are essentially:

Mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydro-naphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, for example amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the compounds of the formula I, as such or dissolved in an oil or solvent, can be homogenized in water by means of wetting agent, tackifier, dispersant or emulsifier.

Alternatively, it is possible to prepare concentrates from active substance, wetting agent, tackifier, dispersant or emulsifier and, if desired, solvent or oil, and these concentrates are suitable for dilution with water.

Suitable surfactants are the alkali metal salts, alkaline earth metal salts and ammonium salts of aromatic sulfonic acids, for example ligno-, phenol-, naphthalene- and dibutylnaphthalene-sulfonic acid, and of fatty acids, of alkyl- and alkylaryl-sulfonates, of alkyl sulfates, lauryl ether sulfates and fatty alcohol sulfates, and the salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitant grinding of the active substances with a solid carrier.

Granules, e.g. coated granules, impregnated granules and homogeneous granules, can be prepared by binding the active compounds to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

The concentrations of the active compounds I in the ready-to-use products can be varied within wide ranges. In general, the formulations comprise from 0.001 to 98% by weight, preferably 0.01 to 95% by weight, of at least one active compound. The active compounds are employed in a purity of from 90% to 100%, preferably 95% to 100% (according to NMR spectrum).

The compounds I according to the invention can be formulated, for example, as follows:

I. 20 parts by weight of the compound of the formula I are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active compound.

II. 20 parts by weight of the compound of the formula I are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil.

Pouring the solution into 100,000 parts by weight of water and finely distributing it therein gives an aqueous dispersion which comprises 0.02% by weight of the active compound.

III. 20 parts by weight of the active compound of the formula I are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active compound.

IV. 20 parts by weight of the active compound of the formula I are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound of the formula I are mixed with 97 parts by weight of finely divided kaolin. This gives a dust which comprises 3% by weight of the active compound.

VI. 20 parts by weight of the active compound of the formula I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound of the formula I is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound of the formula I is dissolved in a mixture composed of 80 parts by weight of cyclohexanone and 20 parts by weight of Wettol® EM 31 (=non-ionic emulsifier based on ethoxylated castor oil). This gives a stable emulsion concentrate.

The herbicidal compositions or the active compounds can be applied pre- or post-emergence or together in the seed of a crop plant. It is also possible to apply the herbicidal compositions or active compounds by applying crop plant seed pretreated with the herbicidal compositions or active compounds. If the active compounds are less well tolerated by certain crop plants, it is possible to use application techniques in which the herbicidal compositions are sprayed, with the aid of the spraying equipment, in such a way that they come into as little contact as possible, if any, with the leaves of the sensitive crop plants while the active compounds reach the leaves of undesirable plants which grow underneath, or the bare soil surface (post-directed, lay-by).

Depending on the intended aim, the season, the target plants and the growth stage, the rates of application of the active compound I are from 0.001 to 3.0, preferably 0.01 to 1.0, kg of active substance (a.s.)/ha.

To widen the spectrum of action and to achieve synergistic effects, the novel compounds of the formula I may be mixed, and applied jointly, with a large number of representatives of other groups of herbicidally or growth-regulating active compounds. Suitable examples of components in mixtures are 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, 2-hetaroyl-1,3-cyclohexanedione, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to apply the compounds I alone or in combination with other herbicides, even in the form of a mixture together with further crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates may also be added.

USE EXAMPLES

The herbicidal activity of the cyclohexenone derivatives of benzazolones of the formula I was demonstrated by the following greenhouse experiments:

The culture containers used were plastic pots containing loamy sand with approximately 3.0% of humus as substrate. The seeds of the test plants were sown separately for each species.

For the pre-emergence treatment, the active compounds, suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants unless this was adversely affected by the active compounds.

For the post-emergence treatment, the test plants were first grown to a plant height of from 3 to 15 cm, depending on the plant habit, and only then treated with the active compounds which had been suspended or emulsified in water. To this end, the test plants were either sown directly and grown in the same containers, or they were first grown separately as seedlings and transplanted into the test containers a few days prior to treatment. The rate of application for the post-emergence treatment was 250, 125, 62.5, 31.3 and/or 15.6 g/ha of active substance (a.s.).

Depending on the species, the plants were kept at from 10 to 25° C., or 20–35° C., respectively. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage, or normal course of growth. A damage of at least 95% corresponds to very good herbicidal action.

The plants used in the greenhouse experiments were of the following species:

| Bayer code | Common name |
|---|---|
| ABUTH | velvet leaf |
| AMARE | redroot pigweed |
| BRAPL | marmalade grass |
| CHEAL | lambs' quarters (goosefoot) |
| ECHCG | barnyard grass |
| LAMAM | henbit |
| MATIN | chamomile, false |
| PHBPU | morning glory, common |
| POLPE | lady's thumb |
| SINAL | white mustard |
| SETFA | giant foxtail |

The following results were obtained by the post-emergence method. At application rates of 125 or 62.5 g/ha (a.s.), the compound I-1a.1129 from Example 1, used by the post-emergence method, showed very good herbicidal action against CHEAL, LAMAM, MATIN and SINAL.

At application rates of 125 or 62.5 g/ha (a.s.), the compound I-1c.1129 from Example 2, used by the post-emergence method, showed very good herbicidal action against CHEAL, ECHCG, PHBPU und POLPE.

At application rates of 31.3 g/ha (a.s.), the compound I-1d.1129 from Example 3, used by the post-emergence method, showed very good herbicidal action against CHEAL, PHBPU and POLPE, good to very good herbicidal action against ECHCG and, at application rates of 16.5 g/ha of a.s., very good herbicidal action against PHBPU and POLPE and good to very good herbicidal action against CHEAL and ECHCG.

At application rates of 125 or 250 g/ha (a.s.), the compound I-1c.1131 from Example 16, used by the post-emergence method, showed very good herbicidal action against CHEAL, ECHCG, SETFA and POLPE.

At application rates of 125 or 250 g/ha (a.s.) the compound I-1x.1131 from Example 17, used by the post-emergence method, showed very good herbicidal action against BRAPL, CHEAL, ECHCG, SETFA and POLPE.

At application rates of 125 or 250 g/ha (a.s.) the compound I-1a.1131 from Example 18, used by the post-emergence method, showed very good herbicidal action against ABUTH, CHEAL, ECHCG and POLPE.

At application rates of 125 or 250 g/ha (a.s.) the compound I-1d.1131 from Example 19, used by the post-emergence method, showed very good herbicidal action against ABUTH, AMARE, CHEAL, ECHCG and SETFA.

At application rates of 125 or 250 g/ha (a.s.) the compound I-1x.1134 from Example 14, used by the post-emergence method, showed very good herbicidal action against ABUTH, CHEAL, ECHCG and SETFA.

At application rates of 125 or 250 g/ha (a.s.) the compound I-1d.1134 from Example 15, used by the post-emergence method, showed very good herbicidal action against ABUTH, AMARE, ECHCG and POLPE.

At application rates of 125 or 250 g/ha (a.s.) the compound I-1a.6 from Example 9, used by the post-emergence method, showed very good herbicidal action against AMARE, CHEAL, ECHCG and POLPE.

At application rates of 125 or 250 g/ha (a.s.) the compound I-1a.29 from Example 11, used by the post-emergence method, showed very good herbicidal action against AMARE, CHEAL, ECHCG and POLPE.

What is claimed is:
1. A cyclohexenone derivative of a benzazolone of the formula I

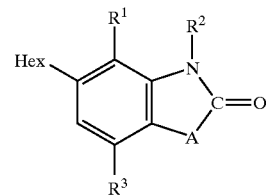

(I)

in which A, $R^1$, $R^2$, $R^3$ and Hex are as defined below:

A is O, S, SO, $SO_2$ or $NR^6$;

$R^1$ is halogen, $C_1$–$C_4$-alkyl, $C_1$–$C_4$-haloalkyl, $C_1$–$C_4$-hydroxyalkyl, $C_1$–$C_4$-alkoxy-$C_1$–$C_4$-alkyl, $C_1$–$C_4$-haloalkoxy-$C_1$–$C_4$-alkyl, $C_1$–$C_4$-haloalkylthio-$C_1$–$C_4$-alkyl, $C_1$–$C_4$-alkylthio-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, $C_1$–$C_4$-alkoxy, $C_1$–$C_4$-hydroxyalkoxy, $C_1$–$C_4$-haloalkoxy, $C_1$–$C_4$-alkoxy-$C_1$–$C_4$-alkoxy, $C_1$–$C_4$-haloalkoxy-$C_1$–$C_4$-alkoxy, $C_1$–$C_4$-alkylthio, $C_1$–$C_4$-haloalkylthio, $C_1$–$C_4$-alkylsulfonyl, $C_1$–$C_4$-haloalkylsulfonyl;

$R^2$ is hydroxyl, nitro, amino, $C_1$–$C_6$-alkylamino, di($C_1$–$C_6$-alkyl)amino, cyno, CHO, $C_1$–$C_6$-alkoxy, $C_1$–$C_6$-alkyl, $C_1$–$C_6$-hydroxyalkyl, $C_1$–$C_6$-haloalkyl, $C_1$–$C_6$-alkoxy-$C_1$–$C_6$-alkyl, $C_1$–$C_6$-haloalkoxy-$C_1$–$C_6$-alkyl, $C_2$–$C_6$-alkenyl, $C_2$–$C_6$-haloalkeny, $C_1$–$C_6$-haloalkoxy-$C_2$–$C_6$-alkenyl, $C_1$–$C_6$-alkoxy-$C_2$–$C_6$-alkenyl, $C_2$–$C_6$-alkynyl, $C_2$–$C_6$-haloalkynyl, $C_1$–$C_6$-haloalkoxy-$C_2$–$C_6$-alkynyl, $C_1$–$C_6$-alkoxy-$C_2$–$C_6$-alkynyl, $C_1$–$C_6$-alkylsulfonyl, $C_1$–$C_6$-haloalkylsulfonyl, ($C_1$–$C_6$-alkyl)carbonyl, $C_1$–$C_6$-haloalkylcarbonyl, hydroxycarbonyl-$C_1$–$C_4$-alkyl, $C_1$–$C_6$-alkoxycarbonyl-$C_1$–$C_6$-alkyl, a radical of the formula $C(O)OR^4$, $CON(R^5)_2$ or $C(=NOR^{4a})R^{4b}$, aryl, aryl-$C_1$–$C_4$-alkyl, arylsulfonyl, arylcarbonyl, $C_3$–$C_6$-cycloalkyl, $C_3$–$C_6$-cycloalkenyl, 3-, 4-, 5-, 6- or 7-membered heterocyclyl, 3-, 4-, 5-, 6- or 7-membered heterocyclyl-$C_1$–$C_6$-alkyl, where each aryl, cycloalkyl, cycloalkenyl and each heterocyclyl radical may be unsubstituted or may carry one, two, three or four substituents, in each case selected from the group consisting of halogen, $C_1$–$C_4$-haloalky, $C_1$–$C_4$-alkoxy and $C_1$–$C_4$-haloalkoxy;

$R^3$ is hydrogen, $C_1$–$C_4$-alkyl, $C_1$–$C_4$-haloalkyl, $C_1$–$C_4$-alkoxy-$C_1$–$C_4$-alkyl, $C_1$–$C_4$-haloalkoxy-$C_1$–$C_4$-alkyl or halogen;

in which $R^4$ is $C_1$–$C_6$-alkyl, $C_1$–$C_6$-haloalkyl, $C_1$–$C_6$-alkoxy-$C_1$–$C_6$-alkyl, $C_1$–$C_6$-haloalkoxy-$C_1$–$C_6$-alkyl, $C_2$–$C_6$-alkenyl, $C_2$–$C_6$-haloalkenyl, $C_1$–$C_6$-haloalkoxy-$C_2$–$C_6$-alkenyl, $C_1$–$C_6$-alkoxy-$C_2$–$C_6$-alkenyl, $C_2$–$C_6$-alkynyl, $C_2$–$C_6$-haloalkynyl, $C_1$–$C_6$-haloalkoxy-$C_2$–$C_6$-alkynyl, $C_1$–$C_6$-alkoxy-$C_2$–$C_6$-alkynyl;

$R^{4a}$, $R^{4b}$ independently of one another may have the meanings mentioned for $R^4$, and $R^{4b}$ may be hydrogen;

$R^5$ independently of one another are hydrogen, $C_1$–$C_6$-alkyl, $C_1$–$C_6$-haloalkyl, $C_1$–$C_6$-alkoxy-$C_1$–$C_6$-alkyl, ($C_1$–$C_6$-haloalkoxy)-$C_1$–$C_6$-alkyl, $C_2$–$C_6$-alkenyl, $C_2$–$C_6$-haloalkenyl, $C_1$–$C_6$-haloalkyl-$C_2$–$C_6$-alkenyl, $C_1$–$C_6$-haloalkoxy-$C_2$–$C_6$-alkenyl, $C_1$–$C_6$-alkoxy-$C_2$–$C_6$-alkenyl, $C_2$–$C_6$-alkynyl, $C_2$–$C_6$-haloalkynyl, $C_1$–$C_6$-haloalkyl-$C_2$–$C_6$-alkynyl, $C_1$–$C_6$-haloalkoxy-$C_2$–$C_6$-alkynyl, $C_1$–$C_6$-alkoxy-$C_2$–$C_6$-alkynyl, or together form a 3- to 7-membered heterocycle which may be partially or fully halogenated and/or may carry one, two or three substituents selected from the group consisting of $C_1$–$C_6$-alkyl, $C_1$–$C_6$-haloalkyl, $C_1$–$C_6$-alkoxy, $C_1$–$C_6$-haloalkoxy;

$R^6$ is hydrogen, $C_1$–$C_4$-alkyl, $C_1$–$C_4$-haloalkyl, $C_1$–$C_4$-haloalkoxy-$C_1$–$C_4$-alkyl, $C_1$–$C_4$-alkoxy-$C_1$–$C_4$-alkyl; and Hex is substituted (3-oxo-1-cyclohexen-2-yl)carbonyl of the formula IIa or substituted (1,3-dioxo-2-cyclohexyl) methylidene of the formula IIb,

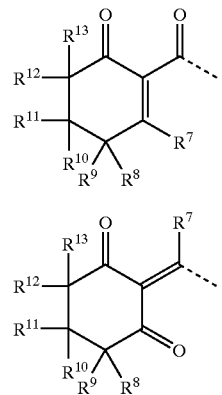

in which the variables $R^7$ to $R^{13}$ are as defined below:

$R^7$ is hydroxyl, mercapto, halogen, $OR^{14}$, $SR^{14}$, $SOR^{15}$, $SO_2R^{15}$, $OSO_2R^{15}$, $P(O)R^{16}R^{17}$, $OP(O)R^{16}R^{17}$, $P(S)R^{16}R^{17}$, $OP(S)R^{16}R^{17}$, $NR^{18}R^{19}$, $ONR^{18}R^{19}$ or N-bonded heterocyclyl which may be partially or fully halogenated an for may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^8$, $R^{12}$ independently of one another are hydrogen, $C_1$–$C_4$-alkyl or $C_1$–$C_4$-alkoxycarbonyl;

$R^9$·$R^{11}R^{13}$ independently of one another are hydrogen or $C_1$–$C_4$-alkyl;

$R^{10}$ is hydrogen, halogen, hydroxyl, $C_1$–$C_6$-alkyl, $C_1$–$C_6$-haloalkyl, di-($C_1$–$C_6$-alkoxy)-methyl,($C_1$–$C_6$-alkoxy)-($C_1$–$C_6$-alkylthio)methyl, di-($C_1$–$C_6$-alkylthio)methyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkoxycarbonyl, $C_1$–$C_6$-haloalkoxycarbonyl;

is 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the six lastmentioned radicals may be substituted by one to three $C_1$–$C_4$-alkyl radicals;

or $R^9$ and $R^{11}$ or $R^{11}$ and $R^{13}$ together form a π bond or a $C_1$–$C_5$-alkylene chain which may carry one, two or three radicals from the following group: halogen, cyano, 1–$C_4$-alkyl, $C_1$–$C_4$-haloalkyl or $C_1$–$C_4$-alkoxycarbonyl;

or $R^9$ and $R^{13}$ together form a $C_1$–$C_4$-alkyl chain which may carry one, two or three radicals from the following group: halogen, cyano, $C_1$–$C_4$-alkyl, $C_1$–$C_4$-haloalkyl or $C_1$–$C_4$-alkoxycarbonyl;

or $R^{10}$ and $R^{11}$ together form a —O—$(CH_2)_p$—O—, —O—$(CH_2)_p$—S—, —S—$(CH_2)_p$—S—, —O—$(CH_2)_q$— or —S—$(CH_2)_q$— chain, in which p is 2, 3, 4 or 5 and q is 2, 3, 4, 5 or 6, which may substituted by one, two or three radicals frclm the following group: halogen, cyano, $C_1$–$C_4$-alkyl, $C_1$–$C_1$–$C_4$-haloalkyl or $C_1$–$C_4$-alkoxycarbonyl;

or $R^{10}$ and $R^{11}$, together with the carbon to which they are attached, form a carbonyl group;

where $R^{14}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)amino-carbonyl, N-($C_3$–$C_6$-alkenyl)-N-($C_1$–$C_6$-alkyl)amino-carbonyl, N-($C_3$–$C_6$-alkynyl)-N-($C_1$–$C_6$-alkyl)amino-carbonyl, N-($C_1$–$C_6$-alkoxy)-N-($C_1$–$C_6$-alkyl)amino-carbonyl, N-($C_3$–$C_6$-alkenyl)-N-($C_1$–$C_6$-alkoxy)amino-carbonyl, N-($C_3$–$C_6$-alkynyl)-N-($C_1$–$C_6$-alkoxy)amino-carbonyl, di($C_1$–$C_6$-alkyl)aminothiocarbonyl, $C_1$–$C_6$-alkoxyimino-$C_1$–$C_6$-alkyl, where the alkyl, cycloalkyl and alkoxy radicals mentioned may be partially or fully halogenated and/or may carry one, two or three of the following groups: cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, hydroxycarbonyl, $C_1$–$C_4$-alkylaminocarbonyl, di($C_1$–$C_4$-alkyl)amino-carbonyl, aminocarbonyl, $C_1$–$C_4$-alkylcarbonyloxyor $C_3$–$C_6$-cycloalkyl;

is phenyl, phenyl-$C_1$–$C_6$-alkyl, phenylcarbonyl-$C_1$–$C_6$-alkyl, phenylcarbonyl, phenoxycarbonyl, phenoxythiocarbonyl, phenylaminocarbonyl, N-($C_1$–$C_6$-alkyl)-N-phenylaminocarbonyl, phenyl-$C_2$–$C_6$-alkenylcarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl, heterocyclylamino-carbonyl, N-($C_1$–$C_6$alkyl)-N-heterocyclyl-aminocarbonyl, or heterocyclyl-$C_1$–$C_6$-alkenylcarbonyl, where the phenyl and the heterocyclyl radical of the 18 lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{15}$ is $C_1$–$C_6$-alkyl, $C_3$–$C_6$-alkenyl, $C_3$–$C_6$-alkynyl or $C_3$–$C_6$-cycloalkyl, where the four radicals mentioned may be partially or fully halogenated and/or may carry one, two or three of the following groups: cyano, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, $C_1$–$C_4$-alkoxycarbonyl or $C_1$–$C_4$-haloalkoxycarbonyl;

is phenyl, phenyl-$C_1$–$C_4$-alkyl, heterocyclyl or heterocyclyl-$C_1$–$C_4$-alkyl, where the phenyl and the heterocyclyl radical of the four lastmentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{16}$, $R^{17}$ independently of one another are hydrogen, hydroxyl, $C_1$–$C_6$alkyl, $C_1$–$C_6$-alkoxy, $C_1$–$C_6$-alkylthio, phenyl, phenyl-$C_1$–$C_4$-alkyl or phenoxy, where the three lastmentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{18}$ is hydrogen, $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di($C_1$–$C_6$-alkyl)amino or $C_1$–$C_6$-alkylcarbonylamino, where the alkyl, cycloalkyl or alkoxy radicals mentioned may be partially or fully halogenated and/or may carry one, two or three of the following radicals: cyano, $C_1$–$C_4$-alkoxycarbonyl, $C_1$–$C_4$-alkylaminocarbonyl, di($C_1$–$C_4$-alkyl)-aminocarbonyl or $C_3$–$C_6$-cycloalkyl;

is phenyl, phenyl-$C_1$–$C_4$-alkyl, phenylcarbonyl, heterocyclyl, heterocyclyl-$C_1$–$C_4$-alkyl or heterocyclylcarbonyl, where the phenyl or heterocyclyl radical of the six lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{19}$ is hydrogen, $C_1$–$C_6$-alkyl, $C_3$–$C_6$-alkenyl or $C_3$–$C_6$-alkynyl;

and its agriculturally useful salts.

2. A cyclohexenone derivative as claimed in claim 1 wherein A in the formula I is oxygen or $NR^6$.

3. A cyclohexenone derivative as claimed in claim 1 wherein A in the formula I is sulfur.

4. A cyclohexenone derivative as claimed in claim 1 where $R^1$ in the formula I is selected from the group consisting of $C_1$–$C_4$-alkyl, halogen and $C_1$–$C_4$-alkoxy.

5. A cyclohexenone derivative as claimed in claim 1 where $R^2$ in the formula I is a heterocycle selected from the group consisting of 4,5-dihydroisoxazol-3-yl, 4,5-dihydroisoxazol-4-yl, isoxazol-3-yl, isoxazol-4-yl, 1,3-dioxolan-2-yl, 1,3-dithiolan-2-yl, 1,3-dioxan-2-yl, 1,3-dithian-2-yl, oxazolin-2-yl and oxazolidin-2-yl, where the abovementioned heterocycles may be mono-, di- or trisubstituted by $C_1$–$C_4$-alkyl.

6. A cyclohexenone derivative as claimed in claim 1, where $R^2$ in the formula I is cyano, $C_1$–$C_4$-alkyl, $C_3$–$C_6$-alkenyl, $C_1$–$C_4$-(halo)alkylcarbonyl, $C_1$–$C_4$-alkoxycarbonyl-$C_1$–$C_4$-alkyl or $C_1$–$C_4$-alkoxycarbonyl.

7. A cyclohexenone derivative as claimed in claim 1 where $R^3$ in the formula I is hydrogen, $C_1$–$C_4$-alkyl or halogen.

8. A cyclohexenone derivative as claimed in claim 1 where Hex in the formula I is a radical of the formula IIa where $R^7$ is selected from the group consisting of hydroxyl, mercapto, halgen, $OR^{14}$, $SR^{14}$, $SO_2R^{15}$, $NR^{18}R^{19}$ and $ONR^{18}R^{19}$, where $R^{14}$, $R^{15}$ and $R^{19}$ are as defined in claim 1.

9. A cyclohexenone derivative as claimed in claim 8 where in the formula IIa or IIb.

$R^7$ is selected from the group consisting of hydroxyl, $C_1$–$C_4$-alkyloxy, $C_1$–$C_4$-alkylamino, di-$C_1$–$C_4$-alkylamino, N-($C_1$–$C_4$-alkyloxy)-N-($C_1$–$C_4$-alkyl) amino, O—$CH_2$-phenyl, phenylthio, phenylcarbonyloxy, 2-, 3- or 4-fluorophenylcarbonyloxy, $C_1$–$C_4$-methylthio, $C_1$–$C_4$-sulfonyloxy, phenylsulfonyloxy and 2-, 3- or 4-ethylphenyl-sulfonyloxy.

10. A cyc;ohexenone derivative as claimed in claim 1 where in the formula IIa or IIb $R^9$, $R^9$, $R^{10}$, $R^{11}$, $R^{12}$ and $R^{13}$ independently of one another are hydrogen or $C_1$–$C_4$-alkyl, $R^{10}$ may also be hydroxyl, $C_1$–$C_4$-alkoxy, $C_1$–$C_4$-alkylthio, haloalkoxy or haloalkylthio, $R^{10}$ and $R^{11}$ together with the carbon atom to which they are attached may also be a carbonyl group or a 1,3-dioxolane, 1,3-dithiolane, 1,3-oxothiolane, 1,3-oxothiane, 1,3-dithiolane or 1,3-dithiane ring, where the 2-position of the six rings mentioned is identical to the carbon to which $R^{10}$ and $R^{11}$ are attached, $R^8$ and $R^{12}$ or $R^9$ and $R^{13}$ may also be a $C_1$–$C_4$-alkylene chain, or $R^9$ and $R^{11}$ or $R^{11}$ and $R^{12}$ together may form a π bond.

11. A benzazolonecarboxylic acid of the formula IVa

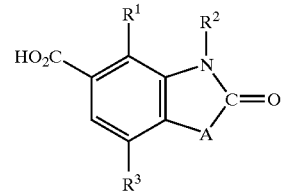

(IVa)

where A, $R^1$, $R^2$ and $R^3$ are defined in claim 1.

12. A composition, comprising at least one cyclohexenone derivative of the formula I or an agriculturally useful salt of I as claimed in claim 1, and custormay auxiliaries.

13. A method for controlling undesirable vegetation, which comprises allowing a herbicidally effective amount of at least one cyclohexenone derivative of the formula I or an agriculturally useful salt of I as claimed in claim 1 to act on plants, their habitat and/or on seed.

* * * * *